US011958900B2

(12) United States Patent
Gruber

(10) Patent No.: US 11,958,900 B2
(45) Date of Patent: *Apr. 16, 2024

(54) ANTI-AGE ANTIBODIES FOR TREATING NEURODEGENERATIVE DISORDERS

(71) Applicant: SIWA Corporation, Chicago, IL (US)

(72) Inventor: Lewis S. Gruber, Chicago, IL (US)

(73) Assignee: SIWA Corporation, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/092,743

(22) PCT Filed: Apr. 14, 2017

(86) PCT No.: PCT/US2017/027773
§ 371 (c)(1),
(2) Date: Oct. 10, 2018

(87) PCT Pub. No.: WO2017/181116
PCT Pub. Date: Oct. 19, 2017

(65) Prior Publication Data
US 2019/0119371 A1  Apr. 25, 2019

Related U.S. Application Data

(60) Provisional application No. 62/323,471, filed on Apr. 15, 2016.

(51) Int. Cl.
*A61P 25/28* (2006.01)
*A61K 35/17* (2015.01)
*C07K 16/24* (2006.01)
*C07K 16/44* (2006.01)
*A61K 38/00* (2006.01)

(52) U.S. Cl.
CPC .............. *C07K 16/24* (2013.01); *A61K 35/17* (2013.01); *A61P 25/28* (2018.01); *C07K 16/44* (2013.01); *A61K 38/00* (2013.01); *C07K 2317/24* (2013.01); *C07K 2317/92* (2013.01)

(58) Field of Classification Search
CPC ........ C07K 16/18; C07K 16/24; C07K 16/44; C07K 2317/24; C07K 2317/92; C07K 2317/569; C07K 2317/73; C07K 2317/732; C07K 2317/734; A61P 25/28; A61P 25/16; A61P 21/00; A61K 35/17; A61K 2039/505; A61K 35/15; A61K 39/0005; A61K 2300/00
See application file for complete search history.

(56) References Cited

U.S. PATENT DOCUMENTS

| | | | |
|---|---|---|---|
| 4,217,344 A | 8/1980 | Vanlerberghe et al. | |
| 4,900,747 A | 2/1990 | Vlassara et al. | |
| 4,911,928 A | 3/1990 | Wallach | |
| 4,917,951 A | 4/1990 | Wallach | |
| 4,965,288 A | 10/1990 | Palfreyman | |
| 5,494,791 A | 2/1996 | Cohen | |
| 5,518,720 A | 5/1996 | Cohen | |
| 5,601,526 A | 2/1997 | Chapelon et al. | |
| 5,620,409 A | 4/1997 | Venuto | |
| 5,620,479 A | 4/1997 | Diederich | |
| 5,664,570 A | 9/1997 | Bishop | |
| 5,693,762 A | 12/1997 | Queen et al. | |
| 5,702,704 A | 12/1997 | Bucala | |
| 5,766,590 A | 6/1998 | Founds et al. | |
| 5,811,075 A | 9/1998 | Vlassara et al. | |
| 5,817,771 A | 10/1998 | Bayley et al. | |
| 5,984,882 A | 11/1999 | Rosenschein et al. | |
| 6,067,859 A | 5/2000 | Kas et al. | |
| 6,090,382 A | 7/2000 | Salfeld et al. | |
| 6,176,842 B1 | 1/2001 | Tachibana et al. | |
| 6,245,318 B1 | 6/2001 | Klibanov et al. | |
| 6,309,355 B1 | 10/2001 | Cain et al. | |
| 6,380,165 B1 | 4/2002 | Al-Abed et al. | |
| 6,387,373 B1 | 5/2002 | Wright et al. | |
| 6,410,598 B1* | 6/2002 | Vitek ..................... | A61K 31/15 514/1.1 |
| 6,670,136 B2 | 12/2003 | Schmidt et al. | |
| 6,676,963 B1 | 1/2004 | Lanza et al. | |
| 6,818,215 B2 | 11/2004 | Smith et al. | |
| 6,821,274 B2 | 11/2004 | McHale et al. | |
| 7,033,574 B1 | 4/2006 | Schneider et al. | |
| 7,101,838 B2 | 9/2006 | Stern et al. | |
| 7,256,273 B2* | 8/2007 | Basi ........................ | A61P 43/00 530/387.3 |
| 7,347,855 B2 | 3/2008 | Eshel et al. | |
| 7,358,226 B2 | 4/2008 | Dayton et al. | |
| 7,367,988 B1 | 5/2008 | Litovitz | |
| 7,470,521 B2 | 12/2008 | O'Keefe | |
| 7,751,057 B2 | 7/2010 | Oldenburg et al. | |
| 7,815,570 B2 | 10/2010 | Eshel et al. | |
| 8,318,164 B2* | 11/2012 | Warne .................... | A61K 47/20 424/133.1 |
| 8,323,651 B2 | 12/2012 | Gu et al. | |
| 8,343,420 B2 | 1/2013 | Cioanta et al. | |
| 8,398,977 B2 | 3/2013 | Bleck et al. | |
| 8,721,571 B2 | 5/2014 | Gruber | |
| 8,977,361 B2 | 3/2015 | Carpentier et al. | |
| 8,981,112 B2 | 3/2015 | Bukhtiyarov et al. | |
| 9,155,805 B2 | 10/2015 | Hamakubo | |
| 9,161,810 B2 | 10/2015 | Gruber | |

(Continued)

FOREIGN PATENT DOCUMENTS

| | | |
|---|---|---|
| AU | 2009/248945 | 5/2014 |
| DE | 102008009461 | 8/2009 |
| EP | 0 259 893 | 3/1988 |
| EP | 1 219 639 | 7/2002 |
| EP | 1 415 997 | 5/2004 |
| EP | 1 867 659 | 12/2007 |

(Continued)

OTHER PUBLICATIONS

Edwards et al. J. Mol. Biol. 2003, 334:103-118. (Year: 2003).*

(Continued)

Primary Examiner — Kimberly Ballard
(74) Attorney, Agent, or Firm — EVAN LAW GROUP LLC

(57) ABSTRACT

A method of treating a neurodegenerative disorder or MD comprises administering to a subject a composition comprising an AGE antibody.

20 Claims, 5 Drawing Sheets

Specification includes a Sequence Listing.

(56) References Cited

U.S. PATENT DOCUMENTS

| | | |
|---|---|---|
| 9,320,919 B2 | 4/2016 | Gruber |
| 9,493,566 B2 | 11/2016 | Ryan |
| 9,493,567 B2 | 11/2016 | Lieberburg |
| 9,649,376 B2 | 5/2017 | Gruber |
| 9,993,535 B2 | 6/2018 | Gruber |
| 10,226,531 B2 | 3/2019 | Gruber |
| 10,584,180 B2 | 3/2020 | Gruber |
| 10,858,449 B1 | 12/2020 | Gruber |
| 10,889,634 B2 | 1/2021 | Gruber |
| 10,919,957 B2 | 2/2021 | Gruber |
| 10,925,937 B1 | 2/2021 | Gruber |
| 10,960,234 B2 | 3/2021 | Gruber |
| 10,961,321 B1 | 3/2021 | Gruber |
| 10,995,151 B1 | 5/2021 | Gruber |
| 11,213,585 B2 | 1/2022 | Gruber |
| 11,261,241 B2 | 3/2022 | Gruber |
| 11,518,801 B1 | 12/2022 | Gruber |
| 11,542,324 B2 | 1/2023 | Gruber |
| 2002/0122799 A1 | 9/2002 | Stern et al. |
| 2002/0193784 A1 | 12/2002 | McHale et al. |
| 2003/0073138 A1 | 4/2003 | Kientsch-Engel et al. |
| 2003/0115614 A1 | 6/2003 | Kanda |
| 2003/0170173 A1 | 9/2003 | Klaveness et al. |
| 2003/0229283 A1 | 12/2003 | Craig et al. |
| 2004/0039416 A1 | 2/2004 | Myhr |
| 2004/0141922 A1 | 7/2004 | Klaveness et al. |
| 2004/0142391 A1 | 7/2004 | Schmidt |
| 2004/0208826 A1 | 10/2004 | Schneider et al. |
| 2004/0210042 A1 | 10/2004 | Tsuchida |
| 2004/0229830 A1 | 11/2004 | Tachibana et al. |
| 2005/0084538 A1 | 4/2005 | Dayton et al. |
| 2005/0283098 A1 | 12/2005 | Conston et al. |
| 2006/0078501 A1 | 4/2006 | Goertz et al. |
| 2006/0122543 A1 | 6/2006 | Mayer et al. |
| 2006/0188883 A1 | 8/2006 | Murray et al. |
| 2006/0222646 A1 | 10/2006 | Treacy |
| 2006/0241524 A1 | 10/2006 | Lee |
| 2007/0059247 A1 | 3/2007 | Lindner et al. |
| 2007/0065415 A1 | 3/2007 | Kleinsek et al. |
| 2007/0065443 A1 | 3/2007 | Tobia |
| 2007/0071675 A1 | 3/2007 | Wu et al. |
| 2007/0078290 A1 | 4/2007 | Esenaliev |
| 2007/0083120 A1 | 4/2007 | Cain et al. |
| 2007/0128117 A1 | 6/2007 | Bettinger et al. |
| 2007/0129633 A1 | 6/2007 | Lee et al. |
| 2007/0225242 A1 | 9/2007 | Erler |
| 2008/0019986 A1 | 1/2008 | Stern et al. |
| 2008/0051680 A1 | 2/2008 | Luebcke |
| 2008/0063603 A1 | 3/2008 | Schneider et al. |
| 2008/0139942 A1 | 6/2008 | Gaud et al. |
| 2008/0160506 A1 | 7/2008 | Liu et al. |
| 2009/0022659 A1 | 1/2009 | Olson et al. |
| 2009/0076390 A1 | 3/2009 | Lee et al. |
| 2009/0306552 A1 | 12/2009 | Furuzono et al. |
| 2010/0028359 A1 | 2/2010 | Gu et al. |
| 2010/0226932 A1 | 9/2010 | Smith et al. |
| 2010/0249038 A1 | 9/2010 | Logsdon |
| 2011/0105961 A1 | 5/2011 | Gruber |
| 2011/0319499 A1 | 12/2011 | Semba et al. |
| 2012/0130287 A1 | 5/2012 | Gruber |
| 2012/0135918 A1 | 5/2012 | Bowers |
| 2012/0156134 A1 | 6/2012 | Squires |
| 2012/0183534 A1 | 7/2012 | Gruber |
| 2013/0058921 A1* | 3/2013 | Van Rhee ............ A61K 31/454 424/133.1 |
| 2013/0131006 A1 | 5/2013 | Hee et al. |
| 2013/0243785 A1 | 9/2013 | Gruber |
| 2013/0288980 A1 | 10/2013 | De Keizer et al. |
| 2014/0234339 A1 | 8/2014 | Ohlsen |
| 2014/0234343 A1 | 8/2014 | Lee et al. |
| 2014/0303526 A1 | 10/2014 | Gruber |
| 2015/0376279 A1 | 12/2015 | Hansen |
| 2016/0038576 A1 | 2/2016 | Vasserot et al. |
| 2016/0083437 A1 | 3/2016 | Cho et al. |
| 2016/0091410 A1 | 3/2016 | Krug |
| 2016/0101299 A1 | 4/2016 | Gruber |
| 2016/0152697 A1 | 6/2016 | Gruber |
| 2016/0175413 A1 | 6/2016 | Gruber |
| 2016/0193358 A1 | 7/2016 | Algate |
| 2016/0215043 A1 | 7/2016 | Gruber |
| 2016/0279261 A1 | 9/2016 | Lee |
| 2016/0311907 A1 | 10/2016 | Brogdon et al. |
| 2016/0339019 A1 | 11/2016 | Laberge et al. |
| 2016/0340418 A1 | 11/2016 | Baron |
| 2017/0216286 A1* | 8/2017 | Kirkland ............... A61K 31/353 |
| 2017/0216435 A1 | 8/2017 | Gruber |
| 2017/0240632 A1 | 8/2017 | Thomas |
| 2017/0247472 A1 | 8/2017 | Gruber |
| 2017/0259086 A1 | 9/2017 | Carpentier et al. |
| 2018/0036558 A1 | 2/2018 | Carpentier et al. |
| 2018/0044411 A1 | 2/2018 | Gruber |
| 2018/0111982 A2 | 4/2018 | Gruber |
| 2018/0298087 A1 | 10/2018 | Gruber |
| 2018/0312577 A1 | 11/2018 | Gruber |
| 2018/0326026 A1 | 11/2018 | Gruber |
| 2019/0031781 A1 | 1/2019 | Gruber |
| 2019/0119371 A1 | 4/2019 | Gruber |
| 2019/0328873 A1 | 10/2019 | Gruber |
| 2019/0328876 A1 | 10/2019 | Gruber |
| 2020/0054682 A1 | 2/2020 | Gojo et al. |
| 2020/0055957 A1 | 2/2020 | Gruber |
| 2020/0150131 A1 | 5/2020 | Gruber |
| 2020/0231706 A1 | 7/2020 | Gruber |
| 2021/0087297 A1 | 3/2021 | Gruber |
| 2021/0208533 A1 | 7/2021 | Gruber |
| 2021/0236860 A1 | 8/2021 | Gruber |
| 2021/0253737 A1 | 8/2021 | Gruber |
| 2021/0253739 A1 | 8/2021 | Gruber |
| 2022/0160869 A1 | 5/2022 | Gruber |
| 2022/0175916 A1 | 6/2022 | Gruber |

FOREIGN PATENT DOCUMENTS

| | | | |
|---|---|---|---|
| EP | 2 294178 | 7/2014 | |
| EP | 2294178 B1 * | 7/2014 | ......... G01N 33/5091 |
| JP | 09178740 | 7/1997 | |
| JP | 11246599 | 9/1999 | |
| JP | 2003/160599 | 6/2003 | |
| JP | 2006-249015 | 9/2006 | |
| JP | 2007-163407 | 6/2007 | |
| JP | 2007277263 | 10/2007 | |
| RU | 2 270 029 | 1/2006 | |
| RU | 2617313 | 4/2017 | |
| WO | 1993/13421 | 7/1993 | |
| WO | 1995/20979 | 8/1995 | |
| WO | WO-9520979 A1 * | 8/1995 | ............. A61K 31/15 |
| WO | 1996/20958 | 7/1996 | |
| WO | 1997/07803 | 3/1997 | |
| WO | 1997/49429 | 12/1997 | |
| WO | 1999/07893 | 2/1999 | |
| WO | 1999/14587 | 3/1999 | |
| WO | 1999/64463 | 12/1999 | |
| WO | 2000/20458 | 4/2000 | |
| WO | 2001/00245 | 1/2001 | |
| WO | 2001/077342 | 10/2001 | |
| WO | 2004/011460 | 2/2004 | |
| WO | 2004/016229 | 2/2004 | |
| WO | 2004/076677 | 9/2004 | |
| WO | 2006/012415 | 2/2006 | |
| WO | 2006/017647 | 2/2006 | |
| WO | 2006/040597 | 4/2006 | |
| WO | 2009/136382 | 11/2009 | |
| WO | 2009/143411 | 11/2009 | |
| WO | 2010/005531 | 1/2010 | |
| WO | 2011/032633 | 3/2011 | |
| WO | 2012/047629 | 4/2012 | |
| WO | 2012/071269 | 5/2012 | |
| WO | 2012/135616 | 10/2012 | |
| WO | 2013/009785 | 1/2013 | |
| WO | 2013/043161 | 3/2013 | |
| WO | 2013/070468 | 5/2013 | |
| WO | 2014/090991 | 6/2014 | |
| WO | 2014/136114 | 9/2014 | |
| WO | 2014/164693 | 10/2014 | |

(56) References Cited

FOREIGN PATENT DOCUMENTS

| | | | |
|---|---|---|---|
| WO | WO-2014164693 A2 * | 10/2014 | ............ C07K 14/25 |
| WO | 2015/112835 | 7/2015 | |
| WO | 2015/116740 | 8/2015 | |
| WO | 2016/044252 | 3/2016 | |
| WO | 2017/065837 | 4/2017 | |
| WO | 2017/143073 | 8/2017 | |
| WO | 2017/181116 | 10/2017 | |
| WO | 2017/222535 | 12/2017 | |
| WO | 2018/191718 | 10/2018 | |
| WO | 2018/204679 | 11/2018 | |
| WO | 2020/023532 | 1/2020 | |
| WO | 2020/041625 | 2/2020 | |
| WO | 2021/222758 | 11/2021 | |
| WO | 2021/247397 | 12/2021 | |
| WO | 2022/093195 | 5/2022 | |

OTHER PUBLICATIONS

Kawaguchi M et al. Glyoxal inactivates glutamate transporter-1 in cultured rat astrocytes. Neuropathology, 2005, 25:27-36. (Year: 2005).*

Lloyd et al. Protein Eng. Design & Select, 2009, 22(3): 159-168. (Year: 2009).*

Scicchitano BM et al. Counteracting muscle wasting in aging and neuromuscular diseases: the critical role of IGF-1, Aging, 2009, 1(5), 451-457. (Year: 2009).*

Southern L et al. Immunohistocheimcal study of N-epsilon-caroxymethl lysine (CML) in human brain: relation to vascular dementia. BMC Neurology, 2007, 7:35. (Year: 2007).*

Haslbeck KM et al. Acta Neuropathol. 2005, 110, 247-254. (Year: 2005).*

Hoenicke et al. Carcinogenesis, 2012, 33(6), 1123-1126. (Year: 2012).*

Malatesta M. Eur. J. Histochem. 2012, 56, e36. (Year: 2012).*

Matias-Guiu JA et al. Front. Neurol. 7:53, 7 pages; published Mar. 31, 2016. (Year: 2016).*

Sternberg Z et al. J. Neuroinflammation, 2010, 7:72. (Year: 2010).*

Wingerchuk et al. Mayo Clinic Proc. 2014, 89(2), 225-240. (Year: 2014).*

Münch G et al. Advanced glycation endproducts and their pathogenic roles in neurological disorders. Amino Acids, 2012, 42(4): 1221-36; Epub Oct. 14, 2010. (Year: 2010).*

Salahuddin P et al. The role of advanced glycation end products in various types of neurodegenerative disease: A therapeutic approach. Cell. Mol. Biol. Lett. 2014, 19, 407-437. (Year: 2014).*

International Search Report dated Jul. 21, 2009 for PCT application No. PCT/US2009/44951.

Lindsey, J.B. et al., "Receptor for advanced glycation end-products (RAGE) and soluble RAGE (sRAGE): Cardiovascular implications", Diabetes Vascular Disease Research, vol. 6, No. 1, pp. 7-14, (2009).

Ando, K. et al., "Membrane proteins of human erythrocytes are modified by advanced glycation end products during aging in the circulation", Biochemical and Biophysical Research Communications, vol. 258, pp. 123-127, (1999).

Jandeleit-Dahm, K. et al., "The AGE/RAGE axis in diabetes-accelerated atherosclerosis", Clinical and Experimental Pharmacology and Physiology, vol. 35, pp. 329-334, (2008).

Sakata, N. et al., "Immunohistochemical localization of different epitopes of advanced glycation end products in human atherosclerotic lesions", Atherosclerosis, vol. 141, pp. 61-75, (1998).

Karachalias, N. et al., "Accumulation of fructosyl-lysine and advanced glycation end products in the kidney, retina and peripheral nerve of streptozotocin-induced diabetic rats", Biochemical Society Transactions, vol. 31, pp. 1423-1425, (2003).

Aroian, R. et al., "Pore-forming toxins and cellular non-immune defenses (CNIDs)", Current Opinion in Microbiology, vol. 10, pp. 57-61, (2007).

Dobson, J., "A twist on tumour targeting", Nature Materials, vol. 9, pp. 95-96, (2010).

Gutensohn, K. et al., "Extracorporeal plateletpheresis induces the interaction of activated platelets with white blood cells", Vox Sanguinis, vol. 78, No. 2, pp. 101-105, (20001.

Horiuchi, S. et al., "Immunochemical approach to characterize advanced glycation end products of the maillard reaction", The Journal of Biological Chemistry, vol. 266, No. 12, pp. 7329-7332, (1991).

Soetanto, K. et al., "Fundamental examination of cattle red blood cells damage with ultrasound exposure microscopic system (UEMS)", Japanese Journal of Applied Physics, vol. 37, part 1, No. 5B, pp. 3070-3073, (1998).

Harja, E. et al., "Vascular and inflammatory stresses mediate atherosclerosis via RAGE and its ligands in apoE-/- mice", The Journal of Clinical Investigation, vol. 118, No. 1, pp. 183-194, (2008).

Carstensen, E.L. et al., "Lysis of erythrocytes by exposure to cw ultrasound", Ultrasound in Medicine and Biology, vol. 19, No. 2, pp. 147-165, (1993).

Miller, M.W. et al., "Comparative sensitivity of human erythrocytes and lymphocytes to sonolysis by 1-MHz ultrasound", Ultrasound in Medicine and Biology, vol. 23, No. 4, pp. 635-638, (1997).

Iwata, H. et al., "Effect of carbonyl compounds on red blood cells deformability", Biochemical and Biophysical Research Communications vol. 321, pp. 700-706, (2004).

Schmitt, A et al., "The binding of advanced glycation end products to cell surfaces can be measured using bead-reconstituted cellular membrane proteins", Biochimica et Biophysica Acta, vol. 1768, pp. 1389-1399, (2007).

Self-Medlin, Y. et al., "Glucose promotes membrane cholesterol crystalline domain formation by lipid peroxidation", Biochimica et Biophysica Acta, vol. 1788, pp. 1398-1403, (2009).

Singh, N. et al., "The PPAR-γ activator, rosiglitazone, inhibits actin polymerisation in monocytes: involvement of Akt and intracellular calcium", Biochemical and Biophysical Research Communications, vol. 333, pp. 455-462, (2005).

Li, Y-M. et al., "Effects of high glucose on mesenchymal stem cell proliferation and differentiation", Biochemical and Biophysical Research Communications, vol. 363, pp. 209-215, (2007).

Takata, K. et al., "Endocytic uptake of nonenzymatically glycosylated proteins is mediated by a scavenger receptor for aldehyde-modified proteins", The Journal of Biological Chemistry, vol. 263, No. 29, pp. 14819-14825, (1988).

Mi, Y. et al., "Apoptosis in leukemia cells is accompanied by alterations in the levels and localization of nucleolin", Journal of Biological Chemistry, vol. 278, pp. 8572-8579, (2003).

Christian, S. et al., "Nucleolin expressed at the cell surface is a marker of endothelial cells in angiogenic blood vessels", Journal of Cell Biology, vol. 163, No. 4, pp. 871-878, (2003).

Loo, T.W. et al., "Identification of residues in the drug translocation pathway of the human multidrug resistance P-glycoprotein by arginine mutagenesis", Journal of Biological Chemistry, vol. 284, No. 36, pp. 24074-24087, (2009).

Brundin, P. et al., "Prion-like transmission of protein aggregates in neurodegenerative diseases", Nature Reviews Molecular Cell Biology, vol. 11, No. 4, pp. 301-307, (2010).

Perez, C. et al., "Translational control of the abundance of cytoplasmic poly(A) binding protein in human cytomegalovirus-infected cells", Journal of Virology, vol. 85, No. 1, pp. 156-164, (2011).

Persson, J. et al., "Interleukin-lbeta and tumour necrosis factor-alpha impede neutral lipid turnover in macrophage-derived foam cells", BMC Immunology, vol. 9, No. 70, pp. 1-11, (2008).

Vergne, I. et al., "Cell biology of *Mycobacterium tuberculosis* phagosome", Annu. Rev. Cell Dev. Biology, vol. 20, pp. 367-394, (2004).

Moskowitz, S.M. et al., "The role of *pseudomonas* lipopolysaccharide in cystic fibrosis airway Infection", Subcell Biochemistry, vol. 53, pp. 241-253, (2010).

Hall-Stoodley, L. et al., "Direct detection of bacterial biofilms on the middle-ear mucosa of children with chronic otitis media", JAMA, vol. 296, No. 2, pp. 202-211, (2006).

(56) References Cited

OTHER PUBLICATIONS

Franke-Fayard, B. et al., "Sequestration and tissue accumulation of human malaria parasites: Can we learn anything from rodent models of malaria?", PLoS Pathogens, vol. 6, issue 9, pp. 1-10, e1001032, (2010).
Zhang, S. et al., "Delineation of diverse macrophage activation programs in response to intracellular parasites and cytokines", PLoS Neglected Tropical Diseases, vol. 4, No. 3, e648 (2010).
Ma, Y. et al., "NS3 helicase domains involved in infectious intracellular hepatitis C virus particle assembly", Journal of Virology, vol. 82, No. 15, pp. 7624-7639, (2008).
Korant, B.D. et al., "Inhibition by zinc of rhinovirus protein cleavage: interaction of zinc with capsid polypeptides", Journal of Virology, vol. 18, No. 1, pp. 298-306, (1976).
Ameli, S. et al., "Effect of immunization with homologous LDL and oxidized LDL on early atherosclerosis in hypercholesterolemic rabbits", Arteriosclerosis, Thrombosis, and Vascular Biology, vol. 16, pp. 1074-1079, (1996).
Nilsson, J. et al., "Inflammation and immunity in diabetic vascular complications", Current Opinion in Lipidology, vol. 19, issue 5, pp. 519-524, (2008).
Schiopu, A. et al., "Recombinant antibodies to an oxidized low-density lipoprotein epitope induce rapid regression of atherosclerosis in apobec-1$^{-/-}$/low-density lipoprotein receptor$^{-/-}$mice", Journal of the American College of Cardiology, vol. 50, No. 24, pp. 2313-2318, (2007).
Schiopu, A. et al., "Recombinant human antibodies against aldehyde-modified apolipoprotein B-100 peptide sequences inhibit atherosclerosis", Circulation, vol. 110, pp. 2047-2052, (2004).
Bassirat, M. et al., "Short- and long-term modulation of microvascular responses in streptozotocin-induced diabetic rats by glycosylated products", Journal of Diabetes and its Complications, vol. 24, pp. 64-72, (2010).
Ge, J. et al., "Advanced glycosylation end products might promote atherosclerosis through inducing the immune maturation of dendritic cells", Arteriosclerosis, Thrombosis, and Vascular Biology, vol. 25, pp. 2157-2163, (2005).
Gugliucci, A. et al., "Circulating advanced glycation peptides in streptozotocin-induced diabetic rats: evidence for preferential modification of IgG light chains", Life Sciences, vol. 62, No. 23, pp. 2141-2150, (1998).
Pullerits, R. et al., "Synovial fluid expression of autoantibodies specific for RAGE relates to less erosive course of rheumatoid arthritis", Rheumatology, vol. 46, pp. 1367-1371, (2007).
Bro, S. et al., "A neutralizing antibody against receptor for advanced glycation end products (RAGE) reduces atherosclerosis in uremic mice", Atherosclerosis, vol. 201, pp. 274-280, (2008).
Turk, Z. et al., "Detection of autoantibodies against advanced glycation endproducts and AGE-immune complexes in serum of patients with diabetes mellitus", Clinica Chimica Acta, vol. 303, pp. 105-115, (2001).
Li, M. et al., "Glycan changes: cancer metastasis and anti-cancer vaccines", Journal of Biosciences, vol. 35, No. 4, pp. 665-673, (2010).
Kyte, J.A. et al., "Third international conference on cancer vaccines/adjuvants/delivery for the next decade (CVADD 2009)", Expert Reviews Vaccines, vol. 9, No. 2, pp. 119-123, (2010).
Akbulut, H. et al., "Chemotherapy targeted to cancer tissue potentiates antigen-specific immune response induced by vaccine for in vivo antigen loading and activation of dendritic cells", Molecular Therapy, vol. 16, No. 10, pp. 1753-1760, (2008).
Li, Y.M. et al., "Glycation products in aged thioglycollate medium enhance the elicitation of peritoneal macrophages", Jounal of Immunological Methods, vol. 201, issue 2, pp. 183-188, (1997).
Poggioli, S. et al., "Age-related increase of protein glycation in peripheral blood lymphocytes is restricted to preferential target proteins", Experimental Gerontology, vol. 37, issue 10-11, pp. 1207-1215, (2002).
Poggioli, S. et al., "Evidence of preferential protein targets for age-related modifications in peripheral blood lymphocytes", Annals of the New York Academy of Sciences, vol. 1019, issue 1, pp. 211-214, (2004).
Dominaitiene, R. et al., "Effects of differently oxidized LDL on the expression of pro-inflammatory molecules in human monocytes in vitro", In Vitro and Molecular Toxicology, vol. 14, No. 2, pp. 83-97, (2001).
Jiang, Z-H. et al., "Synthetic vaccines: the role of adjuvants in immune targeting", Current Medicinal Chemistry, vol. 10, No. 15, pp. 1423-1439, (2003).
Buskas, T. et al., "Immunotherapy for cancer: Synthetic carbohydrate-based vaccines", Chemical Communications, Issue 36, pp. 5335-5349, (2009).
Cohen, M.P. et al., "Amelioration of diabetic nephropathy by treatment with monoclonal antibodies against glycated albumin", Kidney International, vol. 45, pp. 1673-1679, (1994).
Davis, P.J. et al., "How can thermal processing modify the antigenicity of proteins?", Allergy, vol. 56, supplemental 67, pp. 56-60, (2001).
Koga, M. et al. "Clinical impact of glycated albumin as another glycemic control marker", Endocrine Journal, vol. 57, No. 9, pp. 751-762, (2010).
Shcheglova, T. et al., "Reactive immunization suppresses advanced glycation and mitigates diabetic nephropathy", Journal of the American Society of Nephrology, vol. 20, No. 5, pp. 1012-1019, (2009).
Virella, G. et al., "Autoimmune response to advanced glycosylation end-products of human LDL", Journal of Lipid Research, vol. 44, pp. 487-493, (2003).
Ihssen, J. et al., "Production of glycoprotein vaccines in *Escherichia coli*", Microbial Cell Factories, vol. 9, No. 61, pp. 1-13, (2010).
Habets, K.L.L. et al., "Vaccination using oxidized low-density lipoprotein-pulsed dendritic cells reduces atherosclerosis in LDL receptor-deficient mice", Cardiovascular Research, vol. 85, pp. 622-630, (2010).
Mironova, R. et al., "Glycation and post-translational processing of human interferon-γ expressed in *Escherichia coli*", The Journal of Biological Chemistry, vol. 278, No. 51, pp. 51068-51074, (2003).
Vogel, F.R. et al., "A compendium of vaccine adjuvants and excipients", Pharmaceutical Biotechnology, vol. 6, pp. 141-228, (1995).
Monograph series, World Health Organization, "Methods of Vaccine Production", part 4, chapters 18-29, pp. 189-267, (1973).
Cohen, M.P. et al., "Prevention of diabetic nephropathy in db/db mice with glycated albumin antagonists: A novel treatment strategy", The Journal of Clinical Investigation, vol. 95, pp. 2338-2345, (1995).
Naka, Y. et al., "RAGE Axis, Animal models and novel insights into the vascular complications of diabetes", Arteriosclerosis, Thrombosis, and Vascular Biology, vol. 24, pp. 1342-1349, (2004).
European Search Report dated Nov. 8, 2011 for PCT application No. PCT/US2009/044951.
Bierhaus, A. et al., "AGEs and their interaction with AGE-receptors in vascular disease and diabetes mellitus. I. the AGE concept", Cardiovascular Research, vol. 37, No. 3, pp. 586-600, (1998).
Murphy, J.F. "Trends in cancer immunotherapy", Clinical Medicine Insights: Oncology, vol. 4, pp. 67-80, (2010).
Beier, K.C., "Master switches of T-cell activation and differentiation", European Respiratory Journal, vol. 29, pp. 804-812, (2007).
Schmidlin, H., "New insights in the regulation of human B cell differentiation", Trends in Immunology, vol. 30, No. 6, pp. 277-285, (2009).
Coler, R.N. et al., "Development and characterization of synthetic glucopyranosyl lipid adjuvant system as a vaccine adjuvant", PLoS One, vol. 6, No. 1, e16333, pp. 1-12, (2011).
Cheadle, E.J., "Bugs as drugs for cancer", Immunology, vol. 107, pp. 10-19, (2002).
The Pink Book, Epidemiology and Prevention of vaccine preventable diseases, 11$^{th}$ Ed., pp. B7-B13, (2009), Found at www.cdc.gov/vaccines/pubs/pinkbook/downloads/appendices/b/excipient-table-1.pdf.

(56) References Cited

OTHER PUBLICATIONS

The Pink Book, Epidemiology and Prevention of vaccine preventable diseases, 11th Ed., 4 pages, (2009), Found at www.cdc.gov/vaccines/pubs/pinkbook/downloads/appendices/b/excipient-table-2.pdf.
Book Reviews, International Microbiology, vol. 7, pp. 291-295, (2004).
"Glycation: How eating sugar causes wrinkles", www.brighthub.com/health/diet-nutrition/articles/18410.aspx, 1 page, published Oct. 8, 2009.
Ellis, G., "The myth of the glycemic index and its child: good carbs-bad carbs", Targeted Body Systems, www.targetedbodysystems.com/tag/low-carb-diet-plans/, pp. 1-5, published Feb. 16, 2009.
"Diabetic glycation and inflammation—what diabetes does to your coronary arteries", www.rebelheartsurgeon-antioxidants.net/diabetic-glycation.html, pp. 1-9, downloaded Aug. 17, 2010.
Dziarski, R., "Cell-bound albumin is the 70-kDa peptidoglycan-, lipopolysaccharide-, and lipoteichoic acid-binding protein on lymphocytes and macrophages", The Journal of Biological Chemistry, vol. 269, No. 32, pp. 20431-20436, (1994).
Peters Jr. T., "5-Metabolism: Albumin in the body", All About Albumin Biochemistry, Genetics, and Medical Applications, Chapters, pp. 188-250, (1995).
Vlassara, H. et al., "High-affinity-receptor-mediated uptake and degradation of glucose-modified proteins: A potential mechanism for the removal of senescent macromolecules", Proceeding of the National Academy of Science, USA, Biochemistry, vol. 82, pp. 5588-5592, (1985).
Wade, N., "Purging cells in mice is found to combat aging ills", New York Times, found at NYTimes.com, pp. 1-3, (2011).
Roll, P. et al., "Anti-CD20 therapy in patients with rheumatoid arthritis", Arthritis & Rheumatism, vol. 58, No. 6, pp. 1566-1575, (2008).
Kajstura J. et al., "Myocyte turnover in the aging human heart", Circulation Research, vol. 107, pp. 1374-1386, (2010).
Baker, D.J. et al., "Clearance of p16lnk4a-positive senescent cells delays ageing-associated disorders", Nature, vol. 479, pp. 232-236, (2011).
Breyer, V. et al., "Intracellular glycation of nuclear DNA, mitochondrial DNA, and cytosolic proteins during senescence-like growth arrest", DNA Cell Biology, vol. 30, No. 9, pp. 681-689, (2011).
Ravelojaona, V. et al., "Expression of senescence-associated beta-galactosidase (SA-beta-Gal) by human skin fibroblasts, effect of advanced glycation end-products and fucose or rhamnose-rich polysaccharides", Archives of Gerontology and Geriatrics, vol. 48, issue 2, pp. 151-154, (2009).
International Search Report dated Apr. 26, 2012 for PCT application No. PCT/US2011/053399.
International Search Report dated Jun. 13, 2012 for PCT application No. PCT/US2011/061387.
Wautier, J.-L. et al., "Advanced glycation end products (AGEs) on the surface of diabetic erythrocytes bind to the vessel wall via a specific receptor inducing oxidant stress in the vasculature: A link between surface-associated AGEs and diabetic complications", Proc. Natl. Acad. Sci. USA, vol. 91, No. 16, pp. 7742-7746, (1994).
Siegel, R. J. et al., "Ultrasonic plaque ablation: A new method for recanalization of partially or totally occluded arteries", Circulation, vol. 78, No. 6, pp. 1443-1448, (1988).
International Search Report dated Jun. 27, 2012 for PCT application No. PCT/US2012/031446.
Immuno, Catalog No. 637061, 637062, "Mouse, anti-age (advanced glycation end products), monoclonal antibody", www.mpbio.com/detailed_info.php?family_key-0863706, 2 pages, accessed Jul. 26, 2012.
Ahmed, E. K. et al., "Protein modification and replicative senescence of WI-38 human embryonic fibroblasts", Aging Cell, vol. 9, pp. 252-272, (2010).
Vlassara, H. et al., "Advanced glycosylation endproducts on erythrocyte cell surface induce receptor-mediated phagocytosis by macrophages", J. Exp. Med., The Rockefeller University Press, vol. 166, pp. 539-549, (1987).
Yang, Z. et al., "Two novel rat liver membrane proteins that bind advanced glycosylation endproducts; Relationship to macrophage receptor for glucose-modified proteins", J. Exp. Med., The Rockefeller University Press, vol. 174, pp. 515-524, (1991).
Vlassara, H. et al., "Advanced glycation endproducts promote adhesion molecule (VCAM-1, ICAM-1) expression and atheroma formation in normal rabbits", Molecular Medicine, vol. 1, No. 4, pp. 447-456, (1995).
Vaysse, J. et al., "Adhesion and erythrophagocytosis of human senescent erythrocytes by autologous monocytes and their inhibition by β-galactosyl derivatives", Proc. Natl. Acad. Sci. USA, Cell Biology, vol. 83, pp. 1339-1343, (1986).
Li, Y. M. et al., "Prevention of cardiovascular and renal pathology of aging by the advanced glycation inhibitor aminoguanidine", Proc. Natl. Acad. Sci. USA, Medical Sciences, vol. 93, pp. 3902-3907, (1996).
Manesso, E. et al., "Dynamics of β-cell turnover: evidence for β-cell turnover and regeneration from sources of β-cells other than β-cell replication in the HIP rat", American Journal of Physiology—Endocrinology and Metabolism, vol. 297, pp. E323-E330, (2009).
Stepanov, A.V. et al., "Design of targeted B cell killing agents", PLoS ONE, vol. 6, issue 6, e20991, pp. 1-10, (2011).
Fact Sheet, "Targeted Cancer Therapies", www.cancer.gov/cancertopics/factsheet/Therapy/Fs7_49.pdf, pp. 1-8, (2012).
Kay, M.M. "Generation of senescent cell antigen on old cells initiates IgG binding to a neoantigen", Cellular and Molecular Biology (Noisy-le-Grand, France), vol. 39, No. 2, pp. 131-153, (1993), Abstract Only.
Cirocchi, R. et al., "Meta-analysis of thyroidectomy with ultrasonic dissector versus conventional clamp and tie", World Journal of Surgical Oncology, vol. 8, No. 112, pp. 1-7, (2010).
Lingeman, J.E. et al., "Current perspective on adverse effects in shock wave lithotripsy", White Paper, American Urological Association Education and Research, found at www.auanet.org/content/guidelines-and-quality-care/clinical-guidelines/main-reports/whitepaper.pdf, 17 pages, (2009).
De Groot, K. et al., "Vascular endothelial damage and repair in antineutrophil cytoplasmic antibody—associated vasculitis", Arthritis & Rheumatism, vol. 56, No. 11, pp. 3847-3853, (2007).
Imani, F. et al., "Advanced glycosylation endproduct-specific receptors on human and rat t-lymphocytes mediate synthesis of interferon γ: role in tissue remodeling", J. Exp. Med., vol. 178, pp. 2165-2172, (1993).
Kirstein, M. et al., "Receptor-specific induction of insulin-like growth factor I in human monocytes by advanced glycosylation end product-modified proteins", J. Clin. Invest., vol. 90, pp. 439-446, (1992).
Le Grand, F. et al., "Skeletal muscle satellite cells and adult myogenesis", Curr. Opin. Cell Biology, vol. 19, No. 6, pp. 628-633, (2007).
Sasaki, M. et al., "Mesenchymal stem cells are recruited into wounded skin and contribute to wound repair by transdifferentiation into multiple skin cell type", The Journal of Immunology, vol. 180, pp. 2581-2587, (2008).
Misur, I. et al., "Advanced glycation endproducts in peripheral nerve in type 2 diabetes with neuropathy", Acta Diabetol, vol. 41, pp. 158-166, (2004).
Saltykov, B.B., "Mechanisms of development of diabetic macroangiopathy", Arkh Patol., vol. 63, No. 2, pp. 21-26, (2001), Abstract Only.
Grossin, N. et al., "Red blood cell adhesion in diabetes mellitus is mediated by advanced glycation end product receptor and is modulated by nitric oxide", Biorheology, vol. 46, No. 1, pp. 63-72, (2009).
Liang, Y. et al., "Rituximab for children with immune thrombocytopenia: A systematic review", PLoS ONE, vol. 7, issue 1, pp. 1-11, (2012).

(56) References Cited

OTHER PUBLICATIONS

Fehrenbach, H. et al., "Up-regulated expression of the receptor for advanced glycation end products in cultured rat hepatic stellate cells during transdifferentiation to myofibroblasts", Hepatology, vol. 34, No. 5, pp. 943-952, (2001).
Agostini, A. et al., "Targeted cargo delivery in senescent cells using capped mesoporous silica nanoparticles", Angewandte Chemie International Edition, vol. 51, pp. 10556-10560, (2012).
Larson, R.A. et al., "Tumor lysis syndrome: Definition, pathogenesis, clinical manifestations, etiology and risk factors", found at www.uptodate.com/contents/tumor-lysis-syndrome-definition-pathogenesis-clinical-manifestations-etiology-and-risk-factors?detectedLanguage=en&source=search_result&search=tumor+lysis+syndrome&selectedTitle=2~69&provider=noProvider, pp. 1-4, printed on Jun. 11, 2013.
Hansel, T.T. et al., "The safety and side effects of monoclonal antibodies", Nature Reviews, vol. 9, pp. 325-337, (2010).
Nass, N. et al., "Advanced glycation end products, diabetes and ageing", Zeitschrift fur Gerontologie und Geriatrie, vol. 40, issue 5, pp. 349-356, (2007).
Wautier, J-L. et al., Protein Glycation: "A firm link to endothelial cell dysfunction", Circulation Research, Journal of the American Heart Association, vol. 95, pp. 233-238, (2004).
Meuter, A. et al., "Markers of cellular senescence are elevated in murine blastocysts cultured in vitro: molecular consequences of culture in atmospheric oxygen", Journal of Assisted Reproduction and Genetics, vol. 31, issue 10, pp. 1259-1267, (2014).
Freund, A. et al., "Inflammatory networks during cellular senescence: causes and consequences", Trends in Molecular Medicine, vol. 16, No. 5, pp. 238-246, (2010).
Hadrabová, J. et al., "Chicken immunoglobulins for prophylaxis: Effect of inhaled antibodies on inflammatory parameters in rat airways", Journal of Applied Biomedicine, 4 pages, Available online May 5, 2014.
Ferraccioli, G. et al., "Interleukin-1β and lnterleukin-6 in arthritis animal models: Roles in the early phase of transition from acute to chronic inflammation and relevance for human rheumatoid arthritis", Molecular Medicine, vol. 16, issue 11-12, pp. 552-557, (2010).
Zhao, Y. et al., "The bovine antibody repertoire", Developmental & Comparative Immunology, vol. 30, issues 1-2, pp. 175-186, (2006).
Wagner, B. et al. "The complete map of the Ig heavy chain constant gene region reveals evidence for seven IgG isotypes and for IgD in the horse", Journal of Immunology, vol. 173, No. 5, pp. 3230-3242, (2004).
Strietzel, C.J. et al., "In vitro functional characterization of feline IgGs", Veterinary Immunology and Immunopathology, vol. 158, issues 3-4, pp. 214-223, (2014).
Patel, M. et al., "Sequence of the dog immunoglobulin alpha and epsilon constant region genes", Immunogenetics, vol. 41, issue 5, pp. 282-286, (1995).
Maass, D.R. et al., "Alpaca (*Lama pacos*) as a convenient source of recombinant camelid heavy chain antibodies (VHHs)", Journal of Immunology Methods, vol. 324, issues 1-2, pp. 13-25, (2007).
European Search Report dated Sep. 12, 2014 for EP application No. EP14170802.4-1408.
Fessler, J. et al., "Senescent T cells promote bone loss in rheumatoid arthritis", Abstracts of the American College of Rheumatology/Association of Rheumatology Health Professionals, Annual Scientific Meeting, Washington, DC, Nov. 9-14, 2012, Arthritis & Rheumatism, vol. 64, supplement 10, p. 2312, (2012) found at blackwellpublishing.com/acrmeeting/abstract.asp?MeetingID=789&id=103040.
Weyand, C.M. et al., Abstract of "T-cell aging in rheumatoid arthritis", Current Opinion in Rheumatology, vol. 26, No. 1, pp. 93-100, (2014) found at www.ncbi.nlm.nih.gov/m/pubmed/24296720/.
Dvergsten, J. et al., "Prevalence of functionally active, senescent T cells in juvenile idiopathic arthritis", Abstracts of the American College of Rheumatology/Association of Rheumatology Health Professionals, Annual Scientific Meeting, Philadelphia, Oct. 16-21, 2009, Arthritis & Rheumatism, vol. 60, supplement 10, p. 1313, (2009), found at blackwellpublishing.com/acrmeeting/abstract.asp?MeetingID=761&id=80937.
Definition of "Dissociation constant" printed from Wikipedia, the free encyclopedia on Sep. 17, 2014 found at en.wikipedia.org/wiki/Dissociation_constant.
Sigma-Aldrich product specification of "Nα,Nα-Bis(carboxymethyl)-L-lysine trifluoroacetate salt ≥95% (TLC)", found at sigmaaldrich.com/catalog/product/sigma/c3205?lang=en&region=US, printed on Sep. 17, 2014.
"Pulmatrix demonstrates iSPERSE capabilities for inhaled dry powder delivery of antibiotics and antibodies", data presented at Respiratory Drug Delivery 2012, 3 pages, printed on Sep. 4, 2014, found at businesswire.com/news/home/20120515005279/en/Pulmatrix-Demonstrates-iSPERSE-Capabilities-Inhaled-Dry-Powder#.VEgU4hauNbs.
Chan, A.C. et al., "Therapeutic antibodies for autoimmunity and inflammation", Nature Reviews Immunology, vol. 10, pp. 301-316, (2010).
Pradat, P.F. et al., "Abnormalities of satellite cells function in amyotrophic lateral sclerosis", Amyotrophic Lateral Sclerosis, vol. 12, No. 4, pp. 264-271, (2011).
Tchkonia, T. et al., "Cellular senescence and the senescent secretory phenotype: therapeutic opportunities", The Journal of Clinical Investigation, vol. 123, No. 3, pp. 966-972, (2013).
Kitada, K. et al., "Aldosterone induces p21-regulated apoptosis via increased synthesis and secretion of tumour necrosis factor-α in human proximal tubular cells", Clinical and Experimental Pharmacology and Physiology, vol. 39, No. 10, pp. 858-863, (2012).
Definition of "TNF inhibitor", printed from Wikipedia, the free encyclopedia on Oct. 4, 2014, 4 pages, found at http://en.wikipedia.org/wiki/TNF_inhibitor?oldid=628250399.
Definition of "Etanercept", printed from Wikipedia, the free encyclopedia on Aug. 24, 2014, 6 pages, found at http://en.wikipedia.org/wiki/Etanercept?oldid=622648157.
AbbVie, Inc., "Humira adalimumab: Learn about Humira", found at www.humira.com/rheumatoid-arthritis, 7 pages, printed on Aug. 11, 2014.
AbbVie, Inc., "Medication Guide for Humira", found at www.humira.com/rheumatoid-arthritis, 9 pages, printed on Aug. 11, 2014.
AbbVie, Inc., "Humira: A biologic that targets and helps block TNF-alpha", found at www.humira.com/rheumatoid-arthritis/how-humira-works-for-ra, 8 pages, printed on Aug. 11, 2014.
AbbVie, Inc., "How Humira (adalimumab) works video transcript", found at www.humira.com/rheumatoid-arthritis/how-humira-works-video-transcript, 5 pages, printed on Aug. 11, 2014.
AbbVie, Inc., "Humira and methotrexate—a combination that has demonstrated results", found at www.humira.com/rheumatoid-arthritis/humira-and-methotrexate, 7 pages, printed on Aug. 11, 2014.
Madhur, M.S. et al., "Senescent T cells and hypertension: New ideas about old cells", Hypertension, vol. 62, pp. 13-15, (2013).
James, P.E. et al., "Vasorelaxation by red blood cells and impairment in diabetes: Reduced nitric oxide and oxygen delivery by glycated hemoglobin", Circulation Research, vol. 94, pp. 976-983, (2004).
Shibayama, R. et al., "Autoantibody against N(epsilon)-(carboxymethyl)lysine: an advanced glycation end product of the Maillard reaction", Diabetes, vol. 48, No. 9, pp. 1842-1849, (1999).
Bumol, T.F. et al., "Monoclonal antibody and an antibody-toxin conjugate to a cell surface proteoglycan of melanoma cells suppress in vivo tumor growth", Proceeding of the National Academy of Science, vol. 80, pp. 529-533, (1983).
"AGEs (all species) antibody—Product Details", Antibodies Online, 4 pages, found at www.web.archive.org/web/20081229071154/http://www.antibodies-online.com/antibody/289931/AGEs+All+Species/, printed on Dec. 10, 2014.
"Antibody Engineering", Fusion Antibodies, 2 pages, found at www.web.archive.org/web/20080628225818/http://www.fusionantibodies.com/index.cfm/area/information/page/engineering?, printed on Dec. 16, 2014.

(56) References Cited

OTHER PUBLICATIONS

Hargreaves, R.E.G. et al., "Selective depletion of activated T cells: the CD40L-specific antibody experience", Trends in Molecular Medicine, vol. 10, No. 3, pp. 130-135, (2004).
Leinenga, G. et al., "Scanning ultrasound removes amyloid-β and restores memory in an Alzheimer's disease mouse model", Science Translational Medicine, vol. 7, issue 278, pp. 1-11, (2015).
Peppa, M. et al., "Glucose, advanced glycation end products, and diabetes complications: What is new and what works", Clinical Diabetes, vol. 21, No. 4, pp. 186-187, (2003).
Lv, Y. et al., "Low-intensity ultrasound combined with 5-aminolevulinic acid administration in the treatment of human tongue squamous carcinoma", Cellular Physiology and Biochemistry, vol. 30, pp. 321-333, (2012).
Campisi, J. et al., "Cellular senescence: when bad things happen to good cells", Nature Reviews: Molecular Cell Biology, vol. 8, pp. 729-749, (2007).
"ALSUntangled No. 23: The Rife Machine and retroviruses", Amyotrophic Lateral Sclerosis and Frontotemporal Degeneration, vol. 15, pp. 157-159, (2014).
Roylance, D., "Mechanical properties of materials", pp. 1-128, (2008), available at www.web.mit.edu/course/3/3.225/book.pdf.
Vidarsson, G. et al., "IgG subclasses and allotypes: from structure to effector functions", Frontiers in Immunology, vol. 5, article 520, pp. 1-17, (2014).
Lin, H-T. et al., "Stem cell therapy: an exercise in patience and prudence", Philosophical Transactions of the Royal Society B: Biological Sciences 368, (2013).
Waldmann, T.A., "Immunotherapy:past, present and future", Nature Medicine, vol. 9, No. 3, pp. 269-277, (2003).
Okamoto, T. et al., "Advanced glycation end products induce angiogenesis in vivo", Microvascular Research, vol. 63, pp. 186-195, (2002).
Nagal, R. et al., "Application of monoclonal antibody libraries for the measurement of glycation adducts", Biochemical Society Transactions, vol. 31, part 6, pp. 1438-1440, (2003).
De Genst, E. et al., "Antibody repertoire development in camelids", Developmental and Comparative Immunology, vol. 30, pp. 187-198, (2006).
Griffin, L.M. et al., "Analysis of hevy and light chain sequences of conventional camelid antibodies from *Camelus dromedarius* and *Camelus bactrianus* species", Journal of Immunological Methods, vol. 405, pp. 35-46, (2014).
Hamers-Casterman, C. et al., "Naturally occurring antibodies devoid of light chains", Nature, vol. 363, pp. 446-448, (1993).
Muyldermans, S. et al., "Sequence and structure of $V_H$ domain from naturally occurring camel heavy chain immunoglobulins lacking light chains", Protein Engineering, vol. 7, No. 9, pp. 1129-1135, (1994).
Nguyen, V. K. et al., "Camel heavy-chain antibodies: diverse germline VHH and specific mechanisms enlarge the antigen-binding repertoire", The EMBO Journal, vol. 19, No. 5, pp. 921-930, (2000).
Kirstein, et al., "Advanced protein glycosylation induces transendothelial human monocyte chemotaxis and secretion of platelet-derived growth factor: roll in vascular disease of diabetes and aging", PNAS, vol. 87, No. 22, pp. 9010-9014, (1990).
Invitation to Pay Additional Fees and Partial International Search Report dated Jan. 13, 2016 for PCT application No. PCT/US2015/050154.
Feldmann, M. et al., "Anti-TNFalpha therapy of rheumatoid arthritis: What have we learned?", Annual Review of Immunology, vol. 19, pp. 163-196, (2001).
Drinda, S. et al., "Identification of the advanced glycation end products N-carboxymethyllysine in the synovial tissue of patients with rheumatoid arthritis", Annals of the Rheumatic Diseases, vol. 61, No. 6, pp. 488-492, (2002).
Ahmad, S. et al., "Preferential recognition of epitopes on AGE-IgG by the autoantibodies in rheumatoid arthritis patients", Human Immunology, vol. 74, No. 1, pp. 23-27, (2013).

Johns, L.D., "Nonthermal effects of therapeutic ultrasound: The frequency resonance hypothesis", Journal of Athletic Training, vol. 37, No. 3, pp. 293-299, (2002).
Wang, B-L. et al., "Identification of monoclonal antibody of advanced glycation end products", Chinese Journal of Arteriosclerosis, vol. 14, No. 5, pp. 409-412, (2006).
Wang, J.C. et al., "Aging and Atherosclerosis mechanisms, functional consequences, and potential therapeutics for cellular senescence", Circulation Research, vol. 111, pp. 245-259, (2012).
Minamino, T. et al., "Vascular cell senescence contribution to Atherosclerosis", Circulation Research, vol. 100, pp. 15-26, (2007).
Isoda, K. et al., "Glycated LDL increases monocyte CC chemokine receptor 2 expression and monocyte chemoattractant protein-1-mediated chemotaxis", Atherosclerosis, vol. 198, No. 2, pp. 307-312, (2008).
Roos, C.M. et al., "Chronic senolytic treatment alleviates established vasomotor dysfunction in aged or atherosclerotic mice", Aging Cell, 8 pages, (2016).
Hall, B.M. et al., "Aging of mice is associated with p16(Ink4a)- and β-galactosidase-positive macrophage accumulation that can be induced in young mice by senescent cells", Aging, vol. 8, No. 7, pp. 1-18, (2016).
Mera, K. et al., "An autoantibody against $N^e$-(carboxyethyl)lysine (CEL): Possible involvement in the removal of CEL-modified proteins by macrophages", Biochemical and Biophysical Research Communications, vol. 407, pp. 420-425, (2011).
Reddy, S. et al., "$N^e$-(Carboxymethyl)lysine is a dominant advanced glycation end product (AGE) antigen in tissue proteins", Biochemistry, vol. 34, pp. 10872-10878, (1995).
Katcher, H.L., "Studies that shed new light on aging", Biochemistry (Moscow), vol. 78, No. 9, pp. 1061-1070, (2013).
Naylor, R.M. et al., "Senescent Cells: A novel therapeutic target for aging and age-related diseases", Clinical Pharmacology & Therapeutics, vol. 93, No. 1, pp. 105-116, (2013).
Beaulieu, L-P. et al., "Inhibitory effect of the cree traditional medicine wiishichimanaanh (vaccinium vitis-idaea) on advanced glycation endproduct formation: identification of active principles", Phytotherapy Research, vol. 24, pp. 741-747, (2010).
Ulrich, P. et al., "Protein glycation, diabetes, and aging", Recent Progress in Hormone Research, vol. 56, pp. 1-21, (2000).
Van Heijst, J.W.J. et al., "Advanced glycation end products in human cancer tissues: detection of $N^e$-(carboxymethyl)lysine and argpyrimidine", Annals of the New York Academy of Sciences, vol. 1043, pp. 725-733, (2005).
Fielding, R.A. et al., "Sarcopenia: An undiagnosed condition in older adults. Current consensus definition: Prevalence, etiology, and consequences", Journal of the American Medical Directors Association, vol. 12, No. 4, pp. 249-256, (2011).
Definition of "Sarcopenia", printed from Wikipedia, the free encyclopedia on Jul. 25, 2016, 5 pages, found at http://en.wikipedia.org/wiki/Sarcopenia.
"What is Sarcopenia?", International Osteoporosis Foundation, 2 pages, found at www.iofbonehealth.org/what-sarcopenia, (2014).
"Sarcopenia with aging", Webmd, 2 pages, found at www.webmd.com/healthy-aging/sarcopenia-with-aging, (2014).
Definition of "Keyhole limpet hemocyanin", printed from Wikipedia, the free encyclopedia on Jul. 25, 2016, 4 pages, found at en.wikipedia.org/wiki/Keyhole_limpet_hemocyanin.
Cell Biolabs, Inc., "CML-BSA Product Data Sheet", 3 pages, found at www.cellbiolabs.com/sites/default/files/STA-314-cml-bsa.pdf, (2010).
Cell Biolabs, Inc., "CML (N-epsilon-(Caboxymethyl)Lysine) Assays and Reagents", 1 page, found at www.cellbiolabs.com/cml-assays, (2014).
Cruz-Jentoft, A.J. et al., "Sarcopenia: European consensus on definition and diagnosis", Age and Ageing, vol. 39, pp. 412-423, (2010).
Rolland, Y. et al., "Sarcopenia: Its assessment, etiology, pathogenesis, consequences and future perspectives", The Journal of Nutrition, Health & Aging, vol. 12, No. 7, pp. 433-450, (2008).
Centers for Disease Control and Prevention, "Vaccine excipient and media summary", 4 pages, found at www.cdc.gov/vaccines/pubs/pinkbook/downloads/appendices/B/excipient-table-2.pdf?utm_content=buffer4538f&utm_medium=social&utm_source=linkedin.com&utm_campaign=buffer, (2015).

(56) References Cited

OTHER PUBLICATIONS

Definition of "N(6)-Carboxymethyllysine", printed from Wikipedia, the free encyclopedia on Dec. 8, 2013, 1 page, found at en.wikipedia.org/wiki/N(6)-Carboxymethyllysine.
Definition of "Lysine", printed from Wikipedia, the free encyclopedia on Dec. 8, 2013, 1 page, found at en.wikipedia.org/wiki/Lysine.
Jarvis, L.M., "Rethinking antibody-drug conjugates", Chemical & Engineering News, vol. 90, issue 25, pp. 12-18, (2012).
Mullin, R., "Cell-free approach to antibody-drug conjugates", Chemical & Engineering News, vol. 91, issue 44, 2 pages, (2013).
Thayer, A.M., "Building antibody-drug conjugates", Chemical & Engineering News, vol. 92, issue 3, pp. 13-21, (2014).
Feige, M.J. et al., "The structural analysis of shark IgNAR antibodies reveals evolutionary principles of immunoglobulins", Proceedings of the National Academy of Sciences, vol. 111, No. 22, pp. 8155-8160, (2014).
Philipot, D. et al.,"p16$^{INK4a}$ and its regulator miR-24 link senescence and chondrocyte terminal differentiation-associated matrix remodeling in osteoarthritis", Arthritis Research & Therapy, vol. 16, No. 1, pp. 1-12, (2014).
International Search Report and Written Opinion dated Mar. 31, 2016 for PCT application No. PCT/US2015/050154.
Zhu, Y. et al., "The achilles' heel of senescent cells: from transcriptome to senolytic drugs", Aging Cell, vol. 14, pp. 644-658, (2015).
Zhu, L. et al., "Immunization with advanced glycation end products modified low density lipoprotein inhibits atherosclerosis progression in diabetic apoE and LDLR null mice", Cardiovascular Diabetology, vol. 13, No. 151, pp. 1-12, (2014).
DeNardo, S.J. et al., "Development of tumor targeting bioprobes ($^{111}$in-chimeric L6 monoclonal antibody nanoparticles) for alternating magnetic field cancer therapy", Clinical Cancer Research, vol. 11, 19 supplemental, pp. 7087s-7092s, (2005).
Chen, L. et al., "Cytolysis of human erythrocytes by a covalent antibody-selenium immunoconjugate", Free Radical Biology & Medicine, vol. 19, No. 6, pp. 713-724, (1995).
Yuan, Y. et al., "Advanced glycation end products (AGEs) increase human mesangial foam cell formation by increasing Golgi SCAP glycosylation in vitro", American Journal of Physiology—Renal Physiology, vol. 301.1, pp. F236-F243, (2011).
Hashimoto, M. et al., "Elimination of p19$^{ARF}$-expressing cells enhances pulmonary function in mice", JCI Insight, vol. 1, No. 12, pp. 1-15, (2016).
Yan, S.F. et al., "Soluble RAGE: Therapy & biomarker in unraveling the RAGE axis in chronic disease and aging", Biochemical Pharmacology, vol. 79, No. 10, pp. 1379-1386, (2010).
Xue, J. et al., "Advanced glycation end product (AGE) recognition by the receptor for AGEs (RAGE)", Structure, vol. 19, No. 5, pp. 722-732, (2011).
Chang, J. et al., "Clearance of senescent cells by ABT263 rejuvenates aged hematopoietic stem cells in mice", Nature Medicine, vol. 22, No. 1, pp. 78-83, (2016).
Geiger, H., "Depleting senescent cells to combat aging", Nature Medicine, vol. 22, No. 1, pp. 23-24, (2016).
Ni, J. et al., "Plasma protein pentosidine and carboxymethyllysine, biomarkers for age-related macular degeneration", Molecular & Cellular Proteomics, vol. 8, No. 8, pp. 1921-1933, (2009).
R&D Systems, a biotechne brand, product specification of "Carboxymethyl Lysine Antibody", found at www.rndsystems.com/products/carboxymethyl-lysine-antibody-318003_mab3247, 1 page, (2015).
Schalkwijk, C.G. et al., "Increased accumulation of the glycoxidation product N$^ε$-(carboxymethyl)lysine in hearts of diabetic patients: generation and characterization of a monoclonal anti-CML antibody", Biochimica et Biophysica Acta (BBA)—Molecular and Cell Biology of Lipids, vol. 1636, No. 2, pp. 82-89, (2004).
LaPak, K.M. et al., "The molecular balancing act of p16$^{INK4a}$ in cancer and aging", Molecular Cancer Research, vol. 12, No. 2, pp. 167-183, (2013).
Larsen, S.A. et al., "Glucose metabolite glyoxal induces senescence in telomerase-immortalized human mesenchymal stem cells", Chemistry Central Journal, vol. 6, No. 18, pp. 1-13, (2012).
Ahmed, M.U. et al., "N$^ε$-(carboxymethyl)lysine, a product of the chemical modification of proteins by methylglyoxal, increases with age in human lens proteins", Biochemical Journal, vol. 324, pp. 565-570, (1997).
Dunn, J.A. et al., "Age-dependent accumulation of N$^ε$-(Carboxymethyl)lysine and N$^ε$-(Carboxymethyl)hydroxylysine in human skin collagen", Biochemistry, vol. 30, pp. 1205-1210, (1991).
Finco, A.B. et al., "Generation and characterization of monoclonal antibody against advanced glycation end products in chronic kidney disease", Biochemistry and Biophysics Reports, vol. 6, pp. 142-148, (2016).
International Search Report and Written Opinion dated Aug. 10, 2016 for PCT application No. PCT/US2016/034880.
Liu, H. et al., "Abstract 154: Vaccination using advanced glycation end product of low-density lipoprotein pulsed dendritic cells reduces atherosclerosis in diabetic apoe$^{-/-}$ mice", Arteriosclerosis, Thrombosis, and Vascular Biology, pp. 1-4, (2012).
Mashitah, M.W. et al., "Immunization of AGE-modified albumin inhibits diabetic nephropathy progression in diabetic mice", Diabetes, Metabolic Syndrome and Obesity: Targets and Therapy, vol. 8, pp. 347-355, (2015).
Sayej, W.N. et al., "Advanced glycation end products induce obesity and hepatosteatosis in CD-1 wild-type mice", BioMed Research International, vol. 6, No. 39, pp. 1-12, (2016).
Srikanth, V. et al., "Advanced glycation endproducts and their receptor RAGE in alzheimer's disease", Neurobiology of Aging, vol. 32, No. 5, pp. 763-777, (2011).
International Search Report and Written Opinion dated Dec. 2, 2016 for PCT application No. PCT/US2016/039076.
Fu, M-X. et al., "The advanced glycation end product, N-(Carboxymethyl)lysine, is a product of both lipid peroxidation and glycoxidation reactions", The Journal of Biological Chemistry, vol. 271, No. 17, pp. 9982-9986, (1996).
Jorgensen, L. et al., "The relationship between atherosclerosis of the thoracic aorta and renal scarring in an autopsy material", Acta Pathol Microbiol Immunol Scand A., vol. 93, No. 5, pp. 251-255, (1985) Abstract Only.
"Senescent cells drive plaque formation in animal models of atherosclerosis, research shows", Mayo Clinic, pp. 1-2, (2016), found at www.news-medical.net/news/20161027/Senescent-cells-drive-plaque-formation-in-animal-models-of-atherosclerosis-research-shows.aspx.
Baker, D.J. et al., "Naturally occurring p16$^{Ink4a}$-positive cells shorten healthy lifespan", Nature, vol. 530, issue 7589, pp. 184-189, (2016).
Raquib, R., "The key to youth via senescent cell removal", Young Investigators Review, pp. 1-4, (2017), found at sbyireview.com/2017/01/23/the-key-to-youth-via-senescent-cell-removal.
Tiner, S., "Mayo clinic research links senescent cells and atherosclerosis progression", Mayo Clinic News Network, pp. 1-3, (2016), found at newsnetwork.mayoclinic.org/discussion/mayo-clinic-research-links-senescent-cells-and-atherosclerosis-progression.
Wiley, C., "Aging Fundamentals: Cellular senescence", Science of Aging Blog at the Buck Institute, pp. 1-4, (2015), found at sage.buckinstitute.org/aging-fundamentals-cellular-senescence.
Arichika, S. et al., "Correlation of retinal arterial wall thickness with atherosclerosis predictors in type 2 diabetes without clinical retinopathy", British Journal of Ophthalmology, vol. 101, pp. 69-74, (2017).
Lin, Z. et al., "Vaccination against AGE-LDL significant attenuates atherosclerosis in diabetic apoe mice", Heart, vol. 97, No. 21, supplement 3, p. A18, (2011) Abstract Only.
Thompson, L.V., "Age-related muscle dysfunction", Experimental Gerontology, vol. 44, pp. 106-111, (2009).
Sun, K. et al., "Elevated serum carboxymethyl-Lysine, an advanced glycation end product, predicts severe walking disability in older women: The women's health and aging study I", Journal of Aging Research, vol. 2012, pp. 1-8, (2012).
Kislinger, T. et al., "N$^ε$-(Carboxymethyl)Lysine adducts of proteins are ligands for receptor for advanced glycation end products that

(56) References Cited

OTHER PUBLICATIONS activate cell signaling pathways and modulate gene expression", The Journal of Biological Chemistry, vol. 274, No. 44, pp. 31740-31749, (1999).
Nakayama, H. et al., "Production and characterization of antibodies to advanced glycation products on proteins", Biochemical and Biophysical Research Communications, vol. 162, No. 2, pp. 740-745, (1989).
Gupta, R.K., "Aluminum compounds as vaccine adjuvants", Advanced Drug Delivery Review, vol. 32, No. 3, pp. 155-172, (1998), Abstract Only.
Tracy, J.M. et al., "Preservatives for poliomyelitis (Salk) vaccine II: Formaldehyde and esters of p-hydroxybenzoic acid", Journal of Pharmaceutical Sciences, vol. 53, Issue 6, pp. 659-663, (1964), Abstract Only.
Koito, W. et al., "Conventional antibody against $N^\varepsilon$-(Carboxymethyl)Lysine (CML) shows cross-reaction to $N^\varepsilon$-(Carboxyethyl)Lysine (CEL): Immunochemical quantification of CML with a specific antibody", The Journal of Biochemistry, vol. 135, No. 6, pp. 831-837, (2004).
Product Description of "Anti-Advanced Glycation End Products (AGE), Carboxy-Methyl Lysine (CML) [6C7] Antibody", Kerafast, www.kerafast.com/product/1779/anti-advanced-glycation-end-products-age-carboxy-methyl-lysine-cml-6c7-antibody, printed on Feb. 2, 2017.
Ikeda, K. et al., "$N^\varepsilon$-(Carboxymethyl)lysine protein adduct is a major immunological epitope in proteins modified with advanced glycation end products of the maillard reaction", Biochemistry, vol. 35, No. 24, pp. 8075-8083, (1996).
Dunn, J.A. et al., "Oxidation of glycated proteins: Age-dependent accumulation of $N^\varepsilon$-(Carboxymethyl)lysine in lens proteins", Biochemistry, vol. 28, No. 24, pp. 9464-9468, (1989).
Peppa, M. et al., "The role of advanced glycation end products in the development of atherosclerosis", Current Diabetes Reports, vol. 4, pp. 31-36, (2004).
Glenn, J.V. et al., "The role of advanced glycation end products in retinal ageing and disease", Biochimica Et Biophysica Acta, vol. 1790, No. 10. pp. 1109-1116, (2009).
European Search Report dated Feb. 21, 2017 for EP application No. 16198527.0.
Xu, M. et al., "Transplanted senescent cells induce an osteoarthritis-like condition in mice", The Journals of Gerontology Series A: Biological Sciences and Medical Sciences, pp. 1-6, (2016).
Ratliff, M. et al., "In senescence, age-associated B cells secrete TNFα and inhibit survival of B-cell precursors", Aging Cell, vol. 12, pp. 303-311, (2013).
Manestar-Blazic, T. et al., "The dynamic of senescent cells accumulation can explain the age-specific incidence of autoimmune diseases", Medical Hypotheses, vol. 73, pp. 667-669, (2009).
Tchkonia, T. et al., "Fat tissue, aging, and cellular senescence", Aging Cell, vol. 9, pp. 667-684, (2010).
Robbins, P. et al., "Scripps research, Mayo Clinic scientists find new class of drugs that dramatically increases healthy lifespan", The Scripps Research Institute, pp. 1-3, found at www.scripps.edu/news/press/2015/20150309agingcell.html, printed on Mar. 14, 2015.
Dorr, J.R. et al., "Synthetic lethal metabolic targeting of cellular senescence in cancer therapy", Nature, vol. 501, No. 7467, pp. 421-425, (2013).
Xu, M. et al., "Targeting senescent cells enhances adipogenesis and metabolic function in old age", eLife, vol. 4, pp. 1-20, (2015).
Minamino, T. et al., "Endothelial cell senescence in human atherosclerosis: Role of telomere in endothelial dysfunction", Circulation, vol. 105, issue 13, pp. 1541-1544, (2002).
Takino, J-I. et al., "Cancer malignancy is enhanced by glyceraldehyde-derived advanced glycation end-products", Journal of Oncology, vol. 2010, pp. 1-8, (2010).
Laberge, R-M. et al., "Epithelial-mesenchymal transition induced by senescent fibroblasts", Cancer Microenvironment, vol. 5, pp. 39-44, (2012).

Abe, R. et al., "Regulation of human melanoma growth and metastasis by AGE-AGE receptor interactions", Journal of Investigative Dermatology, vol. 122, No. 2, pp. 461-467, (2004).
Porporato, P.E. et al., "A mitochondrial switch promotes tumor metastasis", Cell Reports, vol. 8, pp. 754-766, (2014).
Boquio, A. et al., "Reversible cell cycle inhibition and premature aging features imposed by conditional expression of $p16^{ink4a}$", Aging Cell, vol. 14, pp. 139-147, (2015).
Nelson, G. et al., "A senescent cell bystander effect: senescence-induced senescence", Aging Cell, vol. 11, pp. 345-349, (2012).
Rayess, H. et al., "Cellular senescence and tumor suppressor gene p16", International Journal of Cancer, vol. 130, No. 8, pp. 1715-1725, (2012).
Greenfieldboyce, N., "Boosting life span by clearing out cellular clutter", npr.org, 4 pages, found at www.npr.org/sections/health-shots/2016/02/03/465354874/boosting-lifespan-by-clearing-out-cellular-clutter, printed on Feb. 4, 2016.
Matus, D.Q. et al., "Invasive cell fate requires G1 cell-cycle arrest and histone deacetylase-mediated changes in gene expression", Developmental Cell, vol. 35, pp. 162-174, (2015).
Stony Brook University, "Targeting invasive cells not dividing cells to halt cancer, study suggests", ScienceDaily, pp. 1-2, found at www.sciencedaily.com/releases/2015/10/151026181610.htm, (2015).
Liu, D. et al., "Senescent human fibroblasts increase the early growth of xenograft tumors via matrix metalloproteinase secretion", Cancer Research, vol. 67, No. 7, pp. 3117-3126, (2007).
Hoke, Z. "Belgian researchers discover way to block cancer metastasis", VOZ News, pp. 1-3, found at www.voanews.com/a/belgian-researchers-discover-way-to-block-cancer-metastasis/2453790.html, (2014).
Di, G-H. et al., "IL-6 secreted from senescent mesenchymal stem cells promotes proliferation and migration of breast cancer cells", PloS one, vol. 9, No. 11, pp. 1-15, (2014).
Huang, L-W. et al., "$P16^{ink4a}$ overexpression predicts lymph node metastasis in cervical carcinomas", Journal of Clinical Pathology, vol. 65, pp. 117-121, (2012).
Romagosa, C. et al., "$P16^{ink4a}$ overexpression in cancer: a tumor suppressor gene associated with senescence and high-grade tumors", Oncogene, vol. 30, pp. 2087-2097, (2011).
Terman, A. et al., "Mitochondrial turnover and aging of long-lived postmitotic cells: The mitochondrial-lysosomal axis theory of aging", Antioxidants & Redox Signaling, vol. 12, No. 4, pp. 503-535, (2010).
Ralph, A. et al., "P16 and HPV discordance in metastatic carcinoma of cervical lymph nodes of unknown primary", Clinical Case Reports, vol. 3, No. 10, pp. 817-818, (2015).
Hipkiss, A.R. "Aging, proteotoxicity, mitochondria, glycation, NAD+ and carnosine: possible inter-relationships and resolution of the oxygen paradox", Frontiers in Aging Neuroscience, vol. 2, article 10, pp. 1-6, (2010).
Bakala, H. et al., "Changes in rat liver mitochondria with aging Ion protease-like activity and $N^\varepsilon$-carboxymethyllysine accumulation in the matrix", European Journal of Biochemistry, vol. 270, No. 10, pp. 2295-2302, (2003).
Leslie, M. "Suicide of aging cells prolongs life span in mice", Sciencemag.org, pp. 1-4, found at www.sciencemag.org/news/2016/02/suicide-aging-cells-prolongs-life-span-mice, (2016).
Eto, H. et al., "Selective imaging of malignant ascites in a mouse model of peritoneal metastasis using in vivo dynamic nuclear polarization-magnetic resonance imaging", Analytical Chemistry, vol. 88, pp. 2021-2027, (2016).
May Jr. K.F. et al., "Anti-human CTLA-4 monoclonal antibody promotes T-cell expansion and immunity in a hu-PBL-SCID model: a new method for preclinical screening of costimulatory monoclonal antibodies", Blood, vol. 105, pp. 1114-1120, (2005).
Schmitt, C.A. "Cellular senescence and cancer treatment", Biochimica et Biophysica Acta—Reviews on Cancer, vol. 1775, No. 1, pp. 5-20, (2007).
Gordon, R.R. et al., "Cellular senescence and cancer chemotherapy resistance", Drug Resistance Updates, vol. 15, No. 1-2, pp. 123-131, (2012).
Eyman, D. et al. "CCL5 secreted by senescent aged fibroblasts induces proliferation of prostate epithelial cells and expression of

(56) References Cited

OTHER PUBLICATIONS genes that modulate angiogenesis", Journal of Cellular Physiology, vol. 220, No. 2, pp. 376-381. (2009).
Nguyen, D.X. et al., "Metastasis: from dissemination to organ-specific colonization", Nature Reviews Cancer, vol. 9, No. 4, pp. 274-284, (2009).
Smit, M.A. et al., "Deregulating EMTand senescence: Double impact by a single twist", Cancer Cell, pp. 5-7, (2008).
Degenhardt, T.P. et al., "Chemical modification of proteins by methylglyoxal", Cellular and Molecular Biology (Noisy-le-Grand, France), vol. 44, No. 7, pp. 1139-1145, (1998) Abstract Only.
Gao, S.H. et al., "Monoclonal antibody humanness score and its applications", BMC Biotechnology, vol. 13, No. 1, pp. 1-12, (2013).
ClinicalTrials.gov, "A study evaluating the safety of ABT-263 in combination with etoposide/cisplatin in subjects with cancer", ClinicalTrials.gov, 4 pages, found at clinicaltrials.gov/ct2/show/NCT00878449?term=A+study+evaluating+the+safety+of+ABT-263+in+combination+with+etoposide%2Fcisplatin+in+subjects+with+cancer&rank=1, printed on Aug. 4, 2016.
Keating, D.J. "Mitochondrial dysfunction, oxidative stress, regulation of exocytosis and their relevance to neurodegenerative diseases", vol. 104, No. 2, pp. 298-305, (2008). Abstract Only.
Sas, K. et al., "Mitochondria, metabolic disturbances, oxidative stress and the kynurenine system, with focus on neurodegenerative disorders", Journal of the neurological sciences, vol. 257, No. 1, pp. 221-239, (2007). Abstract Only.
Ott, M. et al., "Mitochondria, oxidative stress and cell death", Apoptosis, vol. 12, No. 5, pp. 913-922, (2007). Abstract Only.
Trushina, E. et al., "Oxidative stress and mitochondrial dysfunction in neurodegenerative diseases", Neuroscience, vol. 145, No. 4, pp. 1233-1248, (2007). Abstract Only.
Moreira, P.I. et al., "Lipoic acid and N-acetyl cysteine decrease mitochondrial-related oxidative stress in Alzheimer disease patient fibroblasts", Journal of Alzheimer's Disease, vol. 12, No. 2, pp. 195-206, (2007). Abstract Only.
Yel, L. et al., "Thimerosal induces neuronal cell apoptosis by causing cytochrome c and apoptosis-inducing factor release from mitochondria", International Journal of Molecular Medicine, vol. 16, No. 6, pp. 971-977, (2005). Abstract Only.
Humphrey, M.L. et al., "Mitochondrial mediated thimerosal-induced apoptosis in a human neuroblastoma cell line (SK-N-SH)", Neurotoxicology, vol. 26, No. 3, pp. 407-416, (2005). Abstract Only.
Makani, S. et al., "Biochemical and molecular basis of thimerosal-induced apoptosis in T cells: a major role of mitochondrial pathway", Genes and Immunity, vol. 3, No. 5, pp. 270-278, (2002). Abstract Only.
Freitag, H. et al., "Inhibition of malate transport and activation of phosphate transport in mitochondria by ethylmercurithiosalicylate", FEBS Letters, vol. 117, No. 1, pp. 149-151, (1980). Citation Only.
Freitag, H. et al., "Ethylmercurithiosalicylate—a new reagent for the study of phosphate transport in mitochondria", FEBS Letters, vol. 114, No. 2, pp. 295-298, (1980). Citation Only.
Windham, G.C. et al., "Autism spectrum disorders in relation to distribution of hazardous air pollutants in the San Francisco bay area", Environmental Health Perspectives, pp. 1438-1444, (2006). Citation Only.
Ooe, H. et al., "Induction of reactive oxygen species by bisphenol A and abrogation of bisphenol A-induced cell injury by DJ-1", Toxicological Sciences, vol. 88, No. 1, pp. 114-126, (2005). Abstract Only.
Hanzel, C.E. et al., "Thallium induces hydrogen peroxide generation by impairing mitochondrial function", Toxicology and Applied Pharmacology, vol. 216, No. 3, pp. 485-492, (2006). Abstract Only.
Murugavel, P. et al., "Cadmium induced mitochondrial injury and apoptosis in vero cells: protective effect of diallyl tetrasufide from garlic", The International Journal of Biochemistry & Cell Biology, vol. 39, No. 1, pp. 161-170, (2007). Abstract Only.

Lasfer, M. et al., "Cadmium induces mitochondria-dependent apoptosis of normal human hepatocytes", Cell Biology and Toxicology, vol. 24, No. 1, pp. 55-62, (2008). Abstract Only.
Gash, D.M. et al., "Trichloroethylene: Parkinsonism and complex 1 mitochondrial neurotoxicity", Annals of neurology, vol. 63, No. 2, pp. 184-192, (2008). Abstract Only.
Banerjee, N. et al., "Arsenic-induced mitochondrial instability leading to programmed cell death in the exposed individuals", Toxicology, vol. 246, No. 2, pp. 101-111, (2008). Abstract Only.
Partridge, M.A. et al., "Arsenic induced mitochondrial DNA damage and altered mitochondrial oxidative function: Implication for genotoxic mechanisms in mammalian cells", Cancer Research, vol. 67, No. 11, pp. 5239-5247, (2007). Abstract Only.
Santra, A. et al., "Arsenic induces apoptosis in mouse liver is mitochondria dependent and is abrogated by N-acetylcysteine", Toxicology and Applied Pharmacology, vol. 220, No. 2, pp. 146-155, (2007). Abstract Only.
Bouchard, H. et al., "Antibody-drug conjugates—A new wave of cancer drugs", Bioorganic & Medicinal Chemistry Letters, vol. 24, pp. 5357-5363, (2014).
Yang, H.M. et al., "Doxorubicin conjugated with a monoclonal antibody directed to a human melanoma-associated proteoglycan suppresses the growth of established tumor xenografts in nude mice", Proceeding of the National Academy of Science, vol. 85, pp. 1189-1193, (1988).
Childs, B.G. et al., "Senescent intimal foam cells are deleterious at all stages of atherosclerosis", Science, vol. 354, No. 6311, pp. 472-477, (2016).
Loaiza, N. et al., "Cellular senescence and tumor promotion: Is aging the key?", Biochimica et Biophysica Acta, vol. 1865, pp. 155-167, (2016).
Rodier, F. et al., "Four faces of cellular senescence", The Journal of Cell Biology, vol. 192, No. 4, pp. 547-556, (2011).
Shay, J.W. et al., "Hallmarks of senescence in carcinogenesis and cancer therapy", Oncogene, vol. 23, pp. 2919-2933, (2004).
Davalos, A.R. et al., "Senescent cells as a source of inflammatory factors for tumor progression", Cancer Metastasis Reviews, vol. 29, pp. 273-283, (2010).
Roninson, I.B., "Tumor cell senescence in cancer treatment", Cancer Research, vol. 63, pp. 2705-2715, (2003).
International Search Report and Written Opinion dated May 17, 2017 for PCT application No. PCT/US2017/018185.
Kobayashi, S. et al., "Overproduction of N(epsilon)—(carboxymethyl) lysine-induced neovascularization in cultured choroidal explant of aged rat", Biological & Pharmaceutical Bulletin, vol. 30, No. 1, pp. 133-138, (2007).
Foster, D. et al., "AGE metabolites: A biomarker linked to cancer disparity?" Cancer Epidemiology, Biomarkers and Prevention, vol. 23, No. 10, pp. 2186-2191, (2014).
Mir, A.R. et al., "Structural changed in histone H2A by methylglyoxal generate highly immunogenic amorphous aggregates with implications in auto-immune response in cancer", Glycobiology, vol. 26, No. 2, pp. 129-141, (2016).
Ko, S-Y. et al., "Cell migration is regulated by AGE-RAGE interaction in human oral cancer cells in vitro", PLOS One, vol. 9, No. 10, pp. 1-9, (2014).
Chen, H. et al., "Advanced glycation end products increase carbohydrate responsive element binding protein expression and promote cancer cell proliferation", Molecular and Cellular Endocrinology, vol. 395, No. 1-2, pp. 69-78, (2014).
Mercado-Pimentel, M.E. et al., "The S100P/RAGE signaling pathway regulates expression of microRNA-21 in colon cancer cells", FEBS Letters, vol. 589, No. 19, pp. 2388-2393, (2015).
Product description, "Carboxymethyl Lysine Antibody", R&D Systems, a biotechne brand, catalog No. MAB3247, 1 page, found at resources.rndsystems.com/pdfs/datasheets/mab3247.pdf, (2015).
Bhat, R. et al., "Astrocyte senescence as a component of Alzheimer's Disease", PLOS One, vol. 7, No. 9, pp. 1-10, (2012).
Flanary, B.E. et al., "Evidence that aging and amyloid promote microglial cell senescence", Rejuvenation Research, vol. 10, No. 1, pp. 61-74, (2007).

(56) References Cited

OTHER PUBLICATIONS

Takeda, A. et al., "Advanced glycation end products co-localize with astrocytes and microglial cells in Alzheimer's disease brain", Acta Neuropathologica, vol. 95, pp. 555-558, (1998).
Chinta, S.J. et al., "Environmental stress, ageing and glial cell senescence: a novel mechanistic link to Parkinson's disease?", Journal of Internal Medicine, vol. 273, pp. 429-436, (2013).
Mori, M., "The Parkinsonian Brain: Cellular senescence and neurodegeneration", SAGE, found at sage.buckinstitute.org/the-parkinsonian-brain-cellular-senescence-and-neurodegeneration, (2015).
Das, M.M. et al., "Astrocytes show reduced support of motor neurons with aging that is accelerated in a rodent model of ALS", Neurobiology of Aging, vol. 36, pp. 1130-1139, (2015).
Luessi, F. et al., "Neurodegeneration in multiple sclerosis: novel treatment strategies", Expert Review of Neurotherapeutics, vol. 12, No. 9, pp. 1061-1077, (2012).
Wright, W.E., "Myoblast senescence in Muscular Dystrophy", Experimental Cell Research, vol. 157, pp. 343-354, (1985).
King, O.D., et al., "The tip of the iceberg: RNA-binding proteins with prion-like domains in neurodegenerative disease", Brain Research, vol. 1462, pp. 61-80, (2012).
Dobson, D.M., "The structural basis of protein folding and its links with human disease", Philosophical Transactions of the Royal Society of London B: Biological Sciences, vol. 356, No. 1406, pp. 133-145, (2001).
Kato, S. et al., "Advanced glycation endproduct-modified superoxide dismutase-1 (SOD1)-positive inclusions are common to familial amyotrophic lateral sclerosis patients with SOD1 gene mutations and transgenic mice expressing human SOD1 with a G85R mutation", Acta Neuropathologica, vol. 100, pp. 490-505, (2000).
International Search Report and Written Opinion dated Sep. 29, 2017 for PCT application No. PCT/US2017/027773.
Capparelli, C. et al., "Autophagy and senescence in cancer-associated fibroblasts metabolically supports tumor growth and metastasis via glycolysis and ketone production", Cell Cycle, vol. 11, No. 12, pp. 2285-2302, (2012).
""Shelf life" of blood? Shorter than we think", Johns Hopkins Medicine, pp. 1-2 found at www.hopkinsmedicine.org/news/media/releases/shelf_life_of_blood_shorter_than_we_think, (2013).
Garay-Sevilla, M.E. et al., "Advanced glycosylation end products in skin, serum, saliva and urine and its association with complications of patients with Type 2 diabetes mellitus", Journal of Endocrinological Investigation, vol. 28, No. 5, pp. 223-230, (2005).
Joyal, S.V., "Aging and Glycation", Life Extension Magazine, issue 4, pp. 1-7, found at www.lifeextension.com/Magazine/2008/4/Aging-And-Glycation/Page-01, (2008).
Egberts, J-H. et al., "Anti-tumor necrosis factor therapy inhibits pancreatic tumor growth and metastasis", Cancer Research, vol. 68, pp. 1443-1450, (2008).
Lowe, R. et al., "Buccals are likely to be a more informative surrogate tissue than blood for epigenome-wide association studies", Epigenetics, vol. 8, No. 4, pp. 445-454, (2013).
Bian, C. et al., "Clinical outcome and expression of mutant P53, P16, and Smad4 in lung adenocarcinoma: a prospective study", World Journal of Surgical Oncology, vol. 13, No. 128, pp. 1-8, (2015).
Tape, C.J. et al., "Oncogenic KRAS regulates tumor cell signaling via stromal reciprocation", Cell, vol. 165, pp. 910-920, (2016).
Product description for "CD8+CD57+ T Cell Isolation Kit, human", Miltenyi Biotec, pp. 1-4, found at www.miltenyibiotec.com/en/products-and-services/macs-cell-separation/cell-separation-reagents/t-cells/cd8-cd57-t-cell-isolation-kit-human.aspx, printed on Aug. 16, 2017.
Warrington, K.J. et al., "CD28 loss in senescent CD4+ T cells: reversal by interleukin-12 stimulation", Blood, vol. 101, No. 9, pp. 3543-3549, (2003).
Kared, H. et al., "CD57 in human natural killer cells and T-lymphocytes", Cancer Immunology, Immunotherapy, vol. 65, issue 4, pp. 441-452, (2016).
Li, Z. et al., "Cdkn2a suppresses metastasis in squamous cell carcinomas induced by the gain-of-function mutant $p53^{R172H}$", The Journal of Pathology, vol. 240, issue 2, pp. 224-234, (2016). (Abstract Only).
Demaria, M. et al., "Cellular senescence promotes adverse effects of chemotherapy and cancer relapse", Cancer Discovery, vol. 7, pp. 165-176, (2017).
Niu, L. et al., "Free and protein-bound $N^\varepsilon$-carboxymethyllysine and $N^\varepsilon$-carboxyethyllysine in fish muscle: Biological variation and effects of heat treatment", Journal of Food Composition and Analysis, vol. 57, pp. 56-63, (2017).
Yoon, M-S. et al., "Characterisation of advanced glycation endproducts in saliva from patients with diabetes mellitus", Biochemical and Biophysical Research Communications, vol. 323, issue 2, pp. 377-381, (2004).
Product description for "Carboxymethyl Lysine (CML) ELISA", Kamiya Biomedical Company, pp. 1-7, found at www.k-assay.com/pdf/KT-32428.pdf, printed on Aug. 16, 2017.
Baar, M.P. et al., "Targeted apoptosis of senescent cells restores tissue homeostasis in response to chemotoxicity and aging", Cell. vol. 169, pp. 132-147, (2017).
Kim, Y.H. et al., "Senescent tumor cells lead the collective invasion in thyroid cancer", Nature Communications, pp. 1-14, (2017).
Ciccone, T.G. et al., "Reversing OA—new treatment on the horizon", Practical Pain Management, pp. 1-5, found at www.practicalpainmanagement.com/resources/news-and-research/reversing-oa-new-treatment-horizon, printed on Aug. 17, 2017.
Cook, L.S., "Learning about blood component therapy", Nursing, vol. 39, No. 4, pp. 30-33, (2009).
Landesberg, R. et al., "The expression of the receptor for glycation endproducts (RAGE) in oral squamous cell carcinomas", Oral Surgery Oral Medicine Oral Pathology Oral Radiology, vol. 105, issue 5, pp. 617-624, (2008).
Zhou, H.W., "Recovery of function in osteoarthritic chondrocytes induced by $p16^{INK4a}$-specific siRNA in vitro", Rheumatology, vol. 43, pp. 555-568, (2004).
Fuijkschot, W.W. et al., "Prevention of age-induced N(ε)-(carboxymethyl)lysine accumulation in the microvasculature", European Journal of Clinical Investigation, vol. 46, issue 4, pp. 334-341, (2016). (Abstract Only).
Rasheed, Z.A. et al., "Pathology of pancreatic stroma in PDAC", Pancreatic Cancer and Tumor Microenvironment, pp. 1-10, (2012).
Morton, J.P. et al., "Mutant p53 drives metastasis and overcomes growth arrest/senescence in pancreatic cancer", PNAS, vol. 107, No. 1, pp. 246-251, (2010).
Verzijl, N. et al., "AGEing and osteoarthritis: a different perspective", Current Opinion in Rheumatology, vol. 15, issue 5, pp. 616-622, (2003).
Frescas, D. et al., "Senescent cells expose and secrete an oxidized form of membrane-bound vimentin as revealed by a natural polyreactive antibody", PNAS, vol. 114, No. 9, pp. E1668-E1677, (2017).
Oren, M. et al., "Mutant p53 gain-of-function in cancer", Cold Spring Harbor Perspectives in Biology, vol. 2, pp. 1-15, (2010).
"Senescence promotes chemotherapy side effects and cancer relapse", Medical Xpress, pp. 1-4, found at m.medicalxpress.com/news/2017-01-senescence-chemotherapy-side-effects-cancer.html, (2017).
Oh, J. et al., "Local clearance of senescent cells attenuates the development of post-traumatic osteoarthritis and creates a pro-regenerative environment", Nature Medicine, vol. 23, No. 6, pp. 1-9, (2017).
Protocols for "Isolation of untouched human T cells from peripheral blood mononuclear cells (PBMC)", Thermo Fisher Scientific, pp. 1-4, found at www.thermofisher.com/us/en/home/references/protocols/proteins-expression-isolation-and-analysis/cell-separation-methods/human-cell-separation-protocols/isolation-of-untouched-human-t-cells-.html, printed on Aug. 17, 2017.
Henrich, C.J. et al., "Isolation and characterization of a glycopeptide from human senescent erythrocytes", Carbohydrate Research, vol. 120, pp. 55-66, (1983).
Yang, S. et al., "Impact of oxidative stress biomarkers and carboxymethyllysine (an advanced glycation end product) on prostate cancer: A prospective study", Clinical Genitourinary Cancer, vol. 13, No. 5, pp. 1-14, (2015).

(56) References Cited

OTHER PUBLICATIONS

Tsai, K.K.C. et al., "Low-dose radiation-induced senescent stromal fibroblasts render nearby breast cancer cells radioresistant", Radiation Research, vol. 172, pp. 306-313, (2009).
Nie, H et al., "Impaired glial glutamate uptake induces extrasynaptic glutamate spillover in the spinal sensory synapses of neuropathic rats", Journal of Neurophysiology, vol. 103, pp. 2570-2580, (2010).
Garcia-Matas, S. et al., "Dysfunction of astrocytes in senescence-accelerated mice SAMP8 reduces their neuroprotective capacity", Aging Cell, vol. 7, pp. 630-640, (2008).
Danysz, W. et al., "Alzheimer's disease, βamyloid, glutamate, NMDA receptors and memantine-searching for the connections", British Journal of Pharmacology, vol. 167, pp. 324-352, (2012).
Blasko, I. et al., "Glial cells: Astrocytes and oligodendrocytes during normal brain aging", Encyclopedia of Neuroscience, pp. 743-747, (2009).
Leonard, B.W. et al., "Subventricular zone neural progenitors from rapid brain autopsies of elderly subjects with and without neurodegenerative disease", The Journal of Comparative Neurology, vol. 515, pp. 269-294, (2009).
Louveau, A. et al., "Structural and functional features of central nervous system lymphatic vessels", Nature, vol. 523, issue 7560, pp. 337-341, (2015).
Torgan, C., "Lymphatic vessels discovered in central nervous system", NIH Research Matters, pp. 1-4, found at www.nih.gov/news-events/nih-research-matters/lymphatic-vessels-discovered-central-nervous-system, Jun. 15, 2015.
Boskovitz, A. et al., "Monoclonal antibodies for brain tumour treatment", Expert Opinion on Biological Therapy, vol. 4, No. 9, pp. 1453-1471, (2004).
Takami, A. et al., "Treatment of primary central nervous system lymphoma with induction of complement-dependent cytotoxicity by intraventricular administration of autologous-serum-supplemented rituximab", Cancer Science, vol. 97, No. 1, pp. 80-83, (2006).
Biran, A. et al., "Senescent cells communicate via intercellular protein transfer", Genes & Development, vol. 29, pp. 791-802, (2015).
Golde, T.E. et al., "Proteinopathy-induced neuronal senescence: a hypothesis for brain failure in Alzheimer's and other neurodegenerative diseases", Alzheimer's Research & Therapy, vol. 1, No. 2, pp. 1-12, (2009).
Ouroboros, "Sweet madness: Sporadic prion disease and age-related changes in protein glycosylation", Research in the Biology of Aging, pp. 1-4, found at ouroboros.wordpress.com/2006/12/14/sweet-madness-sporadic-prion-disease-and-age-related-changes-in-protein-glycosylation/, (2006).
Xellbiogene, "Amyotrophic lateral sclerosis, immunotherapy is offering some hope", Xellbiogene.com, pp. 1-3, (2014).
Definition of "Complement system" printed from Wikipedia, the free encyclopedia on Aug. 4, 2015 found at http://en.wikipedia.org/wiki/Complement_system.
Definition of "Ventricular system" printed from Wikipedia, the free encyclopedia on Oct. 30, 2017 found at http://en.wikipedia.org/wiki/Ventricular_system.
Urushitani, M., "Future perspectives of immunotherapy against ALS", Rinsho Shinkeigaku, vol. 49, No. 11, pp. 818-820, (2009). (Abstract Only).
Cabezas, I.L. et al., "The role of glial cells in Alzheimer disease: potential therapeutic implications", Neurologia, vol. 29, No. 5, pp. 305-309, (2014).
Definition of "Prion" printed from Wikipedia, the free encyclopedia on Nov. 17, 2015 found at en.wikipedia.org/wiki/Prion.
"Prion Diseases", National Institute of Allergy and Infectious Diseases, pp. 1-2, found at www.niaid.nih.gov/diseases-conditions/prion-diseases, printed on Oct. 30, 2017.
"Alzheimer basics: Plaques and tangles", ALZ.org, pp. 1-2, found at www.alz.org/norcal/in_my_community_20545.asp, printed on Nov. 17, 2015.
Definition of "Lewy body" printed from Wikipedia, the free encyclopedia on Nov. 17, 2015 found at en.wikipedia.org/wiki/Lewy_body.
Definition of "Myocyte" printed from Wikipedia, the free encyclopedia on Nov. 17, 2015 found at en.wikipedia.org/wiki/Myocyte.
Definition of "Myosatellite cell" printed from Wikipedia, the free encyclopedia on Nov. 17, 2015 found at en.wikipedia.org/wiki/Myosatellite_cell.
Definition of "Microglia" printed from Wikipedia, the free encyclopedia on Oct. 30, 2017 found at en.wikipedia.org/wiki/Microglia.
Definition of "Astrocyte" printed from Wikipedia, the free encyclopedia on Oct. 30, 2017 found at en.wikipedia.org/wiki/Astrocyte.
Ouroboros, "A role for microglial senescence in Alzheimer's?", Research in the Biology of Aging, pp. 1-3, found at ouroboros.wordpress.com/?s=a+role+for+microglial, (2007).
Chen, K.S. et al., "Monoclonal antibody therapy for malignant glioma", Glioma: Immunotherapeutic Approaches, chapter 10, pp. 121-141, (2012).
Reardon, S., "Alzheimer's drug sneaks through blood-brain barrier", Nature News, pp. 1-4, (2014).
"Astrocytes as a novel target in Alzheimer's disease", Expertsvar, pp. 1-2, (2012).
Myslinski, N., "Alzheimer's disease and the blood-brain barrier", Today's Geriatric Medicine, vol. 7, No. 1, pp. 1-10, (2014).
Hutter-Saunders, J.A.L. et al., "Pathways towards an effective immunotherapy for Parkinson's disease", Expert Reviews in Neurotherapeutics, vol. 11, No. 12, pp. 1703-1715, (2011).
Definition of "Intrathecal administration" printed from Wikipedia, the free encyclopedia on Oct. 30, 2017 found at en.wikipedia.org/wiki/Intrathecal_administration.
"What is ALS?", ALSA.org, found at www.alsa.org/2015-non-responsive-pages/about-als/what-is-als.html, printed on Mar. 31, 2016.
Rouger, K. et al., "Systemic delivery of allogenic muscle stem cells induces long-term muscle repair and clinical efficacy in Duchenne muscular dystrophy dogs", The American Journal of Pathology, vol. 179, No. 5, pp. 2501-2518, (2011).
Anderson, J.L. et al., "Brain function in Duchenne muscular dystrophy", Brain, vol. 125, pp. 4-13, (2002).
Jarius, S. et al., "AQP4 antibodies in neuromyelitis optica: diagnostic and pathogenetic relevance", Nature Reviews, vol. 6, pp. 383-392, (2010).
Wesolowski, J. et al., "Single domain antibodies: promising experimental and therapeutic tools in infection and immunity", Medical Microbiology and Immunology, vol. 198, pp. 157-174, (2009).
Definition of "Antibody" printed from Wikipedia, the free encyclopedia on Sep. 21, 2015 found at en.wikipedia.org/wiki/Antibody.
Definition of "Antibody-dependent cell-mediated cytotoxicity" printed from Wikipedia, the free encyclopedia on Dec. 28, 2015 found at en.wikipedia.org/wiki/Antibody-dependent_cell-mediated_cytotoxicity.
Definition of "Blocking antibody" printed from Wikipedia, the free encyclopedia on Dec. 28, 2015 found at en.wikipedia.org/wiki/Blocking_antibody.
Definition of "Fc receptor" printed from Wikipedia, the free encyclopedia on Dec. 28, 2015 found at en.wikipedia.org/wiki/Fc_receptor.
Definition of "Fragment crystallizable region" printed from Wikipedia, the free encyclopedia on Dec. 28, 2015 found at en.wikipedia.org/wiki/Fragment_crystallizable_region.
Definition of "Neutralizing antibody" printed from Wikipedia, the free encyclopedia on Dec. 28, 2015 found at en.wikipedia.org/wiki/Neutralizing_antibody.
Company Information on "NantKwest", pp. 1-4, found at www.nantkwest.com, printed on Apr. 1, 2016.
Forbes, J.M. et al., "Below the radar: Advanced glycation end products that detour "around the side"", Clinical Biochemist Reviews, vol. 26, pp. 123-134, (2005).
Paul, W.E., "Fundamental immunology, third edition", Raven Press New York, chapter 9, pp. 292-295, (1993).

(56) References Cited

OTHER PUBLICATIONS

Rudikoff, S. et al., "Single amino acid substitution altering antigen-binding specificity", Proceedings of the National Academy of Science USA, vol. 79, pp. 1979-1983, (1982).
Wu, H. et al., "Humanization of a murine monoclonal antibody by simultaneous optimization of framework and CDR residues", Journal of Molecular Biology, vol. 294, pp. 151-162, (1999).
Golay, J. et al., "Mechanism of action of therapeutic monoclonal antibodies: Promises and pitfalls of in vitro and in vivo assays", Archives of Biochemistry and Biophysics, vol. 526, pp. 146-153, (2012).
Tang, S-S. et al., "Reaction of aortic lysyl oxidase with β-Aminopropionitrile", The Journal of Biological Chemistry, vol. 258, No. 7, pp. 4331-4338, (1983).
Saito, H. et al., "Regulation of a novel gene encoding a lysyl oxidase-related protein in cellular adhesion and senescence", The Journal of Biological Chemistry, vol. 272, No. 13, pp. 8157-8160, (1997).
Choi, Y-G. et al., "$N^e$-carboxymethyl modification of lysine residues in pathogenic prion isoforms", Molecular Neurobiology, vol. 53, pp. 3102-3112, (2016).
Wendel, U. et al., "A novel monoclonal antibody targeting carboxymethyllysine, an advanced glycation end product in atherosclerosis and pancreatic cancer", PLoS One, vol. 13, No. 2, pp. 1-22, (2018).
Hsia, T-C. et al., "Carboxymethyllysine, an advanced glycation end-product, promotes the invasion and migration of lung cancer A549 cells", Clinical Medicine Research, vol. 6, No. 5, pp. 149-156, (2017).
Nowotny, K. et al., "Advanced glycation end products and oxidative stress in type 2 diabetes mellitus", Biomolecules, vol. 5, pp. 194-222, (2015).
Yun, M.H. et al., "Recurrent turnover of senescent cells during regeneration of a complex structure", eLIFE, elifesciences.org, pp. 1-16, (2015).
Barja, G., "Aging in vertebrates, and the effect of caloric restriction: a mitochondrial free radical production-DNA damage mechanism?", Biological Reviews, vol. 79, No. 2, pp. 235-251, (2004). Abstract Only.
Pamplona, R. et al., "Aging increases nepsilon-(carboxymethyl)lysine and caloric restriction decreases nepsilon-(carboxyethyl)lysine and nepsilon-(malondialdehyde)lysine in rat heart mitochondrial proteins", Free Radical Research, vol. 36, No. 1, pp. 47-54, (2002). Abstract Only.
Yun, M.H., "Cellular senescence in regeneration", The Node, pp. 1-8, found at http://thenode.biologists.com/cellular-senescence-in-regeneration/research/, Jun. 28, 2015.
Kasper, M. et al., "Age-related changes in cells and tissues due to advanced glycation end products (AGEs)", Archives of Gerontology and Geriatrics, vol. 32, issue 3, pp. 233-243, (2001).
Wang, Z. et al., "Advanced glycation end-product Nε-carboxymethyl-Lysine accelerates progression of atherosclerotic calcification in diabetes", Atherosclerosis, vol. 221, issue 2, pp. 387-396, (2012). Abstract Only.
Draber, P. et al., "Stability of monoclonal IgM antibodies freeze-dried in the presence of trehalose", Journal of Immunological Methods, vol. 181, issue 1, pp. 37-43, (1995).
Kesari, S. et al., "Pritumumab binding to glioma cells induces ADCC and inhibits tumor growth", Journal of Clinical Oncology, vol. 35, No. 15 Supplemental, e14004-e14004, (2017). Abstract Only.
Babic, I. et al., "Pritumumab, the first therapeutic antibody for glioma patients", Human Antibodies, vol. 26, No. 2, pp. 95-101, (2017). Abstract Only.
Riva, P. et al., "Treatment of intracranial human glioblastoma by direct intratumoral administration of $^{131}$I-labelled anti-tenascin monoclonal antibody BC-2", International Journal of Cancer, vol. 51, No. 1, pp. 7-13, (1992). Abstract Only.

Ruster, M. et al., "Detection of elevated $N^e$-carboxymethyllysine levels in muscular tissue and in serum of patients with fibromyalgia", Scandinavian Journal of Rheumatology, vol. 34, issue 6, pp. 460-463, (2005). Abstract Only.
Niwa, H. et al., "Accelerated formation of $N^\varepsilon$-(carboxymethyl) lysine, an advanced glycation end product, by glyoxal and 3-deoxyglucosone in cultured rat sensory neurons", Biochemical and Biophysical Research Communications, vol. 248, issue 1, pp. 93-97, (1998). Abstract Only.
Daly, C. et al., "Monocyte chemoattractant protein-1 (CCL2) in inflammatory disease and adaptive immunity: Therapeutic opportunities and controversies", Microcirculation, vol. 10, pp. 247-257, (2003).
Lee, S.T. et al., "Decreased number and function of endothelial progenitor cells in patients with migraine", Neurology, vol. 70, No. 17, pp. 1510-1517, (2008). Abstract Only.
Brown, J.N. et al., "Class effect of erythropoietin therapy on hemoglobin $A_{1c}$ in a patient with diabetes mellitus and chronic kidney disease not undergoing hemodialysis", Pharmacotherapy, The Journal of Human Pharmacology and Drug Therapy, vol. 29, No. 4, pp. 468-472, (2009). Abstract Only.
Liu, J. et al., "Accelerated senescence of renal tubular epithelial cells is associated with disease progression of patients with immunoglobulin A (IgA) nephropathy", Translational Research, vol. 159, issue 6, pp. 454-463, (2012). Abstract Only.
Khaw, K-T. et al., "Association of hemoglobin $A_{1c}$ with cardiovascular disease and mortality in adults: The European prospective investigation into cancer in Norfolk", Annals of Internal Medicine, vol. 141, pp. 413-420, (2004).
Kohnert, K.D. et al., "Destruction of pancreatic beta cells in rats by complete Freund's adjuvant combined with non-diabetogenic doses of streptozotocin", Diabetes Research, vol. 5, No. 1, pp. 1-11, (1987). Abstract Only.
Staud, R., "Fibromyalgia pain: do we know the source?", Current Opinion in Rheumatology, vol. 16, issue 2, pp. 157-163, (2004). Abstract Only.
Fleurence, J. et al., "Targeting and killing glioblastoma with monoclonal antibody to O-acetyl GD2 ganglioside", Oncotarget, vol. 7, No. 27, pp. 41172-41185, (2016).
Velarde, M.C. et al., "Senescent cells and their secretory phenotype as targets for cancer therapy", Interdisciplinary Topics in Gerontology, vol. 38, pp. 17-27, (2013).
Wang, Z. et al., "CML/RAGE signal induces calcification cascade in diabetes", Diabetology & Metabolic Syndrome, vol. 8, No. 83, pp. 1-12, (2016).
Freise, A.C. et al., "In vivo imaging with antibodies and engineered fragments", Molecular Immunology, vol. 67, issue 2, pp. 142-152, (2015).
Pavlides, S. et al., "The reverse Warburg effect: Aerobic glycolysis in cancer associated fibroblasts and the tumor stroma", Cell Cycle, vol. 8, No. 23, pp. 3984-4001, (2009).
Dunn, G.P. et al., "Principles of immunology and its nuances in the central nervous system", Neuro-Oncology, vol. 17, pp. vii3-vii8, (2015).
Rettig, M.P. et al., "Evaluation of biochemical changes during in vivo erythrocyte senescence in the dog", Blood, vol. 93, No. 1, pp. 376-384, (1999).
Baraibar, M.A. et al., "Proteomic quantification and identification of carbonylated proteins upon oxidative stress and during cellular aging", Journal of Proteomics, vol. 92, pp. 63-70, (2013). Abstract Only.
Chaudhuri, J. et al., "A Caenorhabditis elegans model elucidates a conserved role for TRPA1-Nrf signaling in reactive α-dicarbonyl detoxification", Current Biology, vol. 26, pp. 3014-3025, (2016).
Saleh, T. et al., "Reversibility of chemotherapy-induced senescence is independent of autophagy and a potential model for tumor dormancy and cancer recurrence", bioRxiv, pp. 1-29, 5 figures, (2017).
Hubert, P. et al., "Antibody-dependent cell cytotoxicity in monoclonal antibody-mediated tumor immunotherapy", OncoImmunology, vol. 1, issue 1, pp. 103-105, (2012).

(56) References Cited

OTHER PUBLICATIONS

Ouchi, R. et al., "Senescence from glioma stem cell differentiation promotes tumor growth", Biochemical and Biophysical Research Communications, vol. 470, No. 2, pp. 275-281, (2016).

Evans, A. et al., "Differentiating benign from malignant solid breast masses: value of shear wave elastography according to lesion stiffness combined with greyscale ultrasound according to BI-RADS classification", British Journal of Cancer, vol. 107, pp. 224-229, (2012).

Walen, K.H., "Normal human cell conversion to 3-D cancer-like growth: Genome damage, endopolyploidy, senescence escape, and cell polarity change/loss", Journal of Cancer Therapy, vol. 2, pp. 181-189, (2011).

Virella, G. et al., "Development of capture assays for different modifications of human low-density lipoprotein", Clinical and Diagnostic Laboratory Immunology, vol. 12, No. 1, pp. 68-75, (2005).

Moghaddam, A.E. et al., "Reactive carbonyls are a major Th2-inducing damage-associated molecular pattern generated by oxidative stress", The Journal of Immunology, vol. 187, pp. 1626-1633, (2011).

Kuilman, T. et al., "The essence of senescence", Genes & Development, vol. 24, pp. 2463-2479, (2010).

James, E.L. et al., "Senescent human fibroblasts show increased glycolysis and redox homeostasis with extracellular metabolomes that overlap with those of irreparable DNA damage, aging, and disease", Journal of Proteome Research, vol. 14, pp. 1854-1871, (2015).

Hein, G. et al., "Are advanced glycation end-product-modified proteins of pathogenetic importance in fibromyalgia?" Rheumatology, vol. 41, pp. 1163-1167, (2002).

Beausejour, C.M. et al., "Reversal of human cellular senescence: roles of the p53 and p16 pathways", The EMBO Journal, vol. 22, No. 16, pp. 4212-4222, (2003).

Simpson, R.J., "Aging, persistent viral infections, and immunosenescence: Can exercise "make space"?", Exercise and Sport Sciences Reviews, vol. 39, No. 1, pp. 23-33, (2011).

Gudkov, A., "Andrei Gudkov taped an expanded presentation of the slides he presented at 2017 Biology of Aging conference at Scripps, Florida, Jan. 22-27", Everon Biosciences, found at everonbio.com/Andrei-gudkov-taped-an-expanded-presentation-of-the-slides-he-presented-at-2017-biology-of-aging-conference-at-scripps-florida-22-27-january, 2 pages, Mar. 21, 2017. Abstract Only.

Radoi, V. et al., "Advanced glycation end products in diabetes mellitus: Mechanism of action and focused treatment", Proceedings of the Romanian Academy, Series B, vol. 1, pp. 9-19, (2012).

Sieben, C.J. et al., "Two-step senescence-focused cancer therapies", Trends in Cell Biology, pp. 1-15, (2018).

Gaens, K.H.J. et al., "$N^\varepsilon$-(carboxymethyl)lysine-receptor for advanced glycation end product axis is a key modulator of obesity-induced dysregulation of adipokine expression and insulin resistance", Arteriosclerosis, Thrombosis, and Vascular Biology, vol. 34, issue 6, pp. 1199-1208, pp. s1-s9, (2014).

Semba, R.D. et al., "Relationship of an advanced glycation end product, plasma carboxymethyl-lysine, with slow walking speed in older adults: the inCHIANTI study", European Journal of Applied Physiology, vol. 108, No. 1, pp. 191-195, (2010).

Wu, J. et al., "Sonoporation, anti-cancer drug and antibody delivery using ultrasound", Ultrasonics, vol. 44, supplement, pp. e21-e25, (2006). Abstract Only.

Meerwaldt, R. et al., "Skin autofluorescence is a strong predictor of cardiac mortality in diabetes", Diabetes Care, vol. 30, No. 1, pp. 107-112, (2007).

Nagai, R. et al., "Antibody-based detection of advanced glycation end-products: promises vs. limitations", Glycoconjugate Journal, vol. 33, No. 4, pp. 545-552, (2016).

Schmidt, A.M. et al., "The biology of the receptor for advanced glycation end products and its ligands", Biochimica et Biophysica Acta, vol. 1498, pp. 99-111, (2000).

Berens, M.E. et al., "". . . those left behind." Biology and oncology of invasive glioma cells", Neoplasia, vol. 1, No. 3, pp. 208-219, (1999).

Hansen, K. et al., "Microneedle enabled intradermal delivery of biologies", 3M Drug Delivery Systems, 1 page, printed on Jul. 25, 2018.

Ikeda, K. et al., "Immunochemical approaches to AGE-structures: characterization of anti-AGE antibodies", Journal of Immunological Methods, vol. 215, No. 1-2, pp. 95-104, (1998).

De Vriese, A.S. et al., "Inhibition of the interaction of AGE-RAGE prevents hyperglycemia-induced fibrosis of the peritoneal membrane", Journal of the American Society of Nephrology, vol. 14, pp. 2109-2118, (2003).

Ott, C. et al., "Role of advanced glycation end products in cellular signaling", Redox Biology, vol. 2, pp. 411-429, (2014).

International Search Report and Written Opinion dated Aug. 7, 2018 for PCT application No. PCT/US2018/027653.

International Search Report and Written Opinion dated Sep. 10, 2018 for PCT application No. PCT/US2018/030931.

Edwards, B.M. et al., "The remarkable flexibility of the human antibody repertoire; Isolation of over one thousand different antibodies to a single protein, BLyS", The Journal of Molecular Biology, vol. 334, pp. 103-118, (2003).

Lloyd, C. et al., "Modelling the human immune response: performance of a $10^{11}$ human antibody repertoire against a broad panel of therapeutically relevant antigens", Protein Engineering, Design & Selection, vol. 22, No. 3, pp. 159-168, (2009).

Ansari, N.A. et al., "Glycated lysine residues: A marker for non-enzymatic protein glycation in age-related diseases", Disease Markers, vol. 30, pp. 317-324, (2011).

Blagosklonny, M.V. et al., "Cancerand aging", Cell Cycle, vol. 7, No. 17, pp. 2615-2618, (2008).

Chow, H-M. et al., "Senescent neurons in the alzheimer's brain kill nearby healthy neurons by blocking their WNT lifeline: The continuing saga of the zombie apocalypse", Alzheimer's & Dementia, vol. 12, No. 7(S), p. P658, (2016).

Dvorakova, E. et al., "Development of monoclonal antibodies specific for glycated prion protein", Journal of Toxicology and Environmental Health, Part A, vol. 74, pp. 1469-1475, (2011).

Search Results for "Carboxy Methyl Lysine Anitbody", 7 pages, antibodies-online.com, (2018).

Awwad, S. et al., "Overview of antibody drug delivery", Pharmaceutics, vol. 10, No. 83, pp. 1-24, (2018).

Farr, J.N. et al., "Targeting cellular senescence prevents age-related bone loss in mice", Nature Medicine, vol. 23, No. 9, pp. 1072-1079, (2017).

Hoenicke, L. et al., "Immune surveillance of senescent cells—biological significance in cancer- and non-cancer pathologies", Carcinogenesis, vol. 33, No. 6, pp. 1123-1126, (2012).

Kemmler, W. et al., "Prevalence of sarcopenia in Germany and the corresponding effect of osteoarthritis in females 70 years and older living in the community: results of the FORMOSA study", Clinical Interventions in Aging vol. 10, pp. 1565-1573, (2015).

Myrianthopoulos, V. et al., "Senescence and senotherapeutics: a new field in cancer therapy", Pharmacology & Therapeutics, vol. 193, pp. 31-49, (2019).

Salahuddin, P. et al., "The role of advanced glycation end products in various types of neurodegenerative disease: A therapeutic approach", Cellular & Molecular Biology Letters, vol. 19, pp. 407-437, (2014).

Schosserer, M. et al., "The dual role of cellular senescence in developing tumors and their response to cancer therapy", Frontiers in Oncology, vol. 7, article 278, pp. 1-13, (2017).

Bussian, T.J. et al., "Clearance of senescent glial cells prevents tau-dependent pathology and cognitive decline", Nature Letters, vol. 562, pp. 578-582, (2018).

Penney, J. et al., "Senescence mediates neurodegeneration", Nature, vol. 562, pp. 503-504, (2018).

Trivedi, P.M. et al., "Repurposed JAK1/JAK2 inhibitor reverses established autoimmune insulitis in NOD mice", Diabetes, vol. 66, p. 1650-1660, (2017).

Wang, C. et al., "DNA damage response and cellular senescence in tissues of aging mice", Aging Cell, vol. 8, pp. 311-323, (2009).

(56) References Cited

OTHER PUBLICATIONS

Iizuka, K. et al., "Dasatinib improves insulin sensitivity and affects lipid metabolism in a patient with chronic myeloid leukaemia", BMJ Case Rep, pp. 1-3, (2016).
Jeon, O.H. et al., "Local clearance of senescent cells attenuates the development of post-traumatic osteoarthritis and creates a pro-regenerative environment", Nature Medicine, vol. 23, pp. 775-781, (2017). Abstract Only.
Duke Health News & Media, "Duke team finds missing immune cells that could fight lethal brain tumors", Duke University School of Medicine, pp. 1-5, (2018).
Apple, S., "An old idea, revived: Starve cancer to death", NYTimes.com, pp. 1-15, (2016).
Dock, J.N. et al., "Role of CD8 T cell replicative senescence in human aging and in HIV-mediated immunosenescence", Aging and Disease, vol. 2, No. 5, pp. 382-397, (2011).
Rayavarapu, S. et al., "Idiopathic inflammatory myopathies: pathogenic mechanisms of muscle weakness", Skeletal Muscle, vol. 3, No. 13, pp. 1-13, (2013).
Kudryashova, E. et al., "Satellite cell senescence underlies myopathy in a mouse model of limb-girdle muscular dystrophy 2H", The Journal of Clinical Investigation, vol. 122, No. 5, pp. 1764-1776, (2012).
Ratelade, J. et al., "Neuromyelitis optica IgG and natural killer cells produce NMO lesions in mice without myelin loss", Acta Neuropathologica, vol. 123, issue 6, pp. 861-872, (2012).
Vincent, T. et al., "Functional consequences of neuromyelitis optica-IgG astrocyte interactions on blood-brain barrier permeability and granulocyte recruitment", The Journal of Immunology, vol. 181, pp. 5730-5737, (2008).
Baarine, M. et al., "ABCD1 deletion-induced mitochondrial dysfunction is corrected by SAHA: implication for adrenoleukodystrophy", Journal of Neurochemistry, vol. 133, pp. 380-396, (2015).
Durieu, I. et al., "Subepithelial fibrosis and degradation of the bronchial extracellular matrix in cystic fibrosis", American Journal of Respiratory and Critical Care Medicine, vol. 158, No. 2, pp. 580-588, (1998).
Shapiro, B.L. et al., "Premature senescence in cultured skin fibroblasts from subjects with cystic fibrosis", Science, vol. 203, issue 4386, pp. 1251-1253, (1979). Abstract Only.
Fischer, B.M. et al., "Increased expression of senescence markers in cystic fibrosis airways", American Journal of Physiology Lung Cellular and Molecular Physiology, vol. 304, No. 6, pp. L394-L400, (2013).
Thom, M. et al., "An investigation of the expression of $G_1$-phase cell cycle proteins in focal cortical dysplasia type IIB", Journal of Neuropathology and Experimental Neurology, vol. 66, No. 11, pp. 1045-1055, (2007).
Valdivieso, A.G. et al., "CFTR activity and mitochondrial function", Redox Biology, vol. 1, pp. 190-202, (2013).
Chilosi, M. et al., "Premature lung aging and cellular senescence in the pathogenesis of idiopathic pulmonary fibrosis and COPD/emphysema", Translational Research, vol. 162, issue 3, pp. 156-173, (2013). Abstract Only.
Ribeiro, C.M.P., "The role of intracellular calcium signals in inflammatory responses of polarized cystic fibrosis human airway epithelia", Drugs in R&D, vol. 7, issue 1, pp. 17-31, (2006). Abstract Only.
Velisek L. et al., "Aging: effects of aging on seizures and epilepsy", Encyclopedia of Basic Epilepsy Research, pp. 37-40, (2009). Abstract Only.
Muller, S. et al., "Analysis of senescence markers in rodent pancreatic stellate cells", The Pancreapedia, pp. 1-8, (2013).
Lim, M., "Acute immunology, temporal lobe epilepsy and other disorders", YoungEpilepsy.Org, pp. 1-70, found at youngepilepsy.org.uk/dmdocuments/MIND-THE-GAP2015_Ming%20Lim.pdf, (2015).
Definition of "Cachexia" printed from Wikipedia, the free encyclopedia on Dec. 28, 2015 found at http://en.wikipedia.org/wiki/Cachexia.
Lok, C., "The last illness, researchers are gaining insight into the causes of Cachexia—a devastating form of muscle wasting that is often the final stage of cancer and other diseases", Nature, vol. 528, pp. 182-183, (2015).
Da Rocha, O.M. et al., "Sarcopenia in rheumatoid cachexia: definition, mechanisms, clinical consequences and potential therapies", Revista Brasileira de Reumatologia, vol. 49, No. 3, pp. 294-301, (2009).
Tisdale, M.J., "Biology of Cachexia", Journal of the National Cancer Institute, vol. 89, No. 23, pp. 1763-1773, (1997).
Romanick, M. et al., "Murine models of atrophy, cachexia, and sarcopenia in skeletal muscle", Biochimica et Biophysica Acta—Molecular Basis of Disease, vol. 1832, issue 9, pp. 1410-1420, (2013).
Ali, S. et al., "Sarcopenia, cachexia and aging: Diagnosis, mechanisms and therapeutic options", Gerontology, vol. 60, No. 4, pp. 294-305, (2014).
Angelini, P.D. et al., "Constitutive HER2 signaling promotes breast cancer metastasis through cellular senescence", Cancer Research, vol. 73, No. 1, pp. 450-458, (2013).
Arai, Y. et al., "Inflammation, but not telomere length, predicts successful ageing at extreme old age: A longitudinal study of semi-supercentenarians", EBioMedicine, vol. 2, pp. 1549-1558, (2015).
Bedard, N. et al., "Inactivation of the ubiquitin-specific protease 19 deubiquitinating enzyme protects against muscle wasting", The FASEB Journal, vol. 29, No. 9, pp. 3889-3898, (2016).
Figueroa-Clarevega, A. et al., "Malignant *Drosophila* tumors interrupt insulin signaling to induce cachexia-like wasting", Developmental Cell, vol. 33, pp. 47-55, (2015).
Giacconi, R. et al., "Cellular senescence and inflammatory burden as determinants of mortality in elderly people until the extreme old age", EBioMedicine, vol. 2, pp. 1316-1317, (2015).
Jin, H. et al., "Protein modifications as potential biomarkers in breast cancer", Biomarker Insights, vol. 4, pp. 191-200, (2009).
Lee, S-J. et al., "Treating cancer cachexia to treat cancer", Skeletal Muscle, vol. 1, No. 2, pp. 1-5, (2011).
Mohamed, M.M. et al., "Human monocytes augment invasiveness and proteolytic activity of inflammatory breast cancer", Biological Chemistry, vol. 389, No. 8, pp. 1117-1121, (2008).
Pare, R. et al., "The significance of the senescence pathway in breast cancer progression", Journal of Clinical Pathology, vol. 66, pp. 491-495, (2013). Abstract Only.
Pinto, N.I. et al., "Cancer as a proinflammatory environment: Metastasis and cachexia", Mediators of Inflammation, vol. 2015, pp. 1-13, (2015).
Tesarova, P. et al., "Carbonyl and oxidative stress in patients with breast cancer—is there a relation to the stage of the disease?", Neoplasma, vol. 54, No. 3, pp. 219-224, (2007).
Tseng, Y-C., et al., "Preclinical investigation of the novel histone deacetylase inhibitor AR-42 in the treatment of cancer-induced cachexia", Journal of the National Cancer Institute, vol. 107, No. 12, pp. 1-14, (2015).
Wang, S. et al., "Characterization of IGFBP-3, PAI-1 and SPARC mRNA expression in senescent fibroblasts", Mechanisms of Ageing and Development, vol. 92, issues 2-3, pp. 121-132, (1996). Abstract Only.
Yang, S. et al., "Impact of oxidative stress biomarkers and carboxymethyllysine (an advanced glycation end product) on prostate cancer: A prospective study", Clinical Genitourinary Cancer, vol. 13, issue 5, pp. e347-e351, (2015).
"Global Arthritis Research Network: $4^{th}$ World Congress on Arthritis in Montreal", Arthritis Research & Therapy, vol. 6, supplement 3, meeting abstracts, pp. S1-S41, Sep. 20-22, (2004).
Miller, R.E. et al., "Osteoarthritis joint pain: The cytokine connection", Cytokine, vol. 70, No. 2, pp. 185-193, (2014).
LifeExtension, "Chronic Pain", Lifeextension.com, pp. 1-18, found at www.lifeextension.com/protocols/health-concerns/chronic-pain/page-03, (2016).
Rush University Medical Center, "Scientists home in on cause of osteoarthritis pain". Science Daily, found at www.sciencedaily.com/releases/2012/12/121227173053.htm, pp. 1-4, (2012).

(56) References Cited

OTHER PUBLICATIONS

Kidd, B.L. et al., "Mechanisms of inflammatory pain", British Journal of Anesthesia, vol. 87, No. 1, pp. 3-11, (2001).
Price, J.S. et al., "The role of chondrocyte senescence in osteoarthritis", Aging Cell, vol. 1, pp. 57-65, (2002).
Morales, T.I., "Chondrocyte moves: clever strategies?", OsteoArthritis and Cartilage, vol. 15, pp. 861-871, (2007).
Martin, J.A. et al., "Effects of oxidative damage and telomerase activity on human articular cartilage chondrocyte senescence", Journal of Gerontology: Biological Sciences, vol. 59A, No. 4, pp. 324-337, (2004).
Ang, D.C. et al., "MCP-1 and IL-8 as pain biomarkers in fibromyalgia: A pilot study", Pain Medicine, vol. 12, pp. 1154-1161, (2011).
Burton, D.G.A. et al., "Microarray analysis of senescent vascular smooth muscle cells: A link to atherosclerosis and vascular calcification", Experimental Gerontology, vol. 44, issue 10, pp. 659-665, (2009).
Konttinen, Y.T. et al., "Chondrocyte-mediated collagenolysis correlates with cartilage destruction grades in osteoarthritis", Clinical and Experimental Rheumatology, vol. 23, pp. 19-26, (2005).
"Low back pain", U.S. Department of Health and Human Services, Public Health Service National Institutes of Health, 1-28, (2014).
Bicer, F. "CCL2 (MCP-1) mediates chronic pelvic pain through mast cells in experimental autoimmune cystitis", ETD Archive, pp. 1-120, (2012).
Loeser, R.F. "Aging and osteoarthritis: The role of chondrocyte senescence and aging changes in the cartilage matrix", Osteoarthritis and Cartilage, vol. 17, No. 8, pp. 971-979, (2009).
Zhou, H-W. et al., "Expressions of p16INK4a in healthy and osteoarthritic human articular cartilage and difference analysis", Research Gate, pp. 2148-2149, found at www.researchgate.net/publication/290275008_Expressions_of_p16INK4a_in_healthy_and_osteoarthritic_human_articular_cartilage_and_difference_analysis, (2004). Abstract Only.
Martin, J.A. et al., "Post-traumatic osteoarthritis: the role of accelerated chondrocyte senescence", Biorheology, vol. 41, pp. 479-491, (2004).
Martin, J.A. et al., "Human chondrocyte senescence and osteoarthritis", Biorheology, vol. 39, No. 1,2, pp. 145-152, (2002). Abstract Only.
Forliti, M., "Mayo clinic researchers link senescent cells to most common form of arthritis", Mayo Clinic, pp. 1-2, found at www.eurekalert.org/pub_releases/2016-08/mc-mcr081016.php, (2016).
Roubenoff, R., "Sarcopenic obesity: Does muscle loss cause fat gain? Lessons from Rheumatoid arthritis and osteoarthritis", Annals of the New York Academy of Sciences, vol. 904, pp. 553-557, (2000). Abstract Only.
De Ceuninck, F. et al., "Bearing arms against osteoarthritis and sarcopenia: When cartilage and skeletal muscle find common interest in talking together", Drug Discovery Today, vol. 19, issue 3, pp. 305-311, (2014). Abstract Only.
Chatterjea, D. "Mast cells and pain", Mastcell Basophil, pp. 1-5, found at www.mastcell-basophil.net/wiki/wiki-start/mast-cells-and-pain/, (2013).
Bach, B. "New drug promises relief for inflammatory pain, scientists say", News Center, Stanford Medicine PASiN, found at med.stanford.edu/news/all-news/2014/08/new-drug-promises-relief-for-inflammatory-pain-scientists-say.html, 3 pages, (2014).
Daly, C. et al., "Monocyte chemoattractant protein-1 (CCL2) in inflammatory disease and adaptive immunity: Therapeutic opportunities and controversies", Microcirculation, vol. 10, issue 3-4, pp. 247-257, (2003).
"MMP13 gene", NIH U.S. National Library of Medicine, found at ghr.nlm.nih.gov/gene/MMP13, 4 pages, (2016).
Hayami, T. et al., "MMP-1 (Collagenase-1) and MMP-13 (Collagenase-3) differentially regulate markers of osteoblastic differentiation in osteogenic cells", Matrix Biology, vol. 27, issue 8, pp. 682-692, (2008).
Attur, M.G. et al., "Autocrine production of IL-1 beta by human osteoarthritis-affected cartilage and differential regulation of endogenous nitric oxide, IL-6, prostaglandin E2, and IL-8", Proceedings of the Association of American Physicians, vol. 110, No. 1, pp. 65-72, (1998). Abstract Only.
Xu, Y-K. et al., "The role of MCP-1-CCR2 ligand-receptor axis in chondrocyte degradation and disease progress in knee osteoarthritis", Biological Research, vol. 48, No. 64, pp. 1-8, (2015).
Goldring, M.B., "The role of the chondrocyte in osteoarthritis", Arthritis & Rheumatism, vol. 43, No. 9, pp. 1916-1926, (2000).
Mobasheri, A. et al., "Chondrocyte and mesenchymal stem cell-based therapies for cartilage repair in osteoarthritis and related orthopaedic conditions", Maturitas, vol. 78, pp. 188-198, (2014).
"What are chondrocytes?", wiseGeek, found at www.wisegeek.org/what-are-chondrocytes.htm, 1 page, printed on Nov. 29, 2016.
Woolf, A.D. et al., "Burden of major musculoskeletal conditions", Bulletin of the World Health Organization, vol. 81, No. 9, pp. 646-656, (2003).
Pereira, D. et al., "The effect of osteoarthritis definition on prevalence and incidence estimates: a systematic review", Osteoarthritis and Cartilage, vol. 19, pp. 1270-1285, (2011).
Martin, J.A. et al., "Aging, articular cartilage chondrocyte senescence and osteoarthritis", Biogerontology, vol. 3, pp. 257-264, (2002).
"What is osteoarthritis?", NIH National Institute of Arthritis and Musculoskeletal and Skin Diseases, pp. 1-4, (2014).
Definition of "Osteoarthritis" printed from Wikipedia, the free encyclopedia, found at en.wikipedia.org/wiki/Osteoarthritis, Dec. 13, 2016.
"At a glance 2016, Arthritis, Improving the quality of life for people with arthritis", National Center for Chronic Disease Prevention and Health Promotion, pp. 1-4, (2016).
"IASP Taxonomy", International Association for the Study of Pain, found at www.iasp-pain.org/Taxonomy, pp. 1-9, (2014).
"Pain: Hope through research", National Institute of Neurological Disorders and Stroke, National Institutes of Health, pp. 1-46, (2014).
Definition of "Allodynia" printed from Wikipedia, the free encyclopedia, found at en.wikipedia.org/wiki/Allodynia, Dec. 13, 2016.
Quadros, A.U. et al., "Dynamic weight bearing is an efficient and predictable method for evaluation of arthritic nociception and its pathophysiological mechanisms in mice", Nature, Scientific Reports, pp. 1-11, (2015).
Leung, L. et al., "TNF-α and neuropathic pain—a review", Journal of Neuroinflammation, vol. 7, No. 27, pp. 1-11, (2010).
Schafers, M. et al., "Tumor necrosis factor-α induces mechanical allodynia after spinal nerve ligation by activation of p38 MAPK in primary sensory neurons", The Journal of Neuroscience, vol. 23, No. 7, pp. 2517-2521, (2003).
Sun, J.L. et al., "CX3CL1/CX3CR1 regulates nerve injury-induced pain hypersensitivity through the ERK5 signaling pathway", Journal of Neuroscience Research, vol. 91, No. 4, pp. 545-553, (2013). Abstract Only.
Watkins, L.R. et al., "Mechanisms of tumor necrosis factor-α (TNF-α) hyperalgesia", Brain Research, vol. 692, issues 1-2, pp. 244-250, (1995). Abstract Only.
American Diabetes Association, "Diagnosis and classification of diabetes mellitus", Diabetes Care, vol. 31, supp. 1, pp. S55-S60, (2008).
"Global reporton diabetes", World Health Organization, pp. 1-88, (2016).
"National diabetes statistics report, 2017: Estimates of diabetes and its burden in the United States", U.S. Department of Health and Human Services, Centers for Disease Control and Prevention, pp. 1-20, (2017).
O'Brien, P.D. et al., "Mouse models of diabetic neuropathy", Institute for Laboratory Animal Research Journal, vol. 54, No. 3, pp. 259-272, (2014).
O'Brien, P.D et al., "BTBR ob/ob mice as a novel diabetic neuropathy model: Neurological characterization and gene expression analyses", Neurobiology of Disease, vol. 73, pp. 348-355, (2015).
Alpers, C.E. et al., "Mouse models of diabetic nephropathy", Current Opinion in Nephrology and Hypertension, vol. 20, No. 3, pp. 278-284, (2011).

(56) References Cited

OTHER PUBLICATIONS

Hudkins, K.L. et al., "BTBR ob/ob mutant mice model progressive diabetic nephropathy", Journal of the American Society of Nephrology, vol. 21, pp. 1533-1542, (2010).
O'Brien, K.D. et al., "Divergent effects of vasodilators on cardiac hypertrophy and inflammation in a murine model of diabetic cardiomyopathy", Journal of the American College of Cardiology, vol. 57, issue 17, p. e193, (2011). Abstract Only.
Lee, J-T. et al., "Macrophage metalloelastase (MMP12) regulates adipose tissue expansion, insulin sensitivity, and expression of inducible nitric oxide synthase", Endocrinology, vol. 155, No. 9, pp. 3409-3420, (2014).
Xu, X. et al., "A glimpse of matrix metalloproteinases in diabetic nephropathy", Current Medicinal Chemistry, vol. 21, No. 28, pp. 3244-3260, (2014).
Tsioufis, C. et al., "The role of matrix metalloproteinases in diabetes mellitus", Current Topics in Medicinal Chemistry, vol. 12, No. 10, pp. 1159-1165, (2012). Abstract Only.
Pechhold, K. et al., "Blood glucose levels regulate pancreatic β-cell proliferation during experimentally-induced and spontaneous autoimmune diabetes in mice", PLoS One, vol. 4, No. 3, pp. e4827, (2009).
Oh, K-J. et al., "Metabolic adaptation in obesity and type II diabetes: myokines, adipokines and hepatokines", International Journal of Molecular Sciences, vol. 18, No. 1, article 8, pp. 1-31, (2017).
Micov, A. et al., "Levetiracetam synergises with common analgesics in producing antinociception in a mouse model of painful diabetic neuropathy", Pharmacological Research, vol. 97, pp. 131-142, (2015). Abstract Only.
Feldman, E., "Tail flick assay", Animal Models of Diabetic Complications Consortium, pp. 1-3, (2004).
Bratwur, W., "ABT 263 was formulated in 10 ethano", found at www.selleckchem.com/blog/ABT-263-was-formulated-in-10-ethano.html, (2013). Abstract Only.
"Beta cell dysfunction", Diabetes and the Environment, found at www.diabetesandenvironment.org/home/mech/betacells, pp. 1-7, printed on Feb. 27, 2019.
Edelman, D., "Understanding beta cell exhaustion in Type 2 diabetics", Diabetes Daily, found at www.diabetesdaily.com/blog/2008/06/podcast-understanding-beta-cell-exhaustion-in-type-2-diabetics, pp. 1-6, (2008).
Cao, Y. et al., "Mechanisms of endothelial to mesenchymal transition in the retina in diabetes", Investigative Ophthalmology & Visual Science, vol. 55, pp. 7321-7331, (2014).
Palmer, A.K. et al., "Cellular senescence in Type 2 diabetes: a therapeutic opportunity", Diabetes, vol. 64, pp. 2289-2298, (2015).
Cummings, B.P. et al., "Maternal ileal interposition surgery confers metabolic improvements to offspring independent of effects on maternal body weight in UCD-T2DM rats", Obesity Surgery, vol. 23, No. 12, pp. 2042-2049, (2013).
Cummings, B.P. et al., "Development and characterization of a novel rat model of type 2 diabetes mellitus: the UC Davis type 2 diabetes mellitus UCD-T2DM rat", American Journal of Physiology Regulatory, Integrative and Comparative Physiology, vol. 295, pp. R1782-R1793, (2008).
Cummings, B.P. et al., "Bile-acid-mediated decrease in endoplasmic reticulum stress: a potential contributor to the metabolic benefits of ileal interposition surgery in UCD-T2DM rats", Disease Models & Mechanisms, vol. 6, No. 2, pp. 443-456, (2013).
Cummings, B.P. et al., "Vertical sleeve gastrectomy improves glucose and lipid metabolism and delays diabetes onset in the UCD-T2DM rats", Endocrinology, vol. 153, No. 8, pp. 3620-3632, (2012).
Cummings, B.P. et al., "Ileal interposition surgery improves glucose and lipid metabolism and delays diabetes onset in the UCD-T2DM rat", Gastroenterology, vol. 138, pp. 2437-2446, (2010).
American Diabetes Association, "Standards of medical care in diabetes—2016 abridged for primary care providers", Diabetes, vol. 34, No. 1, pp. 3-21, (2016).

Definition of "Methylglyoxal" printed from Wikipedia, the free encyclopedia, found at en.wikipedia.org/wiki/Methylglyoxal, Jun. 5, 2017.
Boesten, D.M.P.H.J. et al., "Effect of Nε-carboxymethyllysine on oxidative stress and the glutathione system in beta cells", Toxicology Reports, vol. 1, pp. 973-980, (2014).
Molla, B. et al., "Two different pathogenic mechanisms, dying-back axonal neuropathy and pancreatic senescence, are present in the YG8R mouse model of Friedreich ataxia", Disease Models & Mechanisms, vol. 9, pp. 647-657, (2016).
Kender, Z. et al., "Effect of metformin on methylglyoxal metabolism in patients with type 2 diabetes", Experimental and Clinical Endocrinology & Diabetes, vol. 122, No. 5, pp. 316-319, (2014). Abstract Only.
Ehrenmann, F. et al., "IMGT/3Dstructure-DB and IMGT/DomainGapAlign: a database and a tool for immunoglobulins or antibodies, T cell receptors, MHC, IgSF and MhcSF", Nucleic Acids Research, vol. 38, pp. D301-D307, (2010).
Glover, A., "Of mice and men", European Biophamaceutical Review, pp. 30-34, (2016).
"The basic guide to magnetic bead cell separation", Sepmag.eu, pp. 1-15, found at www.sepmag.eu/free-basic-guide-magnetic-bead-cell-separation, (2017).
Su, W-S. et al., "Controllable permeability of blood-brain barrier and reduced brain injury through low-intensity pulsed ultrasound stimulation", Oncotarget, vol. 6, No. 39, pp. 42290-42299, (2015).
Haslbeck, K.M. et al., "The RAGE pathway in inflammatory myopathies and limb girdle muscular dystrophy", Acta Neuropathologica, vol. 110, issue 3, pp. 247-254. (2005).
Sternberg, Z. et al., "AGE-RAGE in multiple sclerosis brain", Immunological Investigations, vol. 40, issue 2, pp. 197-205, (2011). Abstract Only.
Miyata, T. et al., "Increased pentosidine, an advanced glycation end product, in plasma and synovial fluid from patients with rheumatoid arthritis and its relation with inflammatory markers", Biochemical and Biophysical Research Communications, vol. 244, pp. 45-49, (1998).
Mulrennan, S. et al., "The role of receptor for advanced glycation end products in airway inflammation in CF and CF related diabetes", Scientific Reports, vol. 5, No. 8931, pp. 1-9, (2015).
Weber, K. et al., "Distribution of advanced glycation end products in the cerebellar neurons of dogs", Brain Research, vol. 791, pp. 11-17, (1998).
Berg, T.J. et al., "The advanced glycation end product $N^\varepsilon$-(carboxymethyl)lysine is increased in serum from children and adolescents with type 1 diabetes", Diabetes Care, vol. 21, No. 11, pp. 1997-2002, (1998).
Degenhardt, T.P. et al., "The serum concentration of the advanced glycation end-product $N^\varepsilon$-(carboxymethyl)lysine is increased in uremia", Kidney International, vol. 52, pp. 1064-1067, (1997).
Hayase, F. et al., "Aging of proteins: Immunological detection of a glucose-derived pyrrole formed during maillard reaction in vivo", The Journal of Biological Chemistry, vol. 263, No. 7, pp. 3758-3764, (1989).
Ikeda, K. et al., "Immunochemical approaches to AGE-structures: characterization of anti-AGE antibodies", The Maillard Reaction in Foods and Medicine, pp. 310-315, (1998).
Kume, S. et al., "Immunohistochemical and ultrastructural detection of advanced glycation end products in atherosclerotic lesions of human aorta with a novel specific monoclonal antibody", American Journal of Pathology, vol. 147, No. 3, pp. 654-667, (1995).
Makita, A. et al., "Immunochemical detection of advanced glycosylation end products in vivo", The Journal of Biological Chemistry, vol. 267, No. 8, pp. 5133-5138, (1992).
Niwa, T. et al., "Immunohistochemical detection of advanced glycation end products in dialysis-related amyloidosis", Kidney International, vol. 48, pp. 771-778, (1995).
Papanastasiou, P. et al., "Immunological quantification of advanced glycosylation end-products in the serum of patients on hemodialysis of CAPD", Kidney International, vol. 46, pp. 216-222, (1994).

(56) References Cited

OTHER PUBLICATIONS

Schleicher, E.D. et al., "Increased accumulation of the glycoxidation product N(epsilon)-(carboxymethyl)lysine in human tissues in diabetes and aging", The Journal of Clinical Investigation, vol. 99, No. 3, pp. 457-468, (1997).
Takeuchi, M. et al., "Immunological detection of a novel advanced glycation end-product", Molecular Medicine, vol. 7, No. 11, pp. 783-791, (2001).
Kobayashi, S. et al., "N$^\varepsilon$-(Carboxymethyl)lysine-induced choroidal angiogenic potential facilitates retinal neovascularization in advanced-diabetic rat in vitro", The Open Pharmacology Journal vol. 2, pp. 79-85, (2008).
Tamemoto, H. et al., "AGE inhibitor-recent development", Diabetes Frontier, vol. 16, No. 5, pp. 541-546, (2005).
Nagai, R. et al., "Prevention of diabetic complication by AGE inhibitors", Progress of Medicine, vol. 207, No. 9, pp. 663-667, (2003).
Vistoli, G. et al., "Advanced glycoxidation and lipoxidation end products (AGEs and ALEs): an overview of their mechanisms of formation", Free Radical Research, vol. 47, supple. 1, pp. 3-27, (2013).
Bachmeier, B.E. et al., "Maillard products as biomarkers in cancer", Annals of the New York Academy of Sciences, vol. 1126, No. 1, pp. 283-287, (2008). Abstract Only.
Chen, Z. et al., "Senescent cells re-engineered to express soluble programmed death receptor-1 for inhibiting programmed death receptor-1/programmed death ligand-1 as a vaccination approach against breast cancer", Cancer Science, vol. 109, pp. 1753-1763, (2018).
Leontieva, O.V. et al., "Yeast-like chronological senescence in mammalian cells: phenomenon, mechanism and pharmacological suppression", Aging, vol. 3, No. 11, pp. 1-14, (2011).
Moser, A.C. et al., "Immunoaffinity chromatography: an introduction to applications and recent developments", Bioanalysis, vol. 2, No. 4, pp. 769-790, (2010).
Prosser, C.G. et al., "N$^\varepsilon$-carboxymethyllysine in nutritional milk formulas for infants", Food Chemistry, vol. 274, pp. 886-890, (2019).
Takeuchi, M. et al., "Detection of noncarboxymethyllysine and carboxymethyllysine advanced glycation end products (AGE) in serum of diabetic patients", Molecular Medicine, vol. 5, pp. 393-405, (1999).
Teodorowicz, M. et al., Immunomodulation by processed animal feed: The role of maillard reaction products and advanced glycation end-products (AGEs), Frontiers in Immunology, vol. 9, article 2088, pp. 1-15, (2018).
Kwak, T. et al., "Targeting of RAGE-ligand signaling impairs breast cancer cell invasion and metastasis", Oncogene, vol. 11, pp. 1559-1572, (2017). Abstract Only.
Inui, H. et al., "A scFv antibody-based immunoaffinity chromatography column for clean-up of bisphenol a-contaminated water samples", Journal of Agricultural and Food Chemistry, vol. 57, No. 2, pp. 353-358, (2009). Abstract Only.
Casset, F. et al., "A peptide mimetic of an anti-CD4 monoclonal antibody by rational design", Biochemical and Biophysical Research Communications, vol. 307, pp. 198-205, (2003).
Chikazawa, M. et al., "Multispecificity of immunoglobulin M antibodies raised against advanced glycation end products", The Journal of Biological Chemistry, vol. 288, No. 19, pp. 13204-13214, (2013).
De Pascalis, R. et al., "Grafting of "abbreviated" complementarity-determining regions containing specificity-determining residues essential for ligand contact to engineer a less immunogenic humanized monoclonal antibody", The Journal of Immunogeny, vol. 169, pp. 3076-3084, (2002).
Hirose, J. et al., "Immunohistochemical distribution of advanced glycation end products (AFEs) in human osteoarthritic cartilage", Acta Histochemica, vol. 113, No. 6, pp. 613-618, (2011).
Kumar, S. et al., "Molecular cloning and expression of the fabs of human autoantibodies in *Escherichia coli*", The Journal of Biological Chemistry, vol. 275, No. 45, pp. 35129-35136, (2000).
Lamminmaki, U. et al., "Crystal structure of a recombinant anti-estradiol fab fragment in complex with 17β-estradiol", The Journal of Biological Chemistry, vol. 276, No. 39, pp. 36687-36694, (2001).
Padlan, E.A. et al., "Structure of an antibody-antigen complex: Crystal structure of the hyhel-10 fab-lysozyme complex", Proceedings of the National Academy of Science, fol. 86, pp. 5938-5942, (1989).
Schwab, W. et al., "Immunohistochemical demonstration of N$^\varepsilon$-(carboxymethyl)lysine protein adducts in normal and osteoarthritic cartilage", Histochemistry and Cell Biology, vol. 117, issue 6, pp. 541-546, (2002).
Smith-Gill, S.J. et al., "Contributions of immunoglobulin heavy and light chains to antibody specificity for lysozyme and two haptens" The Journal of Immunology, vol. 139, No. 12, pp. 4135-4144, (1987).
Song, M-K, et al., "Light chain of natural antibody plays a dominant role in protein antigen binding", Biochemical and Biophysical Research Communications, vol. 268, pp. 390-394, (2000).
Ward, E.S. et al., "Binding activities of a repertoire of single immunoglobulin variable domains secreted from *Escherichia coli*", Nature, vol. 341, pp. 544-546, (1989).
6 Pages, Jun. 14, 2012, U.S. Appl. No. 12/994,421, US.
19 Pages, Jul. 21, 2009, PCT/US2009/44951, WO.
6 Pages, Dec. 2, 2010, PCT/US2009/44951, WO.
13 Pages, Apr. 26, 2012, PCT/US2011/053399, WO.
3 Pages, Jul. 2, 2012, U.S. Appl. No. 12/951,768, US.
21 Pages, Mar. 30, 2012, U.S. Appl. No. 12/951,768, US.
12 Pages, Jun. 13, 2012, PCT/US2011/061387, WO.
13 Pages, Jun. 27, 2012, PCT/US12/31446, WO.
5 Pages, May 14, 2012, 200980118817.6, CN.
9 Pages, Nov. 8, 2011, 09 751 639.7, EP.
6 Pages, Jun. 12, 2012, 09 751 639.7, EP.
3 Pages, Jul. 20, 2012, U.S. Appl. No. 12/994,421, US.
4 Pages, Jul. 13, 2012, 10-2012-7026063, KR.
27 Pages, Sep. 10, 2012, U.S. Appl. No. 12/994,421, US.
9 Pages, Nov. 5, 2012, U.S. Appl. No. 12/951,768, US.
4 Pages, Nov. 8, 2012, 2009248945, AU.
4 Pages, Aug. 20, 2012, 209513, IL.
6 Pages, Jan. 3, 2013, 09 751 639.7, EP.
10 Pages, Feb. 26, 2013, U.S. Appl. No. 12/994,421, US.
5 Pages, Dec. 25, 2012, 2010152693, RU.
3 Pages, Mar. 21, 2013, U.S. Appl. No. 12/951,768, US.
5 Pages, Feb. 28, 2013, 200980118817.6, CN.
10 Pages, Feb. 28, 2013, 10-2010-7026063, KR.
3 Pages, Mar. 27, 2013, U.S. Appl. No. 12/951,768, US.
3 Pages, Apr. 15, 2013, 2009248945, AU.
3 Pages, May 21, 2013, U.S. Appl. No. 12/994,421, US.
9 Pages, Apr. 23, 2013, 2010152693, RU.
7 Pages, May 30, 2013, PCT/US2011/061387, WO.
3 Pages, May 22, 2013, 209513, IL.
3 Pages, Jul. 18, 2013, U.S. Appl. No. 12/994,421, US.
5 Pages, Jul. 26, 2013, 09751639.7, EP.
7 Pages, Apr. 2, 2013, 11776932.3, WO.
4 Pages, Jul. 16, 2013, 2010/012473, MX.
14 Pages, Jul. 29, 2013, U.S. Appl. No. 12/951,768, US.
5 Pages, Sep. 30, 2013, 10-2010-7026063, KR.
3 Pages, Nov. 15, 2013, U.S. Appl. No. 12/951,768, US.
6 Pages, Oct. 10, 2013, PCT/US2012/031446, WO.
8 Pages, Nov. 19, 2013, 2011-511734, JP.
8 Pages, Oct. 10, 2013, 200980118817.6, CN.
15 Pages, Dec. 20, 2013, U.S. Appl. No. 12/951,768, US.
7 Pages, Dec. 23, 2013, 10-2010-7026063, KR.
6 Pages, Jan. 23, 2014, 09751639.7, EP.
3 Pages, Feb. 4, 2014, 2009248945, AU.
11 Pages, Mar. 18, 2014, 2010/012473, MX.
5 Pages, May 7, 2014, 200980118817.6, CN.
3 Pages, May 25, 2014, 209513, IL.
7 Pages, May 26, 2014, 2010152693, RU.
3 Pages, Jun. 17, 2014, 2010/012473, MX.
3 Pages, Jun. 20, 2014, 2,724,886, CA.

(56) References Cited

OTHER PUBLICATIONS

8 Pages, Jun. 22, 2014, 10-2013-7028228, KR.
3 Pages, Jul. 29, 2014, 10-2010-7026063, KR.
9 Pages, Jul. 29, 2014, 10-2012-7026483, KR.
6 Pages, Sep. 3, 2014, U.S. Appl. No. 13/332,976, US.
30 Pages, Sep. 9, 2014, U.S. Appl. No. 14/247,081, US.
6 Pages, Sep. 12, 2014, 14170802.4, EP.
7 Pages, Oct. 8, 2014, 200980118817.6, CN.
51 Pages, Nov. 18, 2014, U.S. Appl. No. 13/332,976, US.
34 Pages, Nov. 18, 2014, U.S. Appl. No. 12/994,421, US.
3 Pages, Dec. 2, 2014, 209513, IL.
8 Pages, Dec. 3, 2014, 2011-511734, JP.
3 Pages, Jan. 13, 2015, U.S. Appl. No. 14/247,081, US.
5 Pages, Feb. 2, 2015, U.S. Appl. No. 14/247,081, US.
10 Pages, Dec. 16, 2014, 2010152693, RU.
3 Pages, Feb. 5, 2015, 2,724,886, CA.
6 Pages, Feb. 27, 2015, 10-2012-7026483, KR.
5 Pages, Mar. 13, 2015, U.S. Appl. No. 12/994,421, US.
6 Pages, Mar. 13, 2015, U.S. Appl. No. 13/332,976, US.
44 Pages, Mar. 27, 2015, U.S. Appl. No. 12/994,421, US.
25 Pages, Apr. 1, 2015, U.S. Appl. No. 13/332,976, US.
4 Pages, Mar. 26, 2015, 200980118817.6, CN.
3 Pages, Apr. 23, 2015, U.S. Appl. No. 13/332,976, US.
3 Pages, May 1, 2015, U.S. Appl. No. 13/332,976, US.
4 Pages, Apr. 27, 2015, 10-2013-7028228, KR.
29 Pages, May 6, 2015, U.S. Appl. No. 14/247,081, US.
7 Pages, Apr. 20, 2015, 10-2015-7007520, KR.
18 Pages, Jun. 11, 2015, U.S. Appl. No. 13/332,976, US.
3 Pages, Jul. 10, 2015, U.S. Appl. No. 14/247,081, US.
11 Pages, Jul. 21, 2015, U.S. Appl. No. 14/278,081, US.
8 Pages, Jun. 22, 2015, 2015-076575, JP.
3 Pages, Jun. 5, 2015, 2011332143, AU.
3 Pages, Jun. 22, 2015, 2014202548, AU.
5 Pages, Jul. 17, 2015, 14170802.4, EP.
54 Pages, Sep. 10, 2015, U.S. Appl. No. 13/876,157, US.
4 Pages, Sep. 2, 2015, U.S. Appl. No. 12/994,421, US.
5 Pages, Sep. 8, 2015, 2,724,886, CA.
7 Pages, Jul. 27, 2015, MX/a/2013/013310, MX.
4 Pages, Nov. 27, 2015, 10-2015-7007520, KR.
5 Pages, Dec. 10, 2015, 14170802.4, EP.
3 Pages, Jan. 8, 2016, 2014202548, AU.
2 Pages, Jan. 11, 2016, 2011332143, AU.
7 Pages, Jan. 12, 2016, 2015-076575, JP.
35 Pages, Jan. 19, 2016, U.S. Appl. No. 12/994,421, US.
2 Pages, Jan. 25, 2016, 2011332143, AU.
8 Pages, Mar. 30, 2016, U.S. Appl. No. 13/876,157, US.
17 Pages, Mar. 31, 2016, PCT/US2015/050154, WO.
7 Pages, Apr. 6, 2016, MX/a/2013/013310, MX.
5 Pages, Apr. 14, 2016, 2,724,886, CA.
8 Pages, Apr. 28, 2016, 2014202548, AU.
5 Pages, Jun. 20, 2016, 2014202548, AU.
13 Pages, Jun. 15, 2016, 201510303227.8, CN.
4 Pages, Aug. 24, 2016, 2016204196, AU.
4 Pages, Apr. 14, 2016, 240242, IL.
8 Pages, Jul. 19, 2016, 2016-098558, JP.
9 Pages, Jul. 13, 2016, 2015114990, RU.
15 Pages, Oct. 17, 2016, U.S. Appl. No. 13/876,157, US.
5 Pages, Oct. 26, 2016, 2,818,647, CA.
6 Pages, Sep. 22, 2016, U.S. Appl. No. 14/974,095, US.
16 Pages, Dec. 30, 2016, 201510303227.8, CN.
8 Pages, Dec. 29, 2016, 4875/KOLNP/2010, IN.
9 Pages, Jan. 5, 2017, U.S. Appl. No. 13/876,157, US.
16 Pages, Dec. 2, 2016, PCT/US2016/039076, WO.
16 Pages, Aug. 10, 2016, PCT/US2016/034880, WO.
8 Pages, Feb. 21, 2017, 16198527.0, EP.
6 Pages, Mar. 23, 2017, 11776932.3, EP.
4 Pages, Feb. 20, 2017, 2,724,886, CA.
1 Page, May 1, 2017, 2,724,886, CA.
4 Pages, Jan. 23, 2017, 240242, IL.
9 Pages, Dec. 19, 2016, 2016-098558, JP.
9 Pages, Feb. 15, 2017, MX/a/2013/013310, MX.
6 Pages, Jan. 27, 2017, 2015114990, RU.
4 Pages, Apr. 19, 2017, 2,818,647, CA.
45 Pages, Feb. 13, 2017, U.S. Appl. No. 14/974,095, US.
20 Pages, May 17, 2017, PCT/US2017/018185, WO.
8 Pages, Jun. 13, 2017, U.S. Appl. No. 14/974,561, US.
10 Pages, Mar. 30, 2017, PCT/US2015/050154, WO.
5 Pages, Jun. 27, 2017, U.S. Appl. No. 14/974,095, US.
2 Pages, Nov. 24, 2016, 14170802.4, EP.
3 Pages, May 10, 2017, 2017113349, RU.
14 Pages, May 15, 2017, 201510303227.8, CN.
5 Pages, May 29, 2017, 248652, IL.
4 Pages, Aug. 8, 2017, 2015114990, RU.
12 Pages, Aug. 23, 2017, 11776932.3, EP.
25 Pages, Sep. 22, 2017, U.S. Appl. No. 14/974,095, US.
16 Pages, Sep. 29, 2017, PCT/US2017/027773, WO.
4 Pages, Oct. 13, 2017, 2,818,647, CA.
14 Pages, Oct. 18, 2017, 2015114990, RU.
67 Pages, Nov. 15, 2017, U.S. Appl. No. 14/974,561, US.
4 Pages, Nov. 29, 2017, 2,818,647, CA.
7 Pages, Nov. 30, 2017, U.S. Appl. No. 14/932,200, US.
3 Pages, Jan. 11, 2018, U.S. Appl. No. 14/974,095, US.
19 Pages, Jan. 30, 2018, U.S. Appl. No. 14/974,095, US.
5 Pages, Feb. 8, 2018, U.S. Appl. No. 14/974,561, US.
81 Pages, Feb. 21, 2018, U.S. Appl. No. 14/932,200, US.
17 Pages, Mar. 16, 2018, 11776932.3, EP.
7 Pages, Apr. 30, 2018, 2017-086871, JP.
4 Pages, May 11, 2018, U.S. Appl. No. 14/974,095, US.
7 Pages, May 14, 2018, U.S. Appl. No. 14/920,737, US.
27 Pages, May 21, 2018, U.S. Appl. No. 15/511,731, US.
51 Pages, May 21, 2018, U.S. Appl. No. 15/489,624, US.
12 Pages, May 29, 2018, U.S. Appl. No. 14/974,561, US.
1 Page, Jun. 22, 2018, 2,818,647, CA.
1 Page, Jul. 20, 2018, 2,818,647, CA.
11 Pages, Aug. 30, 2018, PCT/U82017/018185, WO.
40 Pages, Sep. 5, 2018, U.S. Appl. No. 14/932,200, US.
51 Pages, Sep. 12, 2018, U.S. Appl. No. 14/920,737, US.
7 Pages, Sep. 14, 2018, 15772116.8, EP.
21 Pages, Sep. 25, 2018, U.S. Appl. No. 14/974,561, US.
13 Pages, Oct. 23, 2018, U.S. Appl. No. 15/489,624, US.
8 Pages, Oct. 25, 2018, PCT/US2017/027773, WO.
18 Pages, Nov. 15, 2018, U.S. Appl. No. 15/511,731, US.
6 Pages, Nov. 28, 2018, U.S. Appl. No. 15/720,912, US.
9 Pages, Dec. 6, 2018, 2017113349, RU.
10 Pages, Dec. 13, 2018, U.S. Appl. No. 14/932,200, US.
3 Pages, Jan. 11, 2019, 17708098.3, EP.
6 Pages, Jan. 23, 2019, U.S. Appl. No. 15/489,624, US.
5 Pages, Feb. 4, 2019, U.S. Appl. No. 15/863,811, US.
5 Pages, Feb. 6, 2019, U.S. Appl. No. 14/974,561, US.
5 Pages, Feb. 11, 2019, U.S. Appl. No. 15/863,784, US.
3 Pages, Feb. 14, 2019, U.S. Appl. No. 15/511,731, US.
12 Pages, Mar. 4, 2019, U.S. Appl. No. 14/920,737, US.
20 Pages, Mar. 12, 2019, U.S. Appl. No. 14/974,561, US.
55 Pages, Mar. 26, 2019, U.S. Appl. No. 15/720,912, US.
13 Pages, Apr. 10, 2019, U.S. Appl. No. 15/863,741, US.
144 Pages, Feb. 25, 2019, 17708098.3, EP.
9 Pages, Dec. 25, 2018, PCT/US2016/039076, WO.
5 Pages, Mar. 20, 2019, U.S. Appl. No. 15/863,828, US.
5 Pages, Mar. 31, 2019, 2017086871, JP.
14 Pages, Apr. 8, 2019, 2017113349, RU.
3 Pages, Jun. 7, 2019, U.S. Appl. No. 14/932,200, US.
9 Pages, Jul. 1, 2019, 2017-515740, JP.
24 Pages, Aug. 15, 2019, U.S. Appl. No. 14/920,737, US.
15 Pages, Jun. 19, 2019, 18184822.7, EP.
15 Pages, Jun. 27, 2019, U.S. Appl. No. 15/511,731, US.
144 Pages, Jul. 19, 2019, 17708098.3, EP.
14 Pages, Sep. 25, 2019, U.S. Appl. No. 15/863,811, US.
3 Pages, Apr. 14, 2016, 14170802.4, EP.
3 Pages, Sep. 8, 2017, 11776932.3, EP.
3 Pages, Jan. 19, 2018, 11776932.3, EP.
3 Pages, Feb. 7, 2018, 11776932.3, EP.
3 Pages, Jan. 30, 2019, 15772116.8, EP.
4 Pages, Aug. 30, 2019, 17737078.0, EP.

(56) References Cited

OTHER PUBLICATIONS

15 Pages, Sep. 30, 2019, U.S. Appl. No. 15/863,784, US.
12 Pages, Oct. 7, 2019, U.S. Appl. No. 15/863,828, US.
6 Pages, Oct. 11, 2019, U.S. Appl. No. 15/953,244, US.
10 Pages, Oct. 11, 2019, U.S. Appl. No. 15/768,425, US.
12 Pages, Oct. 21, 2019, U.S. Appl. No. 15/511,731, US.
38 Pages, Oct. 30, 2019, U.S. Appl. No. 15/720,912, US.
4 Pages, Nov. 1, 2019, U.S. Appl. No. 15/863,811, US.
12 Pages, Nov. 14, 2019, PCT/US2018/030931, WO.
28 Pages, Nov. 20, 2019, U.S. Appl. No. 14/932,200, US.
3 Pages, Nov. 21, 2019, U.S. Appl. No. 15/863,784, US.
4 Pages, Jan. 23, 2019, 18184822.7, EP.
3 Pages, Feb. 4, 2019, 15772116.8, EP.
2 Pages, Feb. 14, 2019, 11776932.3, EP.
U.S. Appl. No. 14/932,200, filed Nov. 4, 2015.
U.S. Appl. No. 15/720,912, filed Sep. 29, 2017.
U.S. Appl. No. 16/265,875, filed Feb. 1, 2019.
U.S. Appl. No. 14/920,737, filed Oct. 22, 2015.
U.S. Appl. No. 16/440,747, filed Jun. 13, 2019.
U.S. Appl. No. 15/511,731, filed Sep. 15, 2015.
U.S. Appl. No. 15/977,587, filed May 11, 2018.
U.S. Appl. No. 16/077,713, filed Feb. 16, 2017.
U.S. Appl. No. 15/768,425, filed May 27, 2016.
U.S. Appl. No. 16/311,149, filed Dec. 18, 2018.
U.S. Appl. No. 15/863,741, filed Jan. 5, 2018.
U.S. Appl. No. 15/863,784, filed Jan. 5, 2018.
U.S. Appl. No. 15/863,811, filed Jan. 5, 2018.
U.S. Appl. No. 15/863,828, filed Jan. 5, 2018.
U.S. Appl. No. 16/228,293, filed Dec. 20, 2018.
U.S. Appl. No. 15/953,244, filed Apr. 13, 2018.
U.S. Appl. No. 16/610,473, filed Nov. 1, 2019, May 3, 2018.
U.S. Appl. No. 16/383,348, filed Apr. 12, 2019.
U.S. Appl. No. 10/358,502, filed Jul. 2019, Gruber.
63 Pages, Dec. 5, 2019, U.S. Appl. No. 15/863,741, US.
8 Pages, Dec. 11, 2019, U.S. Appl. No. 15/977,587, US.
3 Pages, Dec. 11, 2019, 18726656.4, EP.
3 Pages, Dec. 20, 2019, U.S. Appl. No. 15/863,828, US.
3 Pages, Jan. 13, 2020, U.S. Appl. No. 14/920,737, US.
22 Pages, Jan. 29, 2020, 2018110885, RU.
4 Pages, Jan. 29, 2020, 2018110885, RU.
6 Pages, Jan. 27, 2020, U.S. Appl. No. 15/511,731, US.
3 Pages, Feb. 13, 2020, U.S. Appl. No. 15/863,741, US.
7 Pages, Feb. 7, 2020, U.S. Appl. No. 15/863,784, US.
56 Pages, Feb. 11, 2020, U.S. Appl. No. 15/863,811, US.
5 Pages, Jan. 14, 2020, 2017-515740, JP.
8 Pages, Mar. 17, 2020, U.S. Appl. No. 15/768,425, US.
6 Pages, Mar. 20, 2020, U.S. Appl. No. 15/953,244, US.
11 Pages, Mar. 31, 2020, U.S. Appl. No. 14/920,737, US.
16 Pages, Mar. 26, 2020, 2017113349, RU.
79 Pages, Mar. 18, 2020, U.S. Appl. No. 16/092,743, US.
4 Pages, Mar. 5, 2020, 15772116.8, EP.
6 Pages, Mar. 5, 2020, 2018-543120, JP.
7 Pages, Apr. 16, 2020, U.S. Appl. No. 15/863,828, US.
7 Pages, Apr. 20, 2020, U.S. Appl. No. 15/863,741, US.
22 Pages, Apr. 3, 2020, 201580056616.3, CN.
10 Pages, May 12, 2020, 2018-519727, JP.
4 Pages, May 18, 2020, U.S. Appl. No. 15/720,912, US.
17 Pages, May 19, 2020, U.S. Appl. No. 14/932,200, US.
18 Pages, May 28, 2020, 2018132998, RU.
4 Pages, May 25, 2020, 2018-543120, JP.
8 Pages, May 29, 2020, 19210193.9, EP.
76 Pages, May 28, 2020, U.S. Appl. No. 15/977,587, US.
10 Pages, Jun. 2, 2020, U.S. Appl. No. 16/077,713, US.
5 Pages, Jun. 12, 2020, 2015318036, AU.
65 Pages, Jun. 18, 2020, U.S. Appl. No. 15/863,784, US.
8 Pages, Jun. 3, 2020, 258397, IL.
9 Pages, Jun. 8, 2020, 251210, IL.
3 Pages, Jun. 23, 2020, U.S. Appl. No. 14/920,737, US.
4 Pages, Jun. 24, 2020, 17737078.0, EP.
8 Pages, Jun. 26, 2020, 201737009367, IN.
7 Pages, Jun. 15, 2020, 2018-566505, JP.
2 Pages, Jul. 13, 2020, 19210193.9, EP.
2 Pages, Dec. 12, 2019, 17708098.3, EP.
3 Pages, Jul. 23, 2020, U.S. Appl. No. 15/720,912, US.
6 Pages, Jul. 24, 2020, U.S. Appl. No. 15/863,784, US.
14 Pages, Jul. 20, 2020, U.S. Appl. No. 15/863,811, US.
4 Pages, Jul. 24, 2020, 15772116.8, EP.
11 Pages, Aug. 4, 2020, U.S. Appl. No. 14/920,737, US.
65 Pages, Aug. 6, 2020, U.S. Appl. No. 15/953,244, US.
41 Pages, Aug. 12, 2020, U.S. Appl. No. 16/077,713, US.
6 Pages, Aug. 4, 2020, 2020-106264, JP.
65 Pages, Aug. 26, 2020, U.S. Appl. No. 15/768,425, US.
8 Pages, Sep. 9, 2020, U.S. Appl. No. 16/440,747, US.
56 Pages, Sep. 16, 2020, U.S. Appl. No. 15/863,784, US.
5 Pages, Sep. 16, 2020, U.S. Appl. No. 15/953,244, US.
6 Pages, Sep. 29, 2020, U.S. Appl. No. 15/768,425, US.
6 Pages, Sep. 29, 2020, U.S. Appl. No. 15/863,811, US.
67 Pages, Sep. 17, 2020, U.S. Appl. No. 15/863,828, US.
14 Pages, Oct. 13, 2020, U.S. Appl. No. 15/863,741, US.
63 Pages, Oct. 21, 2020, U.S. Appl. No. 16/311,149, US.
11 Pages, Oct. 22, 2020, U.S. Appl. No. 15/863,811, US.
4 Pages, Oct. 27, 2020, U.S. Appl. No. 15/863,828, US.
4 Pages, Oct. 27, 2020, U.S. Appl. No. 15/863,741, US.
3 Pages, Nov. 5, 2020, U.S. Appl. No. 15/863,741, US.
74 Pages, Nov. 6, 2020, U.S. Appl. No. 16/092,743, US.
3 Pages, Nov. 12, 2020, U.S. Appl. No. 15/953,244, US.
47 Pages, Nov. 9, 2020, U.S. Appl. No. 14/920,737, US.
5 Pages, Nov. 19, 2020, U.S. Appl. No. 16/228,293, US.
4 Pages, Nov. 24, 2020, 2020-106264, JP.
5 Pages, Nov. 24, 2020, U.S. Appl. No. 15/768,425, US.
9 Pages, Dec. 3, 2020, U.S. Appl. No. 15/863,784, US.
4 Pages, Dec. 9, 2020, U.S. Appl. No. 15/768,425, US.
7 Pages, Dec. 17, 2020, U.S. Appl. No. 15/863,741, US.
7 Pages, Dec. 17, 2020, U.S. Appl. No. 15/863,784, US.
9 Pages, Dec. 17, 2020, U.S. Appl. No. 15/863,828, US.
7 Pages, Dec. 21, 2020, 2019-230026, JP.
4 Pages, Jan. 8, 2021, 2017219749, AU.
6 Pages, Jan. 13, 2021, U.S. Appl. No. 15/863,741, US.
10 Pages, Jan. 6, 2021, U.S. Appl. No. 15/720,912, US.
5 Pages, Jan. 29, 2021, U.S. Appl. No. 16/092,743, US.
3 Pages, Jan. 12, 2021, 2016800599975, CN.
5 Pages, Feb. 3, 2021, 2016800599975, CN.
6 Pages, Jan. 28, 2021, U.S. Appl. No. 14/920,737, US.
21 Pages, Feb. 3, 2021, U.S. Appl. No. 15/977,587, US.
7 Pages, Feb. 10, 2021, U.S. Appl. No. 14/920,737, US.
3 Pages, Feb. 12, 2021, 2017219749, AU.
21 Pages, Feb. 23, 2021, U.S. Appl. No. 16/077,713, US.
8 Pages, Feb. 10, 2021, U.S. Appl. No. 14/920,737, US.
29 Pages, Mar. 8, 2021, 201580056616.3, CN.
7 Pages, Mar. 12, 2021, U.S. Appl. No. 15/863,784, US.
9 Pages, Mar. 15, 2021, U.S. Appl. No. 16/311,149, US.
5 Pages, Mar. 25, 2021, U.S. Appl. No. 15/863,784, US.
7 Pages, Mar. 17, 2021, 18184822.7, EP.
8 Pages, Apr. 1, 2021, U.S. Appl. No. 16/228,293, US.
5 Pages, Mar. 24, 2021, 18726656.4, EP.
4 Pages, May 12, 2021, 2015318036, AU.
10 Pages, May 18, 2021, 201780024206.X, CN.
1 Pages, May 25, 2021, 2,961,603, CA.
4 Pages, Mar. 7, 2021, 261006, IL.
142 Pages, May 21, 2021, 19210193.9, EP.
6 Pages, May 21, 2021, 3,000,815, CA.
20 Pages, Jun. 17, 2021, U.S. Appl. No. 16/311,149, US.
9 Pages, May 24, 2021, 2018-566505, JP.
4 Pages, Jun. 10, 2021, 2020-085180, JP.
8 Pages, Jun. 29, 2021, U.S. Appl. No. 15/720,912, US.
4 Pages, Jul. 7, 2021, U.S. Appl. No. 15/720,912, US.
3 Pages, Jul. 19, 2021, 2017-515740, JP.
14 Pages, Aug. 6, 2021, U.S. Appl. No. 16/077,713, US.
5 Pages, Aug. 12, 2021, U.S. Appl. No. 15/977,587, US.
4 Pages, Aug. 30, 2021, U.S. Appl. No. 16/077,713, US.
7 Pages, Aug. 27, 2021, 2019139256, RU.
10 Pages, Sep. 7, 2021, 2018110885, RU.
12 Pages, Sep. 24, 2021, U.S. Appl. No. 16/311,149, US.

(56) References Cited

OTHER PUBLICATIONS

9 Pages, Sep. 17, 2021, MX/a/2017/003565, MX.
11 Pages, Oct. 7, 2021, U.S. Appl. No. 16/228,293, US.
11 Pages, Sep. 3, 2021, 201780037571.4, CN.
2 Pages, Sep. 18, 2021, 201580056616.3, CN.
3 Pages, Oct. 20, 2021, U.S. Appl. No. 15/977,587, US.
1 Page, Oct. 18, 2021, 2017-515740, JP.
5 Pages, Oct. 28, 2021, U.S. Appl. No. 16/077,713, US.
24 Pages, Oct. 26, 2021, U.S. Appl. No. 15/720,912, US.
11 Pages, Oct. 28, 2021, U.S. Appl. No. 16/440,747, US.
5 Pages, Sep. 30, 2021, 10-2017-7009539, KR.
5 Pages, Oct. 13, 2021, 3,000,815, CA.
67 Pages, Nov. 15, 2021, U.S. Appl. No. 17/089,999, US.
5 Pages, Nov. 18, 2021, U.S. Appl. No. 16/311,149, US.
24 Pages, Dec. 8, 2021, U.S. Appl. No. 16/092,743, US.
3 Pages, Nov. 18, 2021, 283726, IL.
13 Pages, Dec. 7, 2021, 2018110885, RU.
15 Pages, Dec. 16, 2021, U.S. Appl. No. 16/383,348, US.
6 Pages, Dec. 6, 2021, 2021-155024, JP.
9 Pages, Nov. 11, 2021, 10-2018-7031932, KR.
8 Pages, Dec. 17, 2021, U.S. Appl. No. 15/720,912, US.
2 Pages, Jan. 12, 2022, U.S. Appl. No. 16/228,293, US.
2 Pages, Dec. 23, 2021, 15772116.8, EP.
6 Pages, Dec. 1, 2021, 2019-230026, JP.
19 Pages, Jan. 18, 2022, U.S. Appl. No. 17/089,999, US.
3 Pages, Jan. 6, 2022, 262222, IL.
13 Pages, Feb. 1, 2022, U.S. Appl. No. 15/720,912, US.
15 Pages, Jan. 18, 2022, 2019139256, RU.
7 Pages, Feb. 2, 2022, 251210, IL.
14 Pages, Feb. 14, 2022, 2019-555873, JP.
8 Pages, Feb. 28, 2022, U.S. Appl. No. 16/228,293, US.
1 Page, Feb. 16, 2022, MX/a/2017/003565, MX.
2 Pages, Mar. 11, 2022, 19210193.9, EP.
4 Pages, Mar. 18, 2022, U.S. Appl. No. 17/089,999, US.
8 Pages, Mar. 21, 2022, U.S. Appl. No. 16/610,473, US.
3 Pages, Mar. 21, 2022, U.S. Appl. No. 16/228,293, US.
7 Pages, Mar. 10, 2022, 201827014696, IN.
3 Pages, Mar. 16, 2022, 2018251183, AU.
4 Pages, Mar. 11, 2022, 3,021,150, CA.
96 Pages, Apr. 1, 2022, U.S. Appl. No. 16/077,713, US.
78 Pages, Apr. 11, 2022, U.S. Appl. No. 16/228,293, US.
7 Pages, Apr. 8, 2022, 201780024206.X, CN.
16 Pages, Mar. 22, 2022, 2019-560086, JP.
10 Pages, Apr. 27, 2022, 201780037571.4, CN.
9 Pages, May 6, 2022, 201837030621, IN.
2 Pages, May 30, 2022, 10-2017-7009539, KR.
4 Pages, Jun. 13, 2022, U.S. Appl. No. 17/089,999, US.
5 Pages, Jun. 22, 2022, U.S. Appl. No. 16/228,293, US.
58 Pages, Jun. 23, 2022, U.S. Appl. No. 15/977,587, US.
12 Pages, Jun. 27, 2022, U.S. Appl. No. 16/383,348, US.
6 Pages, May 23, 2022, 16738275.3, EP.
8 Pages, Jun. 30, 2022, U.S. Appl. No. 16/265,875, US.
33 Pages, Jul. 6, 2022, U.S. Appl. No. 16/440,747, US.
7 Pages, Jun. 28, 2022, MX/a/2018/009988, MX.
10 Pages, Jun. 27, 2022, 2021-155024, JP.
11 Pages, Jul. 18, 2022, 2019139256, RU.
13 Pages, Jul. 29, 2022, U.S. Appl. No. 17/089,999, US.
5 Pages, Jul. 23, 2022, P6000510/2018, AE.
4 Pages, Jul. 23, 2022, P6000510/2018, AE.
15 Pages, Aug. 2, 2022, U.S. Appl. No. 16/228,293, US.
6 Pages, Jun. 23, 2022, 10-2018-7026021, KR.
12 Pages, Aug. 18, 2022, U.S. Appl. No. 16/092,743, US.
7 Pages, Jul. 28, 2022, 10-2018-7031932, KR.
11 Pages, Sep. 21, 2022, U.S. Appl. No. 16/610,473, US.
1 Page, Sep. 12, 2022, 3,021,150, CA.
1 Page, Sep. 2, 2022, MX/a/2018/009988, MX.
6 Pages, Oct. 12, 2022, U.S. Appl. No. 16/228,293, US.
5 Pages, Oct. 12, 2022, U.S. Appl. No. 17/089,999, US.
10 Pages, Oct. 14, 2022, U.S. Appl. No. 15/977,587, US.
8 Pages, Oct. 10, 2022, 201780024206.X, CN.
8 Pages, Sep. 6, 2022, 10-2019-7035140, KR.
22 Pages, Sep. 2, 2022, 22157145.8, EP.
23 Pages, Oct. 27, 2022, U.S. Appl. No. 16/077,713, US.
14 Pages, Oct. 20, 2022, 2022-128911, JP.
7 Pages, Oct. 31, 2022, U.S. Appl. No. 17/089,999, US.
5 Pages, Nov. 1, 2022, U.S. Appl. No. 16/228,293, US.
2 Pages, Nov. 17, 2022, U.S. Appl. No. 16/440,747, US.
20 Pages, Nov. 24, 2022, 2019139256, RU.
12 Pages, Nov. 10, 2022, PCT/US2021/030184, WO.
10 Pages, Dec. 9, 2022, U.S. Appl. No. 16/779,369, US.
12 Pages, Dec. 5, 2022, 201780037571.4, CN.
5 Pages, Dec. 15, 2022, U.S. Appl. No. 16/383,348, US.
8 Pages, Dec. 12, 2022, 2019-560086, JP.
7 Pages, Dec. 29, 2022, U.S. Appl. No. 16/440,747, US.
11 Pages, Dec. 30, 2022, U.S. Appl. No. 16/265,875, US.
4 Pages, Jan. 11, 2023, U.S. Appl. No. 16/440,747, US.
9 Pages, Dec. 26, 2022, 2022-168035, JP.
4 Pages, Dec. 14, 2022, 270285, IL.
6 Pages, Dec. 13, 2022, MX/a/2022/014630, MX.
Jeon O.H. et al., "Senescent cells and osteoarthritis: a painful connection", The Journal of Clinical Investigation, vol. 128, No. 4, pp. 1229-1237, (2018).
Guan, Z. et al., "Contemporary views on inflammatory pain mechanisms: TRPing over innate and microglial pathways", F1000Research, vol. 5, pp. 1-11, (2016).
Musi, N. et al., "Tau protein aggregation is associated with cellular senescence in the brain", Aging Cell, vol. 17, pp. 1-13, (2018).
International Search Report and Written Opinion dated Nov. 25, 2019 for PCT application No. PCT/US2019/047762.
Dillon, P., "Focused ultrasound and pembrolizumab in metastatic breast cancer (breast-48)", ClinicalTrials.gov, pp. 1-7. (2017).
Masui, T. et al., "Low-intensity ultrasound enhances the anticancer activity of cetuximab in human head and neck cancer cells", Experimental and Therapeutic Medicine, vol. 5, pp. 11-16, (2013).
Khaibullina, A. et al., "Pulsed high-intensity focused ultrasound enhances uptake of radiolabeled monoclonal antibody to human epidermoid tumor in nude mice", The Journal of Nuclear Medicine, vol. 49, pp. 295-302, (2008).
Liao, A-H. et al., "Enhanced therapeutic epidermal growth factor receptor (EGFR) antibody delivery via pulsed ultrasound with targeting microbubbles for glioma treatment", Journal of Medical and Biological Engineering, vol. 35, pp. 156-164, (2015).
Liu, H-L. et al., "Focused ultrasound enhances central nervous system delivery of bevacizumab for malignant glioma treatment", Radiology, vol. 281, No. 1, pp. 99-108, (2016).
Kobus, T. et al., "Growth inhibition in a brain metastasis model by antibody delivery using focused ultrasound-mediated blood-brain barrier disruption", Journal of Controlled Release, vol. 238, pp. 281-288, (2016).
Linetsky, M. et al., "UVA light-excited kynurenines oxidize ascorbate and modify lens proteins through the formation of advanced glycation end products, Implications for Human Lens Aging and Cataract Formation", Journal of Biological Chemistry, vol. 289, No. 24, pp. 17111-17123, (2014).
Chaudhary, M.K. et al., "Redox imbalance in a model of rat mimicking Hutchinson-Gilford progeria syndrome", Biochemical and Biophysical Research Communications, vol. 491, No. 2, pp. 361-367, (2017). Abstract Only.
Hause F. et al., "Accumulation of glycated proteins suggesting premature ageing in lamin B receptor deficient mice", Biogerontology, vol. 19, No. 1, pp. 95-100, (2017). Abstract Only.
International Search Report and Written Opinion dated Nov. 27, 2019 for PCT application No. PCT/US2019/043071.
Zhang, J-M. et al., "Cytokines, Inflammation and Pain", International Anesthesiology Clinics, vol. 45, No. 2, pp. 27-37, (2007).
Bhatt A.N. et al., "Transient elevation of glycolysis confers radio-resistance by facilitating DNA repair in cells", BMC Cancer, vol. 15, Article 335, pp. 1-12, (2015).
Callier, V., "Cancer cells can't proliferate and invade at the same time", Scientific American, pp. 1-5, (2016), found at www.scientificamerican.com/article/cancer-cells-can-t-proliferate-and-invade-at-the-same-time.

(56) References Cited

OTHER PUBLICATIONS

Drews, G. et al., "Oxidative stress and beta-cell dysfunction", European Journal of Physiology, vol. 460, pp. 703-718, (2010).
Huang, C-C. et al., "Glycolytic inhibitor 2-deoxyglucose simultaneously targets cancer and endothelial cells to suppress neuroblastoma growth in mice", Disease Models and Mechanisms, vol. 8, pp. 1247-1254, (2015).
Kehm, R. et al., "age-related oxidative changes in pancreatic islets are predominantly located in the vascular system", Redox Biology, vol. 15, pp. 387-393, (2018).
Kohrman, A.Q. et al., "Divide or conquer: Cell cycle regulation of invasive behavior", Trends in Cell Biology, vol. 27, issue 1, pp. 12-25, (2017).
Menini, S. et al., "The advanced glycation end-product $N^\varepsilon$-carboxymethyllysine promotes progression of pancreatic cancer: implications for diabetes-associated risk and its prevention", Journal of Pathology, vol. 245, pp. 197-208, (2018).
Wang, J. et al., "Oxidative stress in pancreatic beta cell regeneration", Oxidative Medicine and Cellular Longevity, vol. 2017, Article id 1930261, pp. 1-9, (2017).
Nerlich, A.G. et al., "$N^\varepsilon$-(carboxymethyl)lysine in atherosclerotic vascular lesions as a marker for local oxidative stress", Atherosclerosis, vol. 144, issue 1, pp. 41-47, (1999). Abstract Only.
Soreide, K. et al., "Epidemiological-molecular evidence of metabolic reprogramming on proliferation, autophagy and cell signaling in pancreas cancer", Cancer Letters, vol. 356, issue 2, part A, pp. 281-288, (2015) Abstract Only.
Krautwald, M. et al., "Advanced glycation end products as biomarkers and gerontotoxins—a basis to explore methylglyoxal-lowering agents for Alzheimer's disease?", Experimental Gerontology, vol. 45, issue 10, pp. 744-751, (2010). Abstract Only.
Leclerc, E., "Development of monoclonal antibodies to inhibit RAGE activation in pancreatic tumors", North Dakota State University, Center for diagnostic and therapeutic strategies in pancreatic cancer, 1 page, (2019), found at www.ndsu.edu/centers/pancreaticcancer/former_investigators/leclerc_project/.
Yamagishi, S-I., et al., "DNA-aptamers raised against AGEs as a blocker of various aging-related disorders", Glycoconjugate Journal, vol. 33, pp. 683-690, (2016).
Kawaguchi, M. et al., "Glyoxal inactivates glutamate transporter-1 in cultured rat astrocytes", Neuropathology, vol. 25, pp. 27-36, (2005).
Scicchitano, B.M. et al., "Counteracting muscle wasting in aging and neuromuscular diseases: the critical role of IGF-1", Aging, vol. 1, No. 5, pp. 451-457, (2009).
Southern, L. et al., "Immunohistochemical study of N-epsilon-carboxymethyl lysine (CML) in human brain: relation to vascular dementia", BMC Neuology, vol. 7, article No. 35, pp. 1-8, (2007).
Hanssen, N.M.J. et al., "Higher levels of advanced glycation endproducts in human carotid atherosclerotic plaques are associated with a rupture-prone phenotype", European Heart Journal, vol. 35, pp. 1137-1146, (2014).
Ramunas, J. et al., "Transient delivery of modified mRNA encoding TERT rapidly extends telomeres in human cells", The FASEB Journal, vol. 29, No. 5, pp. 1930-1939, (2015).
Gutierrez-Reyes, G. et al., "Cellular senescence in livers from children with end stage liver disease", Plos One, vol. 5, issue 4, pp. 1-5, (2010).
Extended European Search Report dated May 29, 2020 for European application No. 19210193.9-1111, 8 pages.
Taguchi, A. et al., "Blockade of RAGE-amphoterin signalling suppresses tumour growth and metastases", Nature, vol. 405, pp. 354-360, (2000).
Janeway, C.A. Jr. et al., "Appendix I. Immunologists' toolbox", Immunobiology: The immune system in health and disease, $5^{th}$ edition, Garland Science, (2001), found at www.ncbi.nim.nih.gov/books/NBK10755/, (2001).
Haus, J.M. et al., "Collagen, cross-linking, and advanced glycation end products in aging human skeletal muscle", Journal of Applied Physiology, vol. 103, pp. 2068-2076, (2007).
Yi, H-S. et al., "T-cell senescence contributes to abnormal glucose homeostasis in humans and mice", Cell Death and Disease, vol. 10, No. 249, pp. 1-15, (2019).
Al-Motawa, M. et al., "Vulnerabilities of the SARS-CoV-2 virus to proteotoxicity—opportunity for repurposed chemotherapy of COVID-19 infection", Cell-Reports, 43 pages, found at www.ssrn.com/abstract=3582068, (2020).
D'Adda di Fagagna, F., "Living on a break: cellular senescence as a DNA-damage response", Nature Reviews Cancer, vol. 8, pp. 512-522, (2008).
"New biomarker for the prevention of arteriosclerosis", Atherosclerosis Prevention, vol. 14, No. 1, pp. 22-27, (2015).
Baxevanis, C.N. "Antibody-based cancer therapy", Expert Opinion Drug Discovery, vol. 3, No. 4, pp. 441-452, (2008).
Malatesta, M. "skeletal muscle features in myotonic dystrophy and sarcopenia: do similar nuclear mechanisms lead to skeletal wasting? ", European Journal of Histochemistry, vol. 56, pp. 228-230, (2012).
Wingerchuk, D.M. et al., "Multiple sclerosis: Current and emerging disease-modifying therapies and treatment strategies", Mayo Clinic Proceedings, vol. 89, No. 2, pp. 225-240, (2014).
Matias-Guiu J.A. et al., "Amyloid proteins and their role in multiple sclerosis. Considerations in the use of amyloid-PET imaging", Frontiers in Neurology, vol. 7, article 53, pp. 1-7, (2016).
Sternberg, Z. et al., "Diagnostic potential of plasma carbxymethyllysine and carboxyethyllysine in multiple sclerosis", Journal of Neuroinflammation, vol. 7, No. 72, pp. 1-8, (2010).
Gunawan, M. et al., "A novel human systemic lupus erythematosus model in humanised mice", Nature Scientific Reports, vol. 7, pp. 1-11, (2017).
"Grants for Health Science of the Ministry of Health and Welfare, Comprehensive Research Project on Longevity Science", Long-Term Longitudinal Epidemiology, vol. 5, pp. 223-227, (1998).
Office Action dated Dec. 21, 2020 for Japanese application No. 2019-230026.
Shi, M. et al., "Low intensity-pulsed ultrasound induced apoptosis of human hepatocellular carcinoma cells in vitro", Ultrasonics, vol. 64, pp. 43-53, (2016). abstract only.
Myers, R. et al., "Ultrasound-mediated cavitation does not decrease the activity of small molecule, antibody or viral-based medicines", International Journal of Nanomedicine, vol. 13, pp. 337-349, (2018).
Danno, D. et al., "Effects of ultrasound on apoptosis induced by anti-CD20 antibody in CD20-positive B lymphoma cells", Ultrasonics Sonochemistry, vol. 15, pp. 463-471, (2008). abstract only.
Nande, R. et al., "Ultrasound-mediated oncolytic virus delivery and uptake for increased therapeutic efficacy: state of art", Oncolytic Virotherapy, vol. 4, pp. 193-205, (2015).
Abe, H. et al., "Targeted sonodynamic therapy of cancer using a photosensitizer conjugated with antibody against carcinoembryonic antigen", Anticancer Research, vol. 22, No. 3, pp. 1575-1580, (2002).
Jordao, J.F. et al., "Antibodies targeted to the brain with image-guided focused ultrasound reduces amyloid-β plaque load in the TgCRND8 mouse model of alzheimer's disease", Plos One, vol. 5, issue 5, pp. 1-8, (2010).
Idbaih, A. et al., "Phase I/II study of an implantable device delivering low intensity pulsed ultrasound (LIPU) to disrupt the blood-brain barrier (BBB) followed by intravenous carboplatin chemotherapy in patients with recurrent glioblastoma (GBM)", Journal of Clinical Oncology, vol. 35, issue 15, supplemental 2034, pp. 1-6, (2017). abstract only.
Etame, A.B. et al., "Focused ultrasound disruption of the blood brain barrier: a new frontier for therapeutic delivery in molecular neuro-oncology", Neurosurg Focus, vol. 32, No. 1, pp. 1-17, (2012).
Wang, S. et al., "Pulsed high intensity focused ultrasound increases penetration and therapeutic efficacy of monoclonal antibodies in murine xenograft tumors", Journal of Controlled Release, vol. 162, No. 1, pp. 218-224, (2012).
Miller, D. et al., "Overview of therapeutic ultrasound applications and safety considerations", Journal of Ultrasound in Medicine, vol. 31, No. 4, pp. 623-634, (2012).
Udroiu, I. "Ultrasonic drug delivery in oncology", Journal of the Balkan Union of Oncology, vol. 20, No. 2, pp. 381-390, (2015).

(56) References Cited

OTHER PUBLICATIONS

Yu, T. et al., "Ultrasound: A chemotherapy sensitizer", Technology in Cancer Research and Treatment, vol. 5, No. 1, pp. 51-60, (2006).
Zhang, Z. et al., "Low intensity ultrasound promotes the sensitivity of rat brain glioma to doxorubicin by down-regulating the expressions of P-Glucoprotein and multidrug resistance protein 1 in vitro and in vivo", PLOS One, vol. 8, issue 8, pp. 1-13, (2013).
Sawai, Y. et al., "Effects of low-intensity pulsed ultrasound on osteosarcoma and cancer cells", Oncology Reports, vol. 28, pp. 481-486, (2012).
Takeuchi, R. et al., "Low-intensity pulsed ultrasound activates the phosphatidylinositol 3 kinase/Akt pathway and stimulates the growth of chondrocytes in three-dimensional cultures: a basic science study", Arthritis Research & Therapy, vol. 10, pp. 1-11, (2008).
Cui, J.H. et al., "Effects of low-intensity ultrasound on chondrogenic differentiation of mesenchymal stem cells embedded in polyglycolic acid: an in vivo study", Tissue Engineering, vol. 12, No. 1, pp. 75-82, (2006).
Muhlfeld, J. et al., "Influence of ultrasonic waves and enzymes on antigenic properties of human erythrocytes. I. Ultrasonic waves", Blut., vol. 30, No. 5, pp. 349-352, (1975). Abstract Only.
Rosenfeld, E. et al., "Positive and negative effects of diagnostic intensities of ultrasound on erythrocyte blood group markers", Ultrasonics, vol. 28, issue 3, pp. 155-158, (1990). Abstract Only.
Aviles Jr., F., "Contact low-frequency ultrasound used to accelerate granulation tissue proliferation and rapid removal of nonviable tissue in colonized wounds: A case study", Wound Management and Prevention, pp. 1-6, (2011).
Chen, R. et al., "Ultrasound-accelerated immunoassay, as exemplified by enzyme immunoassay of choriogonadotropin", Clinical Chemistry, vol. 30, No. 9, pp. 1446-1451, (1984).
Lin, C-H. et al., "Advanced glycosylation end products induce nitric oxide synthase expression in C6 glioma cells involvement of a p38 MAP kinase-dependent mechanism", Life Sciences, vol. 69, pp. 2503-2515, (2001).
Stoczynska-Fidelus, E. et al., "Spontaneous in vitro senescence of glioma cells confirmed by an antibody against IDH1$^{R132H}$" Anticancer Research, vol. 34, pp. 2859-2868, (2014).
Kinoshita, M. et al., "Noninvasive localized delivery of Herceptin to the mouse brain by MRI-guided focused ultrasound-induced blood-brain barrier disruption", Proceedings of the National Academy of Science, vol. 103, No. 31, pp. 11719-11723, (2006).
Nisbet, R.M. et al., "Combined effects of scanning ultrasound and a tau-specific single chain antibody in a tau transgenic mouse model", Brain, A Journal of Neurology, vol. 140, pp. 1220-1230, (2017).
Sun, T. et al., "Closed-loop control of targeted ultrasound drug delivery across the blood-brain/tumor barriers in a rat glioma model", Proceedings of the National Academy of Science, pp. e10281-e10290, (2017).
Liu, H-L. et al., "Blood-brain barrier disruption with focused ultrasound enhances delivery of chemotherapeutic drugs for glioblastoma treatment", Radiology, vol. 255, No. 2, pp. 415-425, (2010).
Zhao, B. et al., "Blood-brain barrier disruption induced by diagnostic ultrasound combined with microbubbles in mice", Oncotarget, vol. 9, No. 4, pp. 4897-4914, (2018).
Neergaard, L., "Ultrasound opens brain barrier, a step to better care", AZCentral.com, pp. 1, (2018).
Houston-Edwards, K., "Wave of the Future?", PBS.org, pp. 1-6, found at www.pbs.org/wgbh/nova/article/hifu/, (2016).
Allen, K.D. et al., "Evaluating intra-articular drug delivery for the treatment of osteoarthritis in a rat model", Tissue Engineering: Part B, vol. 16, No. 1, pp. 81-92, (2010).
Eguchi, K. et al., "Whole-brain low-intensity pulsed ultrasound therapy markedly improves cognitive dysfunctions in mouse models of dementia—crucial roles of endothelial nitric oxide synthase", Brain Stimulation, vol. 11, pp. 959-973, (2018).
Ninomiya, K. et al., "Targeted sonodynamic therapy using protein-modified $TiO_2$ nanoparticles", Ultrasonics Sonochemistry, vol. 19, pp. 607-614, (2012).

Watson, K.D. et al., "Ultrasound increases nanoparticle delivery by reducing intratumoral pressure and increasing transport in epithelial and epithelial-mesenchymal transition tumors", Cancer Research, vol. 72, No. 6, pp. 1485-1493, (2012).
Endo, S. et al., "Porphyrin derivatives-mediated sonodynamic therapy for malignant gliomas in vitro", Ultrasound in Medicine and Biology, vol. 41, issue 9, pp. 2458-2465, (2015).
Zhang, Z. et al., "Low frequency and intensity ultrasound induces apoptosis of brain glioma in rats mediated by caspase-3, Bcl-2, and survivin", Brain Research, vol. 1473, pp. 25-34, (2012). Abstract Only.
Wang, P. et al., "Membrane damage effect of continuous wave ultrasound on K562 human leukemia cells", Journal of Ultrasound in Medicine, vol. 31, pp. 1977-1986, (2012).
Wood, A.K.W. et al., "A review of low-intensity ultrasound for cancer therapy", Ultrasound in Medicine and Biology, vol. 41, No. 4, pp. 905-928, (2015).
Lejbkowicz, F. et al., "Distinct sensitivity of normal and malignant cells to ultrasound in vitro", Environmental Health Perspectives, vol. 105, supplements, pp. 1575-1578, (1997).
Purkayastha, S. et al., "Transcranial doppler ultrasound: Technique and application", Seminars in Neurology, vol. 32, No. 4, pp. 411-420, (2012).
Liman, J. et al., "Transcranial ultrasound in adults and children with movement disorders", Perspectives in Medicine, vol. 1, pp. 349-352, (2012).
Product Description of "US 1000 $3^{rd}$ Edition Portable Ultrasound Unit 1-mHz", TENSpros, found at www.tenspros.com/us-1000-3rd-edition-portable-ultrasound-du1025.html, printed on Oct. 24, 2018.
El-Taieb, M.A. et al., "Oxidative stress and acrosomal morphology: A cause of infertility in patients with normal semen parameters", Middle East Fertility Society Journal, vol. 20, pp. 79-85, (2015).
Liu, D.Y. et al., "Defective sperm-zona pellucida interaction: a major cause of failure of fertilization in clinical in-vitro fertilization", Human Reproduction, vol. 15, No. 3, pp. 702-708, (2000).
Uhler, M.L., "Sperm morphology", Fertility Centers of Illinois, pp. 1-2, printed on Apr. 12, 2018.
Mallidis, C. et al., "Advanced glycation end products accumulate in the reproductive tract of men with diabetes", International Journal of Andrology, vol. 32, pp. 295-305, (2008).
Henkel, R.R. et al., "Sperm preparation for ART", Reproductive Biology and Endocrinology, vol. 1, pp. 1-22, (2003).
Ng, K.K. et al., "Sperm output of older men", Human Reproduction, vol. 19, No. 8, pp. 1811-1815, (2004).
Harris, I.D. et al., "Fertility and the aging male", Reviews in Urology, vol. 13, No. 4, pp. e184-e190, (2011).
Almeida, S. et al., "Fertility and sperm quality in the aging male", Current Pharmaceutical Design, vol. 23, issue 30, pp. 4429-4437, (2017). Abstract Only.
Kidd, S.A. et al., "Effects of male age on semen quality and fertility: a review of the literature", Fertility and Sterility, vol. 75, No. 2, pp. 237-248, (2001).
Sugimoto, K. et al., "The application of life style diseases-animal models to the research for sarcopenia", Clinical Calcium, vol. 24, No. 10, pp. 51-58, (2014).
International Search Report and written opinion dated Jul. 16, 2021 for PCT application No. PCT/US2020/057539.
Lilienthal, G-M, et al., "Potential of murine IgG1 and human IgG4 to inhibit the classical complement and Fcγ receptor activation pathways", Frontiers in Immunology, vol. 9, article 958, pp. 1-9, (2018).
Kiyoshi, M. et al., "Affinity improvement of a therapeutic antibody by structure-based computational design: generation of electrostatic interactions in the transition state stabilizes the antibody-antigen complex", Plos One, vol. 9, issue 1, pp. 1-9, (2014).
Yamashita, K. et al., "Kotai antibody builder: automated high-resolution structural modeling of antibodies", Bioinofrmatics, vol. 30, No. 22, pp. 3279-3280, (2014).
Ye, J. et al., "IgBLAST: an immunoglobulin variable domain sequence analysis tool", Nucleic Acids Research, vol. 41, pp. W34-W40, (2013).

(56) References Cited

OTHER PUBLICATIONS

Esquivel, R.O. et al., "Decoding the building blocks of life from the perspective of quantum information", Advances in Quantum Mechanics, chapter 27, pp. 641-669, (2013).
Chilelli, N.C. et al., "AGEs, rather than hyperglycemia, are responsible for microvascular complications in diabetes: a "glycoxidation-centric" point of view", Nutrition, Metabolism & Cardiovascular Diseases, vol. 23, issue 10, pp. 913-919, (2013).
Palmer, A.K. et al., "Targeting senescent cells alleviates obesity-induced metabolic dysfunction", Aging Cell, vol. 18, pp. 1-15, (2019).
Thompson, P.J. et al., "Targeted elimination of senescent beta cells prevents type 1 diabetes", Cell Metabolism, vol. 29, pp. 1045-1060, (2019).
Bardeesy, N. et al., "Both $p16^{Ink4a}$ and the $p19^{Arf}$-p53 pathway constrain progression of pancreatic adenocarcinoma in the mouse", PNAS, vol. 103, No. 15, pp. 5947-5952, (2006).
Sharpless, N.E. et al., "The differential impact of $P16^{Ink4a}$ or $p19^{ARF}$ deficiency on cell growth and tumorigenesis", Oncogene, vol. 23, pp. 379-385, (2004).
Pan, Q. et al., "Blocking neuropilin-1 function has an additive effect with anti-VEGF to inhibit tumor growth", Cancer Cell, vol. 11, pp. 53-67, (2007).
Hung, L-F. et al., "Advanced glycation end products induce T cell apoptosis: Involvement of oxidative stress, caspase and the mitochondrial pathway", Mechanisms of Ageing and Development, vol. 131, pp. 682-691, (2010).
Son, S. et al., "Advanced glycation end products impair NLRP3 inflammasome-mediated innate immune responses in macrophages", Journal of Biological Chemistry, vol. 292, No. 50, pp. 20437-20448, (2017).
Farboud, B. et al., "Development of a polyclonal antibody with broad epitope specificity for advanced glycation endproducts and localization of these epitopes in bruch's membrane of the aging eye", Molecular Vision, vol. 5, No. 11, 6 pages, (1999).
Invitation to Pay Additional Fee and Partial International Search Report dated Aug. 13, 2021 PCT application No. PCT/US2021/030184.
Tamura, M. et al., "Structural correlates of an anticarcinoma antibody: Identification of specificity-determining residues (SDRs) and development of a minimally immunogenic antibody variant by retention of SDRs only", The Journal of Immunology, vol. 164, No. 3, pp. 1432-1441, (2000).
International Search Report and written opinion dated Oct. 18, 2021 for PCT application No. PCT/US2021/030184.
Yamamoto, Y. et al., "Advanced glycation endproducts-receptor interactions stimulate the growth of human pancreatic cancer cells through the induction of platelet-derived growth factor-B", Biochemical and Biophysical Research Communications, vol. 222, pp. 700-705, (1996).
Sellegounder, D. et al., "Advanced glycation end products (AGEs) and its receptor, RAGE, modulate age-dependent COVID-19 morbidity and mortality. A review and hypothesis", International Immunopharmacology, vol. 98, pp. 107806-1-107806-8, (2021).
International Search Report and written opinion dated Nov. 24, 2021 for PCT application No. PCT/US2021/034777.
Graham, F.L. et al., "Characteristics of a human cell line transformed by DNA from human adenovirus type 5", Journal of General Virology, vol. 36, issue 1, pp. 59-74, (1977).
Munch, G. et al., "Advanced glycation endproducts and their pathogenic roles in neurological disorders", Amino Acids, vol. 42, No. 4, pp. 1221-1236, (2010).
Lin, J-A., et al., "Glycative stress from advanced glycation end products (AGEs) and dicarbonyls: An emerging biological factor in cancer onset and progression", Molecular Nutrition & Food Research, vol. 60, No. 8, pp. 1850-1864, (2016).
Muyldermans, S. et al., "Distinct antibody species: Structural differences creating therapeutic opportunities", Current Opinion in Immunology, vol. 40, pp. 7-13, (2016).
Rosenberg, C. et al., "Age is an important determinant in humoral and T cell responses to immunization with hepatitis B surface antigen", Human Vaccines & Immunotherapeutics, vol. 9, No. 7, pp. 1466-1476, (2013).
Choi, Y-G. et al., "Characterization of anti-advanced glycation end product antibodies to nonenzymatically lysine-derived and arginine-derived glycated products", Journal of Immunoassay and Immunochemistry, vol. 30, No. 4, pp. 386-399, (2009).
Kirkland, J.L. et al., "Senolytic drugs: from discovery to translation", Journal of Internal Medicine, vol. 288, No. 5, pp. 518-536, (2020).
Dunbar, J. et al., "SAbPred: a structure-based antibody prediction server", Nucleic Acids Research, vol. 44, Web Server Issue, pp. W474-W478, (2016).
Pedotti, M. et al., "Computational docking of antibody-antigen complexes, opportunities and pitfalls illustrated by influenza hemagglutinin", International Journal of Molecular Sciences, vol. 12, pp. 226-251, (2011).
Drevin, V.E. et al., "Biological age and methods for its determination", Volgograd State Agrarian University, Monograph, Volgograd, pp. 1-143, (2015).
Yabuuchi, J. et al., "Association of advanced glycation end products with sarcopenia and frailty in chronic kidney disease", Scientific Reports, pp. 1-12, (2020).
Zhang, C. et al., "FOXO1 mediates advanced glycation end products induced mouse osteocyte-like MLO-Y4 cell apoptosis and dysfunctions", Journal of Diabetes Research, vol. 2019, article id 6757428, pp. 1-11, (2019).
Dubey, N.K. et al., "Adipose-derived stem cells attenuates diabetic osteoarthritis via inhibition of glycation-mediated inflammatory cascade", Aging and Disease, vol. 10, No. 3, pp. 483-496, (2019).
Tanaka, K. et al., "Nε-(carboxymethyl) lysine represses hair follicle formation by inhibiting sonic hedgehog expression in a NF-κB-independent manner, International Journal of Dermatology and Clinical Research", vol. 5, No. 1, pp. 006-011, (2019).
Bao, Z. et al., "Nε-carboxymethyl-lysine negatively regulates foam cell migration via the vav1/rac1 pathway", Journal of Immunology Research, vol. 2020, article id 1906204, pp. 1-10, (2020).
Upton, J.H. et al., "Oxidative stress-associated senescence in dermal papilla cells of men with androgenetic alopecia", Journal of Investigative Dermatology, vol. 135, pp. 1244-1252, (2015).
Waaijer, M.E.C. et al., "P16INK4a positive cells in human skin are indicative of local elastic fiber morphology, facial wrinkling, and perceived age", Journals of Gerontology: Biological Sciences, vol. 71, No. 8, pp. 1022-1028, (2016).
Scott, A.M. et al., "Antibody therapy of cancer", Nature Reviews, vol. 12, pp. 278-287, (2012).
Allen, T.M. et al., "Humanized immune system mouse models: progress, challenges and opportunities", Nature Immunology, vol. 20, No. 7, pp. 770-774, (2019).
Krtolica, A. et al., "Senescent fibroblasts promote epithelial cell growth and tumorigenesis: A link between cancer and aging", Proceedings of the National Academy of Science, vol. 98, No. 21, pp. 12072-12077, (2001).
Shaw, T.J. et al., "Wound-associated skin fibrosis: mechanisms and treatments based on modulating the inflammatory response", Endocrine, Metabolic & Immune Disorders—Drug Targets, vol. 10, No. 4, pp. 320-330, (2010). Abstract Only.
Bitterman, P.B. et al., "Fibroproliferative disorders", Chest, vol. 99, No. 3, pp. 81S-84S, (1991).
Pan, J. et al., "Inhibition of Bcl-2/xl with ABT-263 selectively kills senescent type II pneumocytes and reverses persistent pulmonary fibrosis induced by ionizing radiation in mice", International Journal of Radiation Oncology, vol. 99, No. 2, pp. 353-361, (2017).
Yilmaz, O. et al., "Dasatinib attenuated bleomycin-induced pulmonary fibrosis in mice", Growth Factors, pp. 1-10, (2015).
Kato, M. et al., "Dasatinib suppresses TGFβ-induced epithelial mesenchymal transition and inhibits pulmonary fibrosis", European Respiratory Journal, vol. 44, pp. 1-4, (2014).
Yagmur, E. et al., "Elevation of Nε-(carboxymethyl)lysine-modified advanced glycation end products in chronic liver disease is an indicator of liver cirrhosis", Clinical Biochemistry, vol. 39, pp. 39-45, (2006).

(56) References Cited

OTHER PUBLICATIONS

Duffield, U.S., "Cellular and molecular mechanisms in kidney fibrosis", The Journal of Clinical Investigation, vol. 124, No. 6, pp. 2299-2306, (2014).
Weiler-Normann, C. et al., "Mouse models of liver fibrosis", Z Gastroenterol, vol. 45, pp. 43-50, (2007).
Midgley, A.C. et al., "Transforming growth factor-β1 (TGF-β1)-stimulated fibroblast to myofibroblast differentiation is mediated by hyaluronan (HA)-facilitated epidermal growth factor receptor (EGFR) and CD44 co-localization in lipid rafts", The Journal of Biological Chemistry, vol. 288, No. 21, pp. 14824-14838, (2013).
Schafer, M.J. et al., "Cellular senescence mediated fibrotic pulmonary disease", Nature Communications, vol. 8, pp. 1-11, (2017).
Harris, W.T. et al., "Myofibroblast differentiation and enhanced Tgf-B signaling in cystic fibrosis lung disease", Plos One, vol. 8, issue 8, pp. 1-8, (2013).
Bataller, R. et al., "Liver fibrosis", The Journal of Clinical Investigation, vol. 115, No. 2, pp. 209-218, (2005).
Wynn, T.A., "Fibrotic disease and the $T_H1/T_H2$ paradigm", Nature Reviews Immunology, vol. 4, No. 8, pp. 583-594, (2004).
Calhoun, C. et al., "Senescent cells contribute to the physiological remodeling of aged lungs", Journals of Gerontology: Biological Sciences, vol. 71, No. 2, pp. 153-160, (2016).
"About PF", The Pulmonary Fibrosis Foundation, pp. 1-9, printed on Jul. 18, 2017.
Definition of "Idiopathic pulmonary fibrosis" printed from Wikipedia, the free encyclopedia on Aug. 4, 2014 found at http://en.wikipedia.org/wiki/Idiopathic_pulmonary_fibrosis.
Definition of "Epithelial-mesenchymal transition" printed from Wikipedia, the free encyclopedia on Apr. 4, 2010 found at http://en.wikipedia.org/wiki/Epithelial-mesenchymal_transition.
Definition of "Pulmonary fibrosis" printed from Wikipedia, the free encyclopedia on Mar. 27, 2022 found at http://en.wikipedia.org/wiki/Pulmonary_fibrosis.
Mayo Clinic Staff, "Myelofibrosis", Mayo Clinic, pp. 1-2, (2017).
Bristol-Myers Squibb, "Safety evaluation of Dasatinib in subjects with scleroderma pulmonary fibrosis", Clinical Trials, 12 pages, (2012).
University of Michigan, "Beneficial effects of quercetin in chronic obstructive pulmonary disease (COPD) (Quercetin)", Clinical Trials, 14 pages, (2012).
Wake Forest University Health Sciences, "Targeting pro-inflammatory cells in idiopathic pulmonary fibrosis: a human trial (IPF)", Clinical Trials, 7 pages, (2017).
Scleroderma Research Foundation, "For patients, current treatments available for scleroderma patients", Scleroderma Research Foundation, pp. 1-2, printed on Feb. 26, 2018.
"Scleroderma, What is it?", National Institute of Arthritis and Musculoskeletal and Skin Diseases, pp. 1-8, printed on Feb. 26, 2018.
Definition of "Progeroid syndromes" printed from Wikipedia, the free encyclopedia on May 25, 2022 found at http://en.wikipedia.org/wiki/Progeroid_syndromes.
Haddadi, G.H. et al., "Hesperidin as radioprotector against radiation-induced lung damage in rat: A histopathological study", Journal of Medical Physics, vol. 42, No. 1, pp. 25-32, (2017).
Wilgus, T.A. et al., "Regulation of scar formation by vascular endothelial growth factor", Laboratory Investigation, vol. 88, pp. 579-590, (2008).
Leeman, K.T. et al., "Lung stem and progenitor cells in tissue homeostasis and disease", Current Topics in Developmental Biology, vol. 107, pp. 207-233, (2014).
Shaw, J.N. et al., "$N^\varepsilon$-(carbosymethyl)lysine (CML) as a biomarker of oxidative stress in long-lived tissue proteins", Methods in Molecular Biology, vol. 186, pp. 129-137, (2002).
Palmer, J.L. et al., "Combined radiation and burn injury results in exaggerated early pulmonary inflammation", Radiation Research, vol. 180, No. 3, pp. 276-283, (2013).

Meng, A. et al., "Ionizing radiation and busulfan induce premature senescence in murine bone marrow hematopoietic cells", Cancer Research, vol. 63, pp. 5414-5419, (2003).
Formenti, S.C. et al., "Combining radiotherapy and cancer immunotherapy: A paradigm shift", Journal of the National Cancer Institute, vol. 105, issue 4, pp. 256-265, (2013).
Flament, F. et al., "Effect of the sun on visible clinical signs of aging in Caucasian skin", Clinical, Cosmetic and Investigational Dermatology, vol. 6, pp. 221-232, (2013).
Richardson, R.B. et al., "Ionizing radiation and aging: rejuvenating an old idea", Aging, vol. 1, No. 11, pp. 887-902, (2009).
Rohani, A. et al., "A case control study of cardiovascular health in chemical war disabled Iranian victims", Indian Journal of Critical Care Medicine, vol. 14, No. 3, pp. 109-112, (2010).
Cupit-Link, M.C. et al., "Biology of premature ageing in survivors of cancer", ESMO Open Cancer Horizons, vol. 2, pp. 1-8, (2017).
Smith, R.L. et al., "Premature and accelerated aging: HIV or HAART?", Frontiers in Genetics, vol. 3, article 328, pp. 1-10, (2013).
Zota, A.R. et al., "Associations of cadmium and lead exposure with leukocyte telomere length: Finding from National Health and Nutrition Examination Survey, 1999-2002", American Journal of Epidemiology, vol. 181, No. 2, pp. 127-136, (2015).
White S.S. et al., "An overview of the effects of dioxins and dioxin-like compounds on vertebrates, as documented in human and ecological epidemiology", Journal of Environmental Science and Health, Part C, Environmental Carcinogenesis and Ecotoxicology Reviews, vol. 27, No. 4, pp. 197-211, (2009).
Ribas, J. et al., "Biomechanical strain exacerbates inflammation on a progeria-on-a-chip model", Small, vol. 13, issue 15, pp. 1-3, (2017). Abstract Only.
D'Orazio, J. et al., "UV radiation and the skin", International Journal of Molecular Sciences, vol. 14, pp. 12222-12248, (2013).
Eisenreich, W. et al., "How viral and intracellular bacterial pathogens reprogram the metabolism of host cells to allow their intracellular replication", Frontiers in Cellular and Infection Microbiology, vol. 9, article 42, pp. 1-24, (2019).
Mayer, K.A. et al., "Hijacking the supplies: Metabolism as a novel facet of virus-host interaction", Frontiers in Immunology, vol. 10, article 1533, pp. 1-9, (2019).
"Covid-19: novel coronavirus, tackling coronavirus with WP1122", Moleculin, pp. 1-10, found at www.moleculin.com/covid-19/, (2020).
Wei, C. et al., "uPAR isoform 2 forms a dimer and induces severe kidney disease in mice", The Journal of Clinical Investigation, vol. 129, No. 5, pp. 1946-1959, (2019).
Wei, C. et al., "Circulating CD40 autoantibody and suPAR synergy drives glomerular injury". Annals of Translational Medicine, vol. 3, No. 19, pp. 1-5, (2015).
Reiser, J., "A humanized mouse model of FSGS", Rush University Medical Center, pp. 1-3, printed on Apr. 10, 2020.
Tanji, N. et al., "Expression of advanced glycation end product and their cellular receptor RAGE in diabetic nephropathy and nondiabetic renal disease", Journal of the American Society of Nephrology, vol. 11, No. 9, pp. 1656-1666, (2000).
Oldfield, M.D. et al., "Advanced glycation end products cause epithelial-myofibroblast transdifferentiation via the receptor for advanced glycation end products (RAGE)", The Journal of Clinical Investigation, vol. 108, No. 12, pp. 1853-1863, (2001).
Suzuki, D. et al., "Immunohistochemical evidence for an increased oxidative stress and carbonyl modification of proteins in diabetic glomerular lesions", Journal of the American Society of Nephrology, vol. 10, pp. 822-832, (1999).
Horie, K. et al., "Immunohistochemical colocalization of glycoxidation products and lipid peroxidation products in diabetic renal glomerular lesions. Implication for glycoxidative stress in the pathogenesis of diabetic nephropathy", The Journal of Clinical Investigation, vol. 100, No. 12, pp. 2995-3004, (1997).
Kushiro, M. et al., "Accumulation of Nsigma-(carboxymethyl)lysine and changes in glomerular extracellular matrix components in Otsuka long-evans tokushima fatty rat: A model of spontaneous NIDDM", Nephron, vol. 79, No. 4, pp. 458-468, (1998). Abstract Only.

(56) References Cited

OTHER PUBLICATIONS

Valentijn, F.A. et al., "Cellular senescence in the aging and diseased kidney", Journal of Cell Communication and Signaling, vol. 12, No. 1, pp. 69-82, (2018).
Wang, W-J. et al., "Cellular senescence, senescence-associated secretory phenotype, and chronic kidney disease", Oncotarget, vol. 8, No. 38, pp. 64520-64533, (2017).
DiCarlo, A.L. et al., "Aging in the context of immunological architecture, function and disease outcomes", Trends in Immunology, vol. 30, No. 7, pp. 293-294, (2009).
Stortz, J.A. et al., "Old mice demonstrate organ dysfunction as well as prolonged inflammation, Immunosuppression, and weight loss in a modified surgical sepsis model", Critical Care Medicine, vol. 47, No. 11, pp. e919-e929, (2019).
Cannizzo, E.S. et al., "Oxidative stress, inflamm-aging and immunosenescence", Journal of Proteomics, vol. 74, issue 11, pp. 2313-2323, (2011).
Bourke, C.D. et al., "Immune dysfunction as a cause and consequence of malnutrition", Trends in Immunology, vol. 37, No. 6, pp. 386-398, (2016).
Aranow, C., "Vitamin D and the immune system", Journal of Investigative Medicine, vol. 59, No. 6, pp. 881-886, (2011).
Taneja, V., "Sex hormones determine immune response", Frontiers in Immunology, vol. 9, article 1931, pp. 1-5, (2018).
Bryant, P.A. et al., "Sick and tired: does sleep have a vital role in the immune system?", Nature Reviews Immunology, vol. 4, pp. 457-467, (2004).
Aw, D. et al., "Immunosenescence: emerging challenges for an ageing population", Immunology, vol. 120, pp. 435-446, (2007).
Traore, K. et al., "Do advanced glycation end-products play a role in malaria susceptibility?", Parasite, vol. 23, No. 15, pp. 1-10, (2016).
Duggal, N.A. et al., "Major features of immunesenescence, including reduced thymic output, are ameliorated by high levels of physical activity in adulthood", Aging Cell, vol. 17, No. 2, pp. 1-13, (2018).
Montecino-Rodriguez, E. et al., "Causes, consequences, and reversal of immune system aging", The Journal of Clinical Investigation, vol. 123, No. 3, pp. 958-965, (2013).
Desai, S. et al., "Early immune senescence in HIV disease", Current HIV/AIDS Reports, vol. 7, No. 1, pp. 4-10, (2010).
Vivier, E., et al., "Innate or adaptive immunity? The example of natural killer cells", Science, vol. 331, No. 6013, pp. 44-49, (2011).
Kvell, K., "Thymic senescence", In tech open, pp. 1-11, found at http://dx.doi.org/10.5772/intechopen.87063, (2019).
Palmer, S. et al., "Thymic involution and rising disease incidence with age", Proceedings of the National Academy of Science, vol. 115, No. 8, pp. 1883-1888, (2018).
Wertheimer, T. et al., "Production of BMP4 by endothelial cells is crucial for endogenous thymic regeneration", Science Immunology, vol. 3, No. 19, pp. 1-11, (2018).
"Oxidative stress and cellular senescence in age-related thymic involution", Fight Aging!, pp. 1-4, found at www.fightaging.org/archives/2020/03/oxidative-stress-and-cellular-senescence-in-age-related-thymic-involution/, (2020).
Barbouti, A. et al., "Implications of oxidative stress and cellular senescence in age-related thymus involution", Oxidative Medicine and Cellular Longevity, vol. 2020, article ID 7986071, pp. 1-14, (2020).
El-Torky, M. et al., "Collagens in scar carcinoma of the lung", The American Journal of Pathology, vol. 121 No. 2, pp. 322-326, (1985).
Machahua, C. et al., "Increased AGE-RAGE ratio in idiopathic pulmonary fibrosis", Respiratory Research, vol. 17, No. 1, pp. 1-11, (2016).
Sirica, A.E. et al., "Desmoplastic stroma and cholangiocarcinoma: Clinical implications and therapeutic targeting", Hepatology, vol. 59, No. 6, pp. 2397-2402, (2014).
Toullec, A. et al., "Oxidative stress promotes myofibroblast differentiation and tumour spreading", EMBO Molecular Medicine, vol. 2, pp. 211-230, (2010).

Oya, T. et al., "Methylglyoxal modification of protein", The Journal of Biological Chemistry, vol. 274, No. 26, pp. 18492-18502, (1999).
Extended European Search Report dated Sep. 2, 2022 for European application No. 22157145.8-1111, 22 pages.
Johmura, Y. et al., "Senolysis by glutaminolysis inhibition ameliorates various age-associated disorders", Science, vol. 371, pp. 265-270, (2021).
Sabbatinelli, J. et al., "Where metabolism meets senescence: Focus on endothelial cells", Frontiers in Physiology, vol. 10, article 1523, pp. 1-17, (2019).
International Search Report and written opinion dated Dec. 2, 2022 for PCT application No. PCT/US2022/020257.
Jensen, A. et al., "SIWA318H, an advanced glycation end product (AGE) targeting antibody, is efficacious in a humanized mouse xenograft model for pancreatic cancer", Cancer Research, vol. 81, 22_Supplement, (2021). Abstract Only.
International Search Report and written opinion dated Nov. 22, 2022 for PCT application No. PCT/US2022/075226.
Liu, R-M. et al., "Cell senescence and fibrotic lung diseases", Experimental Gerontology, vol. 132, pp. 1-7, (2020).
Hernandez-Gonzalez, F. et al., "Cellular senescence in lung fibrosis", International Journal of Molecular Sciences, vol. 22, pp. 1-15, (2021).
Paneni, F. et al., "Advanced glycation endproducts and plaque instability: a link beyond diabetes", European Heart Journal, vol. 35, issue 17, pp. 1095-1097, (2014).
Ahmed, K.A., et al., "$N^{\varepsilon}$-(Carboxymethyl)lysine and coronary atherosclerosis-associated low density lipoprotein abnormalities in type 2 diabetes: current status", Journal of Clinical Biochemistry and Nutrition, vol. 44, No. 1, pp. 14-27, (2009).
Bar, K.J. et al., "Pentosidine and $N^{\varepsilon}$-(Carboxymethyl)lysine in Alzheimer's disease and vascular dementia", Neurobiology of Aging, vol. 24, issue 2, pp. 333-358, (2003).
Begieneman, M.P.V. et al., "Atrial fibrillation coincides with the advanced glycation end product $N^{\varepsilon}$-(Carboxymethyl)lysine in the atrium", The American Journal of Pathology, vol. 185, No. 8, pp. 2096-2104, (2015).
Girones, X. et al., "N epsilon—carboxymethyllysine in brain aging, diabetes mellitus, and Alzheimer's disease", Free Radical Biology & Medicine, vol. 36, No. 10, pp. 1241-1247, (2004). Abstract Only.
Keith, S.W. et al., "Angiotensin blockade therapy and survival in pancreatic cancer: a population study", BMC Cancer, vol. 22, article 150, pp. 1-9, (2022).
Khan, M.A. et al., "Underlying histopathology determines response to oxidative stress in cultured human primary proximal tubular epithelial cells", International Journal of Molecular Sciences, vol. 21, issue 2, pp. 1-15, (2020).
Loperena, R. et al., "Oxidative stress and hypertensive diseases", The Medical Clinics of North America, vol. 101, No. 1, pp. 169-193, (2017).
Mossad, O. et al., "Gut microbiota drives age-related oxidative stress and mitochondrial damage in microglia via the metabolite $N^6$-carboxymethyllysine", Nature Neuroscience, vol. 25, pp. 295-305, (2022). Abstract Only.
Park, J-S. et al., "Blocking microglial activation of reactive astrocytes is neuroprotective in models of Alzheimer's disease", Acta Neuropathologica Communications, vol. 9, No. 1, pp. 1-15, (2021).
Shi, R-Z et al., "Angiotensin II induces vascular endothelial growth factor synthesis in mesenchymal stem cells", Experimental Cell Research, vol. 315, No. 1, pp. 10-15, (2009). Abstract Only.
Takeda, A. et al., "Neuronal and glial advanced glycation end product [Nepsilon-(carboxymethyl)lysine]] in Alzheimer's disease brains", Acta Neuropathologica, vol. 101, No. 1, pp. 27-35, (2001). Abstract Only.
Xu, S-N. et al., "$N^{\varepsilon}$-Carboxymethyl-lysine deteriorates vascular calcification in diabetic atherosclerosis induced by vascular smooth muscle cell-derived foam cells", Frontiers in Pharmacology, vol. 11, article 626, pp. 1-12, (2020).
Eske, J., "What is oxidative stress? Effects on the body and how to reduce", Medical News Today, 4 pages, (2020).
Fuller, S. et al., "Activated astrocytes: a therapeutic target in Alzheimer's disease?", Expert Review of Neurotherapeutics, vol. 9, No. 11, pp. 1585-1594, (2009).

(56) References Cited

OTHER PUBLICATIONS

U.S. Appl. No. 17/177,140, filed Feb. 16, 2021.
U.S. Appl. No. 16/779,369, filed Jan. 31, 2020.
U.S. Appl. No. 17/544,636, filed Dec. 7, 2021.
U.S. Appl. No. 17/262,684, filed Jan. 22, 2021, Jul. 23, 2019.
U.S. Appl. No. 17/209,554, filed Mar. 23, 2021.
U.S. Appl. No. 18/050,915, filed Oct. 28, 2022.
U.S. Appl. No. 18/146,821, filed Dec. 27, 2022.
U.S. Appl. No. 17/268,413, filed Aug. 22, 2019.
U.S. Appl. No. 17/922,264, filed Oct. 28, 2022.

* cited by examiner

ANTI-AGE ANTIBODIES FOR TREATING NEURODEGENERATIVE DISORDERS

BACKGROUND

Advanced glycation end-products (AGEs; also referred to AGE-modified proteins, or glycation end-products) arise from a non-enzymatic reaction of sugars with protein side-chains in aging cells (Ando, K. et al., Membrane Proteins of Human Erythrocytes Are Modified by Advanced Glycation End Products during Aging in the Circulation, *Biochem Biophys Res Commun.*, Vol. 258, 123, 125 (1999)). This process begins with a reversible reaction between the reducing sugar and the amino group to form a Schiff base, which proceeds to form a covalently-bonded Amadori rearrangement product. Once formed, the Amadori product undergoes further rearrangement to produce AGEs. Hyperglycemia, caused by diabetes mellitus (DM), and oxidative stress promote this post-translational modification of membrane proteins (Lindsey J B, et al., "Receptor For Advanced Glycation End-Products (RAGE) and soluble RAGE (sRAGE): Cardiovascular Implications," *Diabetes Vascular Disease Research*, Vol. 6(1), 7-14, (2009)). AGEs have been associated with several pathological conditions including diabetic complications, inflammation, retinopathy, nephropathy, atherosclerosis, stroke, endothelial cell dysfunction, and neurodegenerative disorders (Bierhaus A, "AGEs and their interaction with AGE-receptors in vascular disease and diabetes mellitus. I. The AGE concept," *Cardiovasc Res*, Vol. 37(3), 586-600 (1998)).

Senescent cells are cells that are partially-functional or non-functional and are in a state of irreversible proliferative arrest. Senescence is a distinct state of a cell, and is associated with biomarkers, such as activation of the biomarker $p16^{Ink4a}$, and expression of $\beta$-galactosidase. Senescent cells are also associated with secretion of many factors involved in intercellular signaling, including pro-inflammatory factors; secretion of these factors has been termed the senescence-associated secretory phenotype, or SASP.

AGE-modified proteins are also a marker of senescent cells. This association between glycation end-products and senescence is well known in the art. See, for example, Gruber, L. (WO 2009/143411, 26 Nov. 2009), Ando, K. et al. (Membrane Proteins of Human Erythrocytes Are Modified by Advanced Glycation End Products during Aging in the Circulation, *Biochem Biophys Res Commun.*, Vol. 258, 123, 125 (1999)), Ahmed, E. K. et al. ("Protein Modification and Replicative Senescence of WI-38 Human Embryonic Fibroblasts" *Aging Cells*, vol. 9, 252, 260 (2010)), Vlassara, H. et al. (Advanced Glycosylation Endproducts on Erythrocyte Cell Surface Induce Receptor-Mediated Phagocytosis by Macrophages, *J. Exp. Med., Vol.* 166, 539, 545 (1987)) and Vlassara et al. ("High-affinity-receptor-mediated Uptake and Degradation of Glucose-modified Proteins: A Potential Mechanism for the Removal of Senescent Macromolecules" *Proc. Natl. Acad. Sci. USAI*, Vol. 82, 5588, 5591 (1985)). Furthermore, Ahmed, E. K. et al. indicates that glycation end-products are "one of the major causes of spontaneous damage to cellular and extracellular proteins" (Ahmed, E. K. et al., see above, page 353). Accordingly, the accumulation of glycation end-products is associated with senescence and lack of function.

A recent study has identified a causal link between cellular senescence and age-related disorders, such as sarcopenia. A research team at the Mayo Clinic in Rochester, Minn., demonstrated that effects of aging in mice could be delayed by eliminating senescent cells in their fat and muscle tissues without overt side effects (Baker, D. J. et al., "Clearance of $p16^{Ink4a}$-positive senescent cells delays aging-associated disorders", *Nature*, Vol. 479, pp. 232-236, (2011)). Elimination of senescent cells in transgenic mice was shown to substantially delay the onset of sarcopenia and cataracts, and to reduce senescence indicators in skeletal muscle and the eye. The study established that life-long and late-life treatment of transgenic mice for removal of senescent cells has no negative side effects and selectively delays age-related phenotypes that depend on cells (Id., page 234, col. 2, line 16 through page 235, col. 1, line 2). The authors theorized that removal of senescent cells may represent an avenue for treating or delaying age-related diseases in humans and improving healthy human lifespan (Id., page 235, col. 2, lines 38-51).

Neurodegenerative disorders are associated with abnormal cellular senescence in the central nervous system. Abnormal accumulation of senescent astrocytes has been associated with Alzheimer's disease (AD) (Bhat, R. et al., "Astrocyte Senescence as a Component of Alzheimer's Disease", *PLOS ONE*, Vol. 7(9), e45069, pp. 1-10 (September 2012)). Microglial cell senescence associated with normal aging is exacerbated by the presence of the amyloid plaques indicative of AD (Flanary, B. E. et al., "Evidence That Aging And Amyloid Promote Microglial Cell Senescence", *Rejuvenation Research*, Vol. 10(1), pp. 61-74 (March 2007)). The presence of AGEs with astrocytes and microglial cells in AD is further evidence of the presence of senescent cells (Takeda, A., et al. "Advanced glycation end products co-localize with astrocyes and microglial cells in Alzheimer's disease brain", *Acta Neuropathologica*, Vol. 95, pp. 555-558 (1998)). On the basis of recently reported findings, Chinta et al. proposed that environmental stressors associated with Parkinson's disease (PD) may act in part by eliciting senescence within non-neuronal glial cells, contributing to the characteristic decline in neuronal integrity that occurs in this disorder (Chinta, S. J. et al. "Environmental stress, ageing and glial cell senescence: a novel mechanistic link to Parkinson's disease?", *J Intern Med*, Vol. 273, pp. 429-436 (2013)). Astrocyte senescence is also associated with PD (M. Mori, "The Parkinsonian Brain: Cellular Senescence and Neurodegeneration, SAGE (Jun. 30, 2015) (sage-.buckinstitute.org/the-parkinsonian-brain-cellular-senescence-and-neurodegeneration/). In a rodent model of familial amyotrophic lateral sclerosis (ALS) overexpressing mutant superoxide dismutase-1 (m-SOD1), the rate of astrocytes acquiring a senescent phenotype is accelerated (Das, M. M. and Svendsen, C. N., "Astrocytes show reduced support of motor neurons with aging that is accelerated in a rodent model of ALS", *Neurobiology of Aging*, Vol. 36, pp. 1130-1139 (2015)). Even in multiple sclerosis (MS), microglia and macrophages are shifted toward a strongly proinflammatory phenotype, reminiscent of SASP, and may potentiate neuronal damage by releasing proinflammatory cytokines and molecules (Luessi, F., et al. "Neurodegeneration in multiple sclerosis: novel treatment strategies" *Expert Rev. Neurother.*, Vol 9, pp. 1061-1077 (2012)).

Glial cells, such as astrocytes and microglial cells, provide support for normal brain functions. Astrocytes, also known collectively as astroglia, are star-shaped glial cells found in the brain and spinal cord. Astrocytes perform many functions, such as providing nutrients to nervous tissue, maintaining ion balance in extracellular fluids, and biochemical support of the cells that form the blood-brain barrier. Microglial cells act as macrophages in the brain and spinal cord. Microglial cells scavenge plaques, damaged neurons and infectious agents from the brain and spinal cord.

Some neurodegenerative disorders are also associated with abnormal cellular senescence outside the central nervous system. Most satellite cells, also known as myosatellite cells, present in the muscle tissue of ALS patients exhibit an abnormal senescent-like morphology, although they may be capable of proliferating in vitro (Pradat, P.-F. et al., "Abnormalities of satellite cells function in amyotrophic lateral sclerosis" *Amyotrophic Lateral Sclerosis*, Vol. 12, pp. 264-271 (2011)). Satellite cells are small multipotent cells found in mature muscle, which are able to give rise to additional satellite cells, or differentiate into myoblasts as well as provide additional myonuclei. In an animal model of Duchenne muscular dystrophy (MD), reduced proliferative capacity and premature senescence of myoblasts was observed (Wright, W. E., "Myoblast Senescence in Muscular Dystrophy" *Exp Cell Res*, Vol. 157, pp. 343-354 (1985)). Myoblasts are precursor cells which differentiate into myocytes (also referred to as muscle cells).

Neurodegenerative disorders are also associated with abnormal protein accumulations (King, O. D., et al., "The tip of the iceberg: RNA-binding proteins with prion-like domains in neurodegenerative disease" *Brain Res*. Vol. 1462, pp. 61-80 (2012)). A characteristic of PD and Lewy body dementia is the formation of Lewy bodies that form inside nerve cells. The primary structural component of the Lewy bodies is alpha-synuclein protein, in the form of fibrils. The presence of tangles and plaques are a characteristic of AD, the presence of which is used to definitively diagnose the condition. Plaques, composed of beta-amyloid protein (also referred to as amyloid beta, $A\beta$ or Abeta), accumulate between nerve cells. Tangles, composed of tau protein, form twisted fibers within cells. Prion diseases (also known as transmissible spongiform encephalopathies (TSEs)), include a variety of human and animal disorder such as Creutzfeldt-Jakob disease, variant Creutzfeldt-Jakob disease, bovine spongiform encephalopathy ("mad cow" disease), scrapie (in sheep and goats), chronic wasting disease (in deer and elk), kuru and fatal familial insomnia. Prion protein is a misfolded protein molecule which may propagate by transmitting a misfolded protein state, resulting in the accumulation of the misfolded protein and causing tissue damage and cell death (Dobson, D. M., "The structural basis of protein folding and its links with human disease" *Phil. Trans. R. Soc. Lond*. B, Vol. 356, pp. 133-145 (2001)). In these diseases, it is believed the protein is a normal protein which misfolds or forms an abnormal aggregate. In the case of some patients with familial ALS, a mutated superoxide dismutase-1 (SOD1) forms inclusions and accumulates (Kato, S., et al. "Advanced glycation endproduct-modified superoxide dismutase-1 (SOD1)-positive inclusions are common to familial amyotrophic lateral sclerosis patients with SOD1 gene mutations and transgenic mice expressing human SOD1 with a G85R mutation" *Acta Neuropathol*, Vol. 100, pp. 490-505 (2000)).

In some cases, the proteins are believed to directly cause the death of cells, while in others the protein is believed to cause inflammation indirectly causing death of cells. The inflammation is also believed to induce senescence in cells, which in turn further exacerbates inflammation due to the SASP, leading to a positive feedback advancing neurodegeneration (Golde, T. E., et al. "Proteinopathy-induced neuronal senescence: a hypothesis for brain failure in Alzheimer's and other neurodegenerative diseases" *Alzheimer's Research & Therapy*, Vol. 1, No. 5 (13 Oct. 2009)). Spreading of these inflammation-inducing proteins may also be exacerbated by senescent cells, through intercellular protein transfer (Biran, A., et al. "Senescent cells communicate via intercellular protein transfer" *Genes & Development*, Vol. 29, pp. 791-802 (2015)).

Immunotherapy for neurodegenerative disorders, using antibodies to neurodegenerative proteins associated with the neurodegenerative disorders, is showing some promise. Even when the antibodies are administered peripherally (that is, not into the CNS), positive effects have been observed.

SUMMARY

In a first aspect, the present invention is a method of treating a neurodegenerative disorder or MD comprising administering to a subject a composition comprising an AGE antibody.

In a second aspect, the present invention is a method of killing senescent glial cells comprising administering to a subject a composition comprising an AGE antibody.

In a third aspect, the present invention is a method of killing senescent myoblasts and/or senescent myosatellite cells comprising administering to a subject a composition comprising an AGE antibody.

In a fourth aspect, the present invention is a method of treating a subject with a neurodegenerative disorder or MD comprising a first administering of an AGE antibody; followed by testing the subject for effectiveness of the first administration at treating the neurodegenerative disorder or MD; followed by a second administering of the AGE antibody.

In a fifth aspect, the present invention is a method of treating a neurodegenerative disorder or MD comprising killing or inducing apoptosis in senescent glial cells, senescent myoblasts and/or senescent myosatellite cells.

In a sixth aspect, the present invention is a composition for treating a neurodegenerative disorder comprising (i) an AGE antibody and (ii) serum, immune system cells, or both.

Definitions

The term "neurodegenerative disorder" means disorders which result in neurons losing function and/or dying, in the central nervous system including the brain. Such disorders included central nervous system neurodegenerative disorders such as AD, PD, Lewy body dementia, MS, prion diseases (also known as transmissible spongiform encephalopathies (TSEs), including Creutzfeldt-Jakob disease, variant Creutzfeldt-Jakob disease, bovine spongiform encephalopathy ("mad cow" disease), scrapie (in sheep and goats), chronic wasting disease (in deer and elk), kuru and fatal familial insomnia), and ALS.

The terms "advanced glycation end-product," "AGE," "AGE-modified protein or peptide," "glycation end-product" and "AGE antigen" refer to modified proteins or peptides that are formed as the result of the reaction of sugars with protein side chains that further rearrange and form irreversible cross-links. This process begins with a reversible reaction between a reducing sugar and an amino group to form a Schiff base, which proceeds to form a covalently-bonded Amadori rearrangement product. Once formed, the Amadori product undergoes further rearrangement to produce AGEs. AGE-modified proteins and antibodies to AGE-modified proteins are described in U.S. Pat. No. 5,702,704 to Bucala ("Bucala") and U.S. Pat. No. 6,380,165 to Al-Abed et al. ("Al-Abed"). Glycated proteins or peptides that have not undergone the necessary rearrangement to form AGEs, such as N-deoxyfructosyllysine found on glycated albumin, are not AGEs. AGEs may be identified by the presence of AGE modifications (also referred to as AGE epitopes or AGE moieties) such as 2-(2-furoyl)-4(5)-(2-furanyl)-1H-imidazole ("FFI"); 5-hydroxymethyl-1-alkylpyrrole-2-carbaldehyde ("Pyrraline"); 1-alkyl-2-formyl-3,4-diglycosyl pyrrole ("AFGP"), a non-fluorescent model AGE; carboxymethyllysine; and pentosidine. ALI, another AGE, is described in Al-Abed.

"Neurodegenerative proteins" are proteins which accumulate in a patient having a neurodegenerative disorders and which are associated with the neurodegenerative disorder. Examples include, beta-amyloid protein plaques (associated with AD), tau protein tangles (associated with AD), mutated superoxide dismutase-1 (associated with ALS), prion protein aggregates (associated with TSEs) and alpha-synuclein protein fibrils (associated with PD and Lewy Body dementia). A "neurodegenerative protein" is the form of the protein which accumulates during the neurodegenerative disorder, typically a mutant or mis-folded form.

"An antibody that binds to an AGE-modified protein on a cell", "anti-AGE antibody" or "AGE antibody" means an antibody or other protein that binds to an AGE-modified protein or peptide and includes a constant region of an antibody, where the protein or peptide which has been AGE-modified is a protein or peptide normally found bound on the surface of a cell, preferably a mammalian cell, more preferably a human, cat, dog, horse, camelid (for example, camel or alpaca), cattle, sheep, or goat cell. "An antibody that binds to an AGE-modified protein on a cell", "anti-AGE antibody" or "AGE antibody" does not include an antibody or other protein which binds with the same specificity and selectivity to both the AGE-modified protein or peptide, and the same non-AGE-modified protein or peptide (that is, the presence of the AGE modification does not increase binding). AGE-modified albumin is not an AGE-modified protein on a cell, because albumin is not a protein normally found bound on the surface of cells. "An antibody that binds to an AGE-modified protein on a cell", "anti-AGE antibody" or "AGE antibody" only includes those antibodies which lead to removal, destruction, or death of the cell. Also included are antibodies which are conjugated, for example to a toxin, drug, or other chemical or particle. Preferably, the antibodies are monoclonal antibodies, but polyclonal antibodies are also possible.

The term "senescent cell" means a cell which is in a state of irreversible proliferative arrest and expresses one or more biomarkers of senescence, such as activation of p16$^{Ink4a}$ or expression of β-galactosidase. Also included are cells which express one or more biomarkers of senescence, do not proliferate in vivo, but may proliferate in vitro under certain conditions, such as some satellite cells found in the muscles of ALS patients.

The term "variant" means a nucleotide, protein or amino acid sequence different from the specifically identified sequences, wherein one or more nucleotides, proteins or amino acid residues is deleted, substituted or added. Variants may be naturally-occurring allelic variants, or non-naturally-occurring variants. Variants of the identified sequences may retain some or all of the functional characteristics of the identified sequences.

The term "percent (%) sequence identity" is defined as the percentage of amino acid residues in a candidate sequence that are identical to the amino acid residues in a reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways using publicly available computer software such as BLAST, BLAST-2, ALIGN or Megalign (DNASTAR) software. Preferably, % sequence identity values are generated using the sequence comparison computer program ALIGN-2. The ALIGN-2 sequence comparison computer program is publicly available from Genentech, Inc. (South San Francisco, Calif.), or may be compiled from the source code, which has been filed with user documentation in the U.S. Copyright Office and is registered under U.S. Copyright Registration No. TXU510087. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. Where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained using the ALIGN-2 computer program.

DETAILED DESCRIPTION

Figure 1:
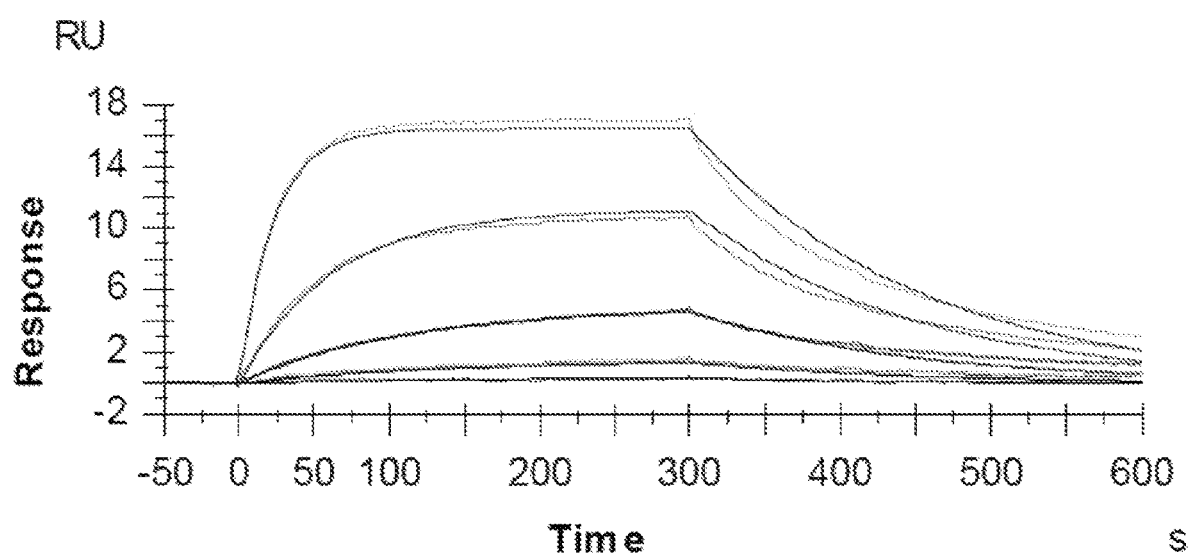
FIG. 1 is a graph of the response versus time in an antibody binding experiment.

The present invention makes use of antibodies that bind to an AGE-modified protein on a cell, to remove or kill senescent glial cells, such as senescent astrocytes, and senescent microglial cells, to treat neurodegenerative disorders such as AD, PD, Lewy body dementia, MS, prion diseases (also known as transmissible spongiform encephalopathies (TSEs), including Creutzfeldt-Jakob disease, variant Creutzfeldt-Jakob disease, bovine spongiform encephalopathy ("mad cow" disease), scrapie (in sheep and goats), chronic wasting disease (in deer and elk), kuru and fatal familial insomnia), and ALS. Preferably, the antibodies are administered into the central nervous system to most efficiently remove these senescent cells; however, peripheral administration (that is, not into the central nervous system but into the peripheral circulatory system) is also effective, since the astrocytes help form the blood-brain barrier. Stem cell present in the patient's central nervous system will then grow and expand to replace cells which were removed. Alternatively, autologous transplantation of the patient's own stem cells, or transplantation of donor stem cells (which may be expanded ex vivo) may also be used to replace cells which were removed.

The present invention also makes use of antibodies that bind to an AGE-modified protein on a cell, to remove or kill senescent glial cells and/or senescent myosatellite cells, to treat ALS. Preferably, the antibodies are administered into the peripheral circulation (such as traditional intravenous administration) to most efficiently remove these senescent cells. The antibodies may also be administered intramuscularly, where the senescent myosatellite cells are found. Stem cell present in the patient's muscles will then grow and expand to replace cells which were removed. Alternatively, autologous transplantation of the patient's own stem cells, or transplantation of donor stem cells (which may be expanded ex vivo) may also be used to replace cells which were removed.

The present invention also makes use of antibodies that bind to an AGE-modified protein on a cell, to remove or kill senescent myoblasts and/or senescent myosatellite cells, to treat MD and ALS. Preferably, the antibodies are administered into the peripheral circulation (such as traditional intravenous administration) to most efficiently remove these senescent cells. The antibodies may also be administered intramuscularly, where the senescent myoblasts and myosatellite cells are found. Stem cell present in the patient's muscles will then grow and expand to replace cells which were removed. Alternatively, autologous transplantation of the patient's own stem cells, or transplantation of donor stem cells (which may be expanded ex vivo) may also be used to replace cells which were removed. See, for example, Rouger et al. "Systemic Delivery of Allogenic Muscle Stem Cells Induces Long-Term Muscle Repair and Clinical Efficacy in Duchenne Muscular Dystrophy Dogs" *The American Journal of Pathology*, Vol. 179, No. 5, 2501-2518 (November 2011).

Senescence begins with damage or stress (such as overstimulation by growth factors) of cells. The damage or stress negatively impacts mitochondrial DNA in the cells to cause them to produce free radicals which react with sugars in the cell to form methyl glyoxal (MG). MG in turn reacts with proteins or lipids to generate advanced glycation end products (AGEs). In the case of the protein component lysine, glyoxal reacts to form carboxymethyllysine, which is an AGE. AGEs also form from non-enzymatic reaction of sugars in the blood with external cell proteins.

Damage or stress to mitochondrial DNA also sets off a DNA damage response which induces the cell to produce cell cycle blocking proteins. These blocking proteins prevent the cell from dividing. Continued damage or stress causes (1) mTOR production, which in turn activates protein synthesis and inactivates protein breakdown, and (2) an SASP (senescence associated secretory phenotype) wherein growth stimulatory and inhibitory factors are secreted to cause senescence in other cells (the senescent cell bystander effect). Further stimulation of the cells leads to programmed cell death (apoptosis).

An antibody that binds to an AGE-modified protein on a cell ("anti-AGE antibody" or "AGE antibody") is known in the art. Examples include those described in U.S. Pat. No. 5,702,704 (Bucala) and U.S. Pat. No. 6,380,165 (Al-Abed et al.). Examples include an antibody that binds to one or more AGE-modified proteins having an AGE modification such as FFI, pyrraline, AFGP, ALI, carboxymethyllysine, carboxyethyllysine and pentosidine, and mixtures of such antibodies. Preferably, the antibody binds carboxymethyllysine-modified proteins. Preferably, the antibody is non-immunogenic to the animal in which it will be used, such as non-immunogenic to humans; companion animals including cats, dogs and horses; and commercially important animals, such camels (or alpaca), cattle (bovine), sheep, and goats. More preferably, the antibody has the same species constant region as antibodies of the animal to reduce the immune response against the antibody, such as being humanized (for humans), felinized (for cats), caninized (for dogs), equuinized (for horses), camelized (for camels or alpaca), bovinized (for cattle), ovinized (for sheep), or caperized (for goats). Most preferably, the antibody is identical to that of the animal in which it will be used (except for the variable region), such as a human antibody, a cat antibody, a dog antibody, a horse antibody, a camel antibody, a bovine antibody, a sheep antibody or a goat antibody. Details of the constant regions and other parts of antibodies for these animals are described below. Preferably, the antibody is a monoclonal antibody.

A particularly preferred AGE antibody is an antibody which binds to a protein or peptide that exhibits a carboxymethyllysine modification. Carboxymethyllysine (also known as CML, N(epsilon)-(carboxymethyl)lysine, N(6)-carboxymethyllysine, or 2-Amino-6-(carboxymethylamino) hexanoic acid) is found on proteins or peptides and lipids as a result of oxidative stress and chemical glycation, and has been correlated with aging. CML-modified proteins or peptides are recognized by the receptor RAGE which is expressed on a variety of cells. CML has been well-studied and CML-related products are commercially available. For example, Cell Biolabs, Inc. sells CML-BSA antigens, CML polyclonal antibodies, CML immunoblot kits, and CML competitive ELISA kits (www.cellbiolabs.com/cml-assays). A particularly preferred antibody includes the variable region of the commercially available mouse anti-glycation end-product antibody raised against carboxymethyl lysine conjugated with keyhole limpet hemocyanin, the carboxymethyl lysine MAb (Clone 318003) available from R&D Systems, Inc. (Minneapolis, Minn.; catalog no. MAB3247), modified to have a human constant region (or the constant region of the animal into which it will be administered). Commercially-available antibodies, such as the carboxymethyl lysine antibody corresponding to catalog no. MAB3247 from R&D Systems, Inc., may be intended for diagnostic purposes and may contain material that is not suited for use in animals or humans. Preferably, commercially-available antibodies are purified and/or isolated prior to use in animals or humans to remove toxins or other potentially-harmful material.

The AGE antibody has low rate of dissociation from the antibody-antigen complex, or $k_d$ (also referred to as $k_{back}$ or off-rate), preferably at most $9\times10^{-3}$, $8\times10^{-3}$, $7\times10^{-3}$ or $6\times10^{-3}$ ($sec^{-1}$). The AGE antibody has a high affinity for the AGE-modified protein of a cell, which may be expressed as a low dissociation constant $K_D$ of at most $9\times10^{-6}$, $8\times10^{-6}$, $7\times10^{-6}$, $6\times10^{-6}$, $5\times10^{-6}$, $4\times10^{-6}$ or $3\times10^{-6}$ (M). Preferably, the binding properties of the AGE antibody is greater than, similar to, or the same as, the carboxymethyl lysine MAb (Clone 318003) available from R&D Systems, Inc. (Minneapolis, Minn.; catalog no. MAB3247), illustrated in FIG. 1.

The anti-AGE antibody may destroy AGE-modified cells through antibody-dependent cell-mediated cytotoxicity (ADCC). ADCC is a mechanism of cell-mediated immune defense in which an effector cell of the immune system actively lyses a target cell whose membrane-surface antigens have been bound by specific antibodies. ADCC may be mediated by natural killer (NK) cells, macrophages, neutrophils or eosinophils. The effector cells bind to the Fc portion of the bound antibody.

The AGE antibody may be conjugated to an agent that causes the destruction of AGE-modified cells. Such agents may be a toxin, a cytotoxic agent, magnetic nanoparticles, and magnetic spin-vortex discs.

A toxin, such as pore-forming toxins (PFT) (Aroian R. et al., "Pore-Forming Toxins and Cellular Non-Immune Defenses (CNIDs)," *Current Opinion in Microbiology*, 10:57-61 (2007)), conjugated to an AGE antibody may be injected into a patient to selectively target and remove AGE-modified cells. The AGE antibody recognizes and binds to AGE-modified cells. Then, the toxin causes pore formation at the cell surface and subsequent cell removal through osmotic lysis.

Magnetic nanoparticles conjugated to the AGE antibody may be injected into a patient to target and remove AGE-modified cells. The magnetic nanoparticles can be heated by applying a magnetic field in order to selectively remove the AGE-modified cells.

As an alternative, magnetic spin-vortex discs, which are magnetized only when a magnetic field is applied to avoid self-aggregation that can block blood vessels, begin to spin when a magnetic field is applied, causing membrane disruption of target cells. Magnetic spin-vortex discs, conjugated to AGE antibodies specifically target AGE-modified cell types, without removing other cells.

Antibodies typically comprise two heavy chains and two light chains of polypeptides joined to form a "Y" shaped molecule. The constant region determines the mechanism used to target the antigen. The amino acid sequence in the tips of the "Y" (the variable region) varies among different antibodies. This variation gives the antibody its specificity for binding antigen. The variable region, which includes the ends of the light and heavy chains, is further subdivided into hypervariable (HV—also sometimes referred to as complementarity determining regions, or CDRs) and framework (FR) regions. When antibodies are prepared recombinantly, it is also possible to have a single antibody with variable regions (or complementary determining regions) that bind to two different antigens, with each tip of the "Y" being specific to each antigen; these are referred to as bi-specific antibodies.

A humanized anti-AGE antibody according to the present invention may have the human constant region sequence of amino acids shown in SEQ ID NO: 22. The heavy chain complementarity determining regions of the humanized anti-AGE antibody may have one or more of the protein sequences shown in SEQ ID NO: 23 (CDR1H), SEQ ID NO: 24 (CDR2H) and SEQ ID NO: 25 (CDR3H). The light chain complementarity determining regions of the humanized anti-AGE antibody may have one or more of the protein sequences shown in SEQ ID NO: 26 (CDR1L), SEQ ID NO: 27 (CDR2L) and SEQ ID NO: 28 (CDR3L).

The heavy chain of human (Homo sapiens) antibody immunoglobulin G1 may have or may include the protein sequence of SEQ ID NO: 1. The variable domain of the heavy chain may have or may include the protein sequence of SEQ ID NO: 2. The kappa light chain of human (Homo sapiens) antibody immunoglobulin G1 may have or may include the protein sequence of SEQ ID NO: 3. The variable domain of the kappa light chain may have or may include the protein sequence of SEQ ID NO: 4. The variable regions may be codon-optimized, synthesized and cloned into expression vectors containing human immunoglobulin G1 constant regions. In addition, the variable regions may be used in the humanization of non-human antibodies.

The antibody heavy chain may be encoded by the DNA sequence of SEQ ID NO: 12, a murine anti-AGE immunoglobulin G2b heavy chain. The protein sequence of the murine anti-AGE immunoglobulin G2b heavy chain encoded by SEQ ID NO: 12 is shown in SEQ ID NO: 16. The variable region of the murine antibody is shown in SEQ ID NO: 20, which corresponds to positions 25-142 of SEQ ID NO: 16. The antibody heavy chain may alternatively be encoded by the DNA sequence of SEQ ID NO: 13, a chimeric anti-AGE human immunoglobulin G1 heavy chain. The protein sequence of the chimeric anti-AGE human immunoglobulin G1 heavy chain encoded by SEQ ID NO: 13 is shown in SEQ ID NO: 17. The chimeric anti-AGE human immunoglobulin includes the murine variable region of SEQ ID NO: 20 in positions 25-142. The antibody light chain may be encoded by the DNA sequence of SEQ ID NO: 14, a murine anti-AGE kappa light chain. The protein sequence of the murine anti-AGE kappa light chain encoded by SEQ ID NO: 14 is shown in SEQ ID NO: 18. The variable region of the murine antibody is shown in SEQ ID NO: 21, which corresponds to positions 21-132 of SEQ ID NO: 18. The antibody light chain may alternatively be encoded by the DNA sequence of SEQ ID NO: 15, a chimeric anti-AGE human kappa light chain. The protein sequence of the chimeric anti-AGE human kappa light chain encoded by SEQ ID NO: 15 is shown in SEQ ID NO: 19. The chimeric anti-AGE human immunoglobulin includes the murine variable region of SEQ ID NO: 21 in positions 21-132.

A humanized anti-AGE antibody according to the present invention may have or may include one or more humanized heavy chains or humanized light chains. A humanized heavy chain may be encoded by the DNA sequence of SEQ ID NO: 30, 32 or 34. The protein sequences of the humanized heavy chains encoded by SEQ ID NOs: 30, 32 and 34 are shown in SEQ ID NOs: 29, 31 and 33, respectively. A humanized light chain may be encoded by the DNA sequence of SEQ ID NO: 36, 38 or 40. The protein sequences of the humanized light chains encoded by SEQ ID NOs: 36, 38 and 40 are shown in SEQ ID NOs: 35, 37 and 39, respectively. Preferably, the humanized anti-AGE antibody maximizes the amount of human sequence while retaining the original antibody specificity. A complete humanized antibody may be constructed that contains a heavy chain having a protein sequence chosen from SEQ ID NOs: 29, 31 and 33 and a light chain having a protein sequence chosen from SEQ ID NOs: 35, 37 and 39.

The protein sequence of an antibody from a non-human species may be modified to include the variable domain of the heavy chain having the sequence shown in SEQ ID NO: 2 or the kappa light chain having the sequence shown in SEQ ID NO: 4. The non-human species may be a companion animal, such as the domestic cat or domestic dog, or livestock, such as cattle, the horse or the camel. Preferably, the non-human species is not the mouse. The heavy chain of the horse (*Equus caballus*) antibody immunoglobulin gamma 4 may have or may include the protein sequence of SEQ ID NO: 5 (EMBL/GenBank accession number AY445518). The heavy chain of the horse (*Equus caballus*) antibody immunoglobulin delta may have or may include the protein sequence of SEQ ID NO: 6 (EMBL/GenBank accession number AY631942). The heavy chain of the dog (*Canis familiaris*) antibody immunoglobulin A may have or may include the protein sequence of SEQ ID NO: 7 (GenBank accession number L36871). The heavy chain of the dog (*Canis familiaris*) antibody immunoglobulin E may have or may include the protein sequence of SEQ ID NO: 8 (GenBank accession number L36872). The heavy chain of the cat (*Felis catus*) antibody immunoglobulin G2 may have or may include the protein sequence of SEQ ID NO: 9 (DDBJ/EMBL/GenBank accession number KF811175).

Animals of the camelid family, such as camels (*Camelus dromedarius* and *Camelus bactrianus*), llamas (*Lama glama, Lama pacos* and *Lama vicugna*), alpacas (*Vicugna pacos*) and guanacos (*Lama guanicoe*), have a unique antibody that is not found in other mammals. In addition to conventional immunoglobulin G antibodies composed of heavy and light chain tetramers, camelids also have heavy chain immunoglobulin G antibodies that do not contain light chains and exist as heavy chain dimers. These antibodies are known as heavy chain antibodies, HCAbs, single-domain antibodies or sdAbs, and the variable domain of a camelid heavy chain antibody is known as the VHH. The camelid heavy chain antibodies lack the heavy chain CH1 domain and have a hinge region that is not found in other species. The variable region of the Arabian camel (*Camelus dromedarius*) single-domain antibody may have or may include the protein sequence of SEQ ID NO: 10 (GenBank accession number AJ245148). The variable region of the heavy chain of the Arabian camel (*Camelus dromedarius*) tetrameric immunoglobulin may have or may include the protein sequence of SEQ ID NO: 11 (GenBank accession number AJ245184).

In addition to camelids, heavy chain antibodies are also found in cartilaginous fishes, such as sharks, skates and rays. This type of antibody is known as an immunoglobulin new antigen receptor or IgNAR, and the variable domain of an IgNAR is known as the VNAR. The IgNAR exists as two identical heavy chain dimers composed of one variable domain and five constant domains each. Like camelids, there is no light chain.

The protein sequences of additional non-human species may be readily found in online databases, such as the International ImMunoGeneTics Information System (www.imgt.org), the European Bioinformatics Institute (www.ebi.ac.uk), the DNA Databank of Japan (ddbj.nig.ac.jp/arsa) or the National Center for Biotechnology Information (www.ncbi.nlm.nih.gov).

Additional DNA and protein sequences may be found in U.S. Provisional Patent Application No. 62/485,246, which is herein incorporated by reference.

An anti-AGE antibody or a variant thereof may include a heavy chain variable region having at least 90%, 91%, 92%, 93%, 94%, 95%, 96%, 97%, 98%, 99%, or 100% sequence identity to the amino acid sequence of SEQ ID NO: 2 or SEQ ID NO: 20, including post-translational modifications thereof. A variable region having at least 90%, 91%, 92%, 93%, 94%, 95%, 96%, 97%, 98%, or 99% sequence identity may contain substitutions (e.g., conservative substitutions), insertions, or deletions relative to the reference sequence, but an anti-AGE antibody including that sequence retains the ability to bind to AGE. The substitutions, insertions, or deletions may occur in regions outside the variable region.

An anti-AGE antibody or a variant thereof may include a light chain variable region having at least 90%, 91%, 92%, 93%, 94%, 95%, 96%, 97%, 98%, 99%, or 100% sequence identity to the amino acid sequence of SEQ ID NO: 4 or SEQ ID NO: 21, including post-translational modifications thereof. A variable region having at least 90%, 91%, 92%, 93%, 94%, 95%, 96%, 97%, 98%, or 99% sequence identity may contain substitutions (e.g., conservative substitutions), insertions, or deletions relative to the reference sequence, but an anti-AGE antibody including that sequence retains the ability to bind to AGE. The substitutions, insertions, or deletions may occur in regions outside the variable region.

Alternatively, the antibody may have the complementarity determining regions of commercially available mouse anti-glycation end-product antibody raised against carboxymethyl lysine conjugated with keyhole limpet hemocyanin (CML-KLH), the carboxymethyl lysine MAb (Clone 318003) available from R&D Systems, Inc. (Minneapolis, Minn.; catalog no. MAB3247).

The antibody may have or may include constant regions which permit destruction of targeted cells by a subject's immune system. Particularly preferred is a monoclonal antibody specific for carboxymethyllysine which is the AGE most commonly found in humans. Preferably, such an antibody includes a complement binding portion (Fc) which stimulates an increase in system natural killer (NK) cell Fc receptors (1) causing the NK cells to bind to the antibody, which in turn, has bound to senescent cells, and (2) initiate a lytic reaction. This causes the senescent cells to undergo apoptosis and be broken up into fragments which are taken up by macrophages, broken down and cleared from the body.

Mixtures of antibodies that bind to more than one type AGE of AGE-modified proteins may also be used.

Bi-specific antibodies, which are AGE antibodies directed to two different epitopes, may also be used. Such antibodies will have a variable region (or complementary determining region) from those of one AGE antibody, and a variable region (or complementary determining region) from a different antibody.

Antibody fragments may be used in place of whole antibodies. For example, immunoglobulin G may be broken down into smaller fragments by digestion with enzymes. Papain digestion cleaves the N-terminal side of inter-heavy chain disulfide bridges to produce Fab fragments. Fab fragments include the light chain and one of the two N-terminal domains of the heavy chain (also known as the Fd fragment). Pepsin digestion cleaves the C-terminal side of the inter-heavy chain disulfide bridges to produce F(ab')$_2$ fragments. F(ab')$_2$ fragments include both light chains and the two N-terminal domains linked by disulfide bridges. Pepsin digestion may also form the Fv (fragment variable) and Fc (fragment crystallizable) fragments. The Fv fragment contains the two N-terminal variable domains. The Fc fragment contains the domains which interact with immunoglobulin receptors on cells and with the initial elements of the complement cascade. Pepsin may also cleave immunoglobulin G before the third constant domain of the heavy chain ($C_H3$) to produce a large fragment F(abc) and a small fragment pFc'. Single domain antibodies, which include a heavy chain CDR and are conjugated to a toxin or other moiety for causing cell death or destruction, may also be used, and are know to pass through the blood-brain barrier. Antibody fragments may alternatively be produced recombinantly.

If additional antibodies are desired, they can be produced using well-known methods. For example, polyclonal antibodies (pAbs) can be raised in a mammalian host by one or more injections of an immunogen, and if desired, an adjuvant. Typically, the immunogen (and adjuvant) is injected in a mammal by a subcutaneous or intraperitoneal injection. The immunogen may be an AGE-modified protein of a cell, such as AGE-antithrombin III, AGE-calmodulin, AGE-insulin, AGE-ceruloplasmin, AGE-collagen, AGE-cathepsin B, AGE-albumin, AGE-crystallin, AGE-plasminogen activator, AGE-endothelial plasma membrane protein, AGE-aldehyde reductase, AGE-transferrin, AGE-fibrin, AGE-copper/zinc SOD, AGE-apo B, AGE-fibronectin, AGE-pancreatic ribose, AGE-apo A-I and II, AGE-hemoglobin, AGE-Na$^+$/K$^+$-ATPase, AGE-plasminogen, AGE-myelin, AGE-lysozyme, AGE-immunoglobulin, AGE-red cell Glu transport protein, AGE-β-N-acetyl hexominase, AGE-apo E, AGE-red cell membrane protein, AGE-aldose reductase, AGE-ferritin, AGE-red cell spectrin, AGE-alcohol dehydrogenase, AGE-haptoglobin, AGE-tubulin, AGE-thyroid hormone, AGE-fibrinogen, AGE-β$_2$-microglobulin, AGE-sorbitol dehydrogenase, AGE-α$_1$-antitrypsin, AGE-carbonate dehydratase, AGE-RNAse, AGE-low density lipoprotein, AGE-hexokinase, AGE-apo C-I, AGE-RNAse, AGE-hemoglobin such as AGE-human hemoglobin, AGE-albumin such as AGE-bovine serum albumin (AGE-BSA) and AGE-human serum albumin, AGE-low density lipoprotein (AGE-LDL) and AGE-collagen IV. AGE-modified cells, such as AGE-modified erythrocytes, whole, lysed, or partially digested, may also be used as AGE antigens. Examples of adjuvants include Freund's complete, monophosphoryl Lipid A synthetic-trehalose dicorynomycolate, aluminum hydroxide (alum), heat shock proteins HSP 70 or HSP96, squalene emulsion containing monophosphoryl lipid A, α2-macroglobulin and surface active substances, including oil emulsions, pleuronic polyols, polyanions and dinitrophenol. To improve the immune response, an immunogen may be conjugated to a polypeptide that is immunogenic in the host, such as keyhole limpet hemocyanin (KLH), serum albumin, bovine thyroglobulin, cholera toxin, labile enterotoxin, silica particles or soybean trypsin inhibitor. Alternatively, pAbs may be made in chickens, producing IgY molecules.

Monoclonal antibodies (mAbs) may also be made by immunizing a host or lymphocytes from a host, harvesting the mAb-secreting (or potentially secreting) lymphocytes, fusing those lymphocytes to immortalized cells (for example, myeloma cells), and selecting those cells that secrete the desired mAb. Other techniques may be used, such as the EBV-hybridoma technique. Techniques for the generation of chimeric antibodies by splicing genes encoding the variable domains of antibodies to genes of the constant domains of human (or other animal) immunoglobulin result in "chimeric antibodies" that are substantially human (humanized) or substantially "ized" to another animal (such as cat, dog, horse, camel or alpaca, cattle, sheep, or goat) at the amino acid level. If desired, the mAbs may be purified from the culture medium or ascites fluid by conventional procedures, such as protein A-sepharose, hydroxylapatite chromatography, gel electrophoresis, dialysis, ammonium sulfate precipitation or affinity chromatography. Additionally, human monoclonal antibodies can be generated by immunization of transgenic mice containing a third copy IgG human trans-loci and silenced endogenous mouse Ig loci or using human-transgenic mice. Production of humanized monoclonal antibodies and fragments thereof can also be generated through phage display technologies.

A "pharmaceutically acceptable carrier" includes any and all solvents, dispersion media, coatings, antibacterial and antifungal agents, isotonic and absorption delaying agents, and the like, compatible with pharmaceutical administration. Preferred examples of such carriers or diluents include water, saline, Ringer's solutions and dextrose solution. Supplementary active compounds can also be incorporated into the compositions. Solutions and suspensions used for parenteral administration can include a sterile diluent, such as water for injection, saline solution, polyethylene glycols, glycerin, propylene glycol or other synthetic solvents; antibacterial agents such as benzyl alcohol or methyl parabens; antioxidants such as ascorbic acid or sodium bisulfite; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injection include sterile aqueous solutions or dispersions for the extemporaneous preparation of sterile injectable solutions or dispersion. Various excipients may be included in pharmaceutical compositions of antibodies suitable for injection. For administration by injection, suitable carriers include physiological saline, bacteriostatic water, CREMOPHOR EL® (BASF; Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. Various antibacterial and anti-fungal agents, for example, parabens, chlorobutanol, phenol, ascorbic acid, and thimerosal, can contain microorganism contamination. Isotonic agents such as sugars, polyalcohols, such as manitol, sorbitol, and sodium chloride can be included in the composition. Compositions that can delay absorption include agents such as aluminum monostearate and gelatin. Sterile injectable solutions can be prepared by incorporating antibodies, and optionally other therapeutic components, in the required amount in an appropriate solvent with one or a combination of ingredients as required, followed by sterilization. Methods of preparation of sterile solids for the preparation of sterile injectable solutions include vacuum drying and freeze-drying to yield a solid.

For administration by inhalation, the antibodies are delivered as an aerosol spray from a nebulizer or a pressurized container that contains a suitable propellant, for example, a gas such as carbon dioxide. Antibodies may also be delivered via inhalation as a dry powder, for example using the iSPERSE™ inhaled drug deliver platform (PULMATRIX, Lexington, Mass.). The use of AGE antibodies which are chicken antibodies (IgY) may be non-immunogenic in a variety of animals, including humans, when administered by inhalation.

An appropriate dosage level of each type of antibody will generally be about 0.01 to 500 mg per kg patient body weight. Preferably, the dosage level will be about 0.1 to about 250 mg/kg; more preferably about 0.5 to about 100 mg/kg. A suitable dosage level may be about 0.01 to 250 mg/kg, about 0.05 to 100 mg/kg, or about 0.1 to 50 mg/kg. Within this range the dosage may be 0.05 to 0.5, 0.5 to 5 or 5 to 50 mg/kg. Although each type of antibody may be administered on a regimen of 1 to 4 times per day, such as once or twice per day, antibodies typically have a long half-life in vivo. Accordingly, each type of antibody may be administered once a day, once a week, once every two or three weeks, once a month, or once every 60 to 90 days.

A subject that receives administration of an AGE antibody may be tested to determine if it has been effective to treat the neurodegenerative disorder, by measuring changes in neurological function or cognitive function, or by the increase or decrease in the presence of a neurodegenerative protein associated with the neurodegenerative disorder. In the case of most neurodegenerative disorders, tests to measure the presence, severity and/or progression of the neurodegenerative disorder are well known. Administration of antibody and subsequent testing may be repeated until the desired therapeutic result is achieved, for example by evaluating the patient for the neurodegenerative disorder or evaluating the patient if the senescent cells have been killed.

Unit dosage forms can be created to facilitate administration and dosage uniformity. Unit dosage form refers to physically discrete units suited as single dosages for the subject to be treated, containing a therapeutically effective quantity of one or more types of antibodies in association with the required pharmaceutical carrier. Preferably, the unit dosage form is in a sealed container and is sterile.

Any mammal that could develop neurodegenerative disorders may be treated by the methods herein described. Humans are a preferred mammal for treatment. Other mammals that may be treated include mice, rats, goats, sheep, cows, horses and companion animals, such as dogs or cats. A subject in need of treatment may be identified by the diagnosis of a neurodegenerative disorder.

In the case of central nervous system neurodegenerative disorders, it may be preferably to administer the composition containing the AGE antibody directly into the central nervous system. Examples of such administration include intrathecal administration; administration into the ventricular system of the brain (intraventricular administration), for example, through a catheter or a permanent shunt, or other administration device which may be placed during a ventriculostomy (see, for example, Takami, A. et al. "Treatment of primary central nervous system lymphoma with induction of complement-dependent cytotoxicity by intraventricular administration of autologous-serum-supplemented rituximab", *Cancer Sci.* Vol. 97, pp. 80-83 (January 2006)); and administered by convection enhanced delivery (CED) (see, for example, Chen, K. S., et al. "MONOCLONAL ANTIBODY THERAPY FOR MALIGNANT GLIOMA" chapter 10 of *Glioma: Immunotherapeutic Approaches*, pp. 132-141 (ed. R. Yamanaka; Landes Bioscience and Springer Science+Business Media, 2012)). All such central nervous system administration may optionally also include administration of a serum supplement (such as autologous serum), to enhance the cell killing properties of the AGE antibody; administration of serum supplement may be prior to, simultaneous with, or subsequent to, the administration of the AGE antibody. Optionally, any of the composition containing AGE antibodies described herein may further contain a serum supplement (such as an autologous serum supplement). In place of a serum supplement, or in addition to a serum supplement, purified immune system cells may also be used, either autologous immune system cells, or immune system cells from a donor; examples of such cells include natural killer cells. In addition to, or instead of, the patient's or a donor's natural killer cells, artificial natural killer cells such as those of NANTKWEST®, engineered to bind directly to antibodies, or engineered to bind directly to an AGE antigen (such as carboxymethyllysine) (see www.nantkwest.com).

The anti-AGE antibodies may be used in cell separation processes, such as magnetic cell separation. In magnetic cell separation, the anti-AGE antibodies are attached to magnetic beads through a process called coating. The coated magnetic beads may then specifically bind to AGE-modified cells. The AGE-modified cells that have bound to anti-AGE antibodies coated on magnetic beads will then respond to an applied magnetic field, allowing the AGE-modified cells to be separated from non-AGE-modified cells. Magnetic cell separation may be used to isolate AGE-modified cells from tissue samples and fluid samples. The magnetic beads may be microbeads (0.5-500 µm) or nanoparticles (5-500 nm). Anti-AGE antibodies coated on magnetic beads may also be used in isolation processes such as immunoassays and immunoprecipitation. Similarly, anti-AGE antibodies coated on magnetic beads may be used to specifically target and separate AGE-modified proteins or peptides from tissue samples and fluid samples. The anti-AGE antibodies may be used in other cell separation processes such as flow cytometry and cell sorting.

The anti-AGE antibodies may be used in cellular purification processes, such as immunopanning and immunoadsorption. Purification processes are useful in isolating desirable or unwanted cells from tissue cultures, cell cultures or blood. Cellular purification may be used in transplantations, such as a bone marrow transplant, or transfusions, such as a blood transfusion. Cellular purification is especially useful in autologous stem cell transplantation during chemotherapy to remove metastasizing malignant cells and concentrate beneficial stem cells. Immunopanning or immunoadsorption using an anti-AGE antibody may isolate AGE-modified cells from a tissue culture, cell culture or blood sample.

The one-letter amino acid sequence that corresponds to SEQ ID NO: 1 is shown below:

```
            10         20         30         40
     MNLLLILTFV AAAVAQVQLL QPGAELVKPG ASVKLACKAS 50         60         70         80
     GYLFTTYWMH WLKQRPGQGL EWIGEISPTN GRAYYNARFK 90        100        110        120
     SEATLTVDKS SNTAYMQLSS LTSEASAVYY CARAYGNYEF 130        140        150        160
     AYWGQGTLVT VSVASTKGPS VFPLAPSSKS TSGGTAALGC 170        180        190        200
     LVKDYFPEPV TVSWNSGALT SGVHTFPAVL QSSGLYSLSS 210        220        230        240
     VVTVPSSSLG TQTYICNVNH KPSNTKVDKK VEPKSCDKTH 250        260        270        280
     TCPPCPAPEL LGGPSVFLFP PKPKDTLMIS RTPEVTCVVV 290        300        310        320
     DVSHEDPEVK FNWYVDGVEV HNAKTKPREE QYNSTYRVVS 330        340        350        360
     VLTVLHQDWL NGKEYKCKVS NKALPAPIEK TISKAKGQPR 370        380        390        400
     EPQVYTLPPS REEMTKNQVS LTCLVKGFYP SDIAVEWESN 410        420        430        440
     GQPENNYKTT PPVLDSDGSF FLYSKLTVDK SRWQQGNVFS 450        460
     CSVMHEALHN HYTQKSLSLS PGK
```

Positions 16-133 of the above amino acid sequence correspond to SEQ ID NO: 2. Positions 46-50 of the above amino acid sequence correspond to SEQ ID NO: 41. Positions 65-81 of the above amino acid sequence correspond to SEQ ID NO: 42. Positions 114-122 of the above amino acid sequence correspond to SEQ ID NO: 43.

The one-letter amino acid sequence that corresponds to SEQ ID NO: 3 is shown below:

```
            10         20         30         40
     MNLLLILTFV AAAVADVVMT QTPLSLPVSL GDQASISCRS 50         60         70         80
     RQSLVNSNGN TFLQWYLQKP GQSPKLLIYK VSLRFSGVPD 90        100        110        120
     RFSGSGSGTD FTLKISRVEA EDLGLYFCSQ STHVPPTFGG
```

```
         130        140        150        160
GTKLEIKRTV AAPSVFIFPP SDEQLKSGTA SVVCLLNNFY 170        180        190        200
PREAKVQWKV DNALQSGNSQ ESVTEQDSKD STYSLSSTLT 210        220        230
LSKADYEKHK VYACEVTHQG LSSPVTKSFN RGEC
```

Positions 16-128 of the above amino acid sequence correspond to SEQ ID NO: 4. Optionally, the arginine (Arg or R) residue at position 128 of SEQ ID NO: 4 may be omitted. Positions 39-54 of the above amino acid sequence correspond to SEQ ID NO: 44. Positions 70-76 of the above amino acid sequence correspond to SEQ ID NO: 45. Positions 109-117 of the above amino acid sequence correspond to SEQ ID NO: 46.

The DNA sequence that corresponds to SEQ ID NO: 12 is shown below:

```
ATGGACCCCAAGGGCAGCCTGAGCTGGAGAATCCTGCTGTTCCTGAGCCT
GGCCTTCGAGCTGAGCTACGGCCAGGTGCAGCTGCTGCAGCCAGGTGCCG
AGCTCGTGAAACCTGGCGCCTCTGTGAAGCTGGCCTGCAAGGCTTCCGGC
TACCTGTTCACCACCTACTGGATGCACTGGCTGAAGCAGAGGCCAGGCCA
GGGCCTGGAATGGATCGGCGAGATCTCCCCCACCAACGGCAGAGCCTACT
ACAACGCCCGGTTCAAGTCCGAGGCCACCCTGACCGTGGACAAGTCCTCC
AACACCGCCTACATGCAGCTGTCCTCCCTGACCTCTGAGGCCTCCGCCGT
GTACTACTGCGCCAGAGCTTACGGCAACTACGAGTTCGCCTACTGGGGCC
AGGGCACCCTCGTGACAGTGTCTGTGGCTAAGACCACCCCTCCCTCCGTG
TACCCTCTGGCTCCTGGCTGTGGCGACACCACCGGATCCTCTGTGACCCT
GGGCTGCCTCGTGAAGGGCTACTTCCCTGAGTCCGTGACCGTGACCTGGA
ACTCCGGCTCCCTGTCCTCCTCCGTGCACACCTTTCCAGCCCTGCTGCAG
TCCGGCCTGTACACCATGTCCTCCAGCGTGACAGTGCCCTCCTCCACCTG
GCCTTCCCAGACCGTGACATGCTCTGTGGCCCACCCTGCCTCTTCCACCA
CCGTGGACAAGAAGCTGGAACCCTCCGGCCCCATCTCCACCATCAACCCT
TGCCCTCCCTGCAAAGAATGCCACAAGTGCCCTGCCCCCAACCTGGAAGG
CGGCCCTTCCGTGTTCATCTTCCCACCCAACATCAAGGACGTGCTGATGA
TCTCCCTGACCCCCAAAGTGACCTGCGTGGTGGTGGACGTGTCCGAGGAC
GACCCTGACGTGCAGATCAGTTGGTTCGTGAACAACGTGGAAGTGCACAC
CGCCCAGACCCAGACACACAGAGAGGACTACAACAGCACCATCAGAGTGG
TGTCTACCCTGCCCATCCAGCACCAGGACTGGATGTCCGGCAAAGAATTC
AAGTGCAAAGTGAACAACAAGGACCTGCCCAGCCCCATCGAGCGGACCAT
CTCCAAGATCAAGGGCCTCGTGCGGGCTCCCCAGGTGTACATTCTGCCTC
CACCAGCCGAGCAGCTGTCCCGGAAGGATGTGTCTCTGACATGTCTGGTC
GTGGGCTTCAACCCCGGCGACATCTCCGTGGAATGGACCTCCAACGGCCA
CACCGAGGAAAACTACAAGGACACCGCCCCTGTGCTGGACTCCGACGGCT
CCTACTTCATCTACTCCAAGCTGAACATGAAGACCTCCAAGTGGGAAAAG
ACCGACTCCTTCTCCTGCAACGTGCGGCACGAGGGCCTGAAGAACTACTA
CCTGAAGAAAACCATCTCCCGGTCCCCCGGCTAG
```

The DNA sequence that corresponds to SEQ ID NO: 13 is shown below:

```
ATGGACCCCAAGGGCAGCCTGAGCTGGAGAATCCTGCTGTTCCTGAGCCT
GGCCTTCGAGCTGAGCTACGGCCAGGTGCAGCTGCTGCAGCCAGGTGCCG
AGCTCGTGAAACCTGGCGCCTCTGTGAAGCTGGCCTGCAAGGCTTCCGGC
TACCTGTTCACCACCTACTGGATGCACTGGCTGAAGCAGAGGCCAGGCCA
GGGCCTGGAATGGATCGGCGAGATCTCCCCCACCAACGGCAGAGCCTACT
ACAACGCCCGGTTCAAGTCCGAGGCCACCCTGACCGTGGACAAGTCCTCC
AACACCGCCTACATGCAGCTGTCCTCCCTGACCTCTGAGGCCTCCGCCGT
GTACTACTGCGCCAGAGCTTACGGCAACTACGAGTTCGCCTACTGGGGCC
AGGGCACCCTCGTGACAGTGTCTGTGGCTAGCACCAAGGGCCCCAGCGTG
TTCCCTCTGGCCCCCAGCAGCAAGAGCACCAGCGGCGGAACCGCCGCCCT
GGGCTGCCTGGTGAAGGACTACTTCCCCGAGCCCGTGACCGTGTCCTGGA
ACAGCGGCGCTCTGACCAGCGGAGTGCACACCTTCCCTGCCGTGCTGCAG
AGCAGCGGCCTGTACTCCCTGAGCAGCGTGGTGACCGTGCCCAGCAGCAG
CCTGGGCACCCAGACCTACATCTGCAACGTGAACCACAAGCCCTCCAACA
CCAAGGTGGACAAGAAGGTGGAGCCTAAGAGCTGCGACAAGACCCACACC
TGCCCTCCCTGCCCCGCCCCCGAGCTGCTGGGCGGACCCAGCGTGTTCCT
GTTCCCTCCCAAGCCCAAGGACACCCTGATGATCAGCCGCACCCCCGAGG
TGACCTGCGTGGTGGTGGACGTGAGCCACGAGGACCCCGAGGTGAAGTTC
AACTGGTACGTGGACGGCGTGGAGGTGCACAACGCCAAGACCAAGCCTCG
GGAGGAGCAGTACAACTCCACCTACCGCGTGGTGAGCGTGCTGACCGTGC
TGCACCAGGACTGGCTGAACGGCAAGGAGTACAAGTGCAAGGTGAGCAAC
AAGGCCCTGCCCGCTCCCATCGAGAAGACCATCAGCAAGGCCAAGGGCCA
GCCCCGGGAGCCTCAGGTGTACACCCTGCCCCCCAGCCGCGACGAGCTGA
CCAAGAACCAGGTGAGCCTGACCTGCCTGGTGAAGGGCTTCTACCCCTCC
GACATCGCCGTGGAGTGGGAGAGCAACGGCCAGCCTGAGAACAACTACAA
GACCACCCCTCCCGTGCTGGACAGCGACGGCAGCTTCTTCCTGTACAGCA
AGCTGACCGTGGACAAGTCCCGGTGGCAGCAGGGCAACGTGTTCAGCTGC
AGCGTGATGCACGAGGCCCTGCACAACCACTACACCCAGAAGAGCCTGAG
CCTGAGCCCCGGATAG
```

The DNA sequence that corresponds to SEQ ID NO: 14 is shown below:

```
ATGGAGACCGACACCCTGCTGCTCTGGGTGCTGCTGCTCTGGGTGCCCGG
CTCCACCGGAGACGTCGTGATGACCCAGACCCCTCTGTCCCTGCCTGTGT
CTCTGGGCGACCAGGCCTCCATCTCCTGCCGGTCTAGACAGTCCCTCGTG
AACTCCAACGGCAACACCTTCCTGCAGTGGTATCTGCAGAAGCCCGGCCA
GTCCCCCAAGCTGCTGATCTACAAGGTGTCCCTGCGGTTCTCCGGCGTGC
CCGACAGATTTTCCGGCTCTGGCTCTGGCACCGACTTCACCCTGAAGATC
TCCCGGGTGGAAGCCGAGGACCTGGGCCTGTACTTCTGCAGCCAGTCCAC
```

-continued
CCACGTGCCCCCTACATTTGGCGGAGGCACCAAGCTGGAAATCAAACGGG

CAGATGCTGCACCAACTGTATCCATCTTCCCACCATCCAGTGAGCAGTTA

ACATCTGGAGGTGCCTCAGTCGTGTGCTTCTTGAACAACTTCTACCCCAA

AGACATCAATGTCAAGTGGAAGATTGATGGCAGTGAACGACAAAATGGCG

TCCTGAACAGTTGGACTGATCAGGACAGCAAAGACAGCACCTACAGCATG

AGCAGCACCCTCACGTTGACCAAGGACGAGTATGAACGACATAACAGCTA

TACCTGTGAGGCCACTCACAAGACATCAACTTCACCCATTGTCAAGAGCT

TCAACAGGAATGAGTGTTGA

The DNA sequence that corresponds to SEQ ID NO: 15 is shown below:

ATGGAGACCGACACCCTGCTGCTCTGGGTGCTGCTGCTCTGGGTGCCCGG

CTCCACCGGAGACGTCGTGATGACCCAGACCCCTCTGTCCCTGCCTGTGT

CTCTGGGCGACCAGGCCTCCATCTCCTGCCGGTCTAGACAGTCCCTCGTG

AACTCCAACGGCAACACCTTCCTGCAGTGGTATCTGCAGAAGCCCGGCCA

GTCCCCCAAGCTGCTGATCTACAAGGTGTCCCTGCGGTTCTCCGGCGTGC

CCGACAGATTTTCCGGCTCTGGCTCTGGCACCGACTTCACCCTGAAGATC

TCCCGGGTGGAAGCCGAGGACCTGGGCCTGTACTTCTGCAGCCAGTCCAC

CCACGTGCCCCCTACATTTGGCGGAGGCACCAAGCTGGAAATCAAGCGGA

CCGTGGCCGCCCCCAGCGTGTTCATCTTCCCTCCCAGCGACGAGCAGCTG

AAGTCTGGCACCGCCAGCGTGGTGTGCCTGCTGAACAACTTCTACCCCCG

CGAGGCCAAGGTGCAGTGGAAGGTGGACAACGCCCTGCAGAGCGGCAACA

GCCAGGAGAGCGTGACCGAGCAGGACTCCAAGGACAGCACCTACAGCCTG

AGCAGCACCCTGACCCTGAGCAAGGCCGACTACGAGAAGCACAAGGTGTA

CGCCTGCGAGGTGACCCACCAGGGACTGTCTAGCCCCGTGACCAAGAGCT

TCAACCGGGGCGAGTGCTAA

The one-letter amino acid sequence that corresponds to SEQ ID NO: 16 is shown below:

MDPKGSLSWRILLFLSLAFELSYGQVQLLQPGAELVKPGASVKLACKASG

YLFTTYWMHWLKQRPGQGLEWIGEISPTNGRAYYNARFKSEATLTVDKSS

NTAYMQLSSLTSEASAVYYCARAYGNYEFAYWGQGTLVTVSVAKTTPPSV

YPLAPGCGDTTGSSVTLGCLVKGYFPESVTVTWNSGSLSSSVHTFPALLQ

SGLYTMSSSVTVPSSTWPSQTVTCSVAHPASSTTVDKKLEPSGPISTINP

CPPCKECHKCPAPNLEGGPSVFIFPPNIKDVLMISLTPKVTCVVVDVSED

DPDVQISWFVNNVEVHTAQTQTHREDYNSTIRVVSTLPIQHQDWMSGKEF

KCKVNNKDLPSPIERTISKIKGLVRAPQVYILPPPAEQLSRKDVSLTCLV

VGFNPGDISVEWTSNGHTEENYKDTAPVLDSDGSYFIYSKLNMKTSKWEK

TDSFSCNVRHEGLKNYYLKKTISRSPG*

The alanine residue at position 123 of the above amino acid sequence may optionally be replaced with a serine residue. The tyrosine residue at position 124 of the above amino acid sequence may optionally be replaced with a phenylalanine residue. Positions 25-142 of the above amino acid sequence correspond to SEQ ID NO: 20. SEQ ID NO: 20 may optionally include the substitutions at positions 123 and 124. SEQ ID NO: 20 may optionally contain one additional lysine residue after the terminal valine residue.

The one-letter amino acid sequence that corresponds to SEQ ID NO: 17 is shown below:

MDPKGSLSWRILLFLSLAFELSYGQVQLLQPGAELVKPGASVKLACKASG

YLFTTYWMHWLKQRPGQGLEWIGEISPTNGRAYYNARFKSEATLTVDKSS

NTAYMQLSSLTSEASAVYYCARAYGNYEFAYWGQGTLVTVSVASTKGPSV

FPLAPSSKSTSGGTAALGCLVKDYFPEPVTVSWNSGALTSGVHTFPAVLQ

SSGLYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSC

SVMHEALHNHYTQKSLSLSPG*

The one-letter amino acid sequence that corresponds to SEQ ID NO: 18 is shown below:

METDTLLLWVLLLWVPGSTGDVVMTQTPLSLPVSLGDQASISCRSRQSLV

NSNGNTFLQWYLQKPGQSPKLLIYKVSLRFSGVPDRFSGSGSGTDFTLKI

SRVEAEDLGLYFCSQSTHVPPTFGGGTKLEIKRADAAPTVSIFPPSSEQL

TSGGASVVCFLNNFYPKDINVKWKIDGSERQNGVLNSWTDQDSKDSTYSM

SSTLTLTKDEYERHNSYTCEATHKTSTSPIVKSFNRNEC*

Positions 21-132 of the above amino acid sequence correspond to SEQ ID NO: 21.

The one-letter amino acid sequence that corresponds to SEQ ID NO: 19 is shown below:

METDTLLLWVLLLWVPGSTGDVVMTQTPLSLPVSLGDQASISCRSRQSLV

NSNGNTFLQWYLQKPGQSPKLLIYKVSLRFSGVPDRFSGSGSGTDFTLKI

SRVEAEDLGLYFCSQSTHVPPTFGGGTKLEIKRTVAAPSVFIFPPSDEQL

KSGTASVVCLLNNFYPREAKVQWKVDNALQSGNSQESVTEQDSKDSTYSL

SSTLTLSKADYEKHKVYACEVTHQGLSSPVTKSFNRGEC*

The one-letter amino acid sequence that corresponds to SEQ ID NO: 22 is shown below:

```
            10         20         30         40
     ASTKGPSVFP LAPCSRSTSE STAALGCLVK DYFPEPVTVS
            50         60         70         80
     WNSGALTSGV HTFPAVLQSS GLYSLSSVVT VPSSNFGTQT
            90        100        110        120
     YTCNVDHKPS NTKVDKTVER KCCVECPPCP APPVAGPSVF
           130        140        150        160
     LFPPKPKDTL MISRTPEVTC VVVDVSHEDP EVQFNWYVDG
           170        180        190        200
     VEVHNAKTKP REEQFNSTFR VVSVLTVVHQ DWLNGKEYKC
           210        220        230        240
     KVSNKGLPAP IEKTISKTKG QPREPQVYTL PPSREEMTKN
```

```
            250        260        270        280
QVSLTCLVKG FYPSDISVEW ESNGQPENNY KTTPPMLDSD 290        300        310        320
GSFFLYSKLT VDKSRWQQGN VFSCSVMHEA LHNHYTQKSL

SLSPGK
```

The one-letter amino acid sequence that corresponds to SEQ ID NO: 23 is

SYTMGVS.

The one-letter amino acid sequence that corresponds to SEQ ID NO: 24 is

TISSGGGSTYYPDSVKG.

The one-letter amino acid sequence that corresponds to SEQ ID NO: 25 is QGGWLPPFAX, where X may be any naturally occurring amino acid.

The one-letter amino acid sequence that corresponds to SEQ ID NO: 26 is

RASKSVSTSSRGYSYMH.

The one-letter amino acid sequence that corresponds to SEQ ID NO: 27 is

LVSNLES.

The one-letter amino acid sequence that corresponds to SEQ ID NO: 28 is

QHIRELTRS.

The one-letter amino acid sequence that corresponds to SEQ ID NO: 29 is

MDPKGSLSWRILLFLSLAFELSYGQVQLVQSGAEVKKPGASVKVSCKASG
YLFTTYWMHWVRQAPGQGLEWMGEISPTNGRAYYNQKFQGRVTMTVDKST
NTVYMELSSLRSEDTAVYYCARAYGNYFAYWGQGTLVTVSSASTKGPSVF
PLAPSSKSTSGGTAALGCLVKDYFPEPVTVSWNSGALTSGVHTFPAVLQS
SGLYSLSSWTVPSSSLGTQTYICNVNHKPSNTKVDKKVEPKSCDKTHTCP
PCPPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKAL
PAPIEKTISKAKGQPREPQVYTLPPSRDELKNQVSLTCLVKGFYPSDIAV
EWESNGQPENNYKTTPPVLDSDGSFFLYSKLTVDKSRWQQGNVFSCSVMH
EALHNHYTQKSLSLSPG.

The DNA sequence that corresponds to SEQ ID NO: 30 is

ATGGACCCCAAGGGCAGCCTGAGCTGGAGAATCCTGCTGTTCCTGAGCCT
GGCCTTCGAGCTGAGCTACGGCCAGGTGCAGCTGGTGCAGTCTGGCGCCG
AAGTGAAGAAACCTGGCGCCTCCGTGAGGTGTCCTGCAAGGCTTCCGGCT
ACCTGTTCACCACCTACTGGATGCACTGGGTGCGACAGGCCCCTGGACAG
GGCCTGGAATGGATGGGCGAGATCTCCCCTACCAACGGCAGAGCCTACTA
CAACAGAAATTCCAGGGCAGAGTGACCATGACCGTGGACAAGTCCACCAA
CACCGTGTACATGGAACTGTCCTCCCTGCGGAGCGAGGACACCGCCGTGT
ACTACTGCGCTAGAGCCTACGGCAACTACGATTCGCCTACTGGGGCCAGG
GCACCCTCGTGACAGTGTCCTCTGCTAGCACCAAGGGCCCCAGCGTGTTC
CCTCTGGCCCCCAGCAGCAAGAGCACCAGCGGCGGAACCGCCGCCCTGGG
CTGCCTGGGAAGGACTACTTCCCCGAGCCCGTGACCGTGTCCTGGAACAG
CGGCGCTCTGACCAGCGGAGTGCACACCTTCCCTGCCGTGCTGCAGAGCA
GCGGCCTGTACTCCCTGAGCAGCGTGGTGACCGTGCCAGCAGCAGCCTGG
GCACCCAGACCTACATCTGCAACGTGAACCACAAGCCCTCCAACACCAAG
GTGGACAAGAAGGTGGAGCCTAAGAGCTGCGACAAGACCCACACCTGCCC
TCCCTGCCCCGCCCCGAGCTGCTGGGCGGACCCAGCGTGTTCCTGTTCCC
TCCCAAGCCCAAGGACACCCTGATGATCAGCCGCACCCCCGAGGTGACCT
GCGTGGTGGTGGACGTGAGCCACGAGGACCCCGAGGTGAGTTCAACTGGT
ACGTGGACGGCGTGGAGGTGCACAACGCCAAGACCAAGCCTCGGGAGGAG
CAGTACAACTCCACCTACCGCGTGGTGAGCGTGCTGACCGTGCTGCACCA
GGACTGGCTGAACGGCAGGAGTACAAGTGCAAGGTGAGCAACAAGGCCCT
GCCCGCTCCCATCGAGAAGACCATCAGCAAGGCCAAGGGCCAGCCCCGGG
AGCCTCAGGTGTACACCCTGCCCCCCAGCCGCGACGAGCTGACAAGAACC
AGGTGAGCCTGACCTGCCTGGTGAAGGGCTTCTACCCCTCCGACATCGCC
GTGGAGTGGGAGAGCAACGGCCAGCCTGAGAACAACTACAAGACCACCCC
TCCCGTGCTGGACAGCGACGCAGCTTCTTCCTGTACAGCAAGCTGACCGT
GGACAAGTCCCGGTGGCAGCAGGGCAACGTGTTCAGCTGCAGCGTGATGC
ACGAGGCCCTGCACAACCACTACACCCAGAAGAGCCTGAGCCTGAGCCCG
GATAGTAA.

The one-letter amino acid sequence that corresponds to SEQ ID NO: 31 is

MDPKGSLSWRILLFLSLAFELSYGQVQLVQSGAEVKKPGASVKVSCKASG
YLFTTYWMHVVVRQAPGQGLEWMGEISPTNGRAYYNAKFQGRVTMTVDKS
TNTAYMELSSLRSEDTAVYYCARAYGNYFAYWGQGTLVTVSSASTKGPSV
FPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHT
CPPCPPELLGGPSVFLFPPKPKDTLMISRTPEVTCVVVDVSHEDPEVKFN
VVYVDGVEVHNAKTKPREEQYNSTYRVVSVLTVLHQDWLNGKEYKCKVSN
KALPAPIEKTISKAKGQPREPQVYTLPPSRDELKNQVSLTCLVKGFYPSD
IAVEWESNGQPENNYKTTPPVLDSDGSFFLYSKLTVDKSRWQQGNVFSCS
VMHEALHNHYTQKSLSLSPG.

The DNA sequence that corresponds to SEQ ID NO: 32 is

ATGGACCCCAAGGGCAGCCTGAGCTGGAGAATCCTGCTGTTCCTGAGCCT
GGCCTTCGAGCTGAGCTACGGCCAGGTGCAGCTGGTGCAGTCTGGCGCCG
AAGTGAAGAAACCTGGCGCCTCCGTGAGGTGTCCTGCAAGGCTTCCGGCT
ACCTGTTCACCACCTACTGGATGCACTGGGTGCGACAGGCCCCTGGACAG
GGCCTGGAATGGATGGGCGAGATCTCCCCTACCAACGGCAGAGCCTACTA
CAACCAAAATTCCAGGGCAGAGTGACCATGACCGTGGACAAGTCCACCAA
CACCGCTTACATGGAACTGTCCTCCCTGCGGAGCGAGGACACCGCCGTGT
ACTACTGCGCTAGAGCCTACGGCAACTACGATTCGCCTACTGGGGCCAGG
GCACCCTCGTGACAGTGTCCTCTGCTAGCACCAAGGGCCCCAGCGTGTTC
CCTCTGGCCCCAGCAGCAAGAGCACCAGCGGCGGAACCGCCGCCCTGGG
CTGCCTGGGAAGGACTACTTCCCCGAGCCCGTGACCGTGTCCTGGAACAG
CGGCGCTCTGACCAGCGGAGTGCACACCTTCCCTGCCGTGCTGCAGAGCA
GCGGCCTGTACTCCCTGAGCAGCGTGGTGACCGTGCCAGCAGCAGCCTGG
GCACCCAGACCTACATCTGCAACGTGAACCACAAGCCCTCCAACACCAAG
GTGGACAAGAAGGTGGAGCCTAAGAGCTGCGACAAGACCCACACCTGCCC
TCCCTGCCCCGCCCCGAGCTGCTGGGCGGACCCAGCGTGTTCCTGTTCCC
TCCCAAGCCCAAGGACACCCTGATGATCAGCCGCACCCCCGAGGTGACCT
GCGTGGTGGTGGACGTGAGCCACGAGGACCCCGAGGTGAGTTCAACTGGT
ACGTGGACGGCGTGGAGGTGCACAACGCCAAGACCAAGCCTCGGGAGGAG
CAGTACAACTCCACCTACCGCGTGGTGAGCGTGCTGACCGTGCTGCACCA
GGACTGGCTGAACGGCAGGAGTACAAGTGCAAGGTGAGCAACAAGGCCCT
GCCCGCTCCCATCGAGAAGACCATCAGCAAGGCCAAGGGCCAGCCCCGGG
AGCCTCAGGTGTACACCCTGCCCCCCAGCCGCGACGAGCTGACAAGAACC
AGGTGAGCCTGACCTGCCTGGTGAAGGGCTTCTACCCCTCCGACATCGCC
GTGGAGTGGGAGAGCAACGGCCAGCCTGAGAACAACTACAAGACCACCCC
TCCCGTGCTGGACAGCGACGCAGCTTCTTCCTGTACAGCAAGCTGACCGT
GGACAAGTCCCGGTGGCAGCAGGGCAACGTGTTCAGCTGCAGCGTGATGC
ACGAGGCCCTGCACAACCACTACACCCAGAAGAGCCTGAGCCTGAGCCCG
GATAGTAA.

The one-letter amino acid sequence that corresponds to SEQ ID NO: 33 is

MDPKGSLSWRILLFLSLAFELSYGQVQLVQSGAEVKKPGASVKVSCKASG
YLFTTYWMHVVRQAPGQGLEWMGEISPTNGRAYYNAKFQGRVTMTVDKS
INTAYMELSRLRSDDTAVYYCARAYGNYFAYWGQGTLVTVSSASTKGPSV
FPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHT
CPPCPPELLGGPSVFLFPPKPKDTLMISRTPEVTCVVVDVSHEDPEVKFN
VVYVDGVEVHNAKTKPREEQYNSTYRVVSVLTVLHQDWLNGKEYKCKVSN
KALPAPIEKTISKAKGQPREPQVYTLPPSRDELKNQVSLTCLVKGFYPSD
IAVEWESNGQPENNYKTTPPVLDSDGSFFLYSKLTVDKSRWQQGNVFSCS
VMHEALHNHYTQKSLSLSPG.

The DNA sequence that corresponds to SEQ ID NO: 34 is

ATGGACCCCAAGGGCAGCCTGAGCTGGAGAATCCTGCTGTTCCTGAGCCT
GGCCTTCGAGCTGAGCTACGGCCAGGTGCAGCTGGTGCAGTCTGGCGCCG
AAGTGAAGAAACCTGGCGCCTCCGTGAGGTGTCCTGCAAGGCTTCCGGCT
ACCTGTTCACCACCTACTGGATGCACTGGGTGCGACAGGCCCCTGGACAG
GGCCTGGAATGGATGGGCGAGATCTCCCCTACCAACGGCAGAGCCTACTA
CAACCAAAATTCCAGGGCAGAGTGACCATGACCGTGGACAAGTCCATCAA
CACCGCTTACATGGAACTGTCCAGACTGCGGAGCGATGACACCGCCGTGT
ACTACTGCGCTAGAGCCTACGGCAACTACGATTCGCCTACTGGGGCCAGG
GCACCCTCGTGACAGTGTCCTCTGCTAGCACCAAGGGCCCCAGCGTGTTC
CCTCTGGCCCCAGCAGCAAGAGCACCAGCGGCGGAACCGCCGCCCTGGG
CTGCCTGGGAAGGACTACTTCCCCGAGCCCGTGACCGTGTCCTGGAACAG
CGGCGCTCTGACCAGCGGAGTGCACACCTTCCCTGCCGTGCTGCAGAGCA
GCGGCCTGTACTCCCTGAGCAGCGTGGTGACCGTGCCAGCAGCAGCCTGG
GCACCCAGACCTACATCTGCAACGTGAACCACAAGCCCTCCAACACCAAG
GTGGACAAGAAGGTGGAGCCTAAGAGCTGCGACAAGACCCACACCTGCCC
TCCCTGCCCCGCCCCGAGCTGCTGGGCGGACCCAGCGTGTTCCTGTTCCC
TCCCAAGCCCAAGGACACCCTGATGATCAGCCGCACCCCCGAGGTGACCT
GCGTGGTGGTGGACGTGAGCCACGAGGACCCCGAGGTGAGTTCAACTGGT
ACGTGGACGGCGTGGAGGTGCACAACGCCAAGACCAAGCCTCGGGAGGAG
CAGTACAACTCCACCTACCGCGTGGTGAGCGTGCTGACCGTGCTGCACCA
GGACTGGCTGAACGGCAGGAGTACAAGTGCAAGGTGAGCAACAAGGCCCT
GCCCGCTCCCATCGAGAAGACCATCAGCAAGGCCAAGGGCCAGCCCCGGG
AGCCTCAGGTGTACACCCTGCCCCCCAGCCGCGACGAGCTGACAAGAACC
AGGTGAGCCTGACCTGCCTGGTGAAGGGCTTCTACCCCTCCGACATCGCC
GTGGAGTGGGAGAGCAACGGCCAGCCTGAGAACAACTACAAGACCACCCC
TCCCGTGCTGGACAGCGACGCAGCTTCTTCCTGTACAGCAAGCTGACCGT
GGACAAGTCCCGGTGGCAGCAGGGCAACGTGTTCAGCTGCAGCGTGATGC
ACGAGGCCCTGCACAACCACTACACCCAGAAGAGCCTGAGCCTGAGCCCG
GATAGTAA.

The one-letter amino acid sequence that corresponds to SEQ ID NO: 35 is

METDTLLLWVLLLWVPGSTGDVVMTQSPLSLPVTLGQPASISCRSSQSLV
NSNGNTFLQWYQQRPGQSPRLLIYKVSLRFSGVPDRFSGSGSGTDFTLKI
SRVEAEDVGVYYCSQSTHVPPTFGGGTVEIKRTVAAPSVFIFPPSDEQLK

-continued

SGTASVVCLLNNFYPREAKVQWKVDNALQSGNSQESVTEQDSKDSTYSLS

STLTLSKADYEKHKVYACEVTHQGLSSPVTKSFNRGEC.

The DNA sequence that corresponds to SEQ ID NO: 36 is

ATGGAGACCGACACCCTGCTGCTCTGGGTGCTGCTGCTCTGGGTGCCCGG

CTCCACCGGAGACGTCGTGATGACCCAGTCCCCTCTGTCCCTGCCTGTGA

CCCTGGGACAGCCTGCCTCCATCTCCTCAGATCCTCCCAGTCCCTCGTGA

ACTCCAACGGCAACACCTTCCTGCAGTGGTATCAGCAGCGGCCTGGCCAG

AGCCCCAGACTGCTGATCTACAAGGTGTCCCTGCGGTTCTCCGGCGTGCC

CGACGATTTTCCGGCTCTGGCTCTGGCACCGACTTCACCCTGAAGATCTC

CCGGGTGGAAGCCGAGGACGTGGGCGTGTACTACTGCTCCCAGAGCACCC

ACGTGCCCCCTACATTTGGCGGAGGCACCAAGTGGAAATCAAGCGGACCG

TGGCCGCCCCCAGCGTGTTCATCTTCCCTCCCAGCGACGAGCAGCTGAAG

TCTGGCACCGCCAGCGTGGTGTGCCTGCTGAACAACTTCTACCCCCGCGA

GGCCAAGGGCAGTGGAAGGTGGACAACGCCCTGCAGAGCGGCAACAGCCA

GGAGAGCGTGACCGAGCAGGACTCCAAGGACAGCACCTACAGCCTGAGCA

GCACCCTGACCCTGAGCAAGGCCGACTACGAGAAGACAAGGTGTACGCCT

GCGAGGTGACCCACCAGGGACTGTCTAGCCCCGTGACCAAGAGCTTCAAC

CGGGGCGAGTGCTAA.

The one-letter amino acid sequence that corresponds to SEQ ID NO: 37 is

METDTLLLWVLLLWVPGSTGDVVMTQSPLSLPVTLGQPASISCRSRQSLV

NSNGNTFLQWYQQRPGQSPRLLIYKVSLRFSGVPDRFSGSGSGTDFTLKI

SRVEAEDVGVYYCSQSTHVPPTFGGGTVEIKRTVAAPSVFIFPPSDEQLK

SGTASVVCLLNNFYPREAKVQWKVDNALQSGNSQESVTEQDSKDSTYSLS

STLTLSKADYEKHKVYACEVTHQGLSSPVTKSFNRGEC.

The DNA sequence that corresponds to SEQ ID NO: 38 is

ATGGAGACCGACACCCTGCTGCTCTGGGTGCTGCTGCTCTGGGTGCCCGG

CTCCACCGGAGACGTCGTGATGACCCAGTCCCCTCTGTCCCTGCCTGTGA

CCCTGGGACAGCCTGCCTCCATCTCCTCAGATCCAGGCAGTCCCTCGTGA

ACTCCAACGGCAACACCTTCCTGCAGTGGTATCAGCAGCGGCCTGGCCAG

AGCCCCAGACTGCTGATCTACAAGGTGTCCCTGCGGTTCTCCGGCGTGCC

CGACGATTTTCCGGCTCTGGCTCTGGCACCGACTTCACCCTGAAGATCTC

CCGGGTGGAAGCCGAGGACGTGGGCGTGTACTACTGCTCCCAGAGCACCC

ACGTGCCCCCTACATTTGGCGGAGGCACCAAGTGGAAATCAAGCGGACCG

TGGCCGCCCCCAGCGTGTTCATCTTCCCTCCCAGCGACGAGCAGCTGAAG

TCTGGCACCGCCAGCGTGGTGTGCCTGCTGAACAACTTCTACCCCCGCGA

GGCCAAGGGCAGTGGAAGGTGGACAACGCCCTGCAGAGCGGCAACAGCCA

GGAGAGCGTGACCGAGCAGGACTCCAAGGACAGCACCTACAGCCTGAGCA

GCACCCTGACCCTGAGCAAGGCCGACTACGAGAAGACAAGGTGTACGCCT

GCGAGGTGACCCACCAGGGACTGTCTAGCCCCGTGACCAAGAGCTTCAAC

CGGGGCGAGTGCTAA.

The one-letter amino acid sequence that corresponds to SEQ ID NO: 39 is

METDTLLLWVLLLWVPGSTGDVVMTQSPLSSPVTLGQPASISCRSSQSLV

NSNGNTFLQWYHQRPGQPPRLLIYKVSLRFSGVPDRFSGSGAGKDFTLKI

SRVEAEDVGVYYCSQSTHVPPTFGQGTLEIKRTVAAPSVFIFPPSDEQLK

SGTASVVCLLNNFYPREAKVQWKVDNALQSGNSQESVTEQDSKDSTYSLS

STLTLSKADYEKHKVYACEVTHQGLSSPVTKSFNRGEC.

The DNA sequence that corresponds to SEQ ID NO: 40 is

ATGGAGACCGACACCCTGCTGCTCTGGGTGCTGCTGCTCTGGGTGCCCGG

CTCCACCGGAGACGTCGTGATGACCCAGTCCCCTCTGTCCAGTCCTGTGA

CCCTGGGACAGCCTGCCTCCATCTCCTCAGATCCTCCCAGTCCCTCGTGA

ACTCCAACGGCAACACCTTCCTGCAGTGGTATCACCAGCGGCCTGGCCAG

CCTCCCAGACTGCTGATCTACAAGGTGTCCCTGCGGTTCTCCGGCGTGCC

CGACGATTTTCCGGCTCTGGCGCTGGCAAGGACTTCACCCTGAAGATCTC

CCGGGTGGAAGCCGAGGACGTGGGCGTGTACTACTGCTCCCAGAGCACCC

ACGTGCCCCCTACATTTGGCCAGGGCACCAACTGGAAATCAAGCGGACCG

TGGCCGCCCCCAGCGTGTTCATCTTCCCTCCCAGCGACGAGCAGCTGAAG

TCTGGCACCGCCAGCGTGGTGTGCCTGCTGAACAACTTCTACCCCCGCGA

GGCCAAGGGCAGTGGAAGGTGGACAACGCCCTGCAGAGCGGCAACAGCCA

GGAGAGCGTGACCGAGCAGGACTCCAAGGACAGCACCTACAGCCTGAGCA

GCACCCTGACCCTGAGCAAGGCCGACTACGAGAAGACAAGGTGTACGCCT

GCGAGGTGACCCACCAGGGACTGTCTAGCCCCGTGACCAAGAGCTTCAAC

CGGGGCGAGTGCTAA.

EXAMPLES

Example 1: Affinity and Kinetics of Test Antibody

The affinity and kinetics of a test antibody were analyzed using Nα,Nα-bis(carboxymethyl)-L-lysine trifluoroacetate salt (Sigma-Aldrich, St. Louis, Mo.) as a model substrate for an AGE-modified protein. Label-free interaction analysis was carried out on a BIACORE™ T200 (GE Healthcare, Pittsburgh, Pa.), using a Series S sensor chip CM5 (GE Healthcare, Pittsburgh, Pa.), with Fc1 set as blank, and Fc2 immodilized with the test antibody (molecular weigh of 150,000 Da). The running buffer was a HBS-EP buffer (10 mM HEPES, 150 mM NaCl, 3 mM EDTA and 0.05% P-20, pH of 7.4), at a temperature of 25° C. Software was BIACORE™ T200 evaluation software, version 2.0. A double reference (Fc2-1 and only buffer injection), was used in the analysis, and the data was fitted to a Langmuir 1:1 binding model.

TABLE 1

Experimental set-up of affinity and kinetics analysis
Association and dissociation

| Flow path | Fc1 and Fc2 |
|---|---|
| Flow rate (μl/min.) | 30 |
| Association time (s) | 300 |
| Dissociation time (s) | 300 |
| Sample concentration (μM) | 20 - 5 - 1.25 (x2) - 0.3125 - 0.078 - 0 |

A graph of the response versus time is illustrated in FIG. 1. The following values were determined from the analysis: $k_a$ (1/Ms)=1.857×10$^3$; $k_d$ (1/s)=6.781×10$^{-3}$; $K_D$ (M)=3.651× 10$^{-6}$; $R_{max}$ (RU)=19.52; and Chi$^2$=0.114. Because the Chi$^2$ value of the fitting is less than 10% of $R_{max}$, the fit is reliable.

Example 2: Construction and Production of Murine Anti-AGE IgG2b Antibody and Chimeric Anti-AGE IgG1 Antibody Murine and chimeric human anti-AGE antibodies were prepared. The DNA sequence of murine anti-AGE antibody IgG2b heavy chain is shown in SEQ ID NO: 12. The DNA sequence of chimeric human anti-AGE antibody IgG1 heavy chain is shown in SEQ ID NO: 13. The DNA sequence of murine anti-AGE antibody kappa light chain is shown in SEQ ID NO: 14. The DNA sequence of chimeric human anti-AGE antibody kappa light chain is shown in SEQ ID NO: 15. The gene sequences were synthesized and cloned into high expression mammalian vectors. The sequences were codon optimized. Completed constructs were sequence confirmed before proceeding to transfection.

HEK293 cells were seeded in a shake flask one day before transfection, and were grown using serum-free chemically defined media. The DNA expression constructs were transiently transfected into 0.03 liters of suspension HEK293 cells. After 20 hours, cells were sampled to obtain the viabilities and viable cell counts, and titers were measured (Octet QKe, ForteBio). Additional readings were taken throughout the transient transfection production runs. The cultures were harvested on day 5, and an additional sample for each was measured for cell density, viability and titer.

The conditioned media for murine and chimeric anti-AGE antibodies were harvested and clarified from the transient transfection production runs by centrifugation and filtration. The supernatants were run over a Protein A column and eluted with a low pH buffer. Filtration using a 0.2 μm membrane filter was performed before aliquoting. After purification and filtration, the protein concentrations were calculated from the OD280 and the extinction coefficient. A summary of yields and aliquots is shown in Table 2:

TABLE 2

Yields and Aliquots

| Protein | Concentration (mg/mL) | Volume (mL) | No. of vials | Total Yield (mg) |
|---|---|---|---|---|
| Murine anti-AGE | 0.08 | 1.00 | 3 | 0.24 |
| Chimeric anti-AGE | 0.23 | 1.00 | 3 | 0.69 |

CE-SDS analysis was performed (LabChip GXII, Perkin Elmer) and the electropherograms were plotted.

Example 3: Binding of Murine (Parental) and Chimeric Anti-AGE Antibodies

The binding of the murine (parental) and chimeric anti-AGE antibodies described in Example 2 was investigated by a direct binding ELISA. An anti-carboxymethyl lysine (CML) antibody (R&D Systems, MAB3247) was used as a control. CML was conjugated to KLH (CML-KLH) and both CML and CML-KLH were coated overnight onto an ELISA plate. HRP-goat anti-mouse Fc was used to detect the control and murine (parental) anti-AGE antibodies. HRP-goat anti-human Fc was used to detect the chimeric anti-AGE antibody.

The antigens were diluted to 1 μg/mL in 1× phosphate buffer at pH 6.5. A 96-well microtiter ELISA plate was coated with 100 μL/well of the diluted antigen and let sit at 4° C. overnight. The plate was blocked with 1× PBS, 2.5% BSA and allowed to sit for 1-2 hours the next morning at room temperature. The antibody samples were prepared in serial dilutions with 1× PBS, 1% BSA with the starting concentration of 50 μg/mL. Secondary antibodies were diluted 1:5,000. 100 μL of the antibody dilutions was applied to each well. The plate was incubated at room temperature for 0.5-1 hour on a microplate shaker. The plate was washed 3 times with 1× PBS. 100 μL/well diluted HRP-conjugated goat anti-human Fc secondary antibody was applied to the wells. The plate was incubated for 1 hour on a microplate shaker. The plate was then washed 3 times with 1× PBS. 100 μL HRP substrate TMB was added to each well to develop the plate. After 3-5 minutes elapsed, the reaction was terminated by adding 100 μL of 1N HCl. A second direct binding ELISA was performed with only CML coating. The absorbance at OD450 was read using a microplate reader.

The OD450 absorbance raw data for the CML and CML-KLH ELISA is shown in the plate map below. 48 of the 96 wells in the well plate were used. Blank wells in the plate map indicate unused wells.

Plate Map of CML and CML-KLH ELISA:

| Conc. (ug/mL) | 1 | 2 | 3 | 4 | 5 | 6 | 7 |
|---|---|---|---|---|---|---|---|
| 50 | 0.462 | 0.092 | 0.42 | | 1.199 | 0.142 | 1.852 |
| 16.67 | 0.312 | 0.067 | 0.185 | | 0.31 | 0.13 | 0.383 |
| 5.56 | 0.165 | 0.063 | 0.123 | | 0.19 | 0.115 | 0.425 |
| 1.85 | 0.092 | 0.063 | 0.088 | | 0.146 | 0.099 | 0.414 |
| 0.62 | 0.083 | 0.072 | 0.066 | | 0.108 | 0.085 | 0.248 |
| 0.21 | 0.075 | 0.066 | 0.09 | | 0.096 | 0.096 | 0.12 |
| 0.07 | 0.086 | 0.086 | 0.082 | | 0.098 | 0.096 | 0.098 |
| 0 | 0.09 | 0.085 | 0.12 | | 0.111 | 0.083 | 0.582 |
| | R&D Positive Control | Parental Anti-AGE | Chimeric Anti-AGE | | R&D Positive Control | Parental Anti-AGE | Chimeric Anti-AGE |
| | CML-KLH Coat | | | | CML Coat | | |

The OD450 absorbance raw data for the CML-only ELISA is shown in the plate map below. 24 of the 96 wells in the well plate were used. Blank wells in the plate map indicate unused wells.

Plate Map of CML-Only ELISA:

| Conc. (ug/mL) | 1 | 2 | 3 | 4 | 5 | 6 | 7 |
|---|---|---|---|---|---|---|---|
| 50 | 1.913 | 0.165 | 0.992 | | | | |
| 16.66667 | 1.113 | 0.226 | 0.541 | | | | |
| 5.555556 | 0.549 | 0.166 | 0.356 | | | | |
| 1.851852 | 0.199 | 0.078 | 0.248 | | | | |
| 0.617284 | 0.128 | 0.103 | 0.159 | | | | |
| 0.205761 | 0.116 | 0.056 | 0.097 | | | | |
| 0.068587 | 0.073 | 0.055 | 0.071 | | | | |
| 0 | 0.053 | 0.057 | 0.06 | | | | |
| | R&D Positive Control | Parental Anti-AGE | Chimeric Anti-AGE | | | | |

The OD450 absorbance data was also plotted against antibody concentration.

The control and chimeric anti-AGE antibodies showed binding to both CML and CML-KLH. The murine (parental) anti-AGE antibody showed very weak to no binding to either CML or CML-KLH. Data from repeated ELISA confirms binding of the control and chimeric anti-AGE to CML. All buffer control showed negative signal.

Example 4: Humanized Antibodies

Humanized antibodies were designed by creating multiple hybrid sequences that fuse select parts of the parental (mouse) antibody sequence with the human framework sequences. Acceptor frameworks were identified based on the overall sequence identity across the framework, matching interface position, similarly classed CDR canonical positions, and presence of N-glycosylation sites that would have to be removed. Three humanized light chains and three humanized heavy chains were designed based on two different heavy and light chain human acceptor frameworks. The amino acid sequences of the heavy chains are shown in SEQ ID NO: 29, 31 and 33, which are encoded by the DNA sequences shown in SEQ ID NO: 30, 32 and 34, respectively. The amino acid sequences of the light chains are shown in SEQ ID NO: 35, 37 and 39, which are encoded by the DNA sequences shown in SEQ ID NO: 36, 38 and 40, respectively. The humanized sequences were methodically analyzed by eye and computer modeling to isolate the sequences that would most likely retain antigen binding. The goal was to maximize the amount of human sequence in the final humanized antibodies while retaining the original antibody specificity. The light and heavy humanized chains could be combined to create nine variant fully humanized antibodies.

The three heavy chains and three light chains were analyzed to determine their humanness. Antibody humanness scores were calculated according to the method described in Gao, S. H., et al., "Monoclonal antibody humanness score and its applications", BMC Biotechnology, 13:55 (Jul. 5, 2013). The humanness score represents how human-like an antibody variable region sequence looks. For heavy chains a score of 79 or above is indicative of looking human-like; for light chains a score of 86 or above is indicative of looking human-like. The humanness of the three heavy chains, three light chains, a parental (mouse) heavy chain and a parental (mouse) light chain are shown below in Table 3:

TABLE 3

Antibody humanness

| Antibody | Humanness (Framework + CDR) |
|---|---|
| Parental (mouse) heavy chain | 63.60 |
| Heavy chain 1 (SEQ ID NO: 29) | 82.20 |
| Heavy chain 2 (SEQ ID NO: 31) | 80.76 |
| Heavy chain 3 (SEQ ID NO: 33) | 81.10 |
| Parental (mouse) light chain | 77.87 |
| Light chain 1 (SEQ ID NO: 35) | 86.74 |
| Light chain 2 (SEQ ID NO: 37) | 86.04 |
| Light chain 3 (SEQ IN NO: 39) | 83.57 |

Full-length antibody genes were constructed by first synthesizing the variable region sequences. The sequences were optimized for expression in mammalian cells. These variable region sequences were then cloned into expression vectors that already contain human Fc domains; for the heavy chain, the IgG1 was used.

Small scale production of humanized antibodies was carried out by transfecting plasmids for the heavy and light chains into suspension HEK293 cells using chemically defined media in the absence of serum. Whole antibodies in the conditioned media were purified using MabSelect SuRe Protein A medium (GE Healthcare).

Nine humanized antibodies were produced from each combination of the three heavy chains having the amino acid sequences shown in SEQ ID NO: 29, 31 and 33 and three light chains having the amino acid sequences shown in SEQ ID NO: 35, 37 and 39. A comparative chimeric parental antibody was also prepared. The antibodies and their respective titers are shown below in Table 4:

TABLE 4

The antibodies and their respective titers

| Antibody | Titer (mg/L) |
|---|---|
| Chimeric parental | 23.00 |
| SEQ ID NO: 29 + SEQ ID NO: 35 | 24.67 |
| SEQ ID NO: 29 + SEQ ID NO: 37 | 41.67 |
| SEQ ID NO: 29 + SEQ ID NO: 39 | 29.67 |
| SEQ ID NO: 31 + SEQ ID NO: 35 | 26.00 |
| SEQ ID NO: 31 + SEQ ID NO: 37 | 27.33 |
| SEQ ID NO: 31 + SEQ ID NO: 39 | 35.33 |
| SEQ ID NO: 33 + SEQ ID NO: 35 | 44.00 |
| SEQ ID NO: 33 + SEQ ID NO: 37 | 30.33 |
| SEQ ID NO: 33 + SEQ ID NO: 39 | 37.33 |

The binding of the humanized antibodies may be evaluated, for example, by dose-dependent binding ELISA or cell-based binding assay.

Example 5: Immunohistochemical Study

Tissue samples were obtained from patients with Alzheimer's disease and Parkinson's disease. Two Alzheimer's disease samples were taken from the hippocampus. One Parkinson's disease sample was taken from the substantia nigra, and a second Parkinson's disease sample was taken from the ventral tegmental area. All cells were stained for carboxymethyllysine (CML) using anti-AGE antibodies as described above. The Alzheimer's disease cells were stained for phosphorylated tau (phospho tau) or separately amyloid precursor protein. The Parkinson's disease cells were stained for alpha synuclein. Nuclear staining of the cells was identified using DAPI counter stain. (Experiments were carried out and images were prepared by Dr. Diego Mastroeni of Arizona State University.)

Figure 2A:
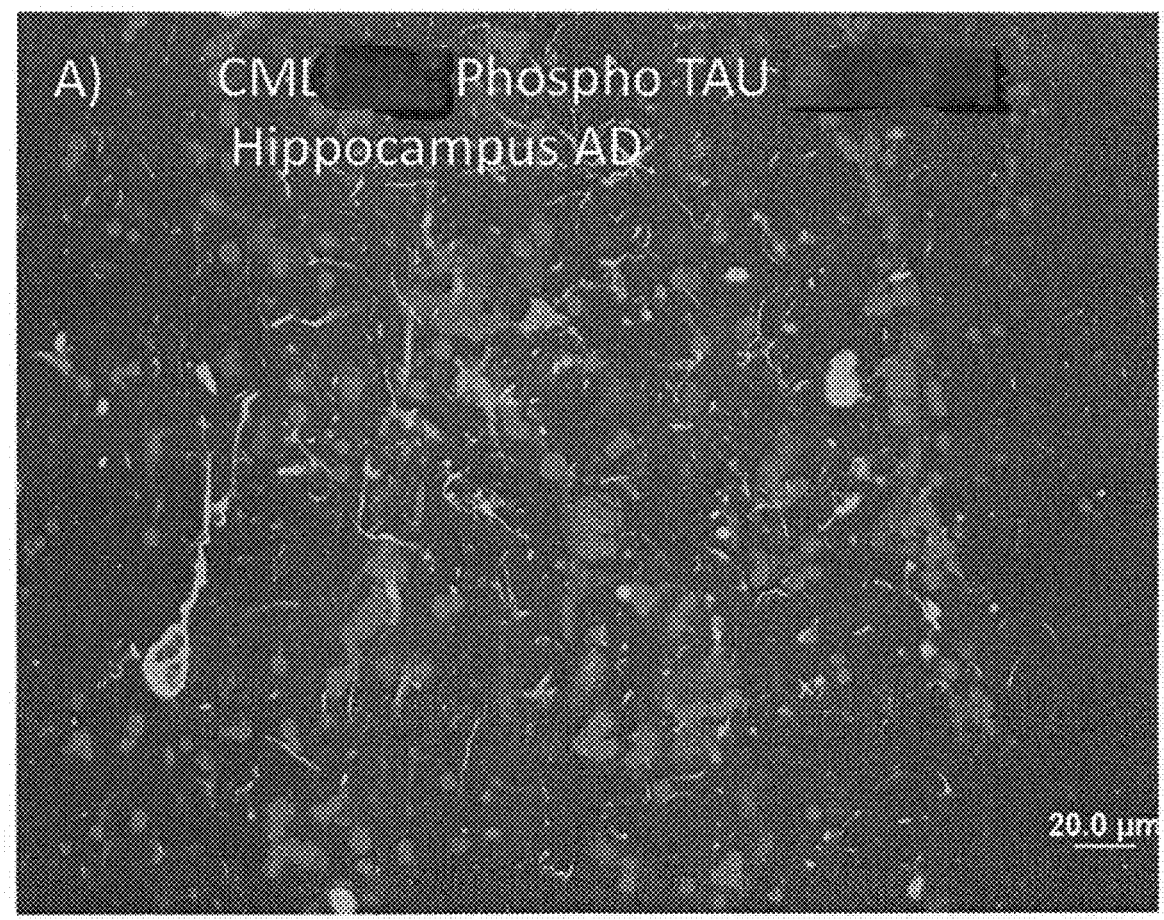
FIG. 2A is a photograph of cells of an Alzheimer's disease sample showing carboxymethyllysine stained gray and phosphorylated tau stained light gray.

FIG. 2A is a photograph of cells of the Alzheimer's disease sample showing carboxymethyllysine stained red and phosphorylated tau stained green.

Figure 2B:
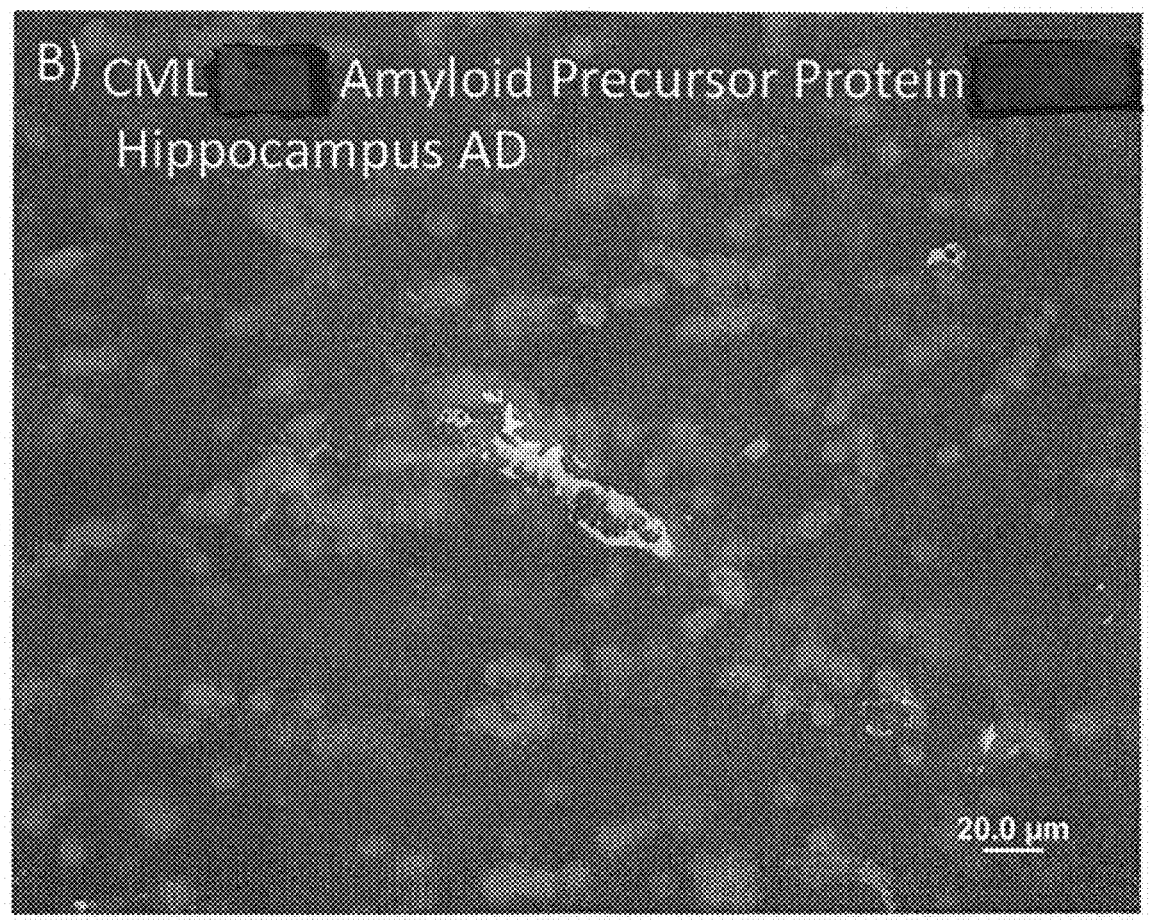
FIG. 2B is a photograph of cells of an Alzheimer's disease sample showing carboxymethyllysine stained gray red and amyloid precursor protein stained light gray.

FIG. 2B is a photograph of cells of the Alzheimer's disease sample showing carboxymethyllysine stained red and amyloid precursor protein stained green.

Figure 2C:
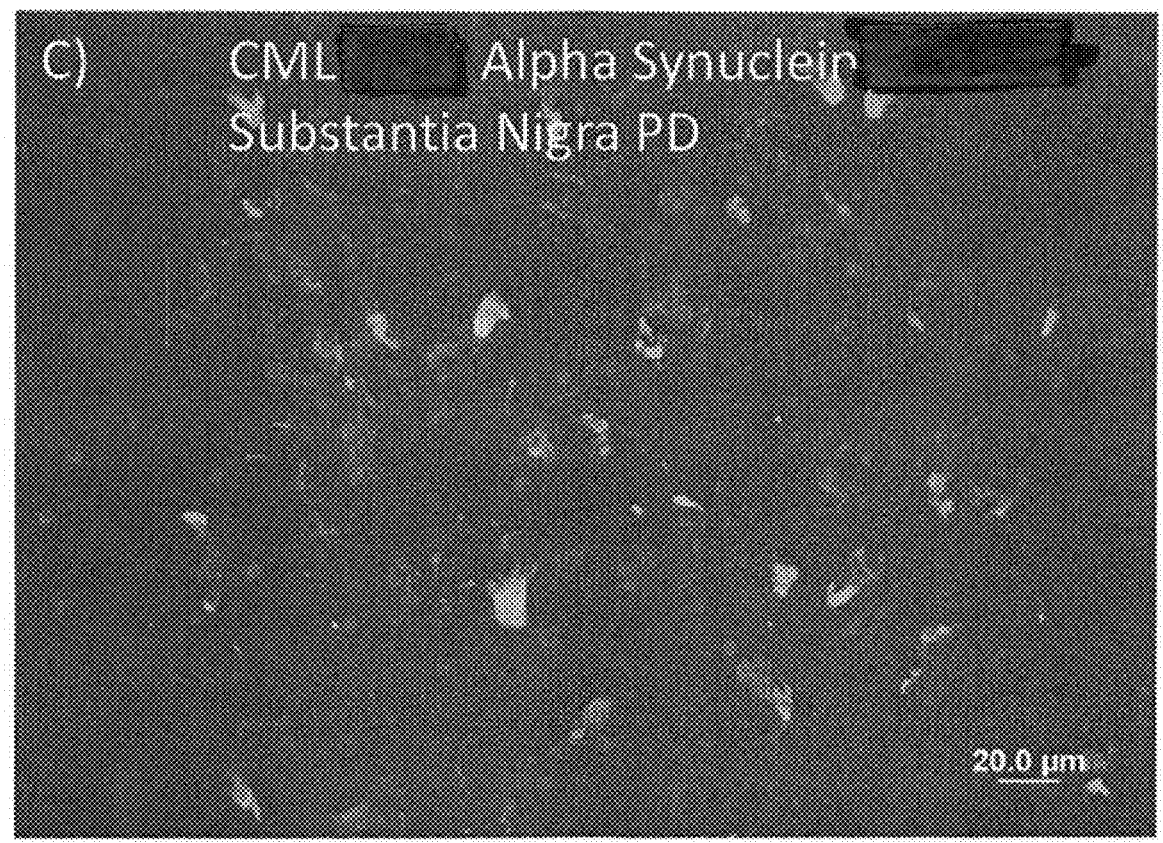
FIG. 2C is a photograph of cells of a Parkinson's disease sample from the substantia nigra showing carboxymethyllysine stained gray and alpha synuclein stained light gray.

FIG. 2C is a photograph of cells of the Parkinson's disease sample from the substantia nigra showing carboxymethyllysine stained red and alpha synuclein stained green.

Figure 2D:
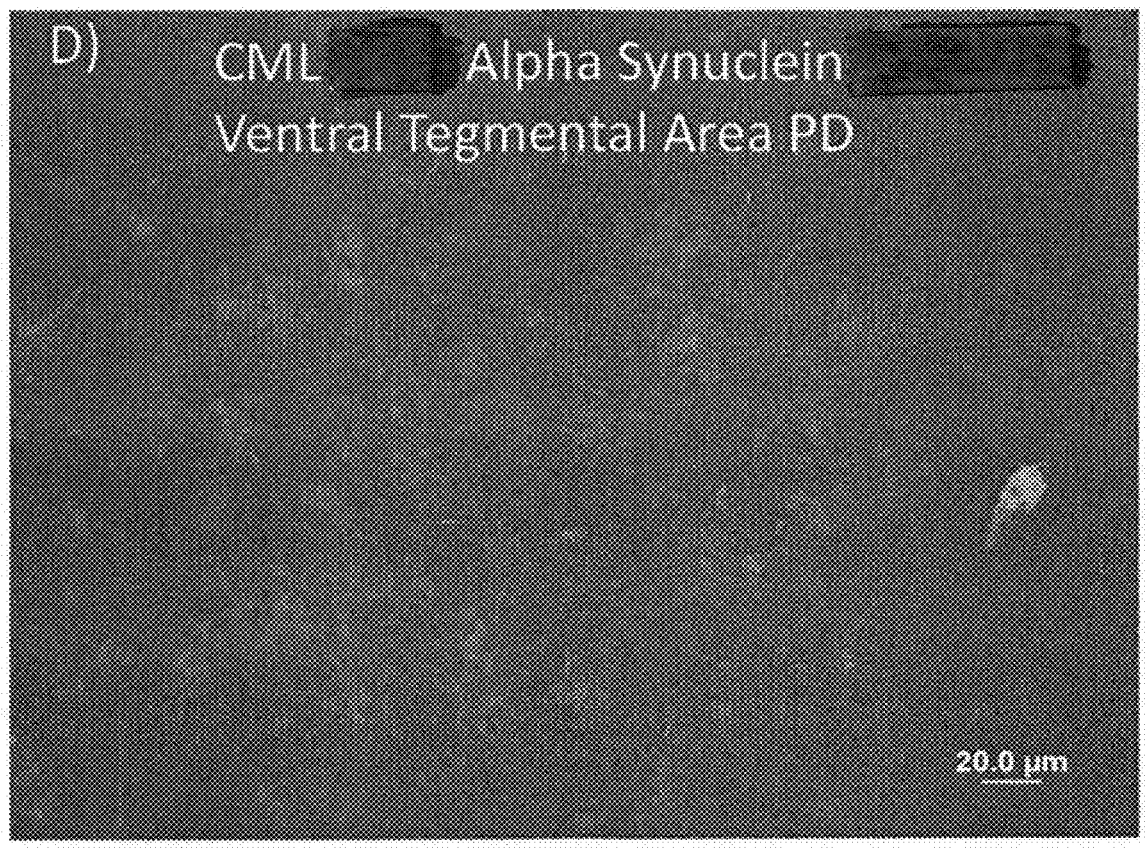
FIG. 2D is a photograph of cells of a Parkinson's disease sample from the ventral tegmental area showing carboxymethyllysine stained gray and alpha synuclein stained light gray.

FIG. 2D is a photograph of cells of the Parkinson's disease sample from the ventral tegmental area showing carboxymethyllysine stained red and alpha synuclein stained green.

CML, a well-known AGE, did not co-localize with established pathologies in Alzheimer's disease and Parkinson's disease. Instead, the CML presented on glial cells. It was suspected that the CML immunoreactivity in the Alzheimer's disease samples was with microglia, and the CML immunoreactivity in the Parkinson's disease samples was with astrocytes. The results demonstrate the presence of senescent glial cells in Alzheimer's disease and Parkinson's disease. Removal of senescent glial cells using an anti-AGE antibody would be expected to result in regeneration of the glial cells by neural stem/progenitor cells. (See, for example, Leonard, B. W. et al., "Subventricular zone neural progenitors from rapid brain autopsies of elderly subjects with and without neurodegenerative disease", The Journal of Comparative Neurology, Vol. 515, pp. 269-294 (2009)).

REFERENCES

1. International Application Pub. No. WO 2009/143411 to Gruber (26 Nov. 2009).
2. U.S. Pat. No. 5,702,704 to Bucala (issued Dec. 30, 1997).
3. U.S. Pat. No. 6,380,165 to Al-Abed et al. (issued Apr. 30, 2002).
4. U.S. Pat. No. 6,387,373 to Wright et al. (issued May 14, 2002).
5. U.S. Pat. No. 4,217,344 to Vanlerberghe et al. (issued Aug. 12, 1980).
6. U.S. Pat. No. 4,917,951 to Wallach (issued Apr. 17, 1990).
7. U.S. Pat. No. 4,911,928 to Wallach (issued Mar. 27, 1990).
8. U.S. Patent Application Publication Pub. No. US 2010/226932 to Smith et al. (Sep. 9, 2010).
9. Ando K, et al., "Membrane Proteins of Human Erythrocytes Are Modified by Advanced Glycation End Products During Aging in the Circulation," *Biochemical and Biophysical Research Communications*, Vol. 258, 123-27 (1999).
10. Lindsey J B, et al., "Receptor For Advanced Glycation End-Products (RAGE) and soluble RAGE (sRAGE): Cardiovascular Implications," *Diabetes Vascular Disease Research*, Vol. 6(1), 7-14, (2009).
11. Bierhaus A, "AGEs and their interaction with AGE-receptors in vascular disease and diabetes mellitus. I. The AGE concept," Cardiovasc Res, Vol. 37(3), 586-600 (1998).
12. Meuter A., et al. "Markers of cellular senescence are elevated in murine blastocysts cultured in vitro: molecular consequences of culture in atmospheric oxygen" J Assist Reprod Genet. 2014 Aug. 10. [Epub ahead of print].
13. Baker, D. J. et al., "Clearance of p16Ink4a-positive senescent cells delays ageing-associated disorders", Nature, vol. 479, pp. 232-236, (2011).
14. Jana Hadrabová, et al. "Chicken immunoglobulins for prophylaxis: Effect of inhaled antibodies on inflammatory parameters in rat airways" Journal of Applied Biomedicine (in press; Available online 5 May 2014).
15. Vlassara, H. et al., "High-affinity-receptor-mediated Uptake and Degradation of Glucose-modified Proteins: A Potential Mechanism for the Removal of Senescent Macromolecules", *Proc. Natl. Acad. Sci. USA*, Vol. 82, 5588, 5591 (1985).
16. Roll, P. et al., "Anti-CD20 Therapy in Patients with Rheumatoid Arthritis", *Arthritis & Rheumatism*, Vol. 58, No. 6, 1566-1575 (2008).
17. Kajstura, J. et al., "Myocite Turnover in the Aging Human Heart", *Circ. Res.*, Vol. 107(11), 1374-86, (2010).
18. de Groot, K. et al., "Vascular Endothelial Damage and Repair in Antineutrophil Cytoplasmic Antibody-Associated Vasculitis", *Arthritis and Rheumatism*, Vol. 56(11), 3847, 3847 (2007).
19. Manesso, E. et al., "Dynamics of β-Cell Turnover: Evidence for β-Cell Turnover and Regeneration from Sources of β-Cells other than β-cell Replication in the HIP Rat", *Am. J. Physiol. Endocrinol. Metab.*, Vol. 297, E323, E324 (2009).
20. Kirstein, M. et al., "Receptor-specific Induction of Insulin-like Growth Factor I in Human Monocytes by Advanced Glycosylation End Product-modified Proteins", *J. Clin. Invest.*, Vol. 90, 439, 439-440 (1992).
21. Murphy, J. F., "Trends in cancer immunotherapy", *Clinical Medical Insights: Oncology*, Vol. 14(4), 67-80 (2010).
22. Virella, G. et al., "Autoimmune Response to Advanced Glycosylation End-Products of Human LDL", *Journal of Lipid Research*, Vol. 44, 487-493 (2003).
23. Ameli, S. et al., "Effect of Immunization With Homologous LDL and Oxidized LDL on Early Atherosclerosis in Hypercholesterolemic Rabbits", *Arteriosclerosis, Thrombosis, and Vascular Biology*, Vol. 16, 1074 (1996).
24. "Sarcopenia", available online at en.wikipedia.org/wiki/Sarcopenia (Nov. 14, 2014).
25. "What is sarcopenia?", available online at www.iofbonehealth.org/what-sarcopenia (2014).
26. Bland, W., "Sarcopenia with aging", available online at www.webmd.com/healthy-aging/sarcopenia-with-aging (Aug. 3, 2014).
27. "Keyhole limpet hemocyanin", available online at en.wikipedia.org/wiki/Keyhole_limpet_hemocyanin (Apr. 18, 2014).
28. "CML-BSA Product Data Sheet", available online at www.cellbiolabs.com/sites/default/files/STA-314-cml-bsa.pdf (2010).
29. "CML (N-epsilon-(Carboxymethyl)Lysine) Assays and Reagents", available online at www.cellbiolabs.com/cml-assays (Accessed on Dec. 15, 2014).
30. Cruz-Jentoft, A. J. et al., "Sarcopenia: European consensus on definition and diagnosis", Age and Ageing, Vol. 39, pp. 412-423 (Apr. 13, 2010).
31. Rolland, Y. et al., "Sarcopenia: its assessment, etiology, pathogenesis, consequences and future perspectives", *J. Nutr. Health Aging*, Vol. 12(7), pp. 433-450 (2008).
32. Mera, K. et al., "An autoantibody against $N^\varepsilon$-(carboxyethyl)lysine (CEL): Possible involvement in the removal of CEL-modified proteins by macrophages", *Biochemical and Biophysical Research Communications*, Vol. 407, pp. 420-425 (Mar. 12, 2011).
33. Reddy, S. et al., "$N^\varepsilon$-(carboxymethyl)lysine is a dominant advanced glycation end product (AGE) antigen in tissue proteins", *Biochemistry*, Vol. 34, pp. 10872-10878 (Aug. 1, 1995).
34. Naylor, R. M. et al., "Senescent cells: a novel therapeutic target for aging and age-related diseases", *Clinical Pharmacology & Therapeutics*, Vol. 93(1), pp. 105-116 (Dec. 5, 2012).
35. Katcher, H. L., "Studies that shed new light on aging", *Biochemistry* (Moscow), Vol. 78(9), pp. 1061-1070 (2013).
36. Ahmed, E. K. et al., "Protein Modification and Replicative Senescence of WI-38 Human Embryonic Fibroblasts", *Aging Cells*, Vol. 9, 252, 260 (2010).

37. Vlassara, H. et al., "Advanced Glycosylation Endproducts on Erythrocyte Cell Surface Induce Receptor-Mediated Phagocytosis by Macrophages", *J. Exp. Med.*, Vol. 166, 539, 545 (1987).
38. Fielding, R. A., et al., "Sarcopenia: an undiagnosed condition in older adults. Current consensus definition: prevalence, etiology, and consequences", *Journal of the American Medical Directors Association*, Vol. 12(4), pp. 249-256 (May 2011).
39. Maass, D. R. et al., "Alpaca (*Lama pacos*) as a convenient source of recombinant camelid heavy chain antibodies (VHHs)", Journal of Immunological Methods, Vol. 324, No. 1-2, pp. 13-25 (Jul. 31, 2007).
40. Strietzel, C. J. et al., "In vitro functional characterization of feline IgGs", Veterinary Immunology and Immunopathology, Vol. 158, pp. 214-223 (2014).
41. Patel, M. et al., "Sequence of the dog immunoglobulin alpha and epsilon constant region genes", Immunogenetics, Vol. 41, pp. 282-286 (1995).
42. Wagner, B. et al., "The complete map of the Ig heavy chain constant gene region reveals evidence for seven IgG isotypes and for IgD in the horse", The Journal of Immunology, Vol. 173, pp. 3230-3242 (2004).
43. Hamers-Casterman, C. et al., "Naturally occurring antibodies devoid of light chains", Nature, Vol. 363, pp. 446-448 (Jun. 3, 1993).
44. De Genst, E. et al., "Antibody repertoire development in camelids", Developmental & Comparative Immunology, Vol. 30, pp. 187-198 (available online Jul. 11, 2005).
45. Griffin, L. M. et al., "Analysis of heavy and light chain sequences of conventional camelid antibodies from *Camelus dromedarius* and *Camelus bactrianus* species", Journal of Immunological Methods, Vol. 405, pp. 35-46 (available online Jan. 18, 2014).
46. Nguyen, V. K. et al., "Camel heavy-chain antibodies: diverse germline $V_H H$ and specific mechanisms enlarge the antigen-binding repertoire", The European Molecular Biology Organization Journal, Vol. 19, No, 5, pp. 921-930 (2000).
47. Muyldermans, S. et al., "Sequence and structure of $V_H$ domain from naturally occurring camel heavy chain immunoglobulins lacking light chains", Protein Engineering, Vol. 7, No. 9, pp. 1129-1135 (1994).
48. Wesolowski, J. et al., "Single domain antibodies: promising experimental and therapeutic tools in infection and immunity", Medical Microbiology and Immunology, Vol. 198, pp. 157-174 (Jun. 16, 2009).
49. Yan, S. F. et al., "Soluble RAGE: therapy & biomarker in unraveling the RAGE axis in chronic disease and aging", Biochemical Pharmacology, Vol. 79, No. 10, pp. 1379-1386 (May 15, 2010).
50. Chen, K. S. et al., "Monoclonal antibody therapy for malignant glioma", Glioma: Immunotherapeutic Approaches, pp. 121-141 (2012).
51. Gao, S. H., et al., "Monoclonal antibody humanness score and its applications", BMC Biotechnology, 13:55 (Jul. 5, 2013).
52. Feige, M. J. et al., "The structural analysis of shark IgNAR antibodies reveals evolutionary principles of immunoglobulins", Proceedings of the National Academy of Sciences of the United States of America, Vol. 111, No. 22, pp. 8155-8160 (Jun. 3, 2014).
53. Romagosa, C. et al., p16$^{Ink4a}$ overexpression in cancer: a tumor suppressor gene associated with senescence and high-grade tumors, Oncogene, Vol. 30, 2087-2097 (2011).
54. Di, G-h. et al. IL-6 Secreted from Senescent Mesenchymal Stem Cells Promotes Proliferation and migration of Breast Cancer Cells, *PLOS One*, Vol. 9, 11, e113572 (2014)
55. Liu, D. et al. Senescent Human Fibroblasts Increase the Early Growth of Xenograft Tumors via Matrix Metalloproteinase Secretion, *Cancer Res*, Vol. 67, 3117-3126 (2007)
56. Nelson, G., A senescent cell bystander effect: senescence-induced senescence, *Aging Cell*, Vol. 11, 345-349 (2012)
57. Rayess, H. et al., Cellular senescence and tumor suppressor gene p16, *Int J Cancer*, Vol. 130, 1715-1725 (2012)
58. Fu, M.-X., et al., The Advanced Glycation End Product, $N^E$-(Carboxymehtyl)lysine, Is a Product of both Lipid Peroxidation and Glycoxidation Reactions, *J. Biol. Chem.*, Vol. 271, 9982-9986 (1996)
59. Matus et al., Invasive Cell Fate Requires G1 Cell-Cycle arrest and Histone Deacetylase-Mediated Changes in Gene Expression, *Developmental Cell*, Vol. 35, 162-174 (2015)
60. Blasko, C. et al., "Glial cells: astrocytes and oligodendrocytes during normal brain aging", Encyclopedia of Neuroscience, Academic Press, pp. 743-747 (2009)
61. Danysz, W. et al., "Alzheimer's disease, β-amyloid, glutamate, NMDA receptors and memantine—searching for the connections", British Journal of Pharmacology, Vol. 167, pp. 324-352 (2012)
62. Garcia-Matas, S. et al., "Dysfunction of astrocytes in senescence-accelerated mice SAM P8 reduces their neuroprotective capacity", Aging Cell, Vol. 7, pp. 630-640 (2008)
63. Nie, H. et al., "Impaired glial glutamate uptake induces extrasynaptic glutamate spillover in the spinal sensory synapses of neuropathic rats", Journal of Neurophysiology, Vol. 103, pp. 2570-2580 (2010)
64. Leonard, B. W. et al., "Subventricular zone neural progenitors from rapid brain autopsies of elderly subjects with and without neurodegenerative disease", The Journal of Comparative Neurology, Vol. 515, pp. 269-294 (2009)

What is claimed is:

1. A method of treating a neurodegenerative disorder, comprising killing or inducing apoptosis in senescent glial cells by administering to a patient in need thereof, a composition comprising an advanced glycation end-product (AGE) antibody,
   wherein the AGE antibody is cytotoxic,
   the AGE antibody binds a carboxymethyllysine-modified protein,
   the neurodegenerative disorder is Alzheimer's disease (AD) or Parkinson's disease (PD),
   the AGE antibody comprises
   a heavy chain, and
   a light chain,
   the heavy chain comprises a sequence selected from the group consisting of SEQ ID NO: 29, SEQ ID NO: 31, and SEQ ID NO: 33, and
   the light chain comprises a sequence selected from the group consisting of SEQ ID NO: 35, SEQ ID NO: 37, and SEQ ID NO: 39.

2. The method of claim 1, wherein the composition further comprises a pharmaceutically acceptable carrier.

3. The method of claim 1, wherein the composition further comprises:
   (i) a pharmaceutically acceptable carrier,
   (ii) serum, and
   (iii) natural killer cells.

4. The method of claim 1, wherein the administering comprises administering the composition to the central nervous system of the patient.

5. The method of claim 4, wherein the composition is administered to the central nervous system of a subject by intrathecal administration, intraventricular administration or by convection enhanced delivery.

6. The method of claim 1, wherein the AGE antibody is a single domain antibody conjugated to an agent selected from the group consisting of a toxin, a cytotoxic agent, magnetic nanoparticles, and magnetic spin-vortex discs.

7. The method of claim 1, wherein the neurodegenerative disorder comprises Alzheimer's disease.

8. The method of claim 7, wherein the senescent glial cells are senescent astrocytes and/or senescent microglial cells.

9. The method of claim 1, wherein
the composition is sterile, and
the composition is in unit dosage form.

10. The method of claim 1, wherein the composition further comprises immune system cells.

11. The method of claim 10, wherein the immune system cells are from the subject.

12. The method of claim 10, wherein the immune system cells comprise natural killer cells.

13. The method of claim 10, wherein the natural killer cells are from the subject.

14. The method of claim 10, wherein the immune cells are natural killer cells, and the natural killer cells comprise artificial natural killer cells.

15. The method of claim 1, wherein the antibody has a rate of dissociation of at most $9 \times 10^{-3}$ sec$^{-1}$.

16. The method of claim 1, wherein the neurodegenerative disorder comprises Parkinson's disease (PD).

17. The method of claim 1, wherein the composition further comprises serum.

18. The method of claim 17, wherein the serum is autologous serum.

19. The method of claim 1, wherein the senescent glial cells are senescent astrocytes and/or senescent microglial cells.

20. The method of claim 1, wherein the patient is a human.

* * * * *

SEQUENCE LISTING

```
<160> NUMBER OF SEQ ID NOS: 40

<210> SEQ ID NO 1
<211> LENGTH: 463
<212> TYPE: PRT
<213> ORGANISM: Artificial sequence
<220> FEATURE:
<223> OTHER INFORMATION: Modified Homo sapiens immunoglobulin G1 heavy
      chain
```

<400> SEQUENCE: 1

```
Met Asn Leu Leu Leu Ile Leu Thr Phe Val Ala Ala Val Ala Gln
1               5                   10                  15

Val Gln Leu Leu Gln Pro Gly Ala Glu Leu Val Lys Pro Gly Ala Ser
            20                  25                  30

Val Lys Leu Ala Cys Lys Ala Ser Gly Tyr Leu Phe Thr Thr Tyr Trp
        35                  40                  45

Met His Trp Leu Lys Gln Arg Pro Gly Gln Gly Leu Glu Trp Ile Gly
    50                  55                  60

Glu Ile Ser Pro Thr Asn Gly Arg Ala Tyr Tyr Asn Ala Arg Phe Lys
65                  70                  75                  80

Ser Glu Ala Thr Leu Thr Val Asp Lys Ser Ser Asn Thr Ala Tyr Met
                85                  90                  95

Gln Leu Ser Ser Leu Thr Ser Glu Ala Ser Ala Val Tyr Tyr Cys Ala
            100                 105                 110

Arg Ala Tyr Gly Asn Tyr Glu Phe Ala Tyr Trp Gly Gln Gly Thr Leu
        115                 120                 125

Val Thr Val Ser Val Ala Ser Thr Lys Gly Pro Ser Val Phe Pro Leu
130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
210                 215                 220

Thr Lys Val Asp Lys Lys Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415
```

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys
        450                 455                 460

<210> SEQ ID NO 2
<211> LENGTH: 118
<212> TYPE: PRT
<213> ORGANISM: Mus musculus

<400> SEQUENCE: 2

Gln Val Gln Leu Leu Gln Pro Gly Ala Glu Leu Val Lys Pro Gly Ala
1               5                   10                  15

Ser Val Lys Leu Ala Cys Lys Ala Ser Gly Tyr Leu Phe Thr Thr Tyr
            20                  25                  30

Trp Met His Trp Leu Lys Gln Arg Pro Gly Gln Gly Leu Glu Trp Ile
        35                  40                  45

Gly Glu Ile Ser Pro Thr Asn Gly Arg Ala Tyr Tyr Asn Ala Arg Phe
    50                  55                  60

Lys Ser Glu Ala Thr Leu Thr Val Asp Lys Ser Ser Asn Thr Ala Tyr
65                  70                  75                  80

Met Gln Leu Ser Ser Leu Thr Ser Glu Ala Ser Ala Val Tyr Tyr Cys
                85                  90                  95

Ala Arg Ala Tyr Gly Asn Tyr Glu Phe Ala Tyr Trp Gly Gln Gly Thr
            100                 105                 110

Leu Val Thr Val Ser Val
        115

<210> SEQ ID NO 3
<211> LENGTH: 234
<212> TYPE: PRT
<213> ORGANISM: Artificial sequence
<220> FEATURE:
<223> OTHER INFORMATION: Modified Homo sapiens immunoglobulin G1 kappa
      light chain

<400> SEQUENCE: 3

Met Asn Leu Leu Leu Ile Leu Thr Phe Val Ala Ala Ala Val Ala Asp
1               5                   10                  15

Val Val Met Thr Gln Thr Pro Leu Ser Leu Pro Val Ser Leu Gly Asp
            20                  25                  30

Gln Ala Ser Ile Ser Cys Arg Ser Arg Gln Ser Leu Val Asn Ser Asn
        35                  40                  45

Gly Asn Thr Phe Leu Gln Trp Tyr Leu Gln Lys Pro Gly Gln Ser Pro
    50                  55                  60

Lys Leu Leu Ile Tyr Lys Val Ser Leu Arg Phe Ser Gly Val Pro Asp
65                  70                  75                  80

Arg Phe Ser Gly Ser Gly Ser Gly Thr Asp Phe Thr Leu Lys Ile Ser
                85                  90                  95

Arg Val Glu Ala Glu Asp Leu Gly Leu Tyr Phe Cys Ser Gln Ser Thr
            100                 105                 110

His Val Pro Pro Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

```
Leu Lys Ser Gly Thr Ala Ser Val Val Cys Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 4
<211> LENGTH: 113
<212> TYPE: PRT
<213> ORGANISM: Mus musculus

<400> SEQUENCE: 4

```
Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val Asn Ser
            20                  25                  30

Asn Gly Asn Thr Phe Leu Gln Trp Tyr Leu Gln Lys Pro Gly Gln Ser
        35                  40                  45

Pro Lys Leu Leu Ile Tyr Lys Val Ser Leu Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Ser Gln Ser
                85                  90                  95

Thr His Val Pro Pro Thr Phe Gly Gly Gly Thr Lys Leu Glu Ile Lys
            100                 105                 110

Arg
```

<210> SEQ ID NO 5
<211> LENGTH: 327
<212> TYPE: PRT
<213> ORGANISM: Equus caballus

<400> SEQUENCE: 5

```
Ala Ser Thr Thr Ala Pro Lys Val Phe Pro Leu Ala Ser His Ser Ala
1               5                   10                  15

Ala Thr Ser Gly Ser Thr Val Ala Leu Gly Cys Leu Val Ser Ser Tyr
            20                  25                  30

Phe Pro Glu Pro Val Thr Val Ser Trp Asn Ser Gly Ala Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ala Ser Ser Leu Lys Ser Gln Thr
65                  70                  75                  80

Tyr Ile Cys Asn Val Ala His Pro Ala Ser Ser Thr Lys Val Asp Lys
                85                  90                  95

Lys Ile Val Ile Lys Glu Cys Asn Gly Gly Cys Pro Ala Glu Cys Leu
            100                 105                 110
```

```
Gln Val Gly Pro Ser Val Phe Ile Phe Pro Pro Lys Pro Lys Asp Val
            115                 120                 125

Leu Met Ile Ser Arg Thr Pro Thr Val Thr Cys Val Val Val Asp Val
130                 135                 140

Gly His Asp Phe Pro Asp Val Gln Phe Asn Trp Tyr Val Asp Gly Val
145                 150                 155                 160

Glu Thr His Thr Ala Thr Thr Glu Pro Lys Gln Gln Phe Asn Ser
            165                 170                 175

Thr Tyr Arg Val Val Ser Val Leu Pro Ile Gln His Lys Asp Trp Leu
                180                 185                 190

Ser Gly Lys Glu Phe Lys Cys Lys Val Asn Asn Lys Ala Leu Pro Ala
            195                 200                 205

Pro Val Glu Arg Thr Ile Ser Lys Pro Thr Gly Gln Pro Arg Glu Pro
210                 215                 220

Gln Val Tyr Val Leu Ala Pro His Arg Asp Glu Leu Ser Lys Asn Lys
225                 230                 235                 240

Val Ser Val Thr Cys Leu Val Lys Asp Phe Tyr Pro Thr Asp Ile Asp
                245                 250                 255

Ile Glu Trp Lys Ser Asn Gly Gln Pro Glu Pro Glu Thr Lys Tyr Ser
            260                 265                 270

Thr Thr Pro Ala Gln Leu Asp Ser Asp Gly Ser Tyr Phe Leu Tyr Ser
        275                 280                 285

Lys Leu Thr Val Glu Thr Asn Arg Trp Gln Gln Gly Thr Thr Phe Thr
            290                 295                 300

Cys Ala Val Met His Glu Ala Leu His Asn His Tyr Thr Glu Lys Ser
305                 310                 315                 320

Val Ser Lys Ser Pro Gly Lys
                325

<210> SEQ ID NO 6
<211> LENGTH: 415
<212> TYPE: PRT
<213> ORGANISM: Equus caballus

<400> SEQUENCE: 6

Ser Leu Glu Asp Thr Ala Val Ile Pro Leu Phe Ser Glu Cys Lys Ala
1               5                   10                  15

Pro Lys Glu Asp Val Val Ser Leu Ala Cys Leu Val Lys Gly Tyr
            20                  25                  30

Phe Pro Glu Pro Val Gln Val Thr Trp Glu Pro Glu Met Gln Asn Gln
        35                  40                  45

Lys Pro Trp Thr Phe Pro Ala Met Lys Lys Gly Gln Glu Tyr Ile His
    50                  55                  60

Val Phe Ser Leu Thr Thr Trp Trp Lys Pro Gly Ser His Ser Cys Thr
65                  70                  75                  80

Val His His Lys Ala Ser Ser Phe Arg Lys Lys Met Thr Phe Gln Glu
                85                  90                  95

Pro Ala Ser Trp Ala Pro Gln Arg Thr Ser Ala Leu Pro Val Thr Ser
            100                 105                 110

Lys Glu Pro Thr Pro Ala Pro Thr Thr Leu Arg Lys Ser Glu Pro Ser
        115                 120                 125

Thr Arg His Thr Gln Pro Glu Thr Gln Lys Pro Arg Ile Pro Val Asp
    130                 135                 140

Thr Pro Leu Lys Glu Cys Gln Ser His Thr His Pro Pro Ser Ile Tyr
145                 150                 155                 160
```

-continued

Leu Leu His Pro Pro Leu Gln Gly Leu Trp Leu Lys Gly Glu Ala Thr
              165                 170                 175

Phe Thr Cys Leu Val Val Gly Asp Asp Leu Lys Asp Ala His Leu Ser
        180                 185                 190

Trp Glu Leu Ser Glu Arg Ser Asn Gly Met Phe Val Glu Ser Gly Pro
            195                 200                 205

Leu Glu Lys His Thr Asn Gly Ser Gln Ser Arg Ser Ser Arg Leu Ala
        210                 215                 220

Leu Pro Arg Ser Ser Trp Ala Met Gly Thr Ser Val Thr Cys Lys Leu
225                 230                 235                 240

Ser Tyr Pro Asn Leu Leu Ser Ser Met Glu Val Val Gly Leu Lys Glu
                245                 250                 255

His Ala Ala Ser Ala Pro Arg Ser Leu Thr Val His Ala Leu Thr Thr
                260                 265                 270

Pro Gly Leu Asn Ala Ser Pro Gly Ala Thr Ser Trp Leu Gln Cys Lys
            275                 280                 285

Val Ser Gly Phe Ser Pro Pro Glu Ile Val Leu Thr Trp Leu Glu Gly
        290                 295                 300

Gln Arg Glu Val Asp Pro Ser Trp Phe Ala Thr Ala Arg Pro Thr Ala
305                 310                 315                 320

Gln Pro Gly Asn Thr Thr Phe Gln Thr Trp Ser Ile Leu Leu Val Pro
                325                 330                 335

Thr Ile Pro Gly Pro Pro Thr Ala Thr Tyr Thr Cys Val Val Gly His
                340                 345                 350

Glu Ala Ser Arg Gln Leu Leu Asn Thr Ser Trp Ser Leu Asp Thr Gly
        355                 360                 365

Gly Leu Ala Met Thr Pro Glu Ser Lys Asp Glu Asn Ser Asp Tyr
370                 375                 380

Ala Asp Leu Asp Asp Ala Gly Ser Leu Trp Leu Thr Phe Met Ala Leu
385                 390                 395                 400

Phe Leu Ile Thr Leu Leu Tyr Ser Gly Phe Val Thr Phe Ile Lys
                405                 410                 415

<210> SEQ ID NO 7
<211> LENGTH: 334
<212> TYPE: PRT
<213> ORGANISM: Canis familiaris

<400> SEQUENCE: 7

Ser Lys Thr Ser Pro Ser Val Phe Pro Leu Ser Leu Cys His Gln Glu
1               5                   10                  15

Ser Glu Gly Tyr Val Val Ile Gly Cys Leu Val Gln Gly Phe Phe Pro
            20                  25                  30

Pro Glu Pro Val Asn Val Thr Trp Asn Ala Gly Lys Asp Ser Thr Ser
        35                  40                  45

Val Lys Asn Phe Pro Pro Met Lys Ala Ala Thr Gly Ser Leu Tyr Thr
    50                  55                  60

Met Ser Ser Gln Leu Thr Leu Pro Ala Ala Gln Cys Pro Asp Asp Ser
65                  70                  75                  80

Ser Val Lys Cys Gln Val Gln His Ala Ser Ser Pro Ser Lys Ala Val
                85                  90                  95

Ser Val Pro Cys Lys Asp Asn Ser His Pro Cys His Pro Cys Pro Ser
            100                 105                 110

Cys Asn Glu Pro Arg Leu Ser Leu Gln Lys Pro Ala Leu Glu Asp Leu
        115                 120                 125

```
Leu Leu Gly Ser Asn Ala Ser Leu Thr Cys Thr Leu Ser Gly Leu Lys
        130                 135                 140

Asp Pro Lys Gly Ala Thr Phe Thr Trp Asn Pro Ser Lys Gly Lys Glu
145                 150                 155                 160

Pro Ile Gln Lys Asn Pro Glu Arg Asp Ser Cys Gly Cys Tyr Ser Val
                165                 170                 175

Ser Ser Val Leu Pro Gly Cys Ala Asp Pro Trp Asn His Gly Asp Thr
            180                 185                 190

Phe Ser Cys Thr Ala Thr His Pro Glu Ser Lys Ser Pro Ile Thr Val
            195                 200                 205

Ser Ile Thr Lys Thr Thr Glu His Ile Pro Pro Gln Val His Leu Leu
210                 215                 220

Pro Pro Pro Ser Glu Glu Leu Ala Leu Asn Glu Leu Val Thr Leu Thr
225                 230                 235                 240

Cys Leu Val Arg Gly Phe Lys Pro Lys Asp Val Leu Val Arg Trp Leu
                245                 250                 255

Gln Gly Thr Gln Glu Leu Pro Gln Glu Lys Tyr Leu Thr Trp Glu Pro
                260                 265                 270

Leu Lys Glu Pro Asp Gln Thr Asn Met Phe Ala Val Thr Ser Met Leu
            275                 280                 285

Arg Val Thr Ala Glu Asp Trp Lys Gln Gly Glu Lys Phe Ser Cys Met
290                 295                 300

Val Gly His Glu Ala Leu Pro Met Ser Phe Thr Gln Lys Thr Ile Asp
305                 310                 315                 320

Arg Leu Ala Gly Lys Pro Thr His Val Asn Val Ser Val Val
                325                 330

<210> SEQ ID NO 8
<211> LENGTH: 426
<212> TYPE: PRT
<213> ORGANISM: Canis familiaris

<400> SEQUENCE: 8

Thr Ser Gln Asp Leu Ser Val Phe Pro Leu Ala Ser Cys Cys Lys Asp
1               5                   10                  15

Asn Ile Ala Ser Thr Ser Val Thr Leu Gly Cys Leu Val Thr Gly Tyr
            20                  25                  30

Leu Pro Met Ser Thr Thr Val Thr Trp Asp Thr Gly Ser Leu Asn Lys
            35                  40                  45

Asn Val Thr Thr Phe Pro Thr Thr Phe His Glu Thr Tyr Gly Leu His
50                  55                  60

Ser Ile Val Ser Gln Val Thr Ala Ser Gly Lys Trp Ala Lys Gln Arg
65                  70                  75                  80

Phe Thr Cys Ser Val Ala His Ala Glu Ser Thr Ala Ile Asn Lys Thr
                85                  90                  95

Phe Ser Ala Cys Ala Leu Asn Phe Ile Pro Pro Thr Val Lys Leu Phe
            100                 105                 110

His Ser Ser Cys Asn Pro Val Gly Asp Thr His Thr Thr Ile Gln Leu
            115                 120                 125

Leu Cys Leu Ile Ser Gly Tyr Val Pro Gly Asp Met Glu Val Ile Trp
130                 135                 140

Leu Val Asp Gly Gln Lys Ala Thr Asn Ile Phe Pro Tyr Thr Ala Pro
145                 150                 155                 160

Gly Thr Lys Glu Gly Asn Val Thr Ser Thr His Ser Glu Leu Asn Ile
                165                 170                 175
```

```
Thr Gln Gly Glu Trp Val Ser Gln Lys Thr Tyr Thr Cys Gln Val Thr
            180                 185                 190

Tyr Gln Gly Phe Thr Phe Lys Asp Glu Ala Arg Lys Cys Ser Glu Ser
        195                 200                 205

Asp Pro Arg Gly Val Thr Ser Tyr Leu Ser Pro Ser Pro Leu Asp
    210                 215                 220

Leu Tyr Val His Lys Ala Pro Lys Ile Thr Cys Leu Val Val Asp Leu
225                 230                 235                 240

Ala Thr Met Glu Gly Met Asn Leu Thr Trp Tyr Arg Glu Ser Lys Glu
                245                 250                 255

Pro Val Asn Pro Gly Pro Leu Asn Lys Lys Asp His Phe Asn Gly Thr
            260                 265                 270

Ile Thr Val Thr Ser Thr Leu Pro Val Asn Thr Asn Asp Trp Ile Glu
        275                 280                 285

Gly Glu Thr Tyr Tyr Cys Arg Val Thr His Pro His Leu Pro Lys Asp
    290                 295                 300

Ile Val Arg Ser Ile Ala Lys Ala Pro Gly Lys Arg Ala Pro Asp
305                 310                 315                 320

Val Tyr Leu Phe Leu Pro Pro Glu Glu Glu Gln Gly Thr Lys Asp Arg
                325                 330                 335

Val Thr Leu Thr Cys Leu Ile Gln Asn Phe Phe Pro Ala Asp Ile Ser
            340                 345                 350

Val Gln Trp Leu Arg Asn Asp Ser Pro Ile Gln Thr Asp Gln Tyr Thr
        355                 360                 365

Thr Thr Gly Pro His Lys Val Ser Gly Ser Arg Pro Ala Phe Phe Ile
    370                 375                 380

Phe Ser Arg Leu Glu Val Ser Arg Val Asp Trp Glu Gln Lys Asn Lys
385                 390                 395                 400

Phe Thr Cys Gln Val Val His Glu Ala Leu Ser Gly Ser Arg Ile Leu
                405                 410                 415

Gln Lys Trp Val Ser Lys Thr Pro Gly Lys
            420                 425

<210> SEQ ID NO 9
<211> LENGTH: 335
<212> TYPE: PRT
<213> ORGANISM: Felis catus

<400> SEQUENCE: 9

Ala Ser Thr Thr Ala Ser Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ser Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Arg Pro Ser Ser Thr Lys Val Asp Lys
                85                  90                  95

Thr Val Pro Lys Thr Ala Ser Thr Ile Glu Ser Lys Thr Gly Glu Gly
            100                 105                 110

Pro Lys Cys Pro Val Pro Glu Ile Pro Gly Ala Pro Ser Val Phe Ile
        115                 120                 125
```

```
Phe Pro Pro Lys Pro Lys Asp Thr Leu Ser Ile Ser Arg Thr Pro Glu
            130                 135                 140

Val Thr Cys Leu Val Val Asp Leu Gly Pro Asp Asp Ser Asn Val Gln
145                 150                 155                 160

Ile Thr Trp Phe Val Asp Asn Thr Glu Met His Thr Ala Lys Thr Arg
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
            195                 200                 205

Val Asn Ser Lys Ser Leu Pro Ser Ala Met Glu Arg Thr Ile Ser Lys
210                 215                 220

Ala Lys Gly Gln Pro His Glu Pro Gln Val Tyr Val Leu Pro Pro Thr
225                 230                 235                 240

Gln Glu Glu Leu Ser Glu Asn Lys Val Ser Val Thr Cys Leu Ile Lys
                245                 250                 255

Gly Phe His Pro Pro Asp Ile Ala Val Glu Trp Glu Ile Thr Gly Gln
                260                 265                 270

Pro Glu Pro Glu Asn Asn Tyr Gln Thr Thr Pro Pro Gln Leu Asp Ser
            275                 280                 285

Asp Gly Thr Tyr Phe Leu Tyr Ser Arg Leu Ser Val Asp Arg Ser His
            290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
                325                 330                 335

<210> SEQ ID NO 10
<211> LENGTH: 96
<212> TYPE: PRT
<213> ORGANISM: Camelus dromedarius

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Arg Glu Arg Glu Gly Val
            35                  40                  45

Ala Ala Ile Asn Ser Gly Gly Gly Ser Thr Tyr Tyr Ala Asp Ser Val
        50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

<210> SEQ ID NO 11
<211> LENGTH: 96
<212> TYPE: PRT
<213> ORGANISM: Camelus dromedarius

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Trp Met Tyr Trp Val Arg Gln Ala Pro Gly Lys Gly Leu Glu Trp Val
             35                  40                  45

Ser Thr Ile Asn Ser Gly Gly Gly Ser Thr Tyr Tyr Ala Asp Ser Val
 50                  55                  60

Lys Gly Arg Phe Thr Ile Ser Arg Asp Asn Ala Lys Asn Met Leu Tyr
 65                  70                  75                  80

Leu Gln Met Asn Ser Leu Lys Pro Glu Asp Thr Ala Met Tyr Tyr Cys
                 85                  90                  95
```

<210> SEQ ID NO 12
<211> LENGTH: 1434
<212> TYPE: DNA
<213> ORGANISM: Artificial sequence
<220> FEATURE:
<223> OTHER INFORMATION: Murine anti-AGE IgG2b heavy chain

<400> SEQUENCE: 12

```
atggacccca agggcagcct gagctggaga atcctgctgt tcctgagcct ggccttcgag     60
ctgagctacg ccaggtgca gctgctgcag ccaggtgccg agctcgtgaa acctggcgcc    120
tctgtgaagc tggcctgcaa ggcttccggc tacctgttca ccacctactg gatgcactgg    180
ctgaagcaga ggccaggcca gggcctggaa tggatcggcg agatctcccc caccaacggc    240
agagcctact acaacgcccg gttcaagtcc gaggccaccc tgaccgtgga caagtcctcc    300
aacaccgcct acatgcagct gtcctccctg acctctgagg cctccgccgt gtactactgc    360
gccagagctt acggcaacta cgagttcgcc tactggggcc agggcaccct cgtgacagtg    420
tctgtggcta agaccacccc tcctccgtg taccctctgg ctcctggctg tggcgacacc    480
accggatcct ctgtgaccct gggctgcctc gtgaagggct acttccctga gtccgtgacc    540
gtgacctgga actccggctc cctgtcctcc tccgtgcaca cctttccagc cctgctgcag    600
tccggcctgt acaccatgtc ctccagcgtg acagtgccct cctccacctg gccttcccag    660
accgtgacat gctctgtggc ccaccctgcc tcttccacca ccgtggacaa gaagctggaa    720
ccctccggcc ccatctccac catcaaccct tgccctccct gcaaagaatg ccacaagtgc    780
cctgccccca acctggaagg cggccctcc gtgttcatct cccacccaa catcaaggac    840 gtgctgatga tctccctgac ccccaaagtg acctgcgtgg tggtggacgt gtccgaggac    900 gacccctgacg tgcagatcag ttggttcgtg aacaacgtgg aagtgcacac cgcccagacc    960
cagacacaca gagaggacta caacagcacc atcagagtgg tgtctaccct gcccatccag   1020
caccaggact ggatgtccgg caaagaattc aagtgcaaag tgaacaacaa ggacctgccc   1080
agccccatcg agcggaccat ctccaagatc aagggcctcg tgcgggctcc ccaggtgtac   1140
attctgcctc caccagccga gcagctgtcc cggaaggatg tgtctctgac atgtctggtc   1200
gtgggcttca accccggcga catctccgtg gaatggacct ccaacggcca caccgaggaa   1260
aactacaagg acaccgcccc tgtgctggac tccgacggct cctacttcat ctactccaag   1320
ctgaacatga gacctccaa gtgggaaaag accgactcct ctcctgcaa cgtgcggcac   1380 gagggcctga gaaactacta cctgaagaaa accatctccc ggtcccccgg ctag         1434
```

<210> SEQ ID NO 13
<211> LENGTH: 1416
<212> TYPE: DNA
<213> ORGANISM: Artificial sequence
<220> FEATURE:
<223> OTHER INFORMATION: Chimeric anti-AGE human IgG1 antibody heavy
      chain

<400> SEQUENCE: 13

```
atggacccca agggcagcct gagctggaga atcctgctgt tcctgagcct ggccttcgag      60
ctgagctacg ccaggtgca gctgctgcag ccaggtgccg agctcgtgaa acctggcgcc     120
tctgtgaagc tggcctgcaa ggcttccggc tacctgttca ccacctactg gatgcactgg     180
ctgaagcaga ggccaggcca gggcctggaa tggatcggcg agatctcccc caccaacggc     240
agagcctact acaacgcccg gttcaagtcc gaggccaccc tgaccgtgga caagtcctcc     300
aacaccgcct acatgcagct gtcctccctg acctctgagg cctccgccgt gtactactgc     360
gccagagctt acggcaacta cgagttcgcc tactggggcc agggcacccc cgtgacagtg     420
tctgtggcta gcaccaaggg ccccagcgtg ttccctctgg cccccagcag caagagcacc     480
agcggcggaa ccgccgccct gggctgcctg gtgaaggact acttccccga gcccgtgacc     540
gtgtcctgga cagcggcgc tctgaccagc ggagtgcaca ccttccctgc cgtgctgcag     600
agcagcggcc tgtactccct gagcagcgtg gtgaccgtgc ccagcagcag cctgggcacc     660
cagacctaca tctgcaacgt gaaccacaag ccctccaaca ccaaggtgga caagaaggtg     720
gagcctaaga gctgcgacaa gacccacacc tgccctccct gccccgcccc cgagctgctg     780
ggcggaccca gcgtgttcct gttccctccc aagcccaagg acaccctgat gatcagccgc     840
acccccgagg tgacctgcgt ggtggtggac gtgagccacg aggaccccga ggtgaagttc     900
aactggtacg tggacggcgt ggaggtgcac aacgccaaga ccaagcctcg ggaggagcag     960
tacaactcca cctaccgcgt ggtgagcgtg ctgaccgtgc tgcaccagga ctggctgaac    1020
ggcaaggagt acaagtgcaa ggtgagcaac aaggccctgc ccgctcccat cgagaagacc    1080
atcagcaagg ccaagggcca gccccgggag cctcaggtgt acaccctgcc ccccagccgc    1140
gacgagctga ccaagaacca ggtgagcctg acctgcctgg tgaagggctt ctaccccctcc   1200
gacatcgccg tggagtggga gagcaacggc cagcctgaga caactacaa gaccacccct    1260
cccgtgctgg acagcgacgg cagcttcttc ctgtacagca agctgaccgt ggacaagtcc    1320
cggtggcagc agggcaacgt gttcagctgc agcgtgatgc acgaggccct gcacaaccac    1380
tacacccaga gagcctgag cctgagcccc ggatag                                1416
```

<210> SEQ ID NO 14
<211> LENGTH: 720
<212> TYPE: DNA
<213> ORGANISM: Artificial sequence
<220> FEATURE:
<223> OTHER INFORMATION: Murine anti-AGE Kappa light chain

<400> SEQUENCE: 14

```
atggagaccg acaccctgct gctctgggtg ctgctgctct gggtgcccgg ctccaccgga      60
gacgtcgtga tgacccagac ccctctgtcc ctgcctgtgt ctctgggcga ccaggcctcc     120
atctcctgcc ggtctagaca gtccctcgtg aactccaacg caacaccctt cctgcagtgg     180
tatctgcaga agcccggcca gtcccccaag ctgctgatca caaggtgtc cctgcggttc     240
tccggcgtgc ccgacagatt tccggctct ggctctggca ccgacttcac cctgaagatc     300
tcccgggtgg aagccgagga cctgggcctg tacttctgca gccagtccac ccacgtgccc     360
cctacatttg gcggaggcac caagctggaa atcaaacggg cagatgctgc accaactgta     420
tccatcttcc caccatccag tgagcagtta acatctggag gtgcctcagt cgtgtgcttc     480
ttgaacaact tctaccccaa agacatcaat gtcaagtgga agattgatgg cagtgaacga     540
caaaatggcg tcctgaacag ttggactgat caggacagca agacagcac ctacagcatg     600
```
agcagcaccc tcacgttgac caaggacgag tatgaacgac ataacagcta tacctgtgag    660
gccactcaca agacatcaac ttcacccatt gtcaagagct caacaggaa tgagtgttga    720

<210> SEQ ID NO 15
<211> LENGTH: 720
<212> TYPE: DNA
<213> ORGANISM: Artificial sequence
<220> FEATURE:
<223> OTHER INFORMATION: Chimeric anti-AGE human kappa light chain

<400> SEQUENCE: 15
atggagaccg acaccctgct gctctgggtg ctgctgctct gggtgcccgg ctccaccgga     60
gacgtcgtga tgacccagac ccctctgtcc ctgcctgtgt ctctgggcga ccaggcctcc    120
atctcctgcc ggtctagaca gtccctcgtg aactccaacg gcaacacctt cctgcagtgg    180
tatctgcaga agcccggcca gtcccccaag ctgctgatct acaaggtgtc cctgcggttc    240
tccggcgtgc ccgacagatt ttccggctct ggctctggca ccgacttcac cctgaagatc    300
tcccgggtgg aagccgagga cctgggcctg tacttctgca gccagtccac ccacgtgccc    360
cctacatttg gcggaggcac caagctggaa atcaagcgga ccgtggccgc ccccagcgtg    420
ttcatcttcc ctcccagcga cgagcagctg aagtctggaa ccgccagcgt ggtgtgcctg    480
ctgaacaact ctacccccg cgaggccaag gtgcagtgga aggtggacaa cgccctgcag    540
agcggcaaca gccaggagag cgtgaccgag caggactcca aggacagcac ctacagcctg    600
agcagcaccc tgaccctgag caaggccgac tacgagaagc acaaggtgta cgcctgcgag    660
gtgacccacc agggactgtc tagccccgtg accaagagct caaccgggg cgagtgctaa    720

<210> SEQ ID NO 16
<211> LENGTH: 477
<212> TYPE: PRT
<213> ORGANISM: Artificial sequence
<220> FEATURE:
<223> OTHER INFORMATION: Murine anti-AGE IgG2b heavy chain

<400> SEQUENCE: 16

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Leu Gln Pro Gly
            20                  25                  30

Ala Glu Leu Val Lys Pro Gly Ala Ser Val Lys Leu Ala Cys Lys Ala
        35                  40                  45

Ser Gly Tyr Leu Phe Thr Thr Tyr Trp Met His Trp Leu Lys Gln Arg
    50                  55                  60

Pro Gly Gln Gly Leu Glu Trp Ile Gly Glu Ile Ser Pro Thr Asn Gly
65                  70                  75                  80

Arg Ala Tyr Tyr Asn Ala Arg Phe Lys Ser Glu Ala Thr Leu Thr Val
                85                  90                  95

Asp Lys Ser Ser Asn Thr Ala Tyr Met Gln Leu Ser Ser Leu Thr Ser
            100                 105                 110

Glu Ala Ser Ala Val Tyr Tyr Cys Ala Arg Ala Tyr Gly Asn Tyr Glu
        115                 120                 125

Phe Ala Tyr Trp Gly Gln Gly Thr Leu Val Thr Val Ser Val Ala Lys
    130                 135                 140

Thr Thr Pro Pro Ser Val Tyr Pro Leu Ala Pro Gly Cys Gly Asp Thr
145                 150                 155                 160

```
Thr Gly Ser Ser Val Thr Leu Gly Cys Leu Val Lys Gly Tyr Phe Pro
            165                 170                 175
Glu Ser Val Thr Val Thr Trp Asn Ser Gly Leu Ser Ser Val
            180                 185                 190
His Thr Phe Pro Ala Leu Leu Gln Ser Gly Leu Tyr Thr Met Ser Ser
            195                 200                 205
Ser Val Thr Val Pro Ser Ser Thr Trp Pro Ser Gln Thr Val Thr Cys
            210                 215                 220
Ser Val Ala His Pro Ala Ser Ser Thr Thr Val Asp Lys Lys Leu Glu
225                 230                 235                 240
Pro Ser Gly Pro Ile Ser Thr Ile Asn Pro Cys Pro Pro Cys Lys Glu
            245                 250                 255
Cys His Lys Cys Pro Ala Pro Asn Leu Glu Gly Gly Pro Ser Val Phe
            260                 265                 270
Ile Phe Pro Pro Asn Ile Lys Asp Val Leu Met Ile Ser Leu Thr Pro
            275                 280                 285
Lys Val Thr Cys Val Val Val Asp Val Ser Glu Asp Asp Pro Asp Val
            290                 295                 300
Gln Ile Ser Trp Phe Val Asn Asn Val Glu Val His Thr Ala Gln Thr
305                 310                 315                 320
Gln Thr His Arg Glu Asp Tyr Asn Ser Thr Ile Arg Val Val Ser Thr
            325                 330                 335
Leu Pro Ile Gln His Gln Asp Trp Met Ser Gly Lys Glu Phe Lys Cys
            340                 345                 350
Lys Val Asn Asn Lys Asp Leu Pro Ser Pro Ile Glu Arg Thr Ile Ser
            355                 360                 365
Lys Ile Lys Gly Leu Val Arg Ala Pro Gln Val Tyr Ile Leu Pro Pro
            370                 375                 380
Pro Ala Glu Gln Leu Ser Arg Lys Asp Val Ser Leu Thr Cys Leu Val
385                 390                 395                 400
Val Gly Phe Asn Pro Gly Asp Ile Ser Val Glu Trp Thr Ser Asn Gly
            405                 410                 415
His Thr Glu Glu Asn Tyr Lys Asp Thr Ala Pro Val Leu Asp Ser Asp
            420                 425                 430
Gly Ser Tyr Phe Ile Tyr Ser Lys Leu Asn Met Lys Thr Ser Lys Trp
            435                 440                 445
Glu Lys Thr Asp Ser Phe Ser Cys Asn Val Arg His Glu Gly Leu Lys
            450                 455                 460
Asn Tyr Tyr Leu Lys Lys Thr Ile Ser Arg Ser Pro Gly
465                 470                 475

<210> SEQ ID NO 17
<211> LENGTH: 471
<212> TYPE: PRT
<213> ORGANISM: Artificial sequence
<220> FEATURE:
<223> OTHER INFORMATION: Chimeric anti-AGE human IgG1 heavy chain

<400> SEQUENCE: 17

Met Asp Pro Lys Gly Ser Leu Ser Trp Arg Ile Leu Leu Phe Leu Ser
1               5                   10                  15
Leu Ala Phe Glu Leu Ser Tyr Gly Gln Val Gln Leu Gln Pro Gly
            20                  25                  30
Ala Glu Leu Val Lys Pro Gly Ala Ser Val Lys Leu Ala Cys Lys Ala
            35                  40                  45
```

-continued

```
Ser Gly Tyr Leu Phe Thr Thr Tyr Trp Met His Trp Leu Lys Gln Arg
 50                  55                  60
Pro Gly Gln Gly Leu Glu Trp Ile Gly Glu Ile Ser Pro Thr Asn Gly
 65                  70                  75                  80
Arg Ala Tyr Tyr Asn Ala Arg Phe Lys Ser Glu Ala Thr Leu Thr Val
                 85                  90                  95
Asp Lys Ser Ser Asn Thr Ala Tyr Met Gln Leu Ser Ser Leu Thr Ser
                100                 105                 110
Glu Ala Ser Ala Val Tyr Tyr Cys Ala Arg Ala Tyr Gly Asn Tyr Glu
                115                 120                 125
Phe Ala Tyr Trp Gly Gln Gly Thr Leu Val Thr Val Ser Val Ala Ser
130                 135                 140
Thr Lys Gly Pro Ser Val Phe Pro Leu Ala Pro Ser Ser Lys Ser Thr
145                 150                 155                 160
Ser Gly Gly Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
                180                 185                 190
His Thr Phe Pro Ala Val Leu Gln Ser Ser Gly Leu Tyr Ser Leu Ser
                195                 200                 205
Ser Val Val Thr Val Pro Ser Ser Leu Gly Thr Gln Thr Tyr Ile
210                 215                 220
Cys Asn Val Asn His Lys Pro Ser Asn Thr Lys Val Asp Lys Lys Val
225                 230                 235                 240
Glu Pro Lys Ser Cys Asp Lys Thr His Thr Cys Pro Pro Cys Pro Ala
                245                 250                 255
Pro Glu Leu Leu Gly Gly Pro Ser Val Phe Leu Phe Pro Pro Lys Pro
                260                 265                 270
Lys Asp Thr Leu Met Ile Ser Arg Thr Pro Glu Val Thr Cys Val Val
                275                 280                 285
Val Asp Val Ser His Glu Asp Pro Glu Val Lys Phe Asn Trp Tyr Val
290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
                340                 345                 350
Leu Pro Ala Pro Ile Glu Lys Thr Ile Ser Lys Ala Lys Gly Gln Pro
                355                 360                 365
Arg Glu Pro Gln Val Tyr Thr Leu Pro Pro Ser Arg Asp Glu Leu Thr
370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
                420                 425                 430
Ser Lys Leu Thr Val Asp Lys Ser Arg Trp Gln Gln Gly Asn Val Phe
                435                 440                 445
```

Ser Cys Ser Val Met His Glu Ala Leu His Asn His Tyr Thr Gln Lys
            450                 455                 460

Ser Leu Ser Leu Ser Pro Gly
465                 470

<210> SEQ ID NO 18
<211> LENGTH: 239
<212> TYPE: PRT
<213> ORGANISM: Artificial sequence
<220> FEATURE:
<223> OTHER INFORMATION: Murine anti-AGE kappa light chain

<400> SEQUENCE: 18

Met Glu Thr Asp Thr Leu Leu Leu Trp Val Leu Leu Leu Trp Val Pro
1               5                   10                  15

Gly Ser Thr Gly Asp Val Val Met Thr Gln Thr Pro Leu Ser Leu Pro
            20                  25                  30

Val Ser Leu Gly Asp Gln Ala Ser Ile Ser Cys Arg Ser Arg Gln Ser
        35                  40                  45

Leu Val Asn Ser Asn Gly Asn Thr Phe Leu Gln Trp Tyr Leu Gln Lys
    50                  55                  60

Pro Gly Gln Ser Pro Lys Leu Leu Ile Tyr Lys Val Ser Leu Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Leu Gly Leu Tyr Phe
            100                 105                 110

Cys Ser Gln Ser Thr His Val Pro Pro Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235

<210> SEQ ID NO 19
<211> LENGTH: 239
<212> TYPE: PRT
<213> ORGANISM: Artificial sequence
<220> FEATURE:
<223> OTHER INFORMATION: Chimeric anti-AGE human kappa light chain

<400> SEQUENCE: 19

Met Glu Thr Asp Thr Leu Leu Leu Trp Val Leu Leu Leu Trp Val Pro
1               5                   10                  15

Gly Ser Thr Gly Asp Val Val Met Thr Gln Thr Pro Leu Ser Leu Pro
            20                  25                  30

Val Ser Leu Gly Asp Gln Ala Ser Ile Ser Cys Arg Ser Arg Gln Ser
        35                  40                  45

Leu Val Asn Ser Asn Gly Asn Thr Phe Leu Gln Trp Tyr Leu Gln Lys
 50                  55                  60

Pro Gly Gln Ser Pro Lys Leu Leu Ile Tyr Lys Val Ser Leu Arg Phe
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Leu Gly Leu Tyr Phe
                100                 105                 110

Cys Ser Gln Ser Thr His Val Pro Pro Thr Phe Gly Gly Gly Thr Lys
                115                 120                 125

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
                180                 185                 190

Ser Lys Asp Ser Thr Tyr Ser Leu Ser Ser Thr Leu Thr Leu Ser Lys
                195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 20
<211> LENGTH: 118
<212> TYPE: PRT
<213> ORGANISM: Artificial sequence
<220> FEATURE:
<223> OTHER INFORMATION: Murine anti-AGE IgG2b heavy chain (variable
      region)

<400> SEQUENCE: 20

Gln Val Gln Leu Leu Gln Pro Gly Ala Glu Leu Val Lys Pro Gly Ala
1               5                   10                  15

Ser Val Lys Leu Ala Cys Lys Ala Ser Gly Tyr Leu Phe Thr Thr Tyr
                20                  25                  30

Trp Met His Trp Leu Lys Gln Arg Pro Gly Gln Gly Leu Glu Trp Ile
            35                  40                  45

Gly Glu Ile Ser Pro Thr Asn Gly Arg Ala Tyr Tyr Asn Ala Arg Phe
     50                  55                  60

Lys Ser Glu Ala Thr Leu Thr Val Asp Lys Ser Ser Asn Thr Ala Tyr
65                  70                  75                  80

Met Gln Leu Ser Ser Leu Thr Ser Glu Ala Ser Ala Val Tyr Tyr Cys
                85                  90                  95

Ala Arg Ala Tyr Gly Asn Tyr Glu Phe Ala Tyr Trp Gly Gln Gly Thr
                100                 105                 110

Leu Val Thr Val Ser Val
            115

<210> SEQ ID NO 21
<211> LENGTH: 112
<212> TYPE: PRT
<213> ORGANISM: Artificial sequence
<220> FEATURE:
<223> OTHER INFORMATION: Murine anti-AGE kappa light chain (variable
      region)

```
<400> SEQUENCE: 21

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val Asn Ser
            20                  25                  30

Asn Gly Asn Thr Phe Leu Gln Trp Tyr Leu Gln Lys Pro Gly Gln Ser
        35                  40                  45

Pro Lys Leu Leu Ile Tyr Lys Val Ser Leu Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Leu Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 22
<211> LENGTH: 326
<212> TYPE: PRT
<213> ORGANISM: Artificial sequence
<220> FEATURE:
<223> OTHER INFORMATION: Human constant region

<400> SEQUENCE: 22

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65              70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145             150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225             230                 235                 240
```

```
Gln Val Ser Leu Thr Cys Leu Val Lys Gly Phe Tyr Pro Ser Asp Ile
            245                 250                 255

Ser Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 23
<211> LENGTH: 7
<212> TYPE: PRT
<213> ORGANISM: Artificial sequence
<220> FEATURE:
<223> OTHER INFORMATION: CDR1H (heavy chain)

<400> SEQUENCE: 23

Ser Tyr Thr Met Gly Val Ser
1               5

<210> SEQ ID NO 24
<211> LENGTH: 17
<212> TYPE: PRT
<213> ORGANISM: Artificial sequence
<220> FEATURE:
<223> OTHER INFORMATION: CDR2H (heavy chain)

<400> SEQUENCE: 24

Thr Ile Ser Ser Gly Gly Gly Ser Thr Tyr Tyr Pro Asp Ser Val Lys
1               5                   10                  15

Gly

<210> SEQ ID NO 25
<211> LENGTH: 10
<212> TYPE: PRT
<213> ORGANISM: Artificial sequence
<220> FEATURE:
<223> OTHER INFORMATION: CDR3H (heavy chain)
<220> FEATURE:
<221> NAME/KEY: misc_feature
<222> LOCATION: (10)..(10)
<223> OTHER INFORMATION: Xaa can be any naturally occurring amino acid

<400> SEQUENCE: 25

Gln Gly Gly Trp Leu Pro Pro Phe Ala Xaa
1               5                   10

<210> SEQ ID NO 26
<211> LENGTH: 17
<212> TYPE: PRT
<213> ORGANISM: Artificial sequence
<220> FEATURE:
<223> OTHER INFORMATION: CDR1L (light chain)

<400> SEQUENCE: 26

Arg Ala Ser Lys Ser Val Ser Thr Ser Ser Arg Gly Tyr Ser Tyr Met
1               5                   10                  15

His
```

```
<210> SEQ ID NO 27
<211> LENGTH: 7
<212> TYPE: PRT
<213> ORGANISM: Artificial sequence
<220> FEATURE:
<223> OTHER INFORMATION: CDR2L (light chain)

<400> SEQUENCE: 27

Leu Val Ser Asn Leu Glu Ser
1               5

<210> SEQ ID NO 28
<211> LENGTH: 9
<212> TYPE: PRT
<213> ORGANISM: Artificial sequence
<220> FEATURE:
<223> OTHER INFORMATION: CDR3L (light chain)

<400> SEQUENCE: 28

Gln His Ile Arg Glu Leu Thr Arg Ser
1               5

<210> SEQ ID NO 29
<211> LENGTH: 468
<212> TYPE: PRT
<213> ORGANISM: Artificial Sequence
<220> FEATURE:
<223> OTHER INFORMATION: Humanized heavy chain

<400> SEQUENCE: 29

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Tyr Leu Phe Thr Thr Tyr Trp Met His Trp Val Arg Gln Ala
    50                  55                  60

Pro Gly Gln Gly Leu Glu Trp Met Gly Glu Ile Ser Pro Thr Asn Gly
65                  70                  75                  80

Arg Ala Tyr Tyr Asn Gln Lys Phe Gln Gly Arg Val Thr Met Thr Val
                85                  90                  95

Asp Lys Ser Thr Asn Thr Val Tyr Met Glu Leu Ser Ser Leu Arg Ser
            100                 105                 110

Glu Asp Thr Ala Val Tyr Tyr Cys Ala Arg Ala Tyr Gly Asn Tyr Phe
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240
```

```
Pro Lys Ser Cys Asp Lys Thr His Thr Cys Pro Pro Cys Pro Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly
465

<210> SEQ ID NO 30
<211> LENGTH: 1408
<212> TYPE: DNA
<213> ORGANISM: Artificial Sequence
<220> FEATURE:
<223> OTHER INFORMATION: Humanized heavy chain

<400> SEQUENCE: 30
atggacccca agggcagcct gagctggaga atcctgctgt cctgagcct  ggccttcgag      60 ctgagctacg ccaggtgca  gctggtgcag tctggcgccg aagtgaagaa acctggcgcc     120
tccgtgaggt gtcctgcaag gcttccggct acctgttcac cacctactgg atgcactggg     180
tgcgacaggc ccctggacag ggcctggaat ggatgggcga gatctcccct accaacggca     240
gagcctacta caacagaaat tccagggcag agtgaccatg accgtggaca gtccaccaa      300 caccgtgtac atggaactgt cctccctgcg gagcgaggac accgccgtgt actactgcgc     360
tagagcctac ggcaactacg attcgcctac tggggccagg gcaccctcgt gacagtgtcc     420
tctgctagca ccaagggccc cagcgtgttc cctctggccc ccagcagcaa gagcaccagc     480
ggcggaaccg ccgccctggg ctgcctggga aggactactt ccccgagccc gtgaccgtgt     540
cctggaacag cggcgctctg accagcggag tgcacacctt cctgccgtg  ctgcagagca     600 gcggcctgta ctccctgagc agcgtggtga ccgtgccagc agcagcctgg gcacccagac     660
ctacatctgc aacgtgaacc acaagccctc caacaccaag gtggacaaga aggtggagcc     720
```

```
taagagctgc gacaagaccc acacctgccc tccctgcccc gccccgagct gctgggcgga    780
cccagcgtgt tcctgttccc tcccaagccc aaggacaccc tgatgatcag ccgcaccccc    840
gaggtgacct gcgtggtggt ggacgtgagc cacgaggacc ccgaggtgag ttcaactggt    900
acgtggacgg cgtggaggtg cacaacgcca agaccaagcc tcgggaggag cagtacaact    960
ccacctaccg cgtggtgagc gtgctgaccg tgctgcacca ggactggctg aacggcagga   1020
gtacaagtgc aaggtgagca acaaggccct gcccgctccc atcgagaaga ccatcagcaa   1080
ggccaagggc cagccccggg agcctcaggt gtacaccctg cccccagcc gcgacgagct   1140 gacaagaacc aggtgagcct gacctgcctg gtgaagggct tctacccctc cgacatcgcc   1200
gtggagtggg agagcaacgg ccagcctgag aacaactaca agaccacccc tcccgtgctg   1260
gacagcgacg gcagcttctt ctgtacagca agctgaccgt ggacaagtcc cggtggcagc   1320
agggcaacgt gttcagctgc agcgtgatgc acgaggccct gcacaaccac tacacccaga   1380
agagcctgag cctgagcccg gatagtaa                                      1408

<210> SEQ ID NO 31
<211> LENGTH: 468
<212> TYPE: PRT
<213> ORGANISM: Artificial Sequence
<220> FEATURE:
<223> OTHER INFORMATION: Humanized heavy chain

<400> SEQUENCE: 31

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
                20                  25                  30

Ala Glu Val Lys Lys Pro Gly Ala Ser Val Lys Val Ser Cys Lys Ala
            35                  40                  45

Ser Gly Tyr Leu Phe Thr Thr Tyr Trp Met His Trp Val Arg Gln Ala
        50                  55                  60

Pro Gly Gln Gly Leu Glu Trp Met Gly Glu Ile Ser Pro Thr Asn Gly
65                  70                  75                  80

Arg Ala Tyr Tyr Asn Ala Lys Phe Gln Gly Arg Val Thr Met Thr Val
                85                  90                  95

Asp Lys Ser Thr Asn Thr Ala Tyr Met Glu Leu Ser Ser Leu Arg Ser
            100                 105                 110

Glu Asp Thr Ala Val Tyr Tyr Cys Ala Arg Ala Tyr Gly Asn Tyr Phe
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240
```

```
Pro Lys Ser Cys Asp Lys Thr His Thr Cys Pro Pro Cys Pro Pro Glu
            245                 250                 255

Leu Leu Gly Gly Pro Ser Val Phe Leu Phe Pro Pro Lys Pro Lys Asp
        260                 265                 270

Thr Leu Met Ile Ser Arg Thr Pro Glu Val Thr Cys Val Val Val Asp
    275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 32
<211> LENGTH: 1408
<212> TYPE: DNA
<213> ORGANISM: Artificial Sequence
<220> FEATURE:
<223> OTHER INFORMATION: Humanized heavy chain

<400> SEQUENCE: 32
atggacccca agggcagcct gagctggaga atcctgctgt tcctgagcct ggccttcgag      60
ctgagctacg ccaggtgca gctggtgcag tctggcgccg aagtgaagaa acctggcgcc     120
tccgtgaggt gtcctgcaag gcttccggct acctgttcac cacctactgg atgcactggg     180
tgcgacaggc ccctggacag ggcctggaat ggatgggcga gatctcccct accaacggca     240
gagcctacta caaccaaaat tccagggcag agtgaccatg accgtggaca gtccaccaa     300 caccgcttac atggaactgt cctccctgcg gagcgaggac accgccgtgt actactgcgc     360
tagagcctac ggcaactacg attcgcctac tggggccagg gcaccctcgt gacagtgtcc     420
tctgctagca ccaagggccc cagcgtgttc cctctggccc ccagcagcaa gagcaccagc     480
ggcggaaccg ccgccctggg ctgcctggga aggactactt ccccgagccc gtgaccgtgt     540
cctggaacag cggcgctctg accagcggag tgcacacctt ccctgccgtg ctgcagagca     600
gcggcctgta ctccctgagc agcgtggtga ccgtgccagc agcagcctgg cacccagac     660 ctacatctgc aacgtgaacc acaagccctc caacaccaag gtggacaaga aggtggagcc     720
```

-continued

```
taagagctgc gacaagaccc acacctgccc tccctgcccc gccccgagct gctgggcgga    780
cccagcgtgt tcctgttccc tcccaagccc aaggacaccc tgatgatcag ccgcaccccc    840
gaggtgacct gcgtggtggt ggacgtgagc cacgaggacc ccgaggtgag ttcaactggt    900
acgtggacgg cgtggaggtg cacaacgcca agaccaagcc tcgggaggag cagtacaact    960
ccacctaccg cgtggtgagc gtgctgaccg tgctgcacca ggactggctg aacggcagga   1020
gtacaagtgc aaggtgagca acaaggccct gcccgctccc atcgagaaga ccatcagcaa   1080
ggccaagggc cagccccggg agcctcaggt gtacaccctg cccccagcc gcgacgagct   1140 gacaagaacc aggtgagcct gacctgcctg gtgaagggct tctacccctc cgacatcgcc   1200
gtggagtggg agagcaacgg ccagcctgag aacaactaca agaccacccc tcccgtgctg   1260
gacagcgacg cagcttcttc ctgtacagca agctgaccgt ggacaagtcc cggtggcagc   1320
agggcaacgt gttcagctgc agcgtgatgc acgaggccct gcacaaccac tacacccaga   1380
agagcctgag cctgagcccg gatagtaa                                        1408
```

<210> SEQ ID NO 33
<211> LENGTH: 468
<212> TYPE: PRT
<213> ORGANISM: Artificial Sequence
<220> FEATURE:
<223> OTHER INFORMATION: Humanized heavy chain

<400> SEQUENCE: 33

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Tyr Leu Phe Thr Thr Tyr Trp Met His Trp Val Arg Gln Ala
    50                  55                  60

Pro Gly Gln Gly Leu Glu Trp Met Gly Glu Ile Ser Pro Thr Asn Gly
65                  70                  75                  80

Arg Ala Tyr Tyr Asn Ala Lys Phe Gln Gly Arg Val Thr Met Thr Val
                85                  90                  95

Asp Lys Ser Ile Asn Thr Ala Tyr Met Glu Leu Ser Arg Leu Arg Ser
            100                 105                 110

Asp Asp Thr Ala Val Tyr Tyr Cys Ala Arg Ala Tyr Gly Asn Tyr Phe
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240
```

```
Pro Lys Ser Cys Asp Lys Thr His Thr Cys Pro Pro Cys Pro Pro Glu
            245                 250                 255

Leu Leu Gly Gly Pro Ser Val Phe Leu Phe Pro Pro Lys Pro Lys Asp
        260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 34
<211> LENGTH: 1408
<212> TYPE: DNA
<213> ORGANISM: Artificial Sequence
<220> FEATURE:
<223> OTHER INFORMATION: Humanized heavy chain

<400> SEQUENCE: 34
atggacccca agggcagcct gagctggaga atcctgctgt tcctgagcct ggccttcgag      60
ctgagctacg ccaggtgca gctggtgcag tctggcgccg aagtgaagaa acctggcgcc     120
tccgtgaggt gtcctgcaag gcttccggct acctgttcac cacctactgg atgcactggg     180
tgcgacaggc ccctggacag ggcctggaat ggatgggcga gatctcccct accaacggca     240
gagcctacta caaccaaaat tccagggcag agtgaccatg accgtggaca gtccatcaa     300 caccgcttac atggaactgt ccagactgcg gagcgatgac accgccgtgt actactgcgc     360
tagagcctac ggcaactacg attcgcctac tggggccagg gcaccctcgt gacagtgtcc     420
tctgctagca ccaagggccc cagcgtgttc cctctggccc ccagcagcaa gagcaccagc     480
ggcggaaccg ccgccctggg ctgcctggga aggactactt ccccgagccc gtgaccgtgt     540
cctggaacag cggcgctctg accagcggag tgcacacctt ccctgccgtg ctgcagagca     600
gcggcctgta ctccctgagc agcgtggtga ccgtgccagc agcagcctgg gcacccagac     660
ctacatctgc aacgtgaacc acaagccctc caacaccaag gtggacaaga aggtggagcc     720
```

```
taagagctgc gacaagaccc acacctgccc tccctgcccc gccccgagct gctgggcgga    780
cccagcgtgt tcctgttccc tcccaagccc aaggacaccc tgatgatcag ccgcacccc     840 gaggtgacct gcgtggtggt ggacgtgagc cacgaggacc ccgaggtgag ttcaactggt    900
acgtggacgg cgtggaggtg cacaacgcca agaccaagcc tcgggaggag cagtacaact    960
ccacctaccg cgtggtgagc gtgctgaccg tgctgcacca ggactggctg aacggcagga   1020
gtacaagtgc aaggtgagca acaaggccct gcccgctccc atcgagaaga ccatcagcaa   1080
ggccaagggc cagccccggg agcctcaggt gtacaccctg cccccagcc cgacgagct    1140 gacaagaacc aggtgagcct gacctgcctg gtgaagggct tctaccccct cgacatcgcc   1200
gtggagtggg agagcaacgg ccagcctgag aacaactaca agaccacccc tcccgtgctg   1260
gacagcgacg gcagcttcttc ctgtacagca agctgaccgt ggacaagtcc cggtggcagc   1320
agggcaacgt gttcagctgc agcgtgatgc acgaggccct gcacaaccac tacacccaga   1380
agagcctgag cctgagcccg gatagtaa                                     1408
```

<210> SEQ ID NO 35
<211> LENGTH: 238
<212> TYPE: PRT
<213> ORGANISM: Artificial Sequence
<220> FEATURE:
<223> OTHER INFORMATION: Humanized light chain

<400> SEQUENCE: 35

```
Met Glu Thr Asp Thr Leu Leu Leu Trp Val Leu Leu Leu Trp Val Pro
1               5                   10                  15

Gly Ser Thr Gly Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Val Asn Ser Asn Gly Asn Thr Phe Leu Gln Trp Tyr Gln Gln Arg
    50                  55                  60

Pro Gly Gln Ser Pro Arg Leu Leu Ile Tyr Lys Val Ser Leu Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Val Pro Pro Thr Phe Gly Gly Gly Thr Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205
```

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 36
<211> LENGTH: 715
<212> TYPE: DNA
<213> ORGANISM: Artificial Sequence
<220> FEATURE:
<223> OTHER INFORMATION: Humanized light chain

<400> SEQUENCE: 36

```
atggagaccg acaccctgct gctctgggtg ctgctgctct gggtgcccgg ctccaccgga      60
gacgtcgtga tgacccagtc ccctctgtcc ctgcctgtga ccctgggaca gcctgcctcc     120
atctcctcag atcctcccag tccctcgtga actccaacgg caacaccttc ctgcagtggt     180
atcagcagcg gcctggccag agccccagac tgctgatcta caaggtgtcc ctgcggttct     240
ccggcgtgcc cgacgatttt ccggctctgg ctctggcacc gacttcaccc tgaagatctc     300
ccgggtggaa gccgaggacg tgggcgtgta ctactgctcc cagagcaccc acgtgccccc     360
tacatttggc ggaggcacca gtggaaatc aagcggaccg tggccgcccc cagcgtgttc     420
atcttccctc ccagcgacga gcagctgaag tctggcaccg ccagcgtggt gtgcctgctg     480
aacaacttct accccgcga ggccaagggc agtggaaggt ggacaacgcc ctgcagagcg     540
gcaacagcca ggagagcgtg accgagcagg actccaagga cagcacctac agcctgagca     600
gcaccctgac cctgagcaag gccgactacg agaagacaag gtgtacgcct gcgaggtgac     660
ccaccaggga ctgtctagcc ccgtgaccaa gagcttcaac cggggcgagt gctaa          715
```

<210> SEQ ID NO 37
<211> LENGTH: 238
<212> TYPE: PRT
<213> ORGANISM: Artificial Sequence
<220> FEATURE:
<223> OTHER INFORMATION: Humanized light chain

<400> SEQUENCE: 37

Met Glu Thr Asp Thr Leu Leu Leu Trp Val Leu Leu Leu Trp Val Pro
1               5                   10                  15

Gly Ser Thr Gly Asp Val Val Met Thr Gln Ser Pro Leu Ser Leu Pro
            20                  25                  30

Val Thr Leu Gly Gln Pro Ala Ser Ile Ser Cys Arg Ser Arg Gln Ser
        35                  40                  45

Leu Val Asn Ser Asn Gly Asn Thr Phe Leu Gln Trp Tyr Gln Gln Arg
    50                  55                  60

Pro Gly Gln Ser Pro Arg Leu Leu Ile Tyr Lys Val Ser Leu Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Val Pro Pro Thr Phe Gly Gly Gly Thr Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

```
Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 38
<211> LENGTH: 715
<212> TYPE: DNA
<213> ORGANISM: Artificial Sequence
<220> FEATURE:
<223> OTHER INFORMATION: Humanized light chain

<400> SEQUENCE: 38

```
atggagaccg acaccctgct gctctgggtg ctgctgctct gggtgcccgg ctccaccgga    60
gacgtcgtga tgacccagtc ccctctgtcc ctgcctgtga ccctgggaca gcctgcctcc   120
atctcctcag atccaggcag tccctcgtga actccaacgg caacaccttc tgcagtggt    180
atcagcagcg gcctggccag agccccagac tgctgatcta caaggtgtcc ctgcggttct   240
ccggcgtgcc cgacgatttt ccggctctgg ctctggcacc gacttcaccc tgaagatctc   300
ccgggtggaa gccgaggacg tgggcgtgta ctactgctcc cagagcaccc acgtgccccc   360
tacatttggc ggaggcacca gtggaaatc aagcggaccg tggccgcccc cagcgtgttc    420
atcttcccte ccagcgacga gcagctgaag tctggcaccg ccagcgtggt gtgcctgctg   480
aacaacttct accccgcga ggccaagggc agtggaaggt ggacaacgcc ctgcagagcg    540
gcaacagcca ggagagcgtg accgagcagg actccaagga cagcacctac agcctgagca   600
gcaccctgac cctgagcaag gccgactacg agaagacaag gtgtacgcct gcgaggtgac   660
ccaccaggga ctgtctagcc ccgtgaccaa gagcttcaac cggggcgagt gctaa        715
```

<210> SEQ ID NO 39
<211> LENGTH: 238
<212> TYPE: PRT
<213> ORGANISM: Artificial Sequence
<220> FEATURE:
<223> OTHER INFORMATION: Humanized light chain

<400> SEQUENCE: 39

```
Met Glu Thr Asp Thr Leu Leu Leu Trp Val Leu Leu Leu Trp Val Pro
1               5                   10                  15

Gly Ser Thr Gly Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Val Asn Ser Asn Gly Asn Thr Phe Leu Gln Trp Tyr His Gln Arg
    50                  55                  60

Pro Gly Gln Pro Pro Arg Leu Leu Ile Tyr Lys Val Ser Leu Arg Phe
65                  70                  75                  80

Ser Gly Val Pro Asp Arg Phe Ser Gly Ser Gly Ala Gly Lys Asp Phe
                85                  90                  95

Thr Leu Lys Ile Ser Arg Val Glu Ala Glu Asp Val Gly Val Tyr Tyr
            100                 105                 110
```

```
Cys Ser Gln Ser Thr His Val Pro Pro Thr Phe Gly Gln Gly Thr Leu
        115                 120                 125

Glu Ile Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
                180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 40
<211> LENGTH: 715
<212> TYPE: DNA
<213> ORGANISM: Artificial Sequence
<220> FEATURE:
<223> OTHER INFORMATION: Humanized light chain

<400> SEQUENCE: 40
atggagaccg acaccctgct gctctgggtg ctgctgctct gggtgcccgg ctccaccgga      60
gacgtcgtga tgacccagtc ccctctgtcc agtcctgtga ccctgggaca gcctgcctcc     120
atctcctcag atcctcccag tccctcgtga actccaacgg caacaccttc ctgcagtggt     180
atcaccagcg gcctggccag cctcccagac tgctgatcta caaggtgtcc ctgcggttct     240
ccggcgtgcc cgacgatttt ccggctctgg cgctggcaag gacttcaccc tgaagatctc     300
ccgggtggaa gccgaggacg tgggcgtgta ctactgctcc cagagcaccc acgtgccccc     360
tacatttggc cagggcacca actggaaatc aagcggaccg tggccgcccc cagcgtgttc     420
atcttccctc ccagcgacga gcagctgaag tctggcaccg ccagcgtggt gtgcctgctg     480
aacaacttct accccgcga ggccaagggc agtggaaggt ggacaacgcc ctgcagagcg      540
gcaacagcca ggagagcgtg accgagcagg actccaagga cagcacctac agcctgagca     600
gcaccctgac cctgagcaag gccgactacg agaagacaag gtgtacgcct gcgaggtgac     660
ccaccaggga ctgtctagcc ccgtgaccaa gagcttcaac cggggcgagt gctaa           715
```